United States Patent [19]

Matsui et al.

[11] Patent Number: 5,858,270

[45] Date of Patent: Jan. 12, 1999

[54] DIFLUOROOXYMETHANE DERIVATIVE AND LIQUID CRYSTAL COMPOSITION

[75] Inventors: Shuichi Matsui; Kazutoshi Miyazawa, both of Chiba; Noriyuki Ohnishi, Kumamoto; Yasuhiro Haseba, Chiba; Yasuyuki Goto, Chiba; Etsuo Nakagawa, Chiba; Shinichi Sawada, Chiba, all of Japan

[73] Assignee: Chisso Corporation, Osaka, Japan

[21] Appl. No.: 776,298

[22] PCT Filed: Oct. 13, 1995

[86] PCT No.: PCT/JP95/02099

§ 371 Date: Jan. 30, 1997

§ 102(e) Date: Jan. 30, 1997

[87] PCT Pub. No.: WO96/11897

PCT Pub. Date: Apr. 25, 1996

[30] Foreign Application Priority Data

Oct. 13, 1994 [JP] Japan .............................. Hei 6-274511
Aug. 11, 1995 [JP] Japan .............................. Hei 7-205531

[51] Int. Cl.$^6$ .......................... C09K 19/52; C09K 19/34; C09K 19/30; C07C 19/08
[52] U.S. Cl. ................................ 252/299.01; 252/299.61; 252/299.63; 252/299.66; 570/127; 570/128; 570/129; 570/130; 570/131
[58] Field of Search ......................... 252/299.01, 299.61, 252/299.63, 299.66; 570/127, 128, 129, 130, 131

[56] References Cited

U.S. PATENT DOCUMENTS 5,045,229 9/1991 Bartmann et al. .................. 252/299.01
5,589,102 12/1996 Bartmann et al. .................. 252/299.01

FOREIGN PATENT DOCUMENTS 5-112778 5/1993 Japan .

Primary Examiner—Shean C. Wu
Attorney, Agent, or Firm—Wenderoth, Lind & Ponack, L.L.P.

[57] ABSTRACT

In order to provide novel compounds which are useful as liquid crystal materials for low voltages in several liquid crystal displays, have a large dielectric anisotropy, and are low in viscosity; and to improve characteristics of liquid crystal compositions, difluorooxymethane derivatives expressed by the following general formula (I) and liquid crystal compositions containing the compound are proposed

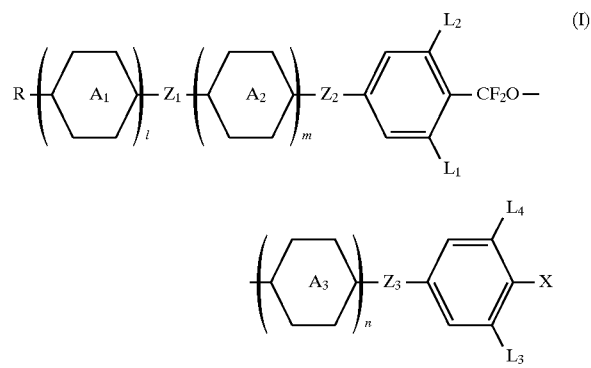

wherein each of $l$, $m$, and $n$ is 0 or 1, rings $A_1$ to $A_3$ independently represent six-membered rings such as trans-1,4-cyclohexylene and 1,4-phenylene, $Z_1$ to $Z_3$ independently represent a bonding group such as covalent bond and —$CH_2CH_2$—, $L_1$ to $L_4$ independently represent hydrogen atom or halogen atom, and X represents a group such as halogen atom and $OCF_3$.

They are useful as liquid crystal materials for low voltages in several modes such as active matrix mode and STN mode.

40 Claims, No Drawings

DIFLUOROOXYMETHANE DERIVATIVE AND LIQUID CRYSTAL COMPOSITION

TECHNICAL FIELD

The present invention relates to a difluoromethane derivative as a liquid crystalline compound suitable as a liquid crystal material in several liquid crystal displays and a liquid crystal composition containing the derivative.

BACKGROUND ART

Liquid crystal display devices employ optical anisotropy and dielectric anisotropy of liquid crystal materials. As display mode, twisted nematic (TN) mode, super twisted nematic (STN) rode, dynamic scattering (DS) mode, guest-host (G-H) mode, and DAP mode are known. Further, as driving mode of the devices, static driving mode, time division driving mode, active matrix driving mode, and dual frequency driving mode are know,. While the properties of liquid crystal materials used for such liquid crystal display devices are different depending on their applications, it is required to any liquid crystal material that the material is stable against external environmental factors such as moisture, air, heat, and light, that the material exhibits a liquid crystal phase at a range of temperatures as wide as possible with room temperature being at its center, that the material has a low viscosity, and that the material is low in its driving voltage. Besides, liquid crystal materials used for liquid crystal display devices are usually composed of several kinds or 10-odd kinds of liquid crystalline compounds in order to obtain optimum dielectric anisotropy ($\Delta\epsilon$) or optical anisotropy ($\Delta n$) required to each display device. Accordingly, the miscibility with other liquid crystal compounds, miscibility at low temperatures is desired for liquid crystal materials from the recent needs of being used under several environments in particular.

On the other hand, active matrix mode, particularly TFT (thin film transistor) mode is popularly adopted recent years as a display mode for television or viewfinder from the aspect of display performances such as contrast, display capacity, and response time. Also, STN mode which is simple in manufacturing process and less expensive in production cost while having a large display capacity is largely adopted as display for personal computers and others.

As the trend in recent years, development in this field is being advanced with miniaturization of liquid crystal display devices or their downsizing to portable dimensions being centered, as typified by televisions which are characterized in that they are small-sized, light weight, and portable, and by notebook type personal computers. From the aspect of materials, development is being carried out with liquid crystalline compounds and liquid crystal composition having a low driving voltage, that is, a low threshold voltage as its center from the aspect of withstand voltage of IC.

It is known that threshold voltage can be expressed by the following equation (H. J. Deuling et al., Mol. Cryst. Liq. Cryst., 27 (1975) 81):

$$V_{th}=\pi(K/\epsilon 0\Delta\epsilon)^{1/2}$$

wherein K is an elastic constant and $\epsilon 0$ is a dielectric constant in vacuum. From the equation mentioned above, it is a common way to use a material having a large dielectric anisotropy ($\Delta\epsilon$) in order to reduce the threshold voltage, and thus, development of compounds having a large value of dielectric anisotropy is being actively carried out.

On the other hand, in liquid crystalline compounds having fluorine atom as substituent, it is known to be effective to increase the number of substitution on the molecule with fluorine atom for increasing dielectric anisotropy. However, the number of substitution on the molecule of compounds with fluorine atom has a proportional relationship with viscosity, and it is also empirically known among the person skilled in the art that when the number of substitution with fluorine atom is increased, mesomorphic range will be narrowed. Accordingly, it is considered to be difficult to increase only dielectric anisotropy while suppressing the raising of viscosity and narrowing of mesomorphic range.

As examples of conventional liquid crystalline compounds substituted with multiple number of fluorine atoms, the followings are disclosed:

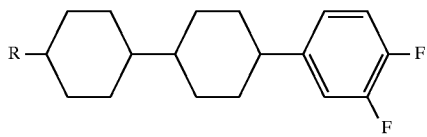

(a)  U.S. Pat. No. 4,405,488

-continued

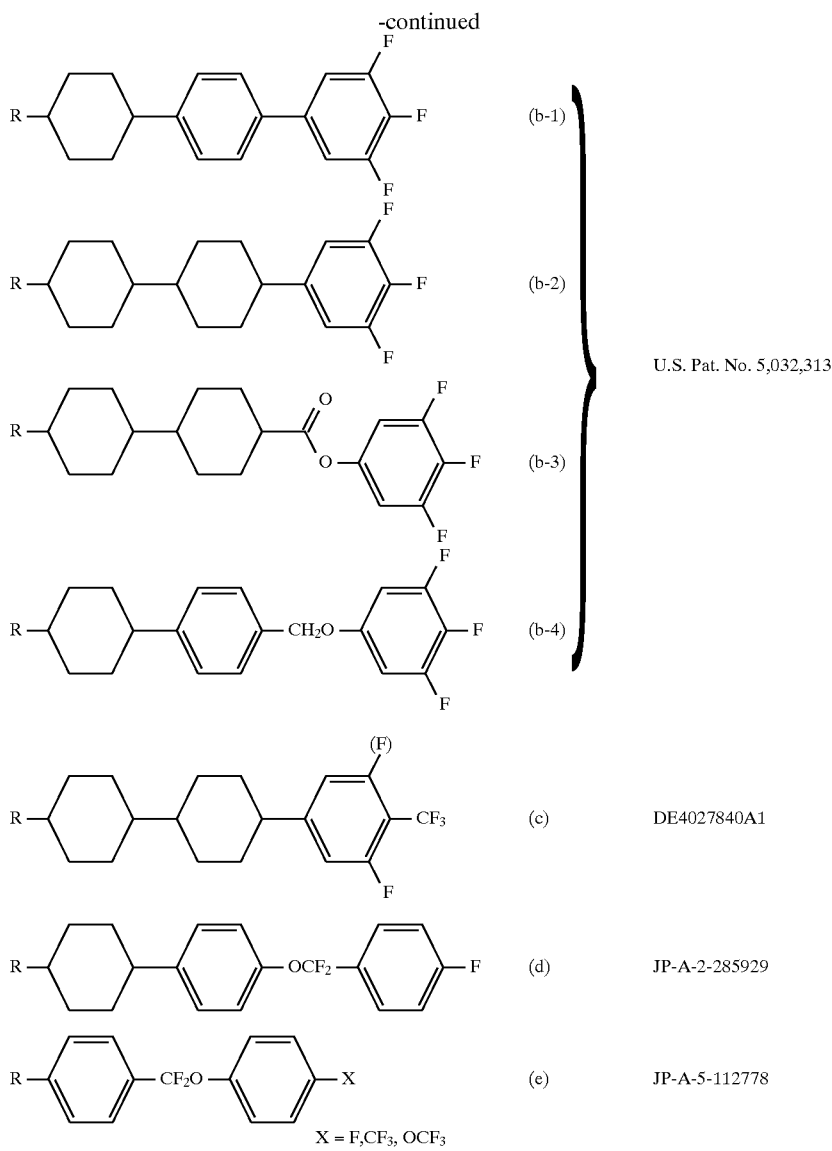

Any of compounds (a) and (b-1) to (b-4) has several fluorine atoms at the terminal of the molecule. The value of dielectric anisotropy of the compounds are compared and arranged in the order of the value as follows:

(b-3)>>(b-1), (b-2), (b-4)>(a)

Compound (b-3) has an ester bond as bonding group between molecular skeletons. It is considered that the large polarization of an ester carbonyl group effectively contributes to the dielectric constant of major axis of compound molecule and thus the compound exhibit an extremely large dielectric anisotropy. On the other hand, however, (b-3) can not be said to be preferable compound in the aspect of response speed from the fact that the compound has a remarkably high viscosity than (a), (b-1), (b-2), and (b-4). With respect to compound (c), it can not be said to be the compound which satisfies the requirements since it has a viscosity as high as (b-3) while (c) has a comparatively high dielectric anisotropy.

In this connection, compounds having —CF$_2$O— at a terminal of the molecule have already been disclosed in patent publications as the compounds having a partial structure of —CF$_2$O— in the molecule in liquid crystalline compounds. However, as the compounds having a partial structure which crosslinked two benzene rings as a bonding group in the structure of the compound, only compounds (d) and (e) shown above have been disclosed in Japanese Patent Application Laid-open Nos. 2-289529 and 5-112778, respectively. Besides, whereas the structural formula of the compounds have been described, physical data of the compounds and specific value of physical properties for evaluating the utility as liquid crystalline compound have not been disclosed in the publications. Accordingly, the properties of liquid crystalline compounds having a partial structure in which two benzene rings are bonded with —CF$_2$O— group are not known at all. The present inventors had presumed that the dielectric constant in the direction of major axis of the molecule is offset in compound (d) since the polarization of —CF$_2$O— group which is a bonding group in the molecule is arranged toward the direction opposite to the polarization of fluorine atom at the terminal of the molecule, and thus a large dielctric anisotropy can not be expected. Even with respect to compound (e), it was considered that a high clearing point can not be expected since it is a bicyclic compound in its skeltal structure while a comparatively large dielectric anisotropy can be expected from the contribution of polarization of —$CF_2O$— group. As explained above, it was the actual situation that the effect of —$CF_2O$— bonding group as well as the effect of compounds (d) and (e), particularly the knowledge on the relationship between dielectric anisotropy and viscosity were not known at all.

DISCLOSURE OF THE INVENTION

An object of the present invention is to provide a novel liquid crystalline compound having a large dielectric anisotropy and extremely low viscosity, as a liquid crystalline compound for low voltages in several modes including active matrix mode and STN mode, and to provide a liquid crystal composition containing the liquid crystalline compound.

As a result of the research by the present inventors on the physical properties of novel difluorooxymethane derivative which can be derived from a phenyl benzoate derivative, it has been found that the direction of dipole moment with polarization of two fluorine atoms in difluoromethoxy group which is a bonding group effectively contributes to the increase of dielectric constant in the direction of major axis of the molecule in the difluorooxymethane derivative, and thus the derivative has a large dielectric anisotropy, and that the derivative is extremely low in viscosity despite of the existence of fluorine atom in its molecule.

Also, it has been found that the compounds in which fluorine substituent is selected as their terminal substituent and the other compounds in which one of other substituents typified by cyano group is selected are novel, useful liquid crystalline compounds for low voltages, with the former in active matrix mode and the latter in several modes including STN mode, leading to the accomplishment of the present invention.

The invention claimed in the present application is summarized as follows:

(1) A difluorooxymethane derivative expressed by the general formula

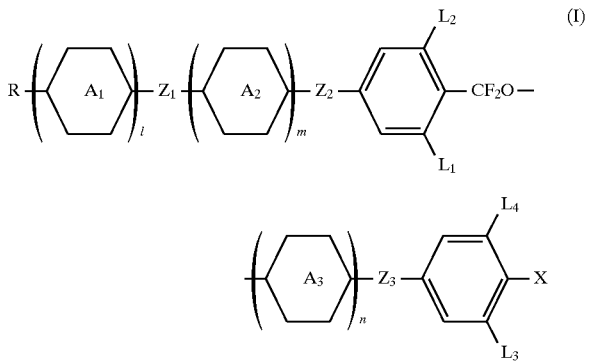

wherein each of l, m, and n is 0 or 1, rings $A_1$ and $A_2$ independently represent trans-1,4-cyclohexylene group, 1,4-phenylene group one or more hydrogen atoms in which six-membered ring may be replaced by halogen atom, trans-1,3-dioxane-2,5-diyl, or pyrimidine-2,5-diyl, ring A3 represents 1,4-phenylene group one or more hydrogen atoms in which six-membered ring may be replaced by halogen atom, trans-1,3-dioxane-2,5-diyl, or pyrimidine-2,5-diyl, $Z_1$, $Z_2$, and $Z_3$ independently represent a covalent bond, $CHCH_2$—, —COO—, —$CF_2O$—, —$OCF_2$—, —$CH_2O$—, —$OCH_2$—, —CH=CH—, or —C≡C—, $L_1$, $L_2$, $L_3$, and $L_4$ independently represent hydrogen atom or halogen atom, respectively, X is halogen atom, CN, CF3, OCF3, $OCHF_2$, $OCH_2F$, or a linear or branched alkyl group, alkenyl group, or alkoxy group having 1 to 10 carbon atoms, and R is a linear or branched alkyl group or alkenyl group having 1 to 10 carbon atoms, one or not adjacent 2 or more $CH_2$ groups in the R may be replaced by oxygen atom, provided that in no case is X an alkyl group, alkenyl group, or alkoxy group except in the case where $Z_1$, $Z_2$, or $Z_3$ is —$CF_2O$—or —$OCF_2$—; that in no case are all of $Z_1$, $Z_2$, and $Z_3$ a covalent bond, and rings $A_1$, $A_2$, and $A_3$ are 1,4-cyclohexylene group or 1,4-phenylene group which is not substituted by a halogen atom in one of the cases where l, m, and n are 0, where l and m are 0, and n is 1, where l and n are 0, and m is 1, and where l and n are 1, and m is 0; that in no case are all of $L_1$, L2, $L_3$, and $L_4$ hydrogen atom, and X is fluorine atom or CN; that in no case are all of $Z_1$, $Z_2$, and $Z_3$ a covalent bond, and rings $A_1$, $A_2$, and $A_3$ are 1,4-cyclohexylene group or 1,4-phenylene group which is not substituted by a halogen atom in one of the cases where l, m, and n are 0, where l and m are 0, and n is 1, and where l and n are 1, and m is 0; and that in no case are all of $L_1$, L2, $L_3$, and $L_4$ hydrogen atom, and X is $CF_3$ or $OCF_3$.

(2) The difluorooxymethane derivative recited in (1) wherein l=1, m=0, n is 0 or 1, $Z_1$ is covalent bond or —$CH_2CH_2$—, both $Z_2$ and $Z_3$ are covalent bond, $A_1$ is trans-1,4-cyclohexylene group, $A_3$ is 1,4-phenylene group, and R is a linear alkyl group or alkenyl group having 1 to 10 carbon atoms, in the general formula (I).

(3) The difluorooxymethane derivative recited in (1) or (2) wherein at least one of $L_3$ and $L_4$ is halogen atom.

(4) The difluorooxymethane derivative recited in (1) wherein l=m=n=0, and all of $Z_1$, $Z_2$, and $Z_3$ are covalent bond, in the general formula (I).

(5) The difluorooxymethane derivative recited in (1) wherein l=1, m=n=0, and both of $Z_2$ and $Z_3$ are covalent bond, in the general formula (I).

(6) The difluorooxymethane derivative recited in any one of (1) to (5) wherein all of $L_3$, $L_4$, and X are fluorine atom, in the general formula (I).

(7) The difluorooxymethane derivative recited in (5) wherein X is $OCF_3$ in the general formula (I).

(8) The difluorooxymethane derivative recited in (5) wherein X is CN, in the general formula (I).

(9) The difluorooxymethane derivative recited in (1) wherein l=1, ring $A_1$ is 1,4-phenylene group one or more hydrogen atom in which 6-membered ring may be replaced by halogen atom, $Z_1$ is —$OCF_2$—, both of $Z_2$ and $Z_3$ are covalent bond, and X is a linear or branched alkyl group, alkenyl group, or alkoxy group having 1 to 10 carbon atoms, in the general formula (I)

(10) The difluorooxymethane derivative recited in (1) wherein l=m=0, n=1, both of $Z_1$ and $Z_2$ are covalent bond, and ring $A_3$ is 1,4-phenylene group, in the general formula (I).

(11) The difluorooxymethane derivative recited in (10) wherein $Z_3$ is covalent bond, in the general formula (I).

(12) The difluorooxymethane derivative recited in (10) wherein $Z_3$ is —$CH_2CH_2$—, in the general formula (I).

(13) A liquid crystal composition containing at least one kind of difluorooxymethane derivative recited in any one of (1) to (12).

(14) A liquid crystal composition containing, as a first component, at least one kind of difluorooxymethane derivative recited in any one of (1) to (12) and containing, as a second component, at least one kind of compound selected from the group of compounds expressed by general formula (II), (III), or (IV)

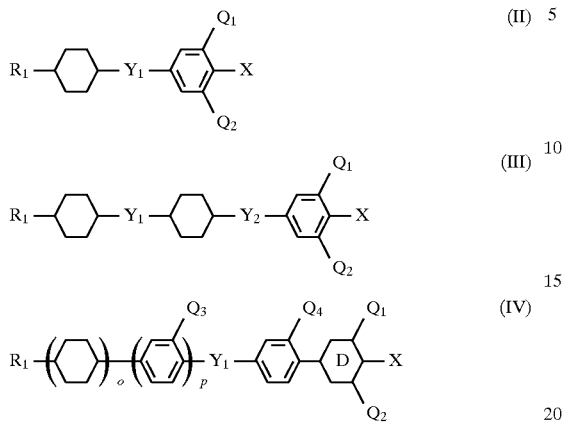

wherein $R_1$ represents an alkyl group having 1 to 10 carbon atoms, X represents F, Cl, $CF_3$, $OCF_3$, $OCF_2H$, or an alkyl group having 1 to 10 carbon atoms, $Q_1$, $Q_2$, and $Q_3$, $Q_4$ independently represent H or F, o represents 1 or 2, p represents 0 or 1, $Y_1$ and $Y_2$ independently represent —$CH_2CH_2$—, —CH=CH—, or covalent bond, and ring D represents trans-1,4-cyclohexylene group or 1,4-phenylene group.

(15) A liquid crystal composition containing, as a first component, at least one kind of difluorooxymethane derivative recited in any one of (1) to (12), containing, as a second component, at least one kind of compound selected from the group of compounds expressed by general formula (V), (VI), (VII), (VIII), or (IX)

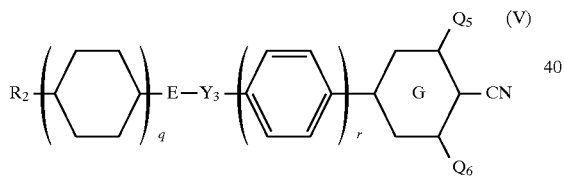

wherein $R_2$ represents fluorine atom, an alkyl group having 1 to 10 carbon atoms, or an alkenyl group having 2 to 10 carbon atoms, in any case, one or not adjacent two or more $CH_2$ groups in the alkyl or alkenyl group may be replaced by oxygen atom, $Y_3$ represents —$CH_2CH_2$—, —COO—, or covalent bond, $Q_5$ and $Q_6$ independently represent hydrogen atom or fluorine atom, E represents trans-1,4-cyclohexylene, 1,4-phenylene, or trans-1,3-dioxane-2,5-diyl, ring G represents trans-1,4-cyclohexylene or 1,4-phenylene, and q and r independently represent 0 or 1,

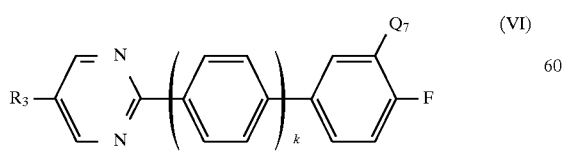

wherein $R_3$ represents an alkyl group having 1 to 10 carbon atoms, $Q_7$ represents hydrogen atom or fluorine atom, and k represents 0 or 1,

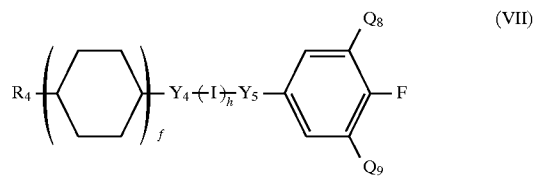

wherein $R_4$ represents an alkyl group having 1 to 10 carbon atoms, I represents trans-1,4-cyclohexylene or 1,4-phenylene, $Q_8$ and $Q_9$ represent hydrogen atom or fluorine atom, $Y_4$ represents —COO— or —C≡C—, and f and h independently represent 0 or 1,

wherein $R_5$ and $R_6$ independently represent an alkyl group, alkoxy group, or alkoxymethyl group having 1 to 10 carbon atoms, J represents trans-1,4-cyclohexylene, 1,3-pyrimidine-2,5-diyl, or 1,4-phenylene, K represents trans-1,4-cyclohexylene or 1,4-phenylene, $Y_6$ represents —C≡C—, —COO—, —$CH_2CH_2$—, or covalent bond,

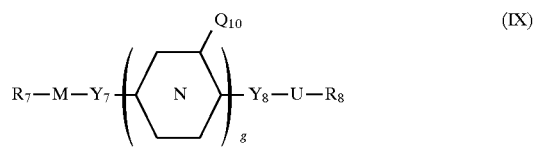

wherein $R_7$ represents an alkyl group or alkoxy group having 1 to 10 carbon atoms, $R_8$ represents an alkyl group having 1 to 10 carbon atoms, one or not adjacent two or more $CH_2$ groups in which alkyl group may be replaced by oxygen atom, M represents trans-1,4-cyclohexylene or 1,3-pyrimidine-2,5-diyl, rings N and U independently represent trans-1,4-cyclohexylene or 1,4-phenylene, $Y_7$ represents —$CH_2CH_2$—, —COO—, or covalent bond, $Y_8$ represents C≡C—, —COO—, or covalent bond, g represents 0 or 1, and $Q_{10}$ represents hydrogen atom or fluorine atom.

(16) A liquid crystal composition containing, as a first component, at least one kind of difluorooxymethane derivative recited in any one of (1) to (12), containing, as a part of the second component, at least one kind of compound selected from a group of compounds expressed by the general formula (II), (III), or (IV), and containing, as other part of the second component, at least one compound selected from a group of compounds expressed by the general formula (V), (VI), (VII), (VIII), or (IX).

(17) A liquid crystal display device composed by using a liquid crystal composition recited in any one of (13) to (16).

BEST MODE FOR CARRYING OUT THE INVENTION

In the present invention, preferable embodiments of difluorooxymethane derivatives expressed by the general formula (I) include compounds expressed by any one of the following general formulas (1a) to (1e):

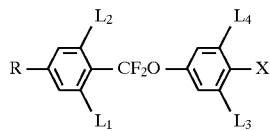 (Ia)
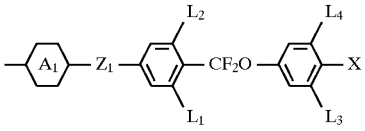 (Ib)
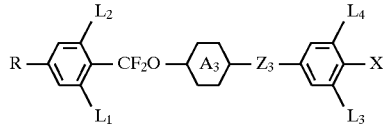 (Ic)
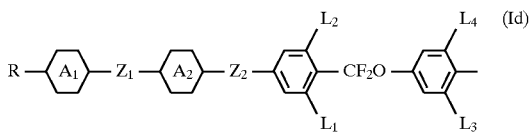 (Id)
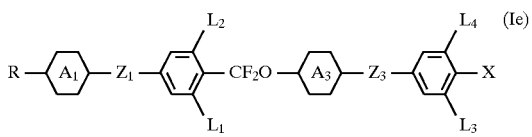 (Ie)
As specific examples of difluorooxymethane derivatives expressed by the general formulas (1a) to (1e), the following compounds (1) to (661) can further be mentioned:
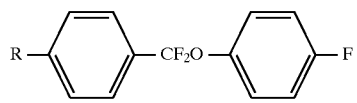 (1)
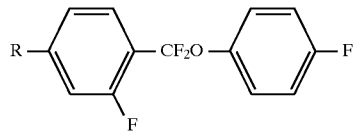 (2)
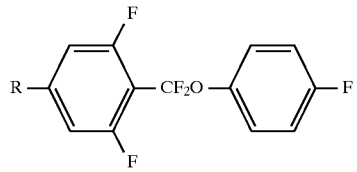 (3)
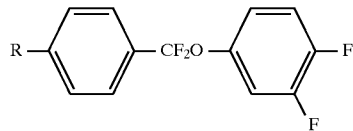 (4)
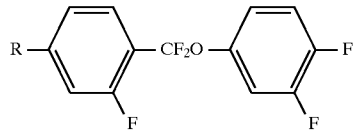 (5)
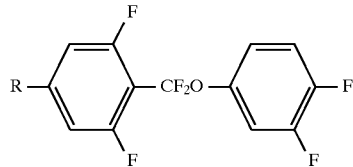 (6)
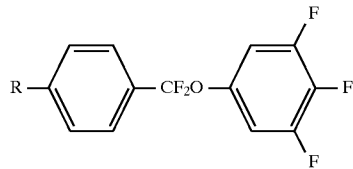 (7)

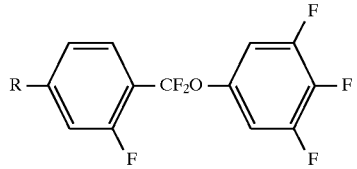
(8)
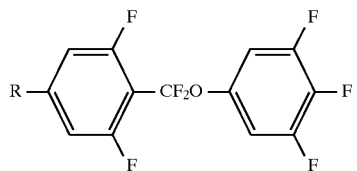
(9)
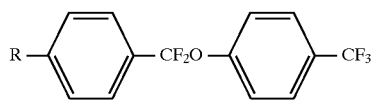
(10)
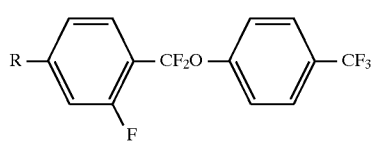
(11)
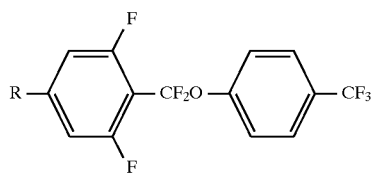
(12)
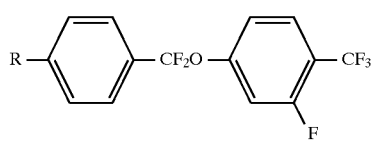
(13)
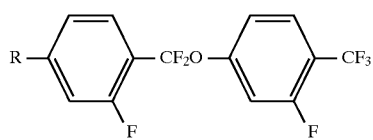
(14)
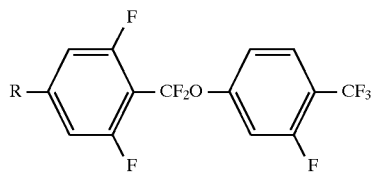
(15)
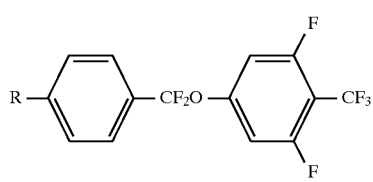
(16)
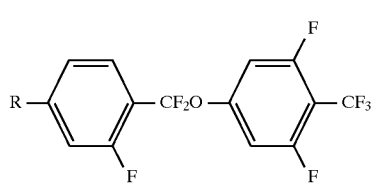
(17)

-continued
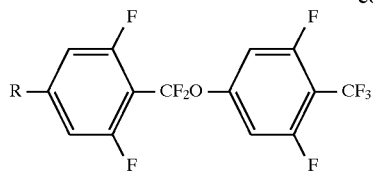
(18)
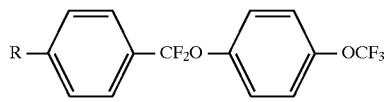
(19)
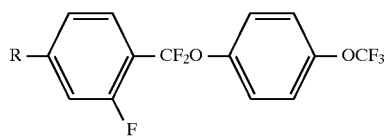
(20)
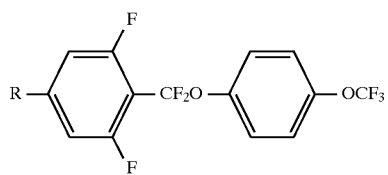
(21)
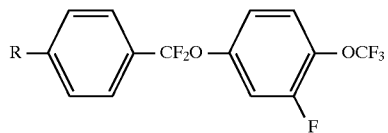
(22)
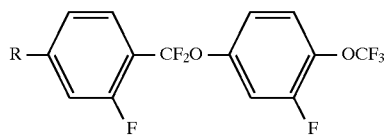
(23)
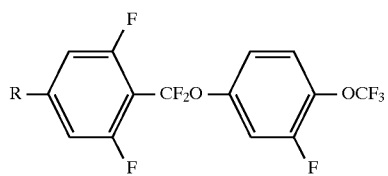
(24)
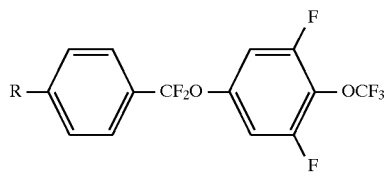
(25)
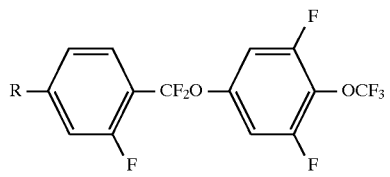
(26)
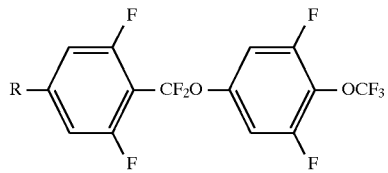
(27)

-continued
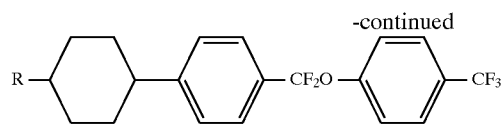 (28)
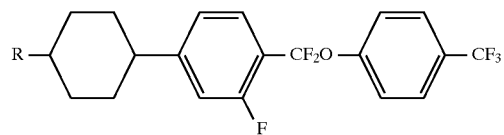 (29)
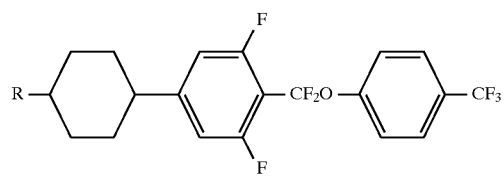 (30)
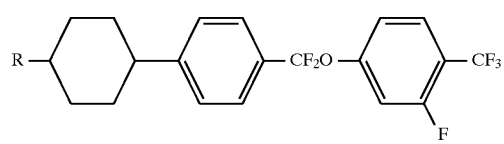 (31)
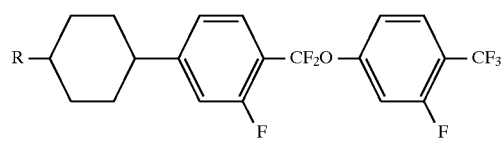 (32)
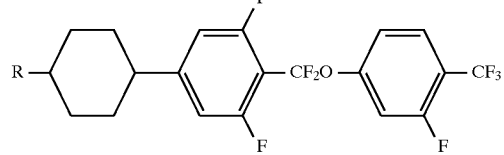 (33)
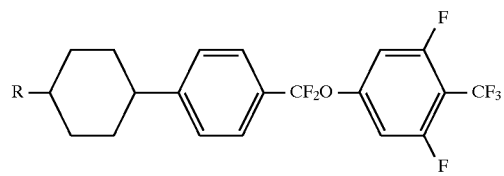 (34)
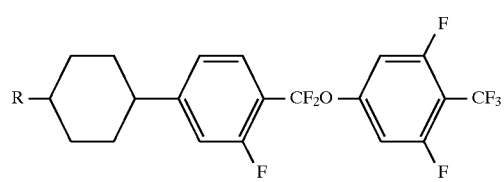 (35)
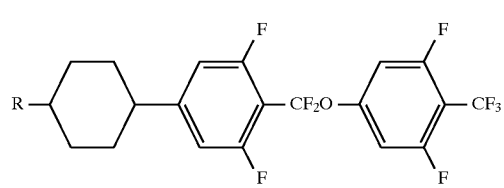 (36)
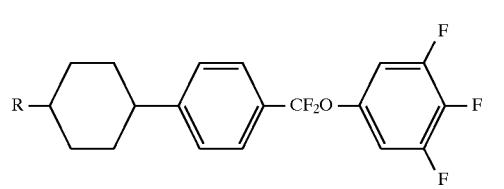 (37)

-continued
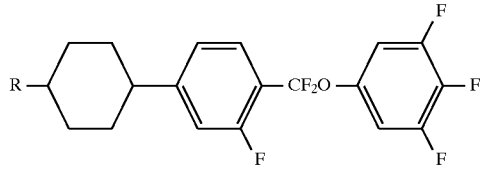 (38)
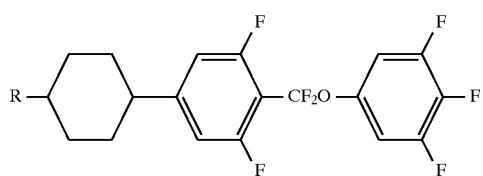 (39)
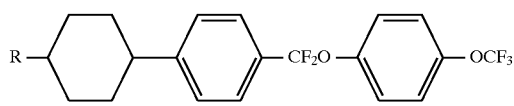 (40)
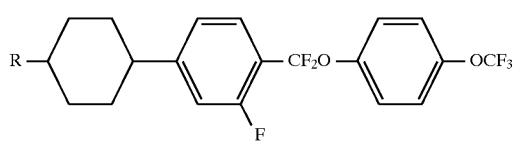 (41)
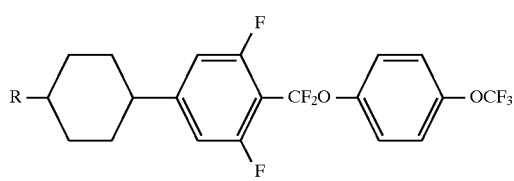 (42)
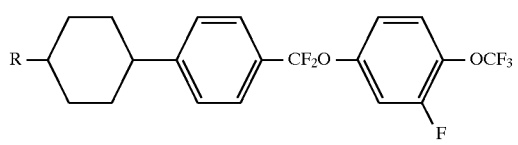 (43)
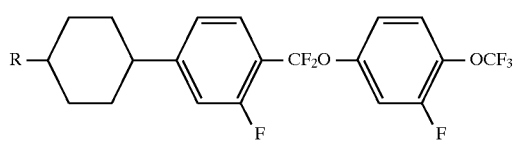 (44)
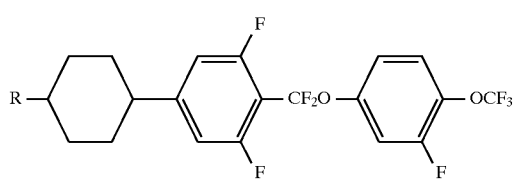 (45)
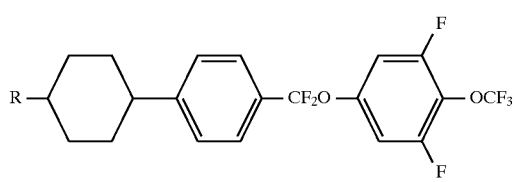 (46)
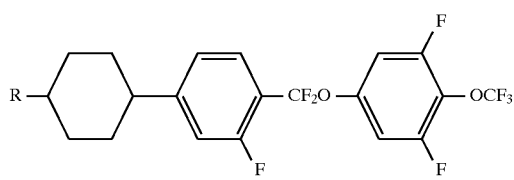 (47)

-continued
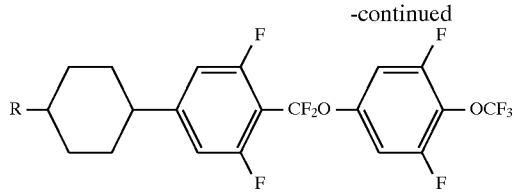 (48)
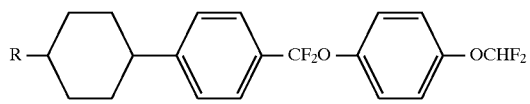 (49)
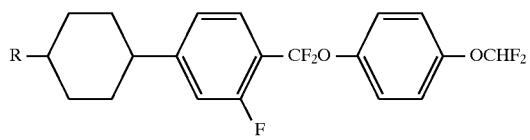 (50)
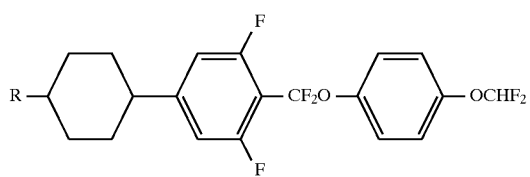 (51)
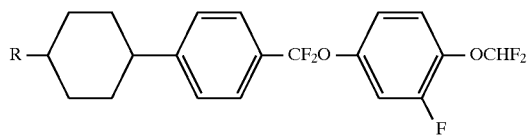 (52)
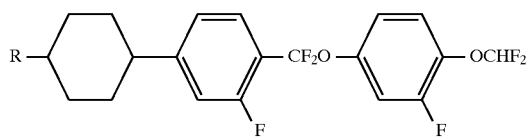 (53)
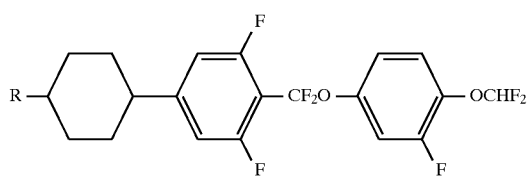 (54)
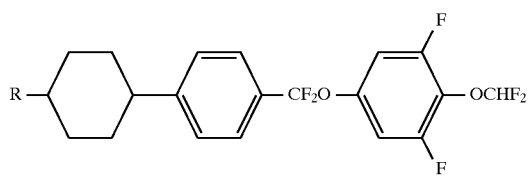 (55)
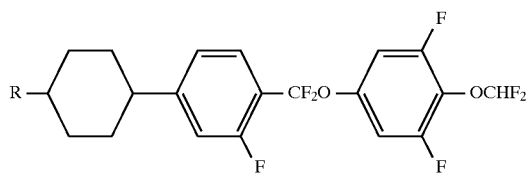 (56)
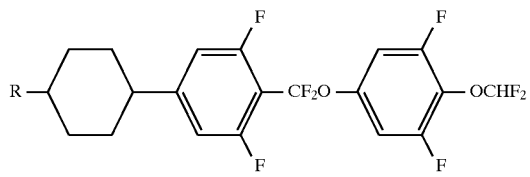 (57)

-continued
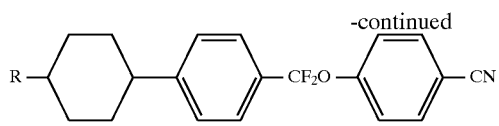 (58)
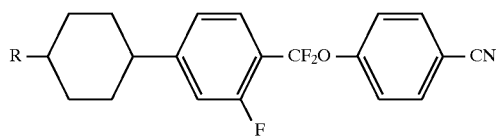 (59)
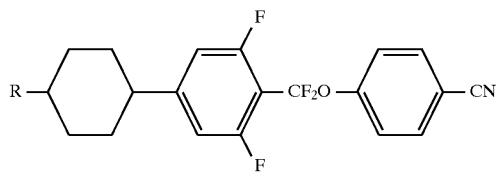 (60)
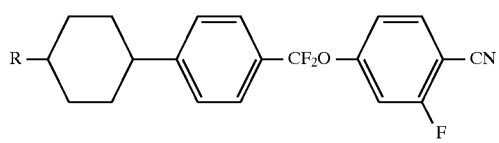 (61)
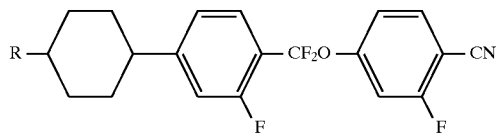 (62)
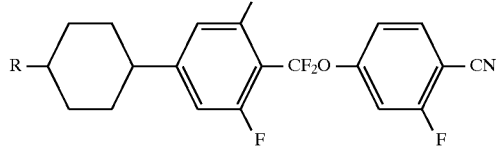 (63)
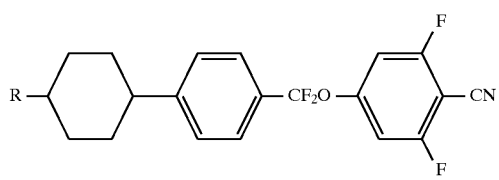 (64)
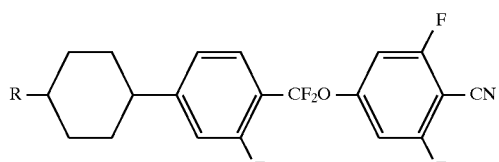 (65)
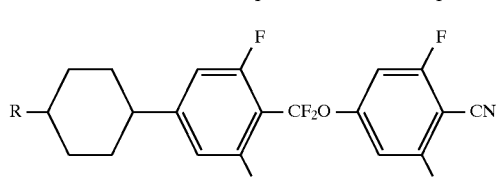 (66)
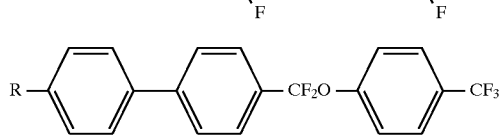 (67)
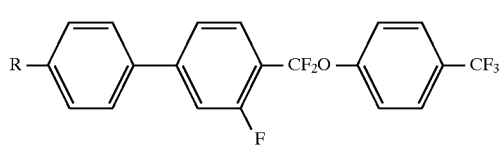 (68)

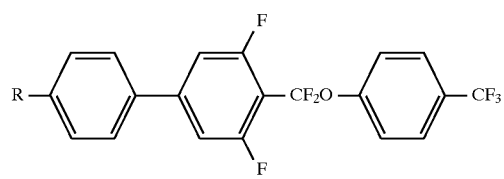 (69)
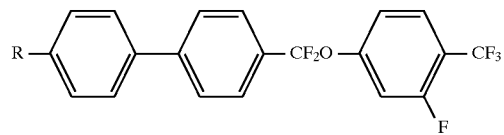 (70)
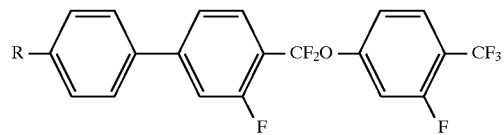 (71)
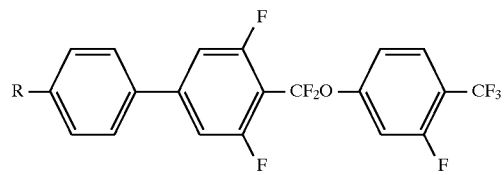 (72)
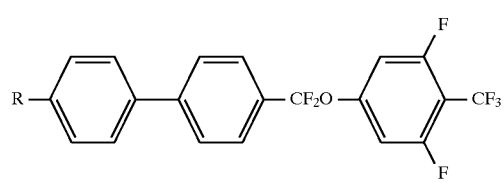 (73)
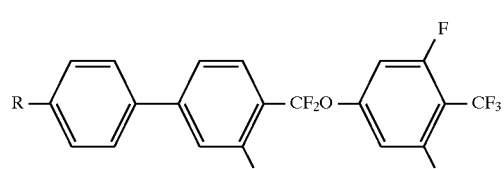 (74)
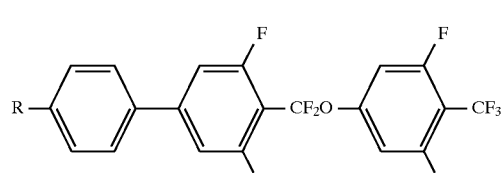 (75)
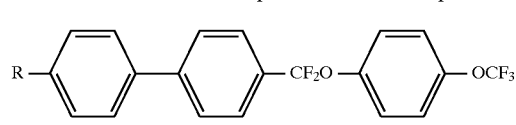 (76)
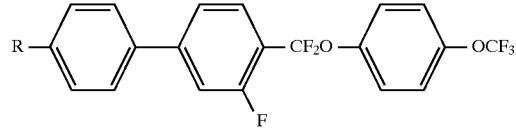 (77)
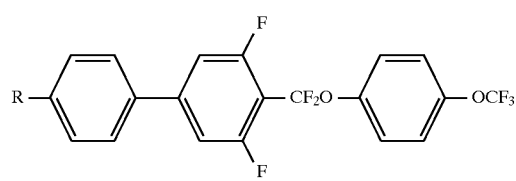 (78)

-continued
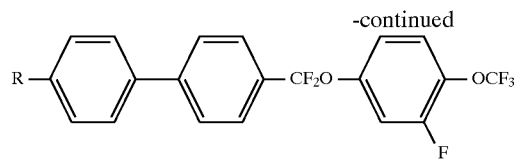 (79)
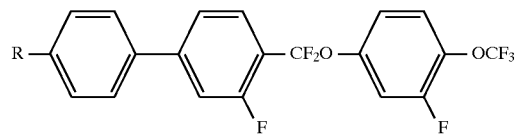 (80)
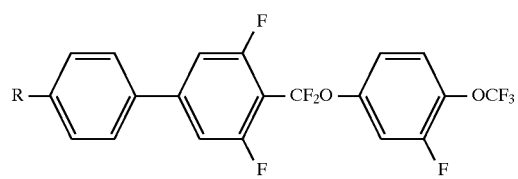 (81)
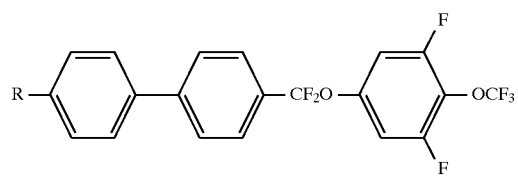 (82)
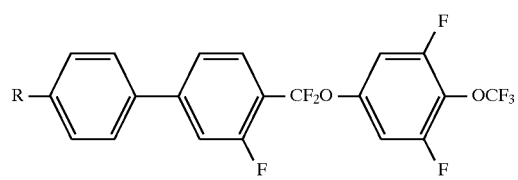 (83)
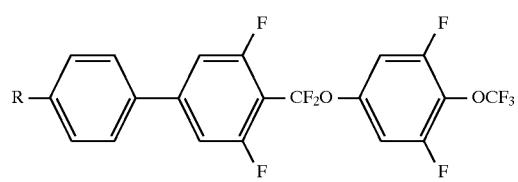 (84)
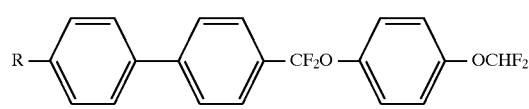 (85)
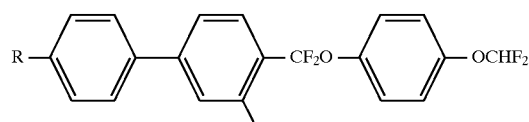 (86)
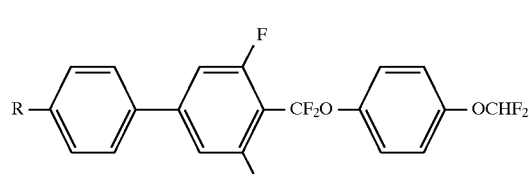 (87)
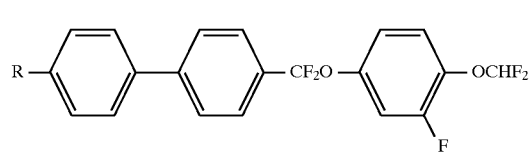 (88)

-continued
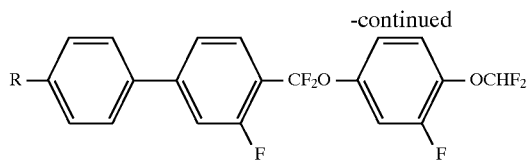
(89)
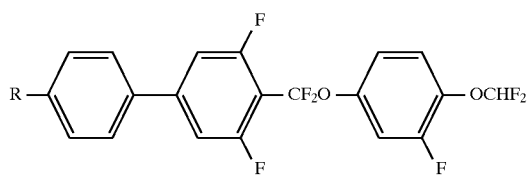
(90)
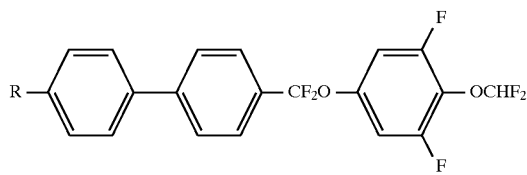
(92)
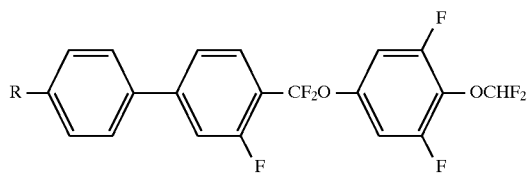
(93)
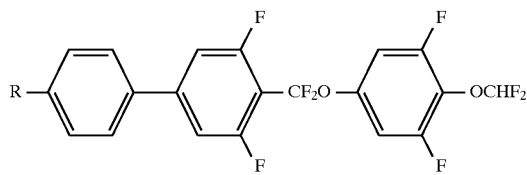
(94)
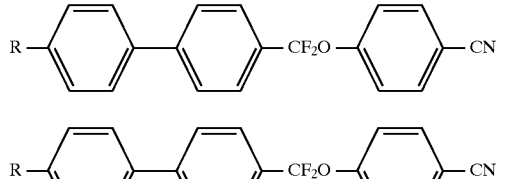
(95)
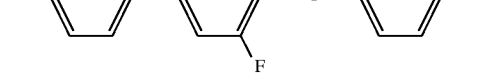
(96)
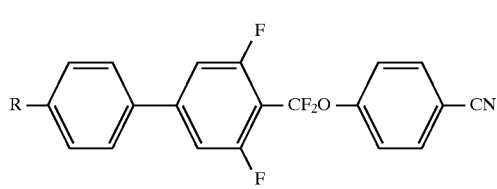
(97)
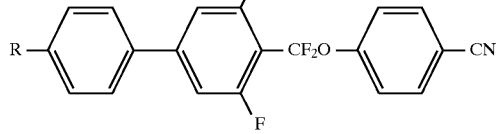
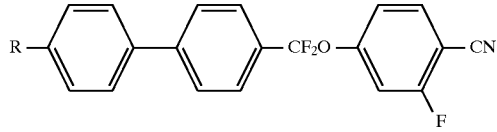
(98)
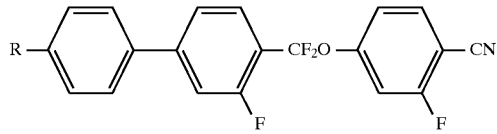
(99)

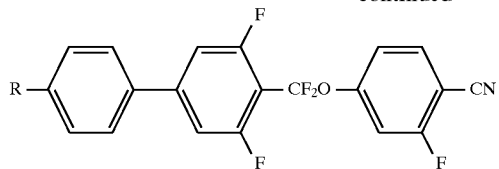
(100)
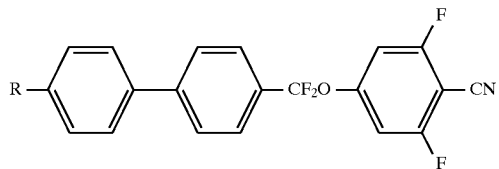
(101)
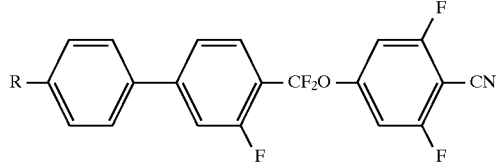
(102)
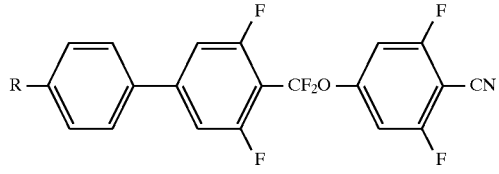
(103)
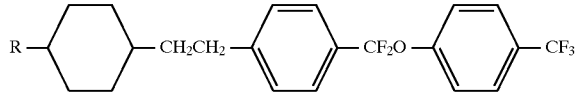
(104)
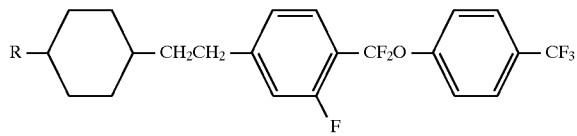
(105)
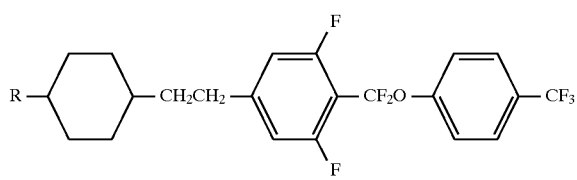
(106)
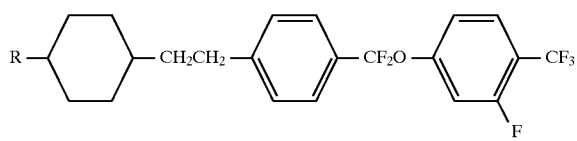
(107)
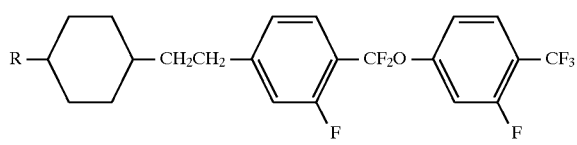
(108)
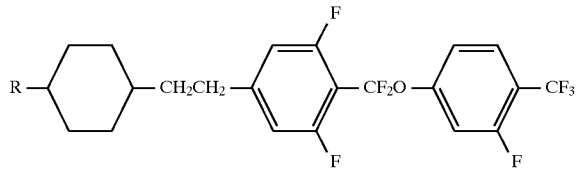
(109)

-continued
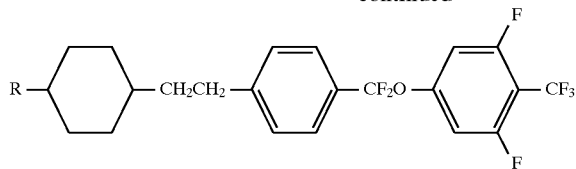 (110)
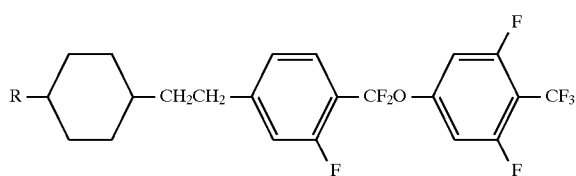 (111)
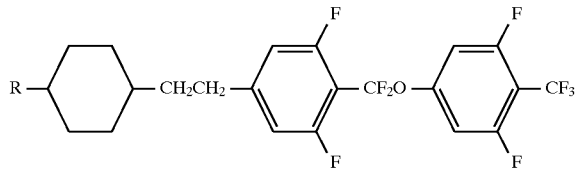 (112)
 (113)
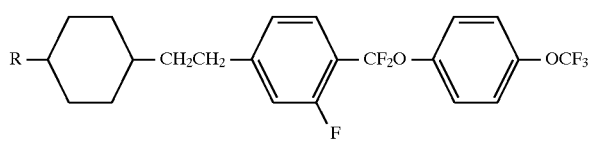 (114)
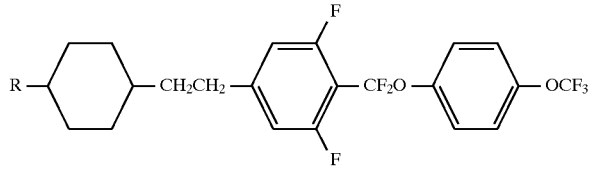 (115)
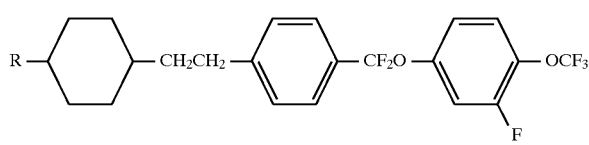 (116)
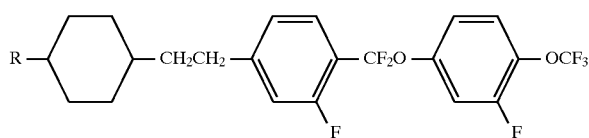 (117)
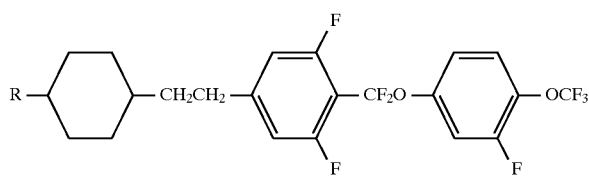 (118)
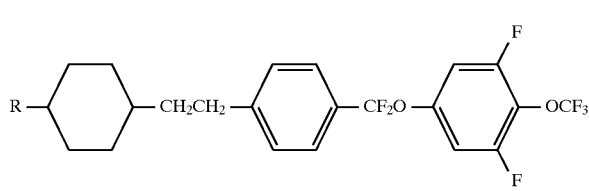 (119)

-continued
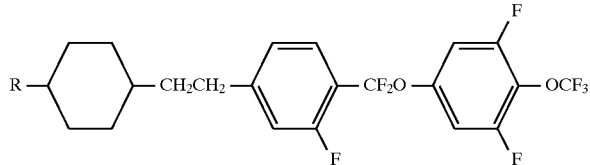 (120)
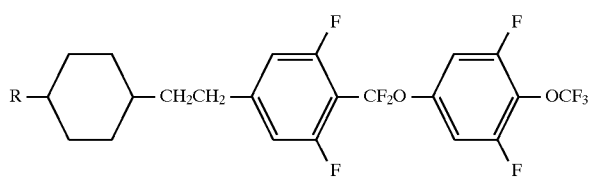 (121)
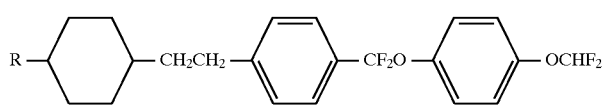 (122)
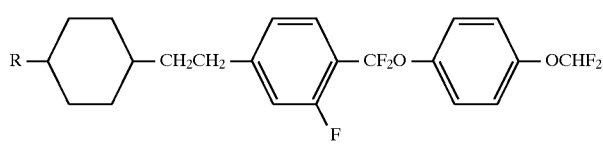 (123)
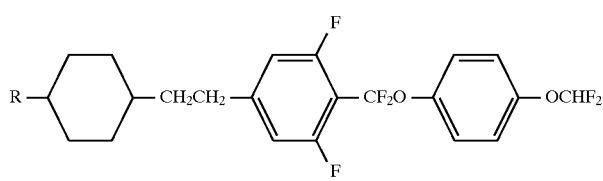 (124)
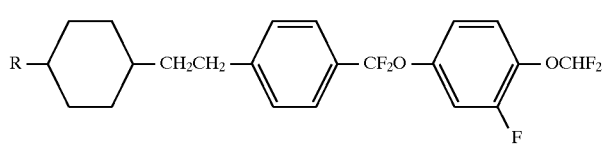 (125)
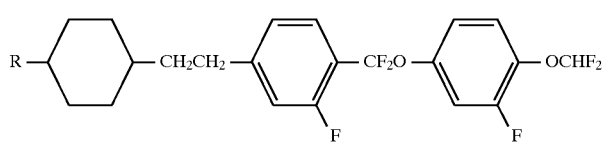 (126)
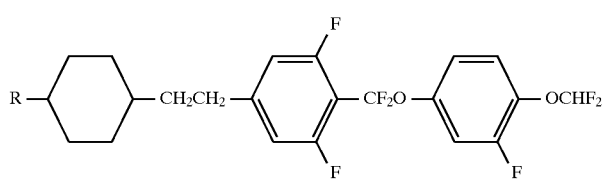 (127)
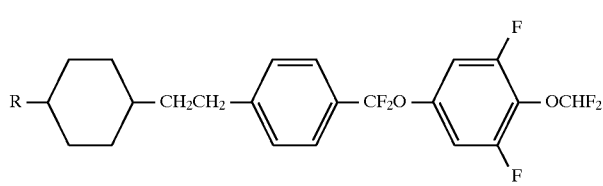 (128)
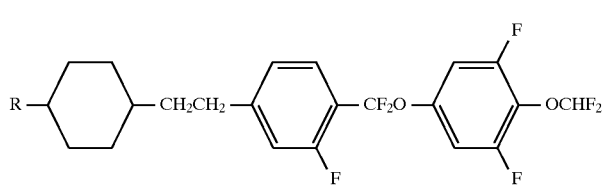 (129)

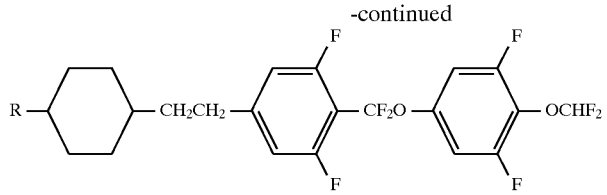
(130)
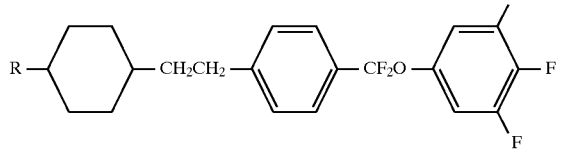
(131)
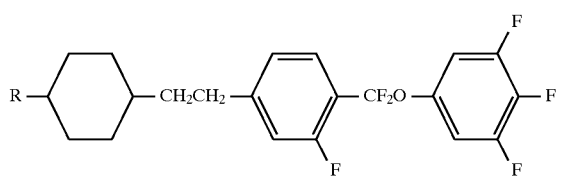
(132)
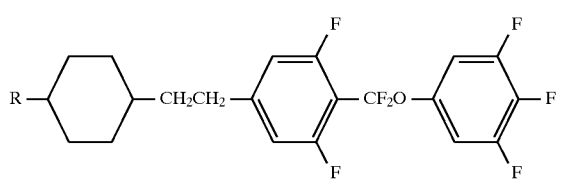
(133)
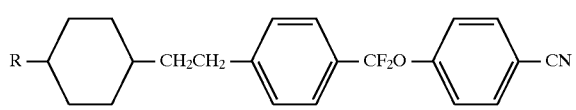
(134)
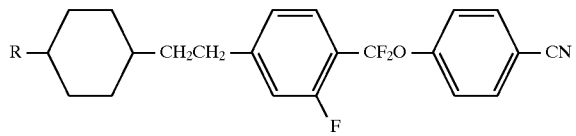
(135)
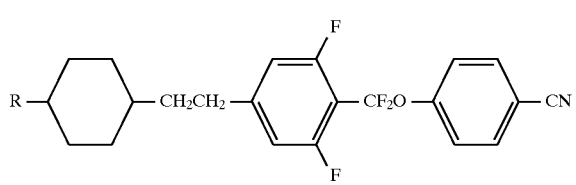
(136)
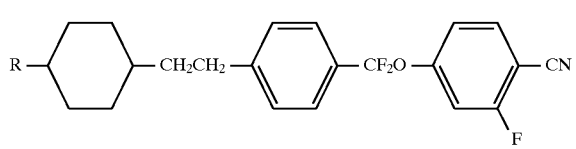
(137)
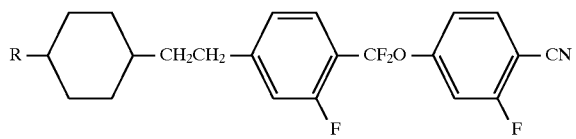
(138)
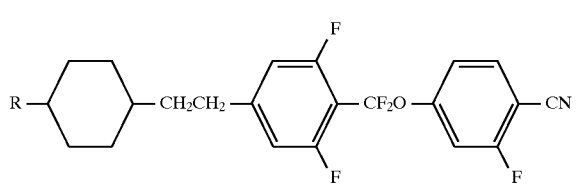
(139)

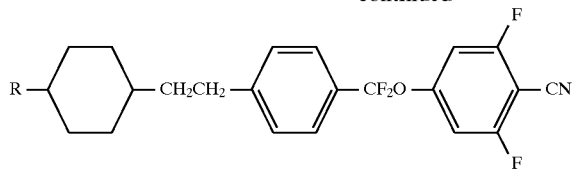
(140)
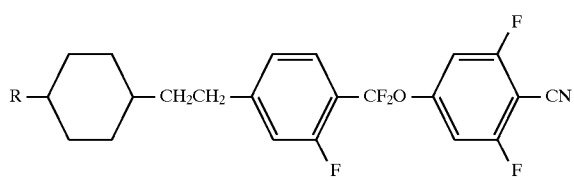
(141)
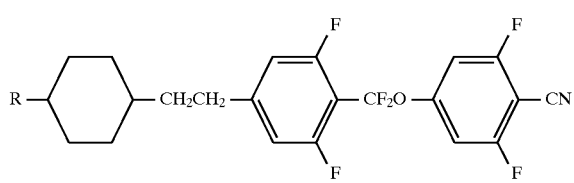
(142)
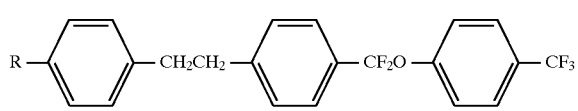
(143)
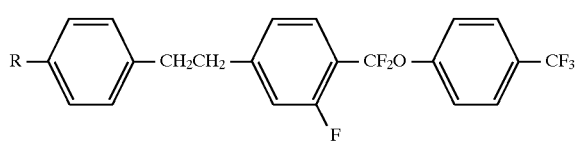
(144)
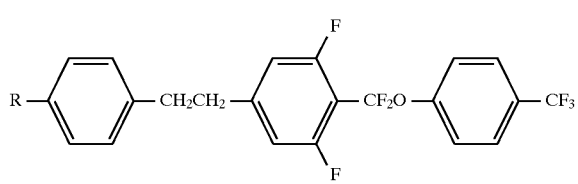
(145)
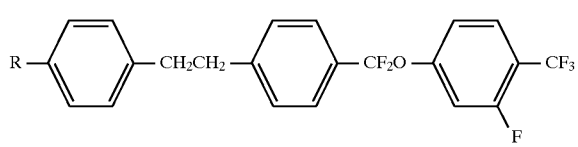
(146)
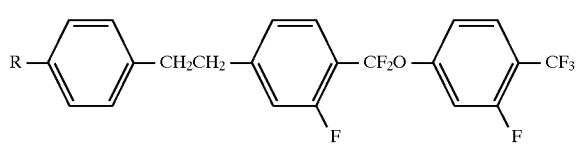
(147)
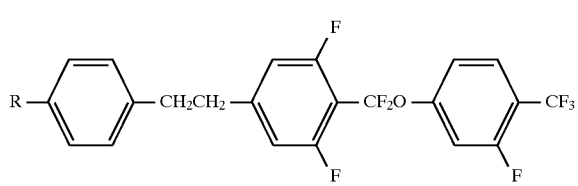
(148)
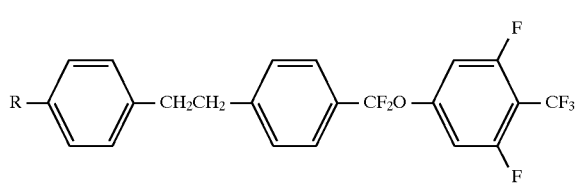
(149)

-continued
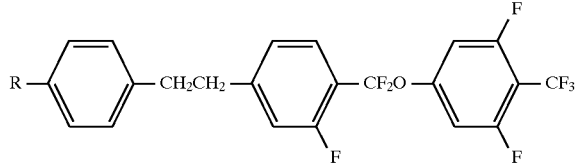 (150)
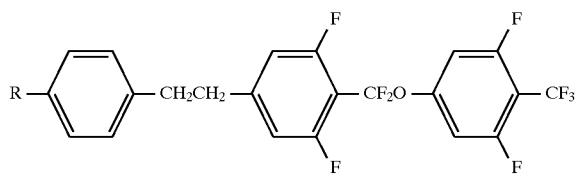 (151)
 (152)
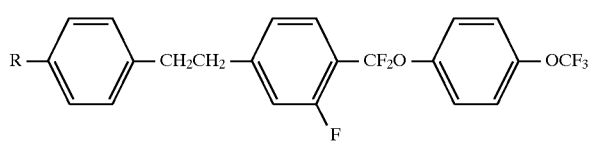 (153)
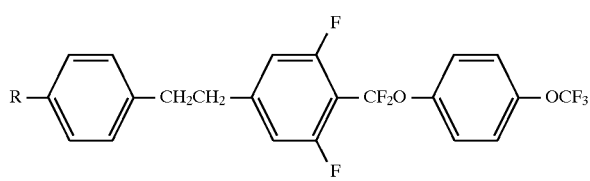 (154)
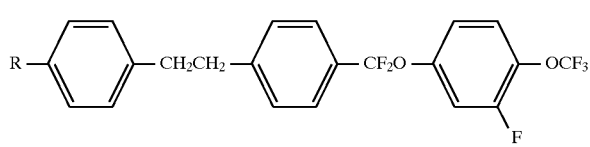 (155)
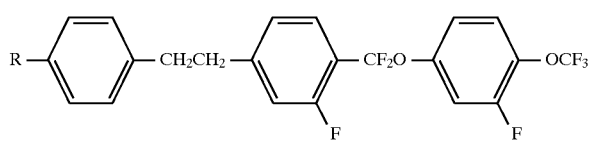 (156)
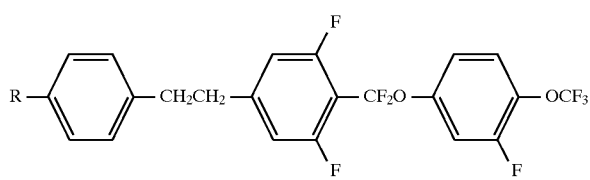 (157)
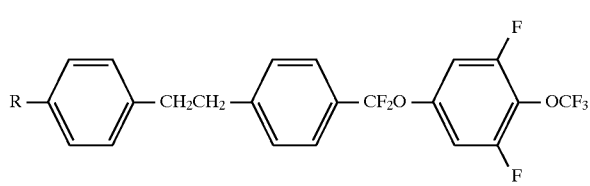 (158)
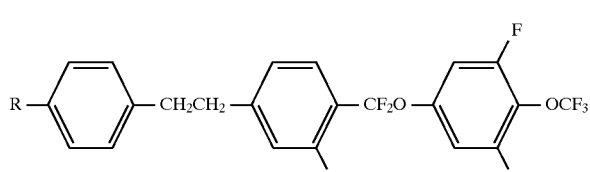 (159)

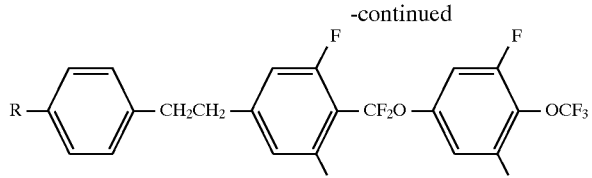 (160)
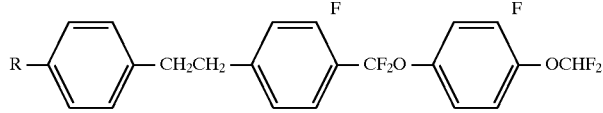 (161)
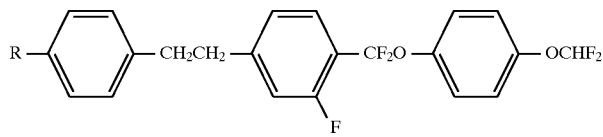 (162)
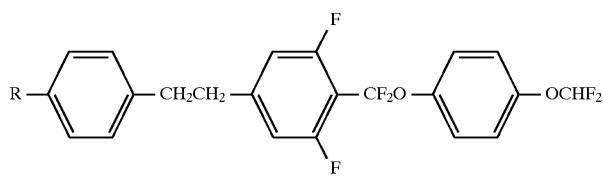 (163)
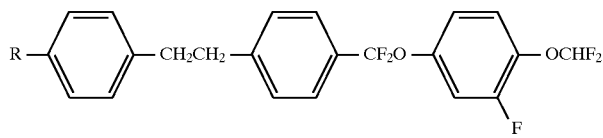 (164)
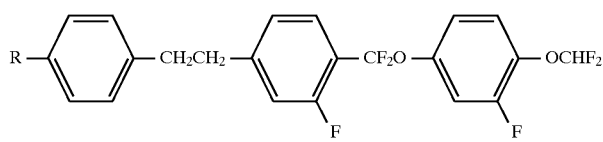 (165)
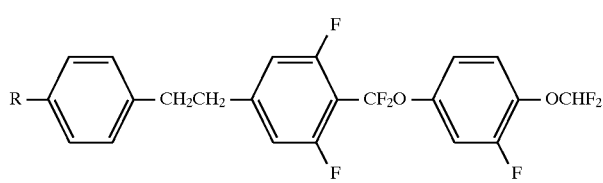 (166)
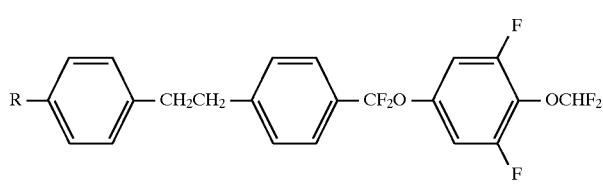 (167)
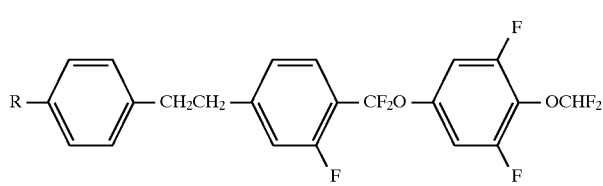 (168)
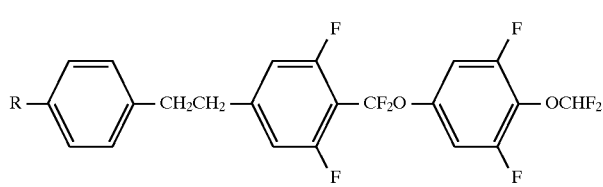 (169)

-continued
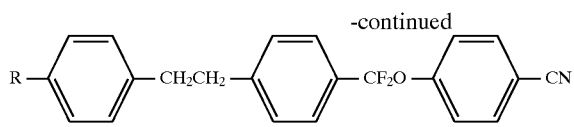
(170)
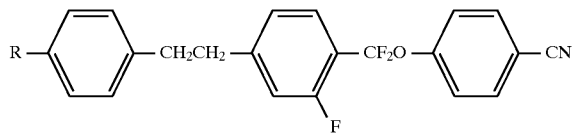
(171)
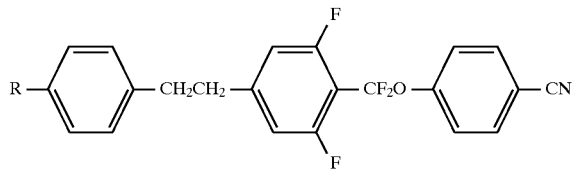
(172)
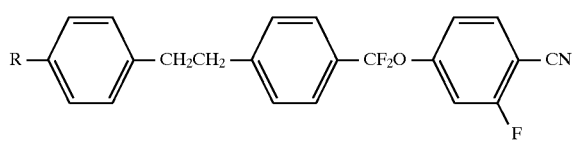
(173)
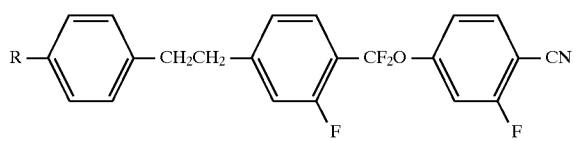
(174)
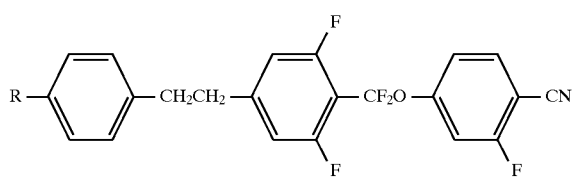
(175)
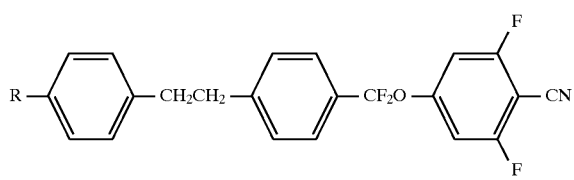
(176)
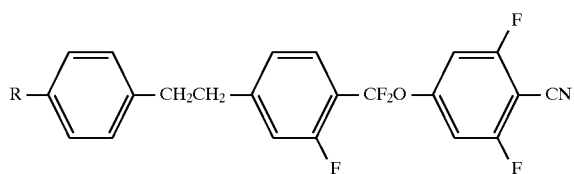
(177)
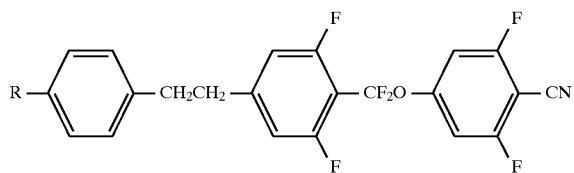
(178)
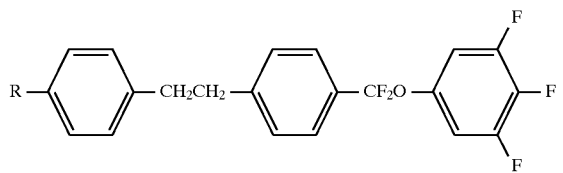
(179)

-continued
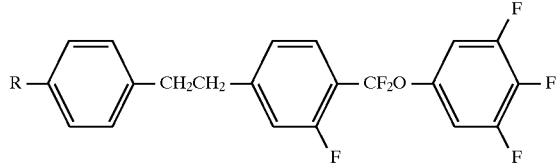
(180)
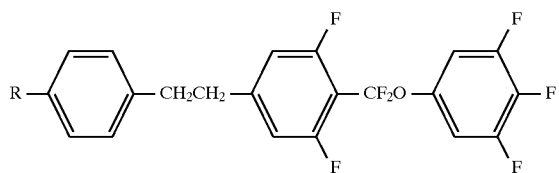
(181)
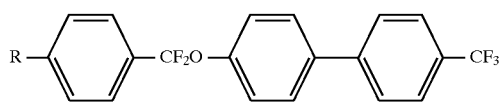
(182)
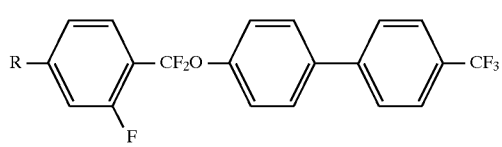
(183)
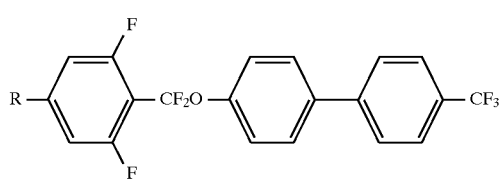
(184)
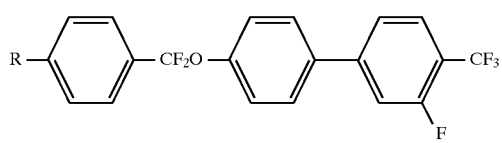
(185)
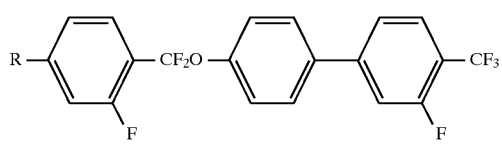
(186)
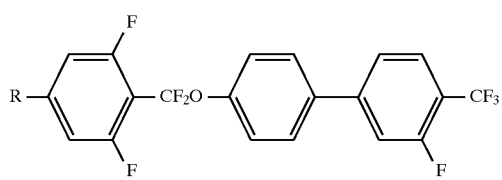
(187)
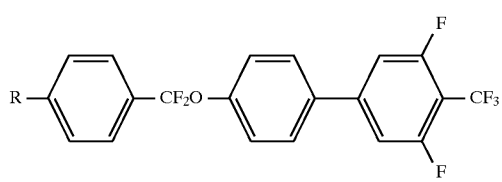
(188)
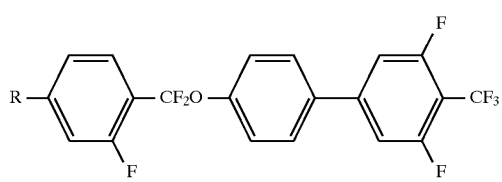
(189)

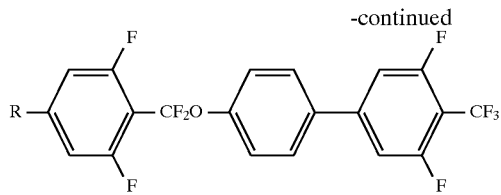 (190)
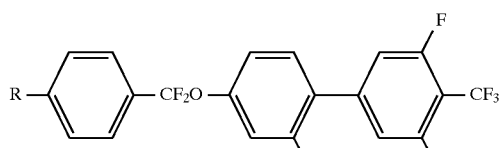 (191)
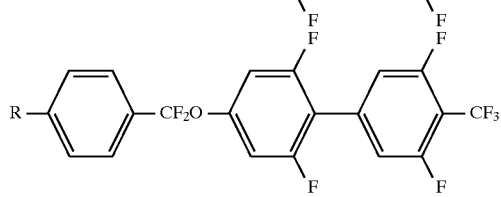 (192)
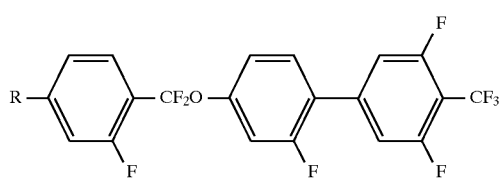 (193)
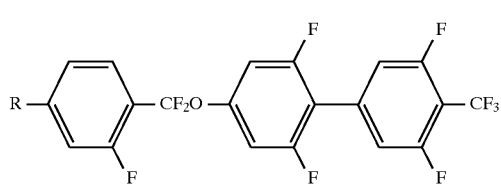 (194)
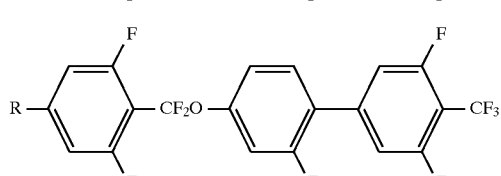 (195)
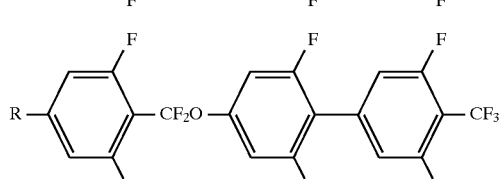 (196)
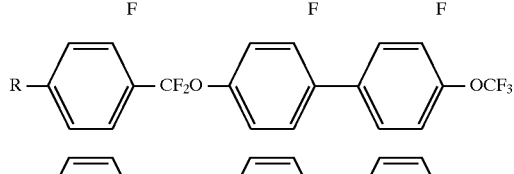 (197)
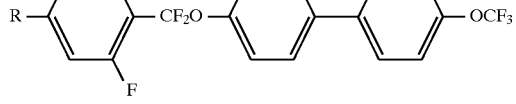 (198)
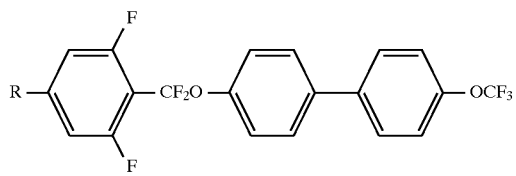 (199)

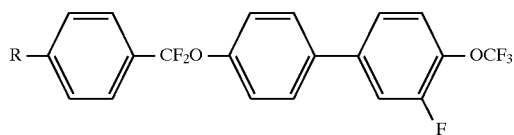 (200)
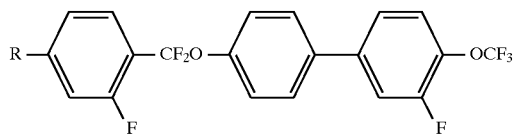 (201)
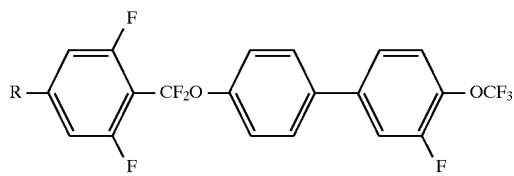 (202)
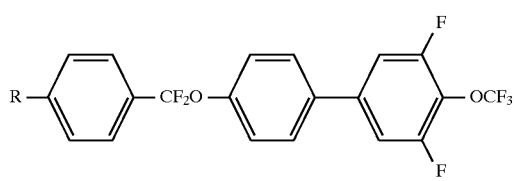 (203)
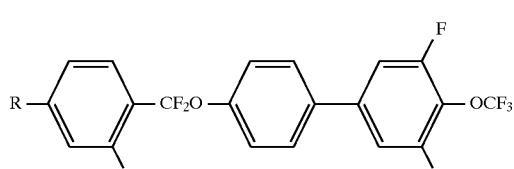 (204)
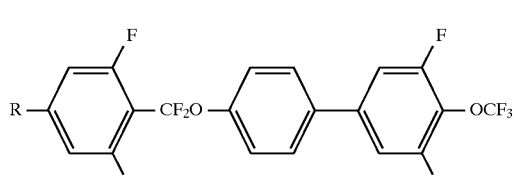 (205)
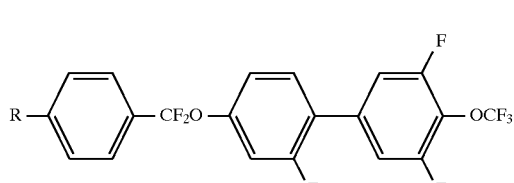 (206)
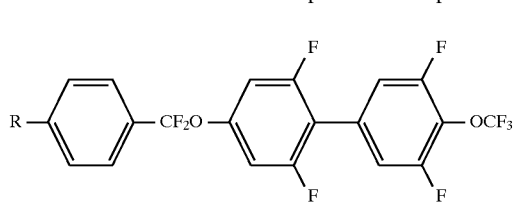 (207)
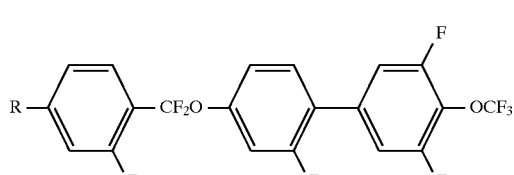 (208)

-continued
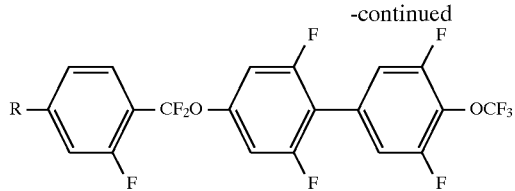 (209)
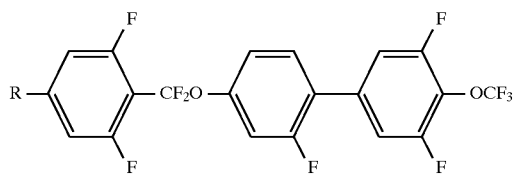 (210)
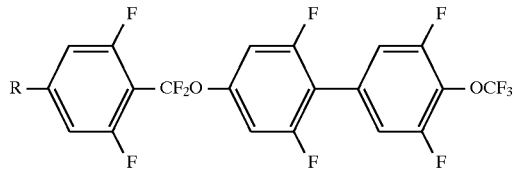 (211)
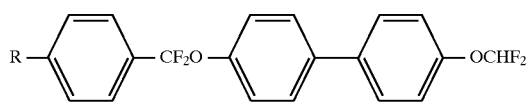 (212)
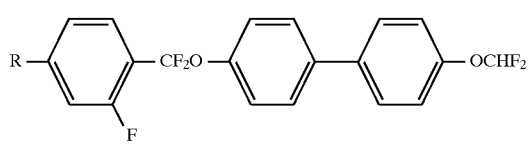 (213)
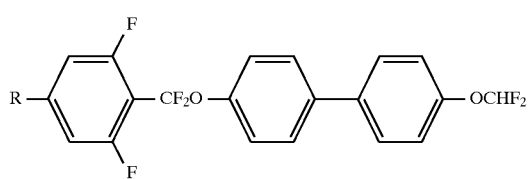 (214)
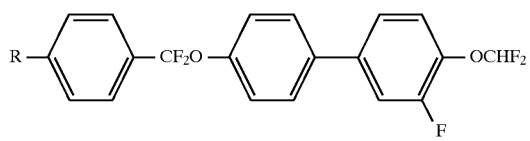 (215)
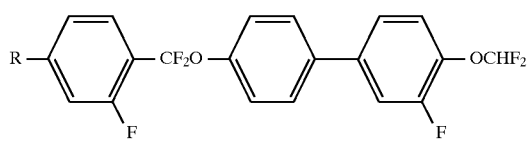 (216)
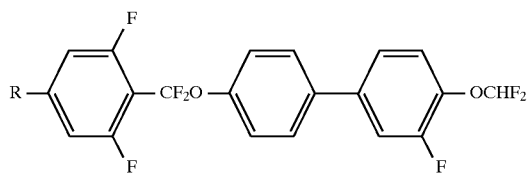 (217)
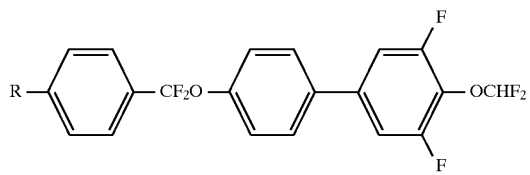 (218)

-continued
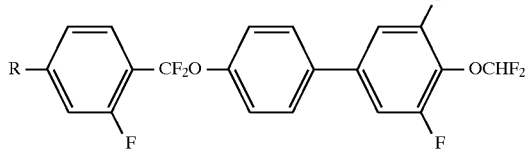
(219)
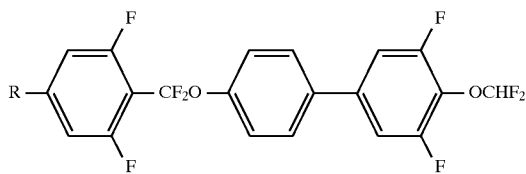
(220)
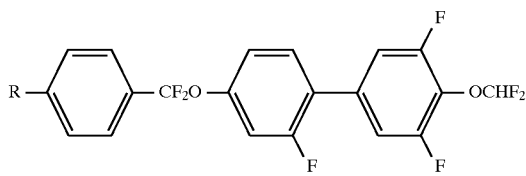
(221)
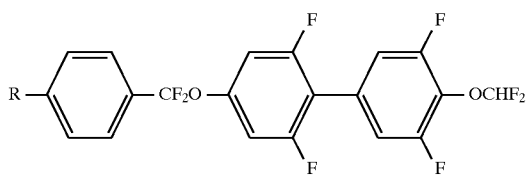
(222)
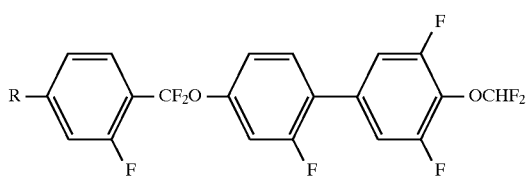
(223)
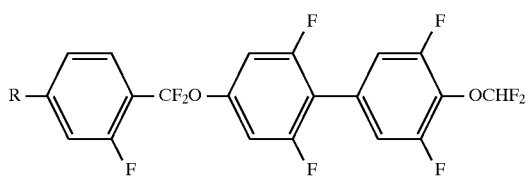
(224)
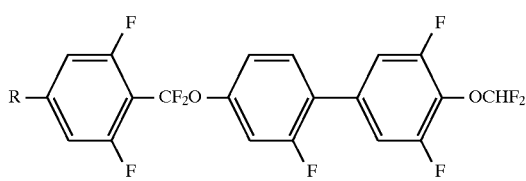
(225)
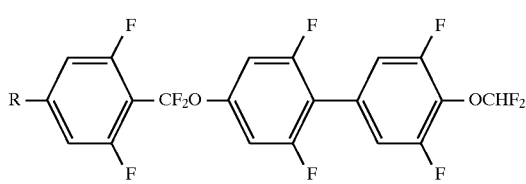
(226)
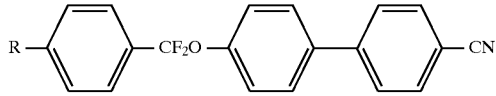
(227)
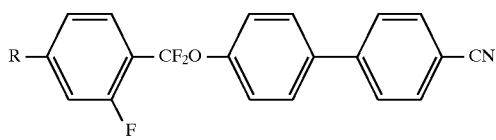
(228)

-continued
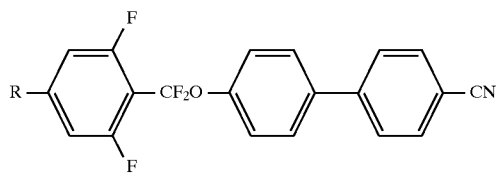 (229)
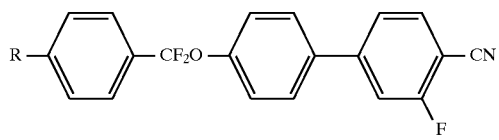 (230)
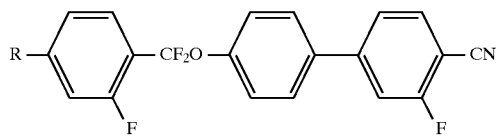 (231)
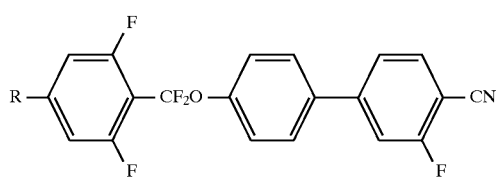 (232)
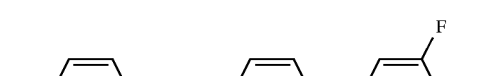 (233)
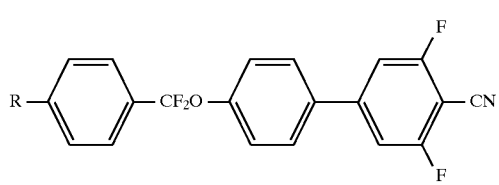 (234)
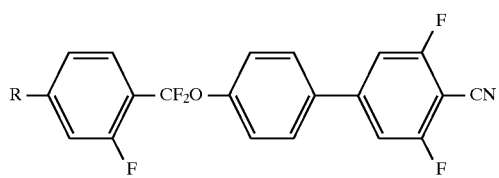 (235)
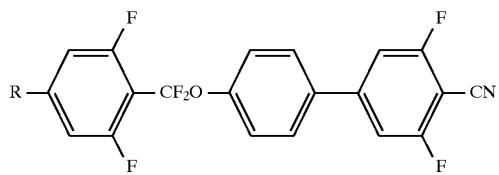 (236)
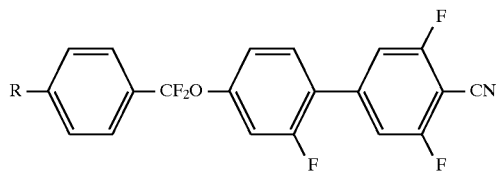 (237)
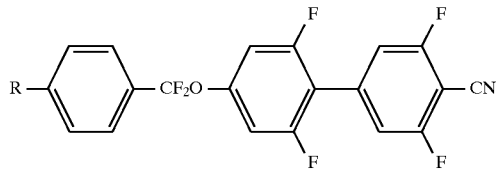

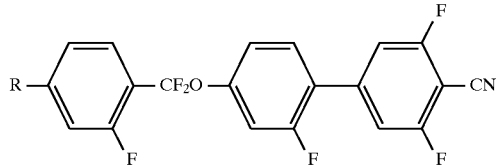 (238)
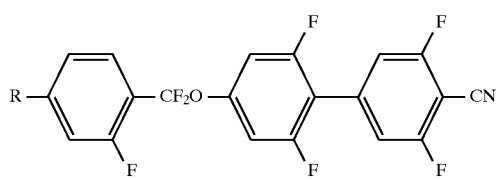 (239)
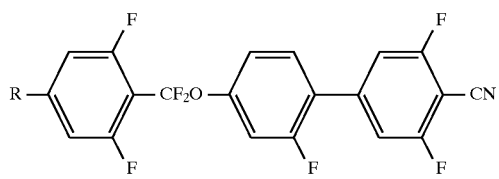 (240)
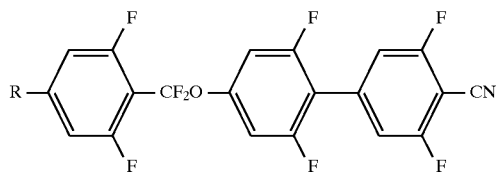 (241)
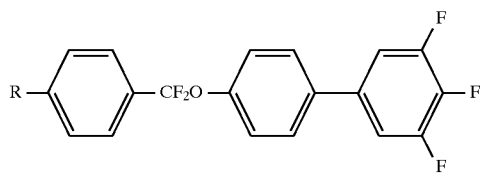 (242)
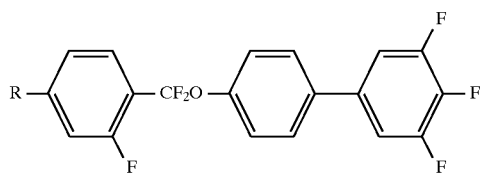 (243)
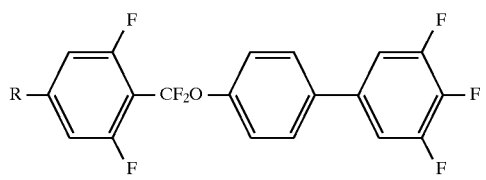 (244)
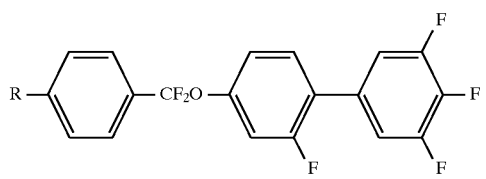 (245)
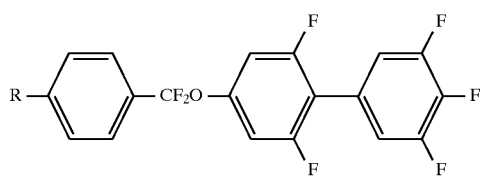 (246)

-continued
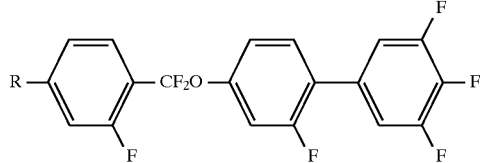 (247)
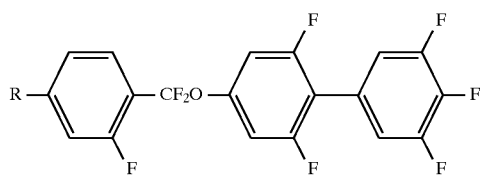 (248)
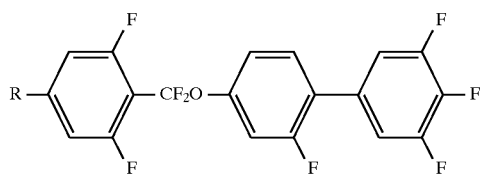 (249)
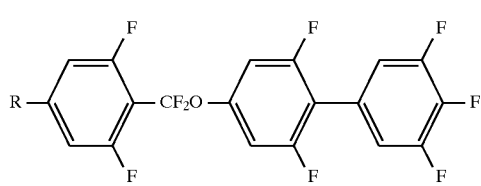 (250)
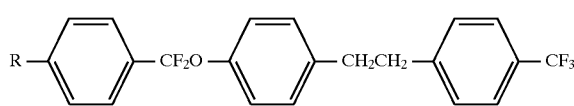 (251)
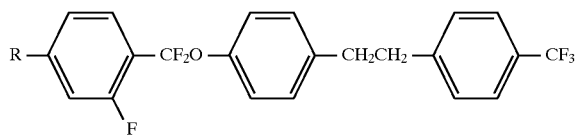 (252)
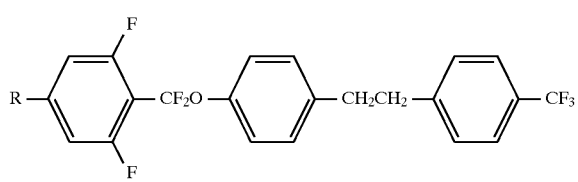 (253)
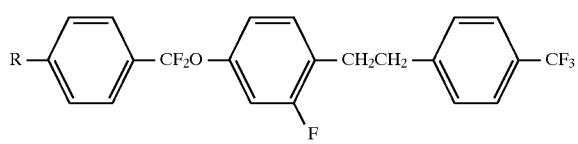 (254)
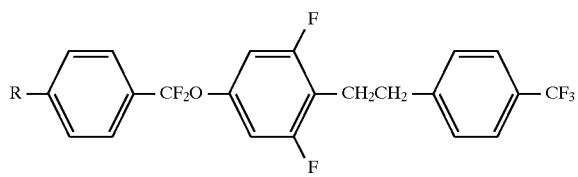 (255)
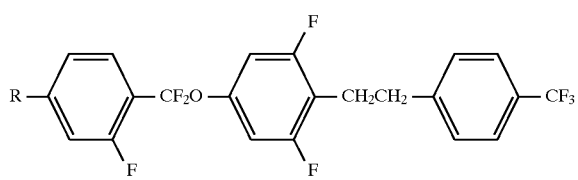 (256)

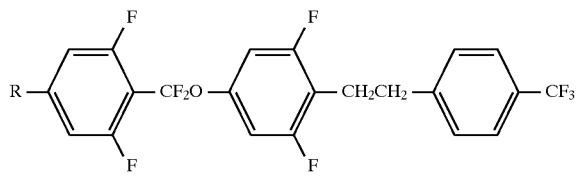 (257)
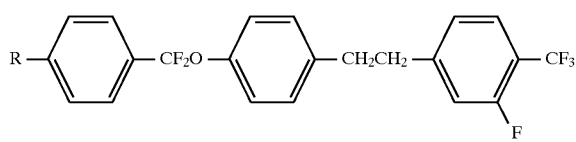 (258)
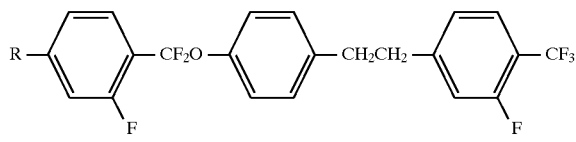 (259)
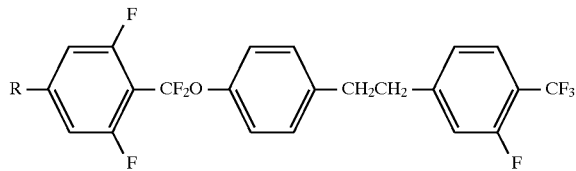 (260)
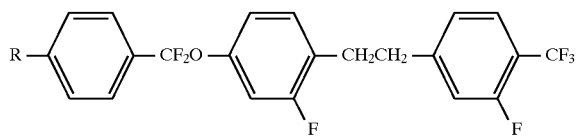 (261)
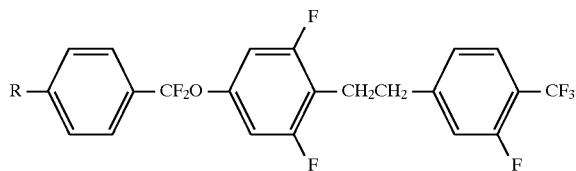 (262)
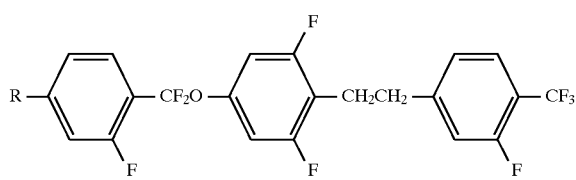 (263)
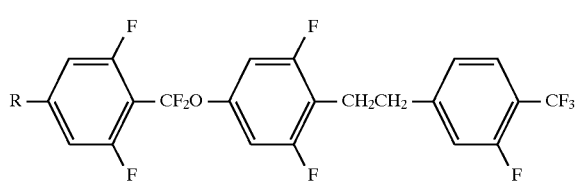 (264)
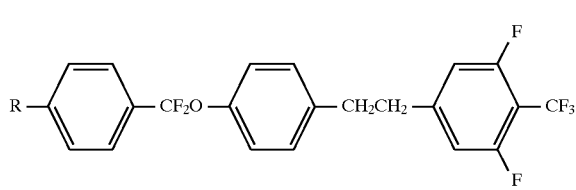 (265)

-continued
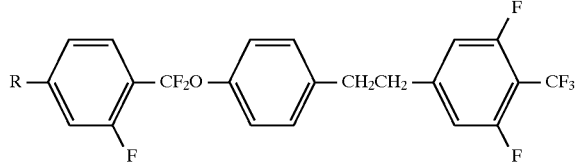
(266)
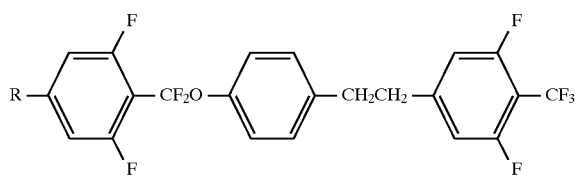
(267)
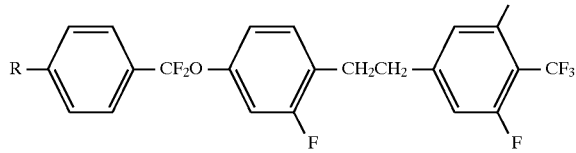
(268)
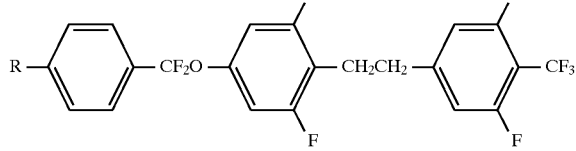
(269)
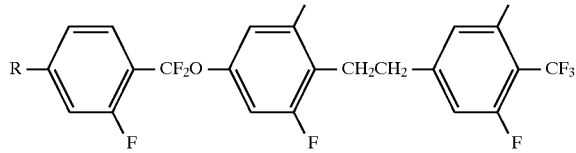
(270)
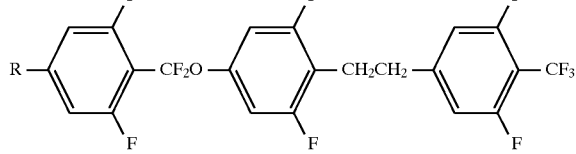
(271)
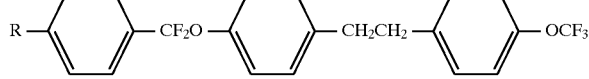
(272)
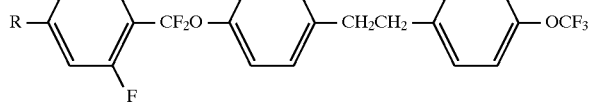
(273)
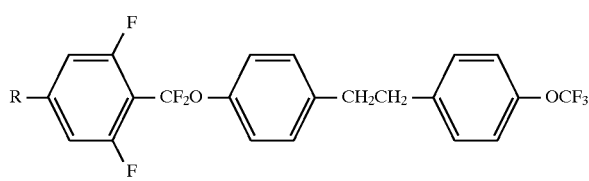
(274)
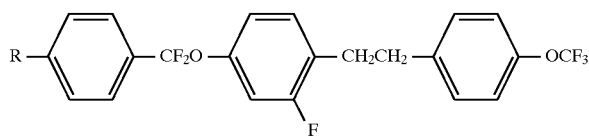
(275)

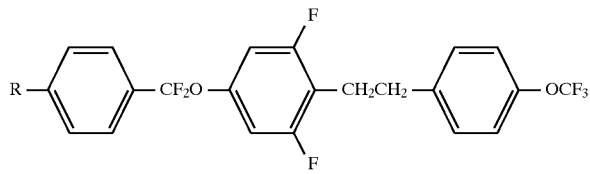 (276)
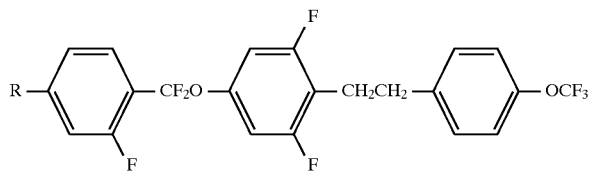 (277)
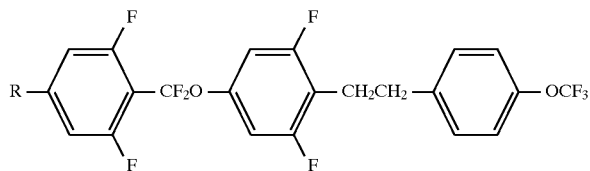 (278)
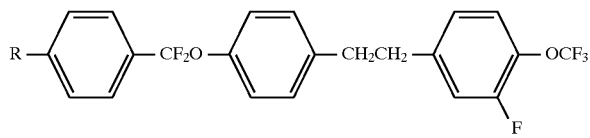 (279)
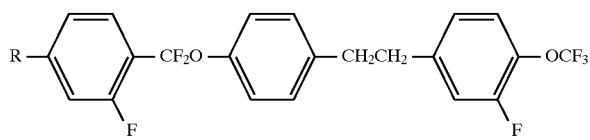 (280)
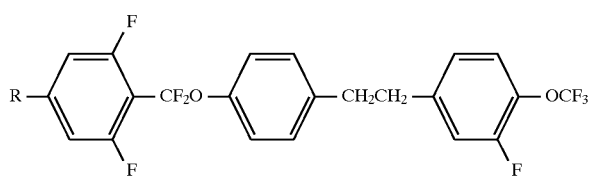 (281)
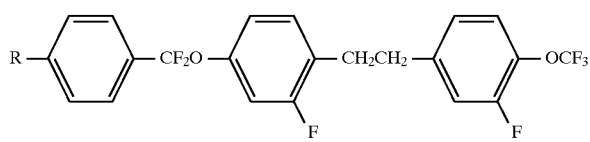 (282)
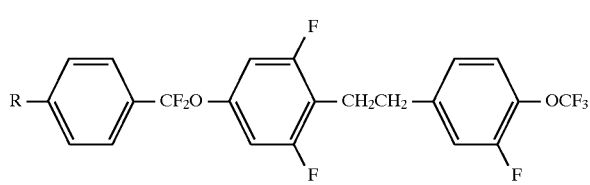 (283)
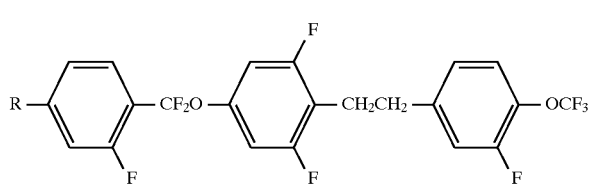 (284)

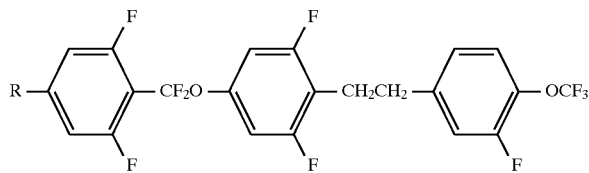 (285)
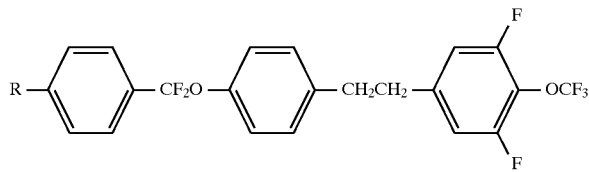 (286)
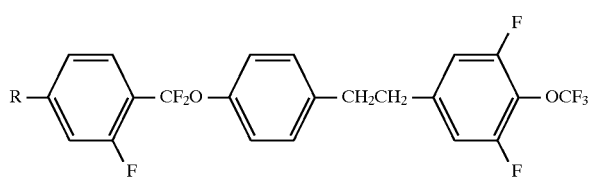 (287)
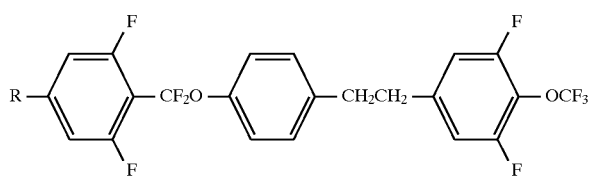 (288)
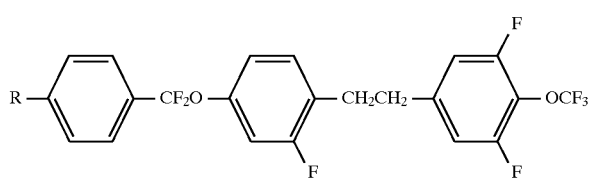 (289)
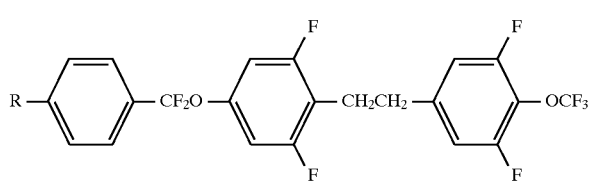 (290)
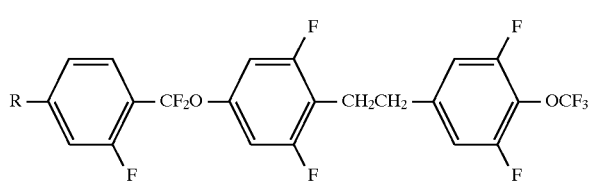 (291)
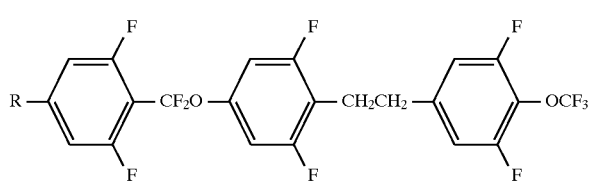 (292)
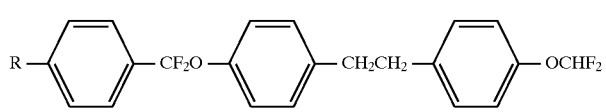 (293)

-continued
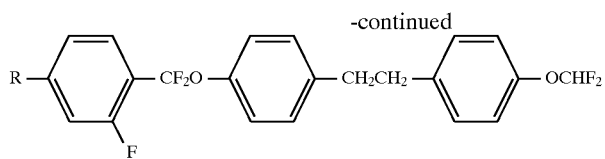 (294)
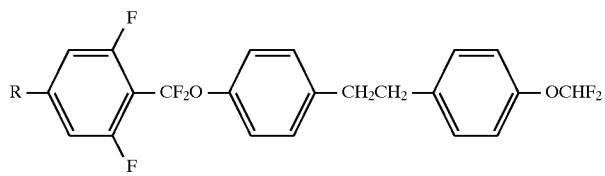 (295)
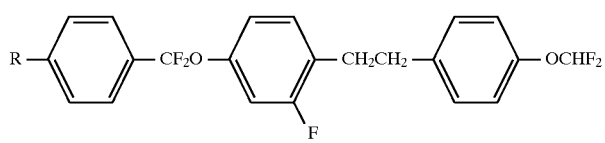 (296)
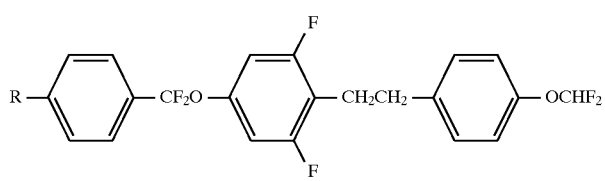 (297)
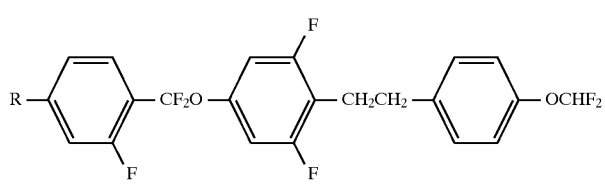 (298)
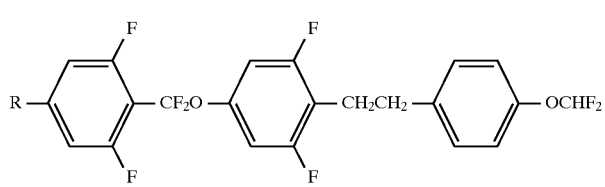 (299)
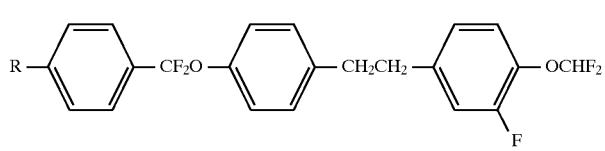 (300)
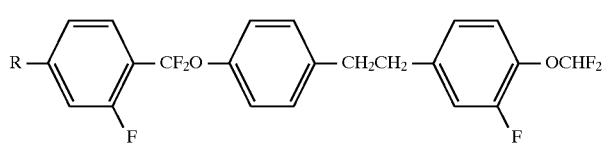 (301)
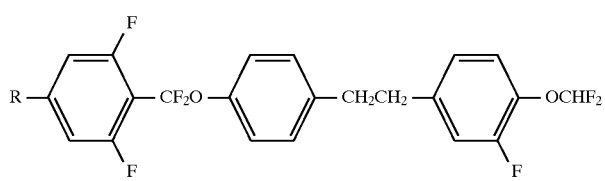 (302)
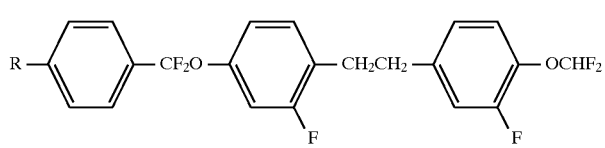 (303)

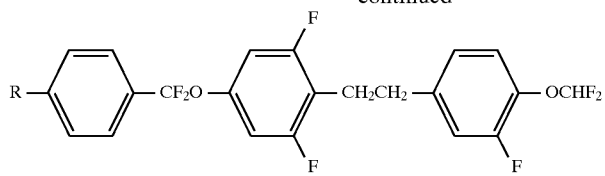
(304)
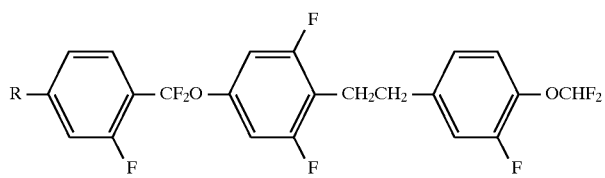
(305)
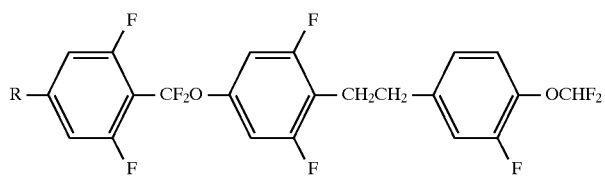
(306)
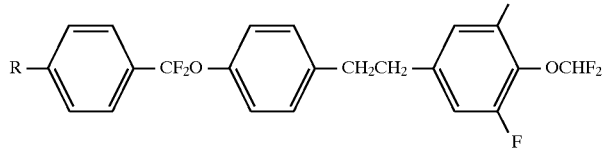
(307)
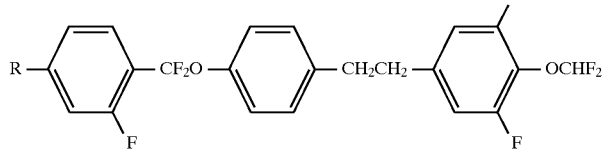
(308)
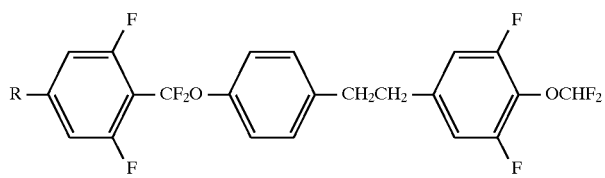
(309)
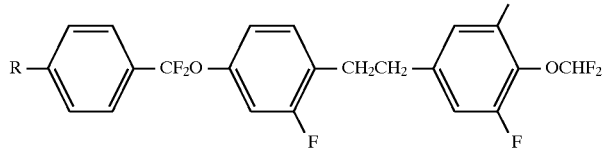
(310)
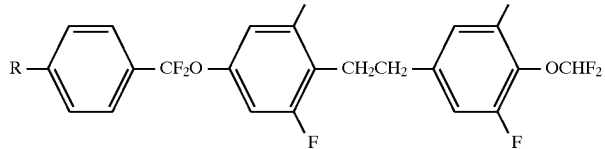
(311)
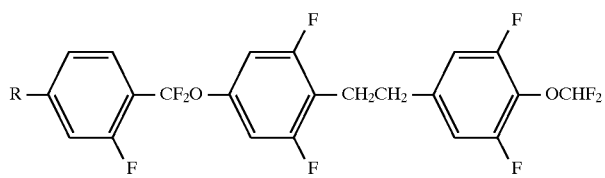
(312)

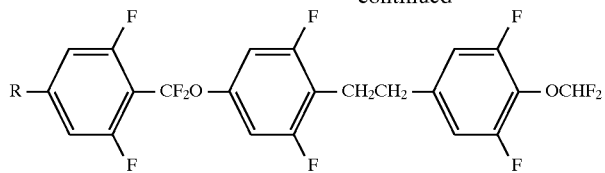 (313)
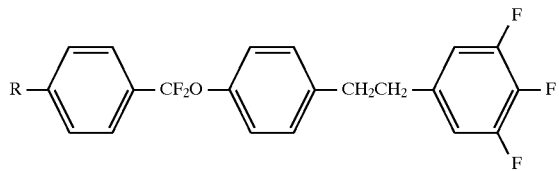 (314)
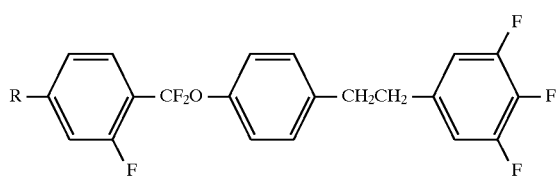 (315)
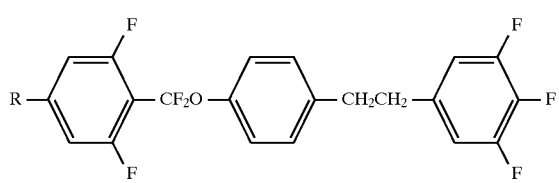 (316)
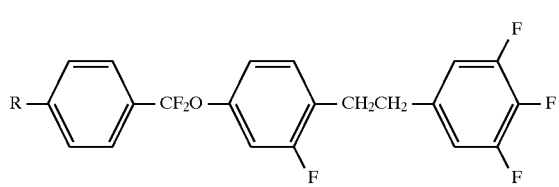 (317)
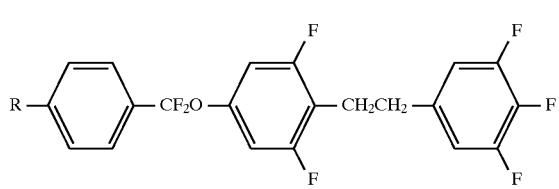 (318)
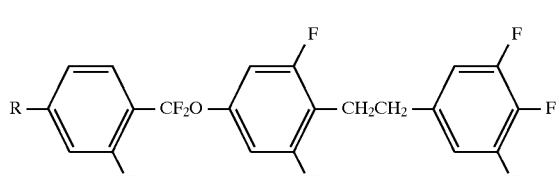 (319)
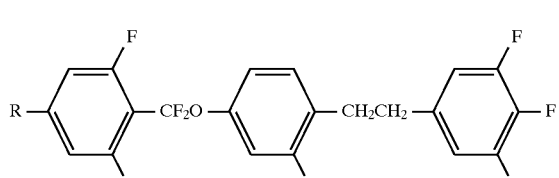 (319a)
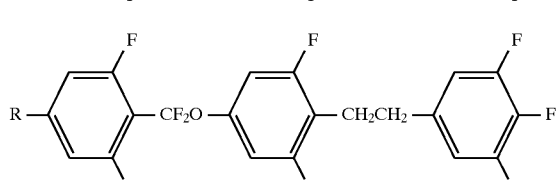 (320)

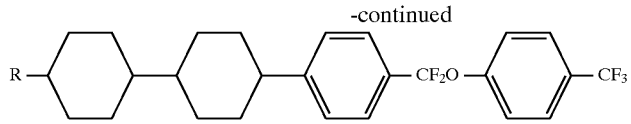 (321)
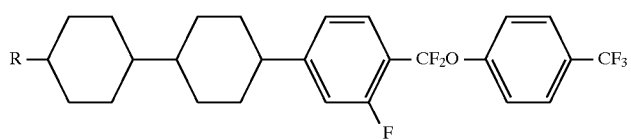 (322)
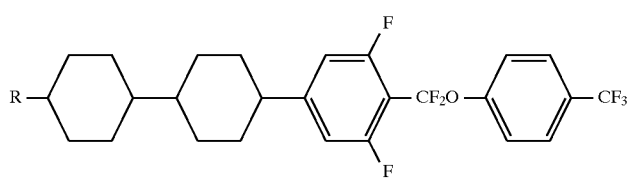 (323)
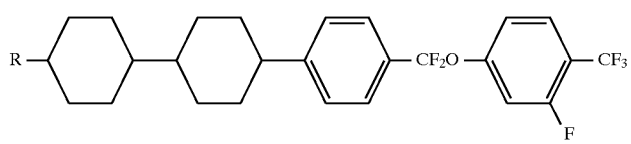 (324)
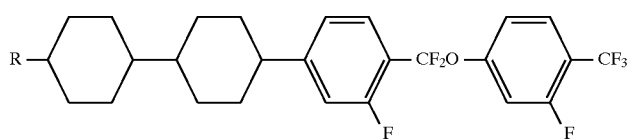 (325)
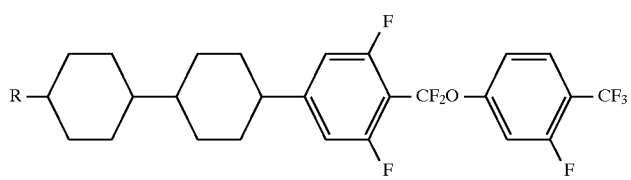 (326)
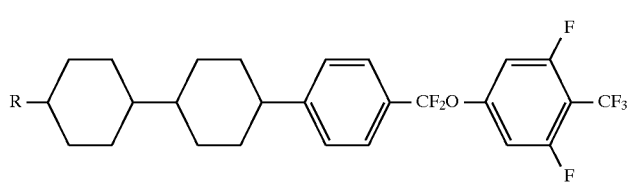 (327)
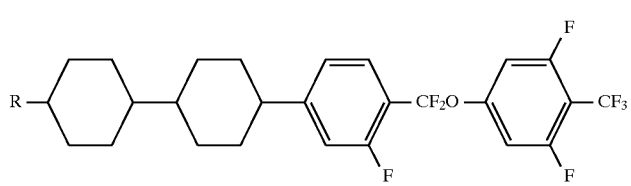 (328)
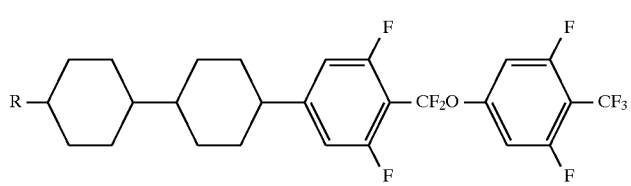 (329)
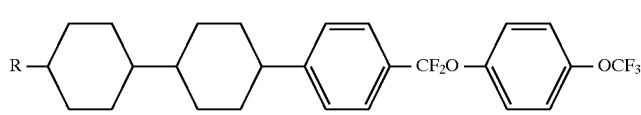 (330)

-continued
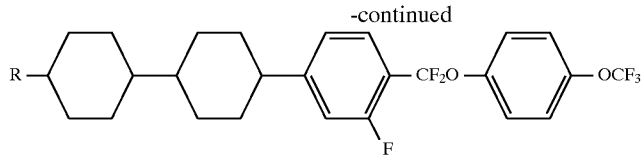 (331)
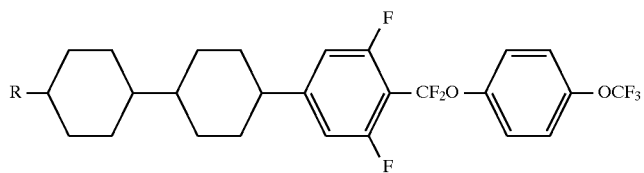 (332)
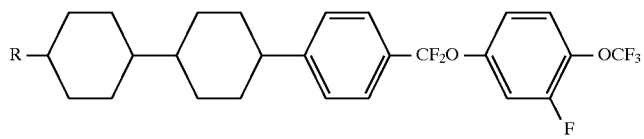 (333)
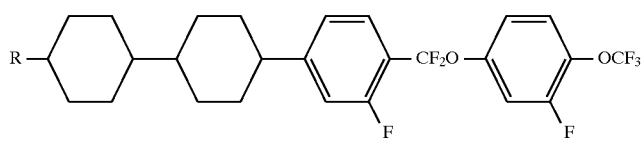 (334)
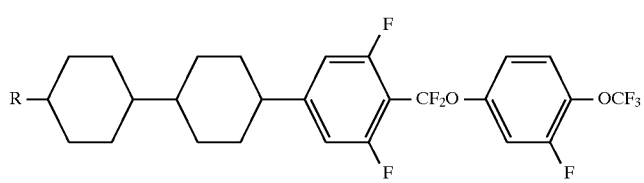 (335)
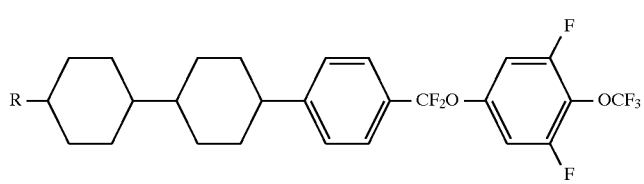 (336)
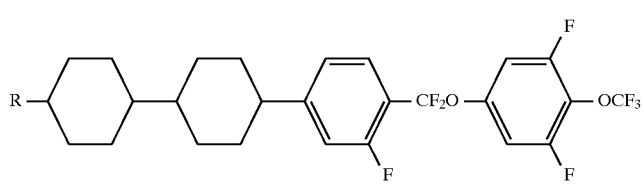 (337)
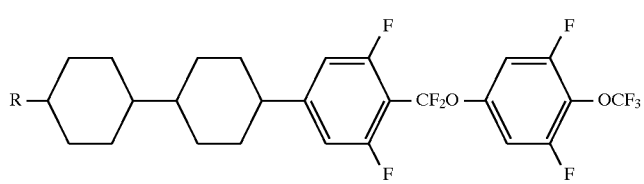 (338)
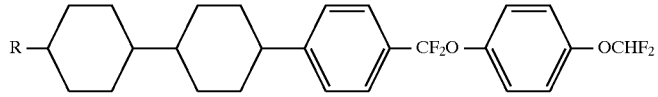 (339)
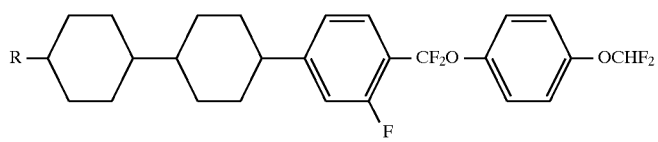 (340)

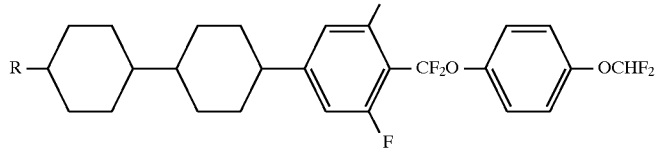
(341)
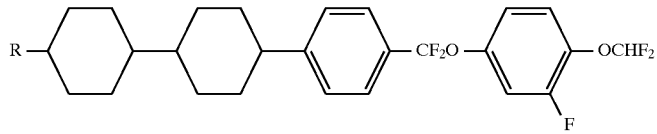
(342)
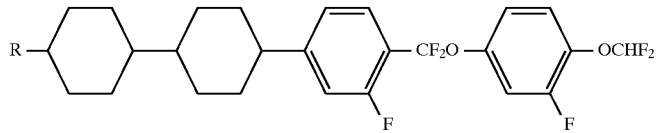
(343)
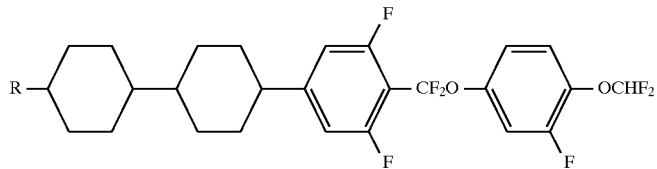
(344)
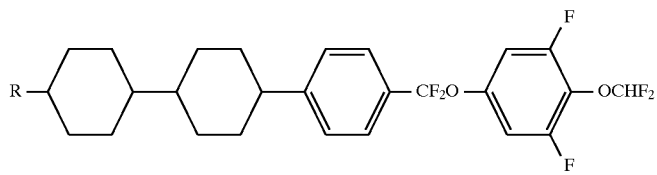
(345)
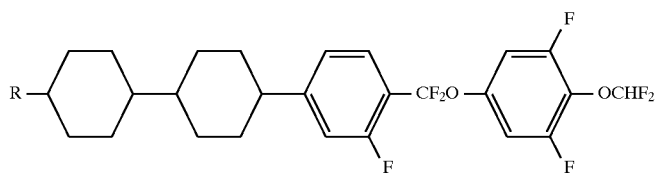
(346)
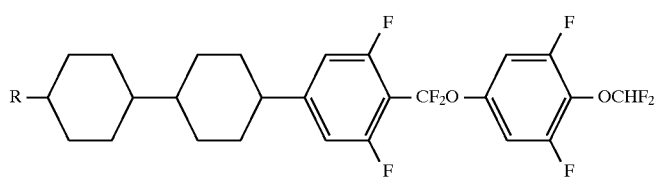
(347)
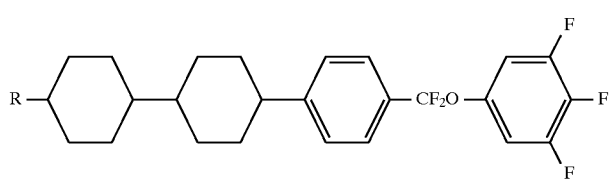
(348)
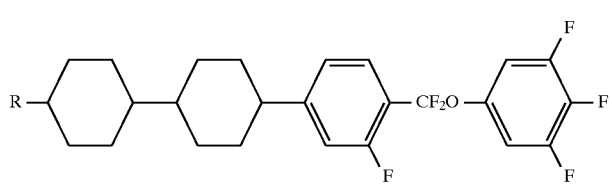
(349)

-continued
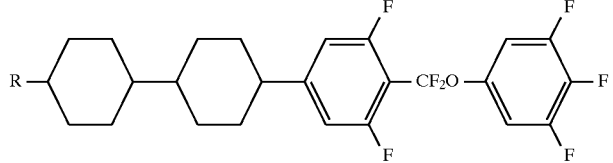 (350)
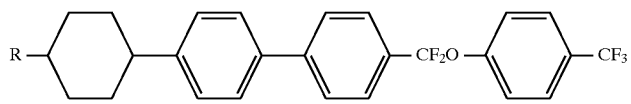 (351)
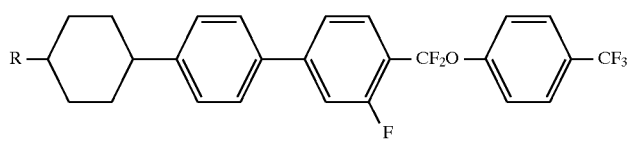 (352)
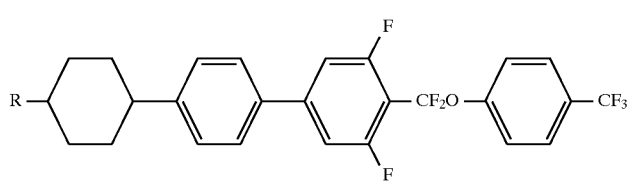 (353)
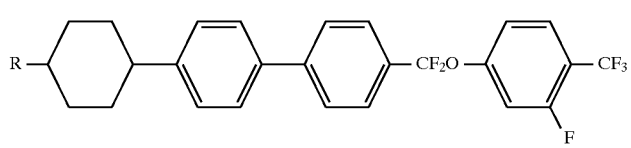 (354)
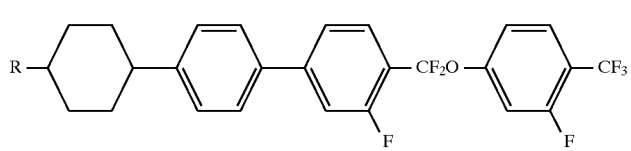 (355)
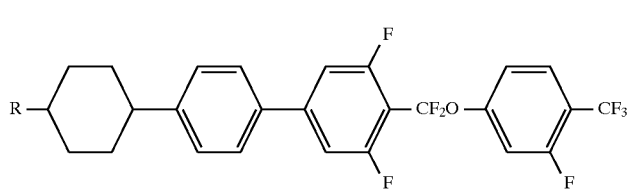 (356)
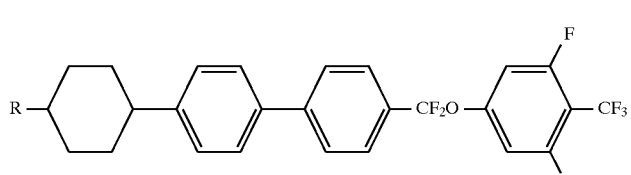 (357)
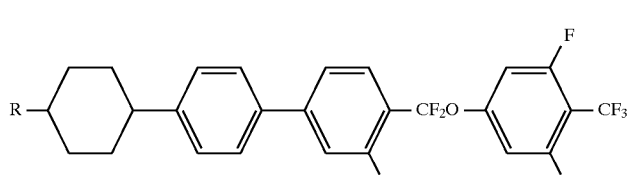 (358)
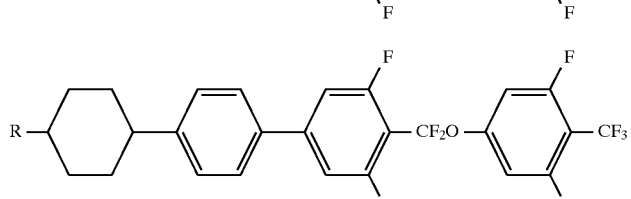 (359)

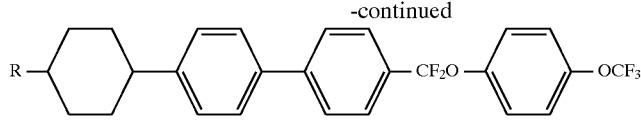 (360)
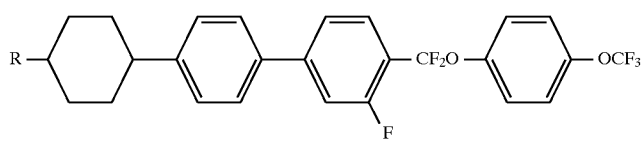 (361)
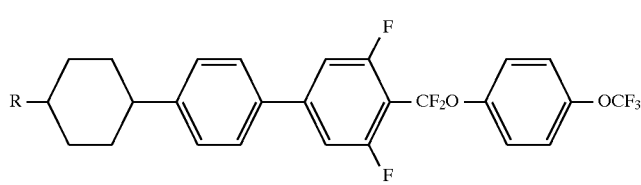 (362)
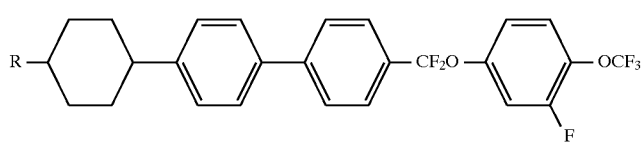 (363)
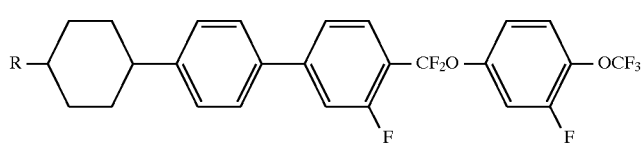 (364)
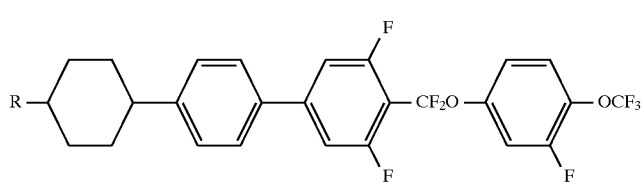 (365)
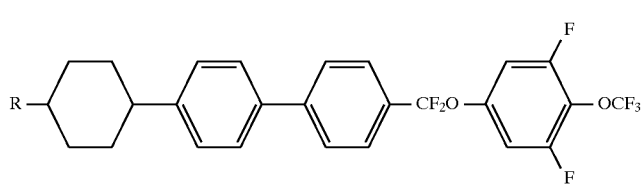 (366)
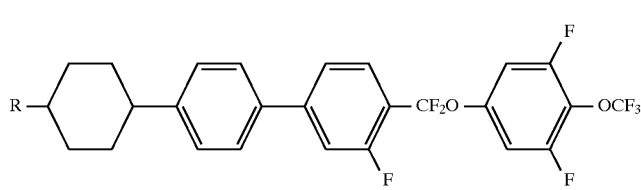 (367)
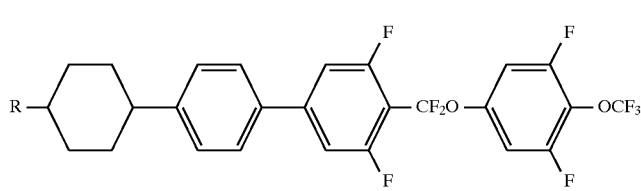 (368)
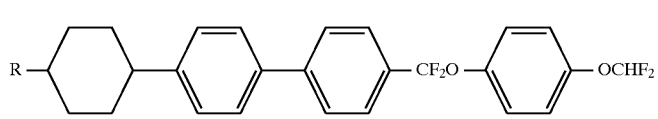 (369)

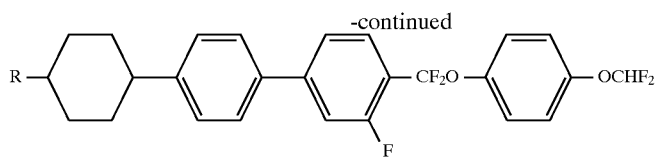
(370)
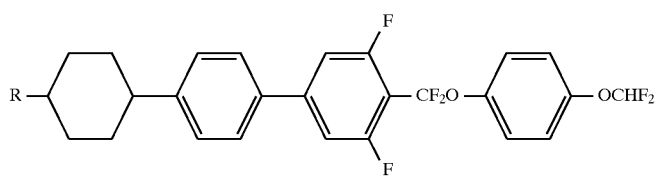
(371)
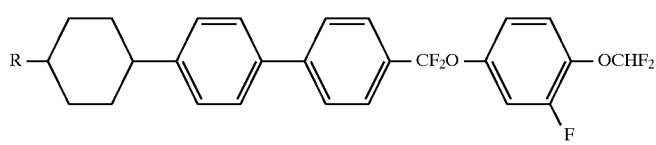
(372)
(373)
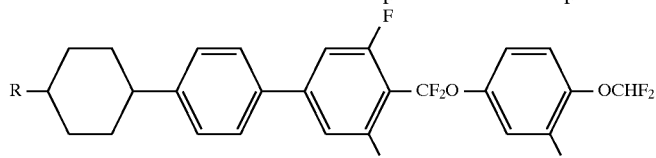
(374)
(375)
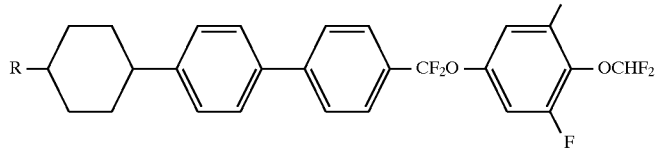
(376)
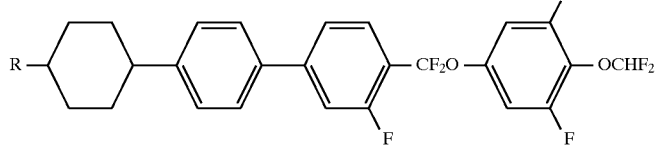
(377)
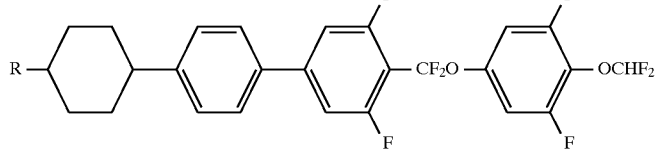
(378)
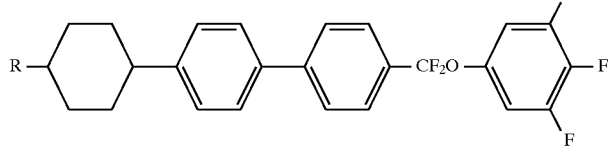
(379)
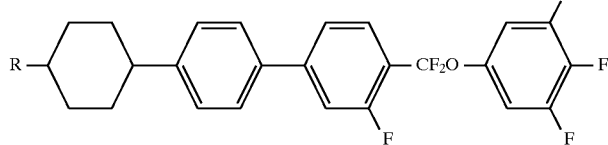

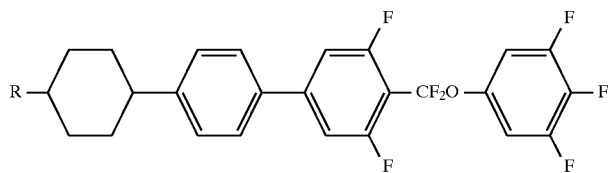 (380)
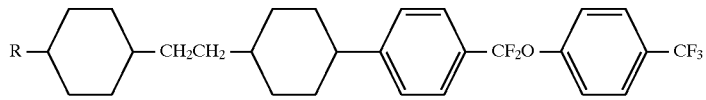 (381)
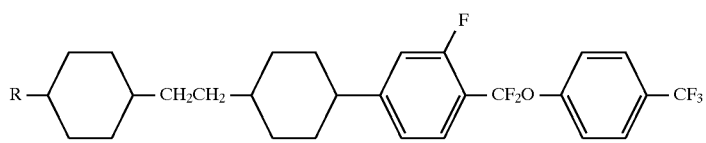 (382)
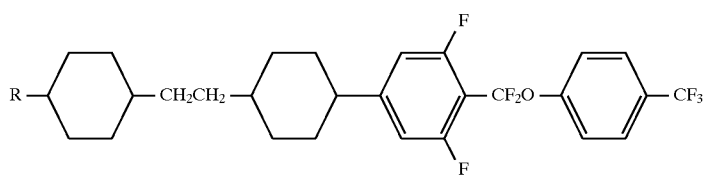 (383)
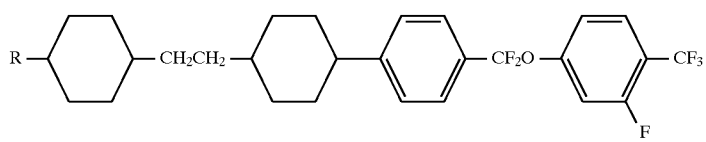 (384)
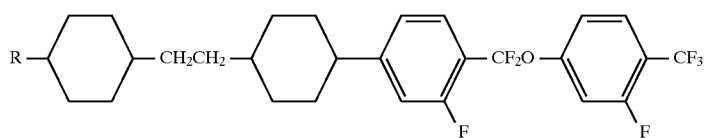 (385)
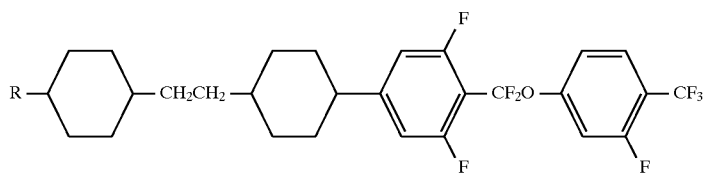 (386)
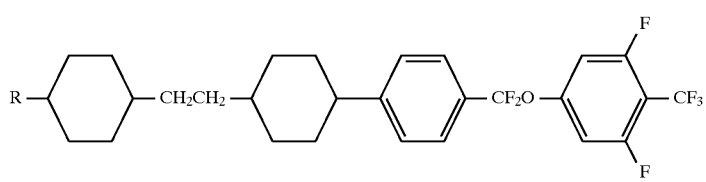 (387)
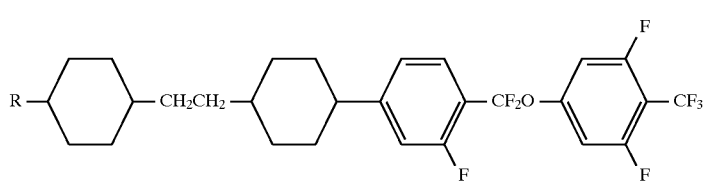 (388)
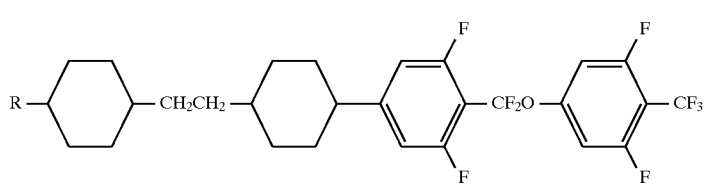 (389)

-continued
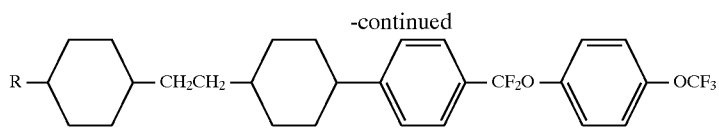 (390)
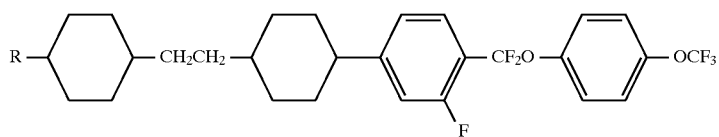 (390a)
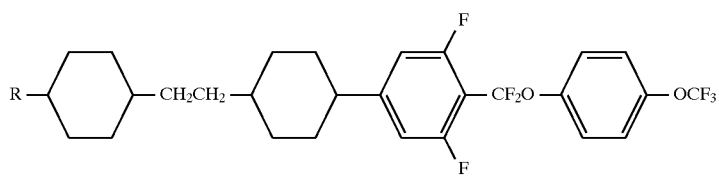 (391)
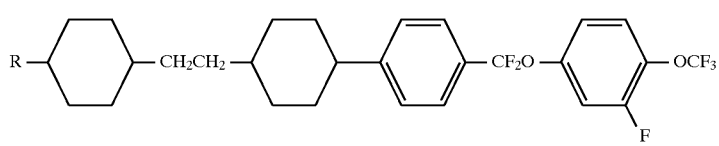 (392)
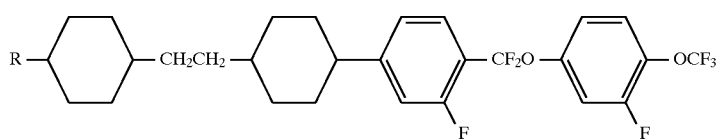 (393)
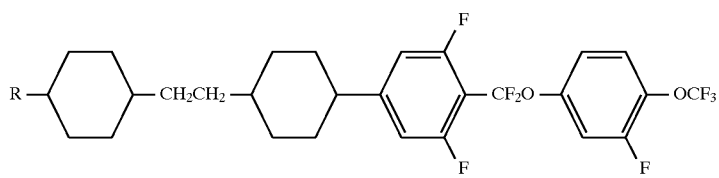 (394)
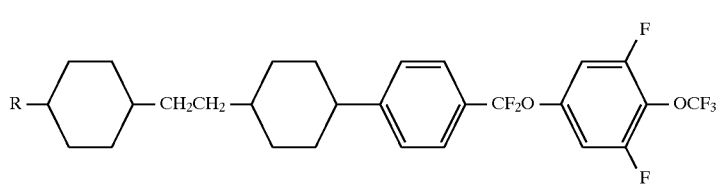 (395)
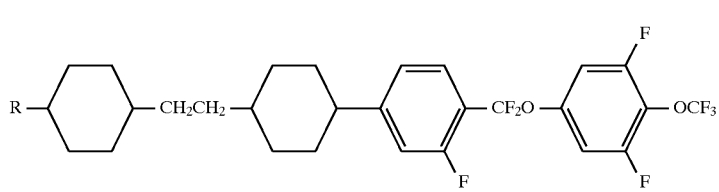 (396)
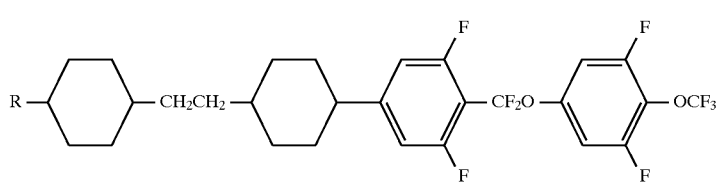 (397)
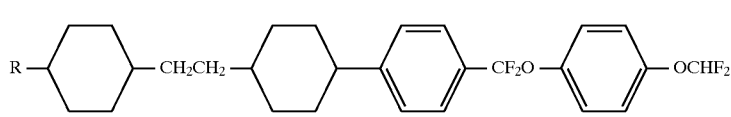 (398)

-continued
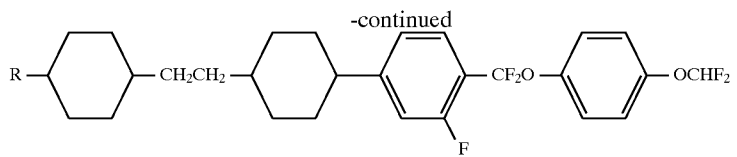 (399)
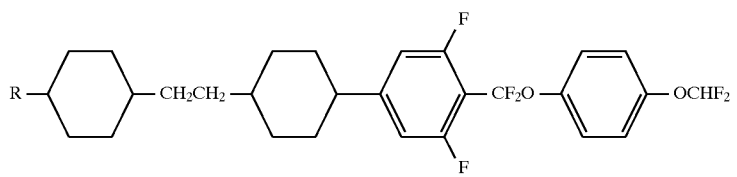 (400)
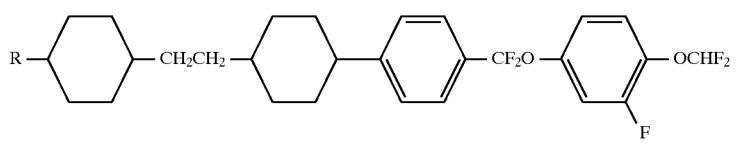 (401)
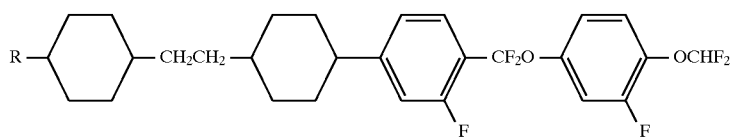 (402)
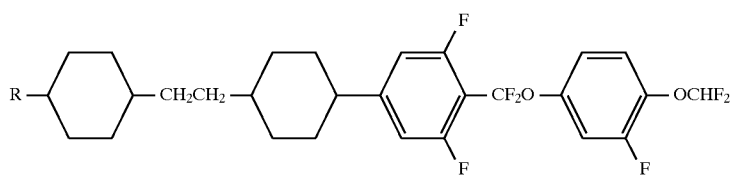 (403)
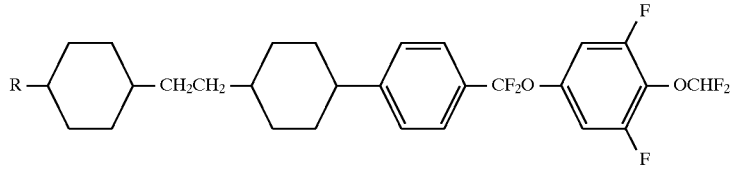 (404)
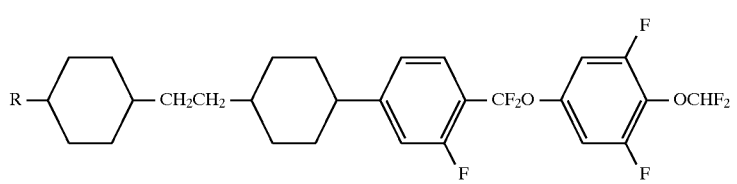 (405)
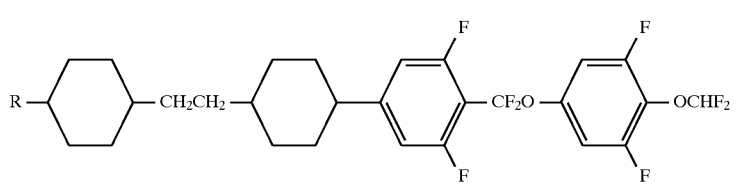 (406)
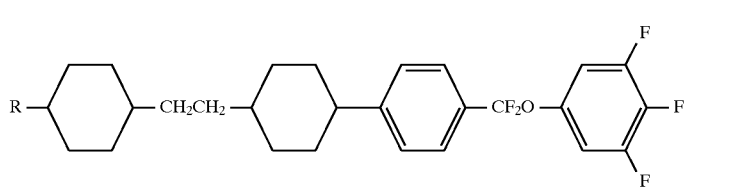 (407)
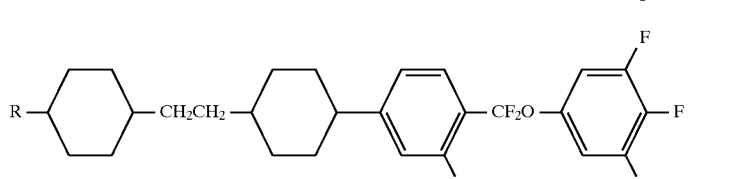 (408)

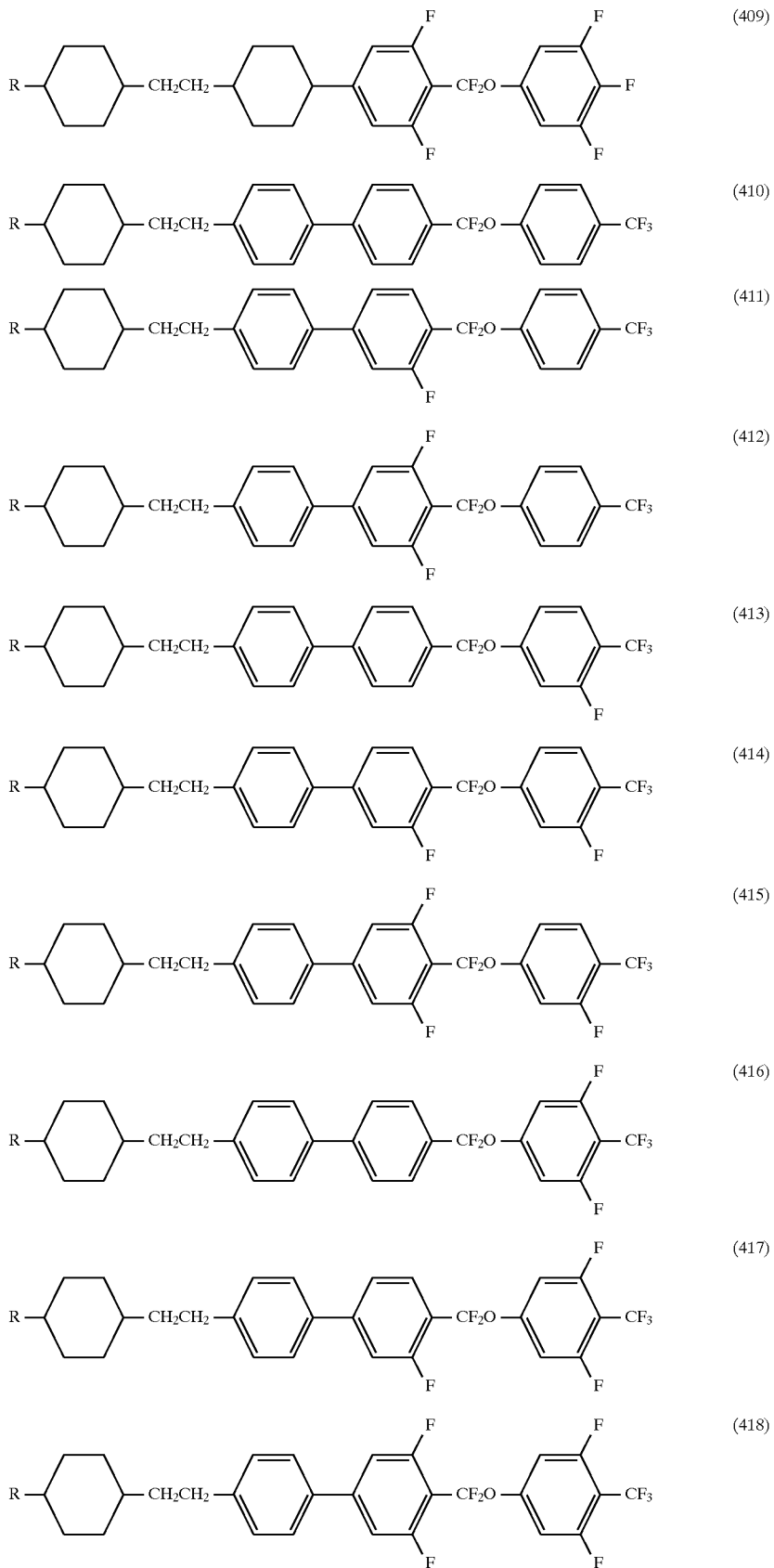

-continued
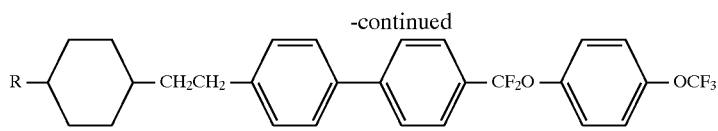  (419)
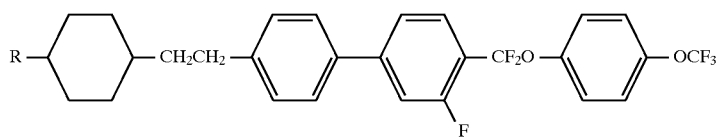  (420)
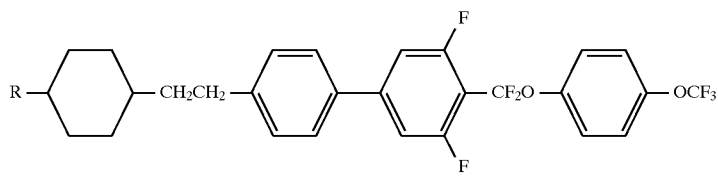  (421)
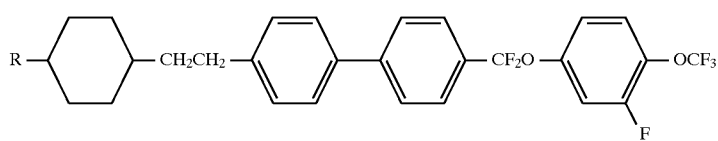  (422)
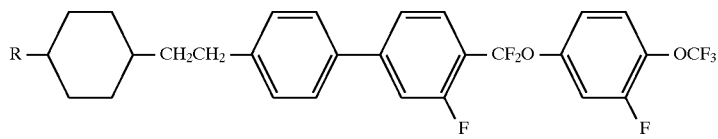  (423)
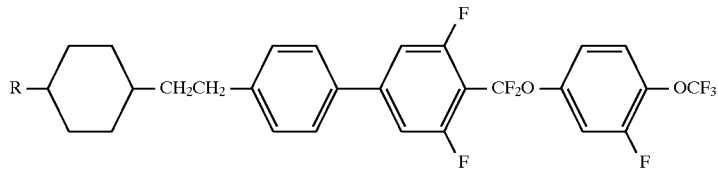  (424)
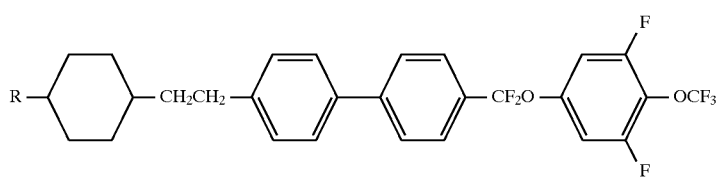  (425)
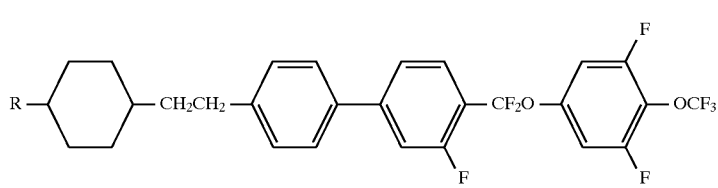  (426)
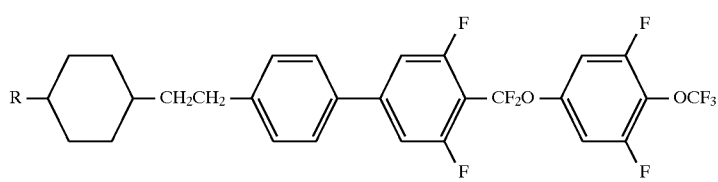  (427)
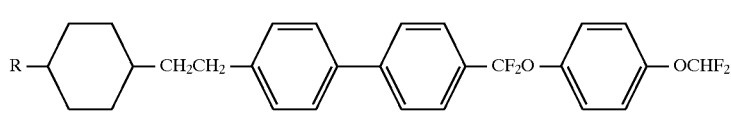  (428)

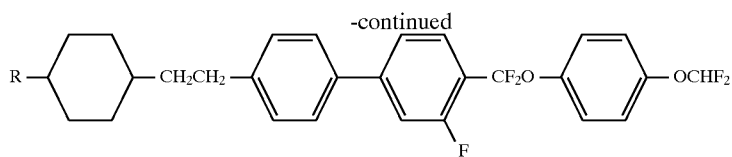
(429)
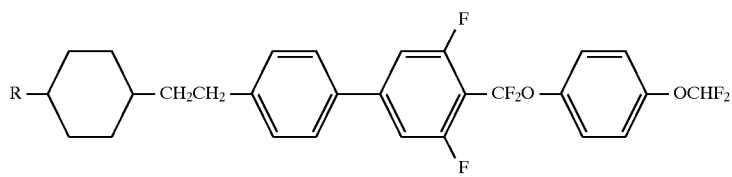
(430)
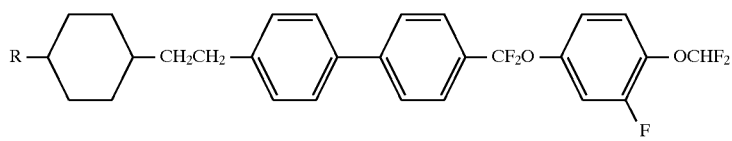
(431)
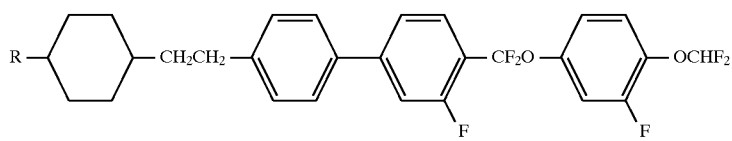
(432)
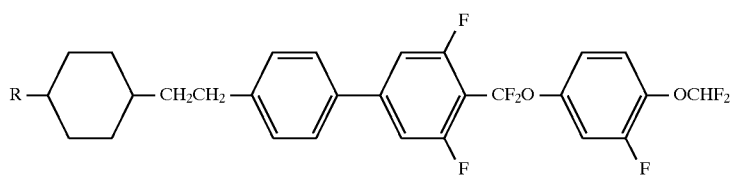
(433)
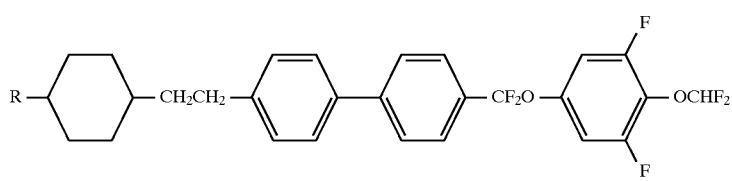
(434)
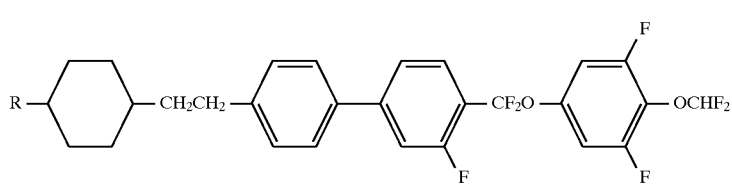
(435)
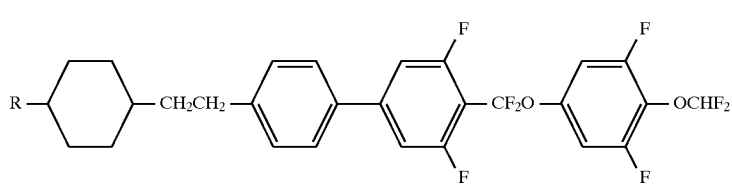
(436)
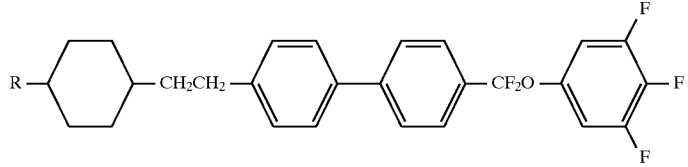
(437)
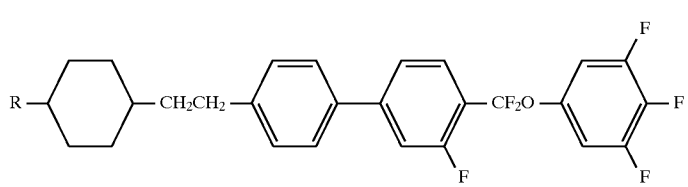
(438)

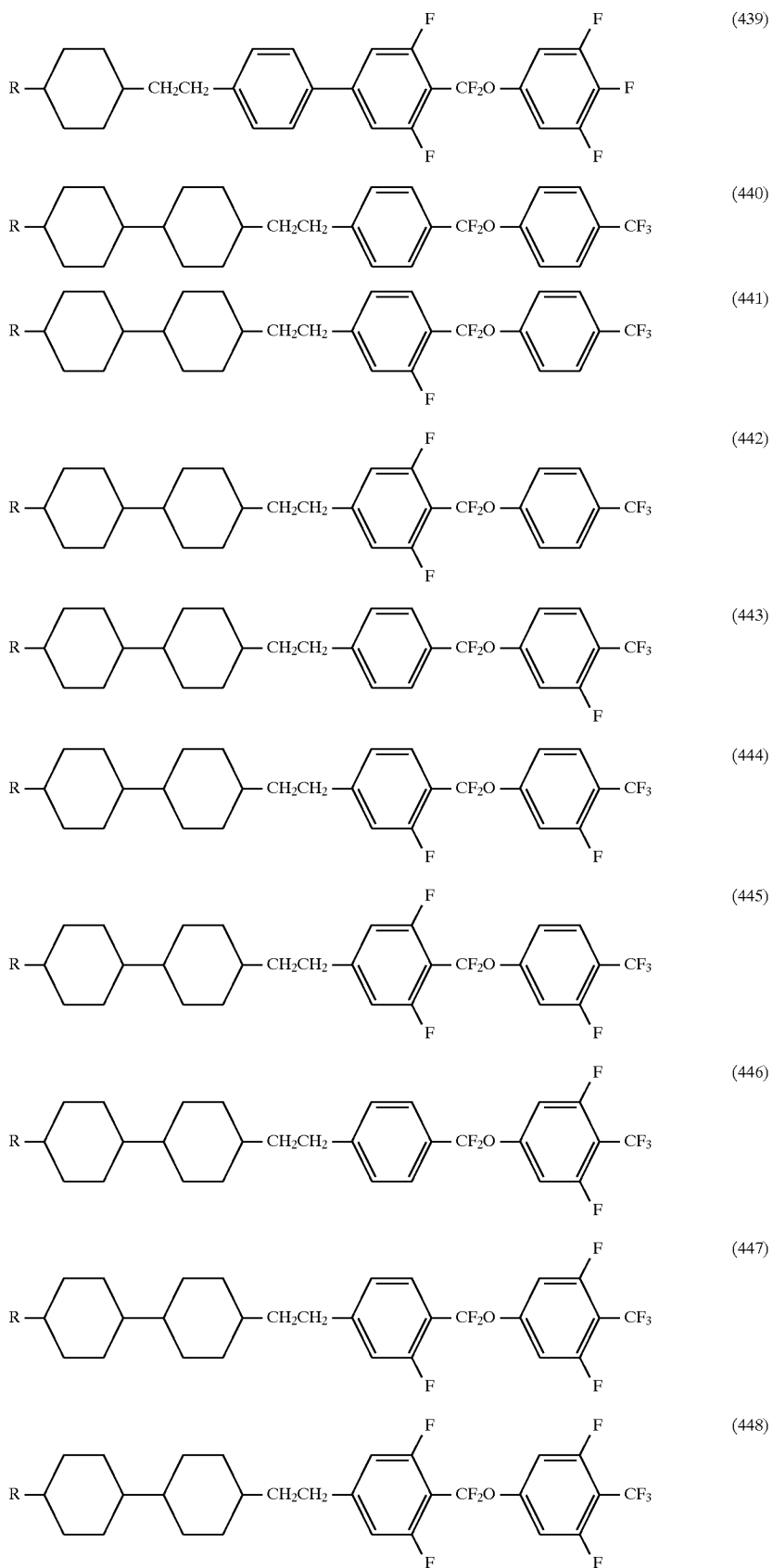

-continued
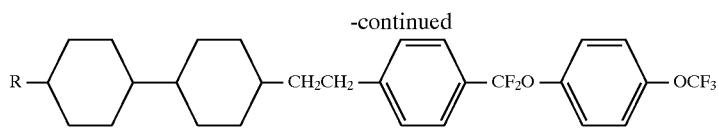 (449)
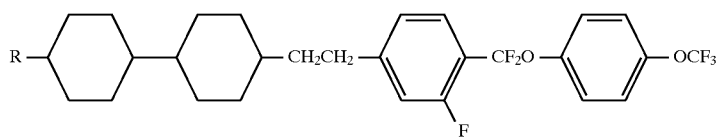 (450)
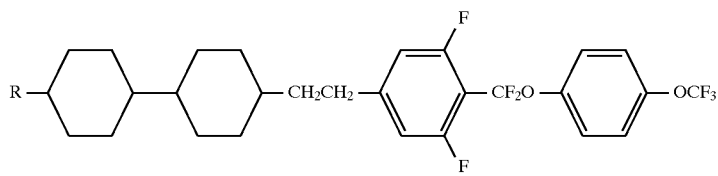 (451)
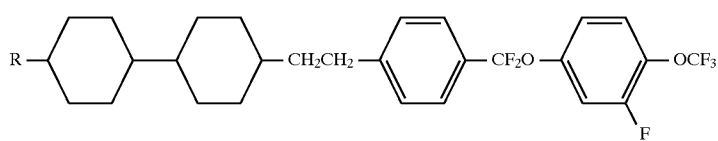 (452)
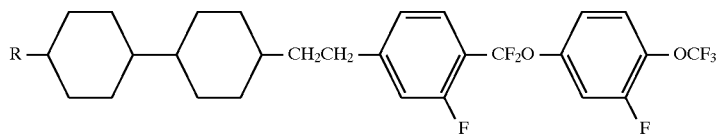 (453)
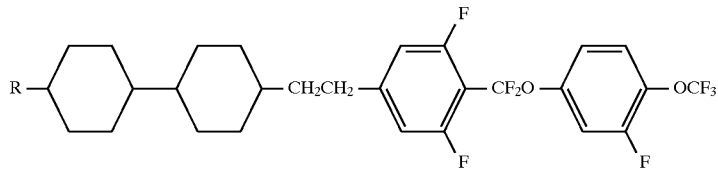 (454)
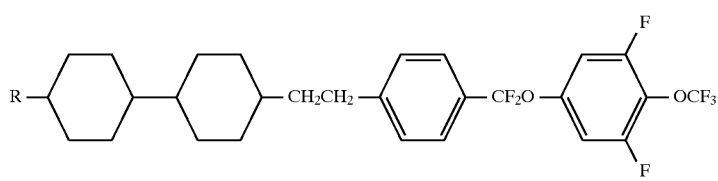 (455)
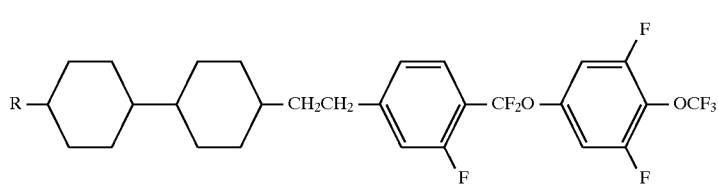 (455a)
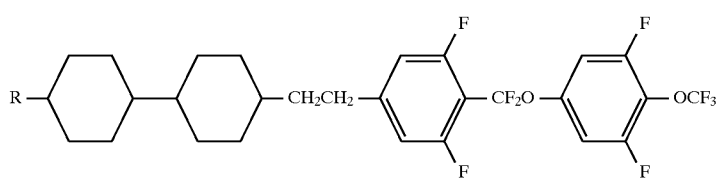 (455b)
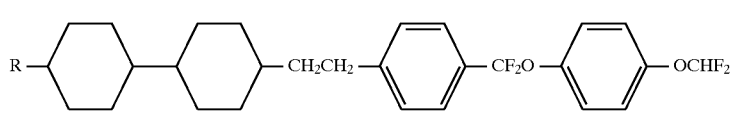 (456)

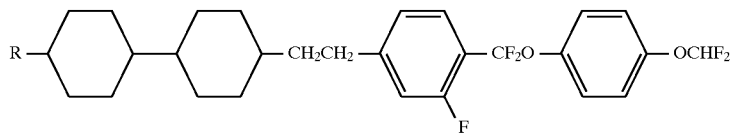 (457)
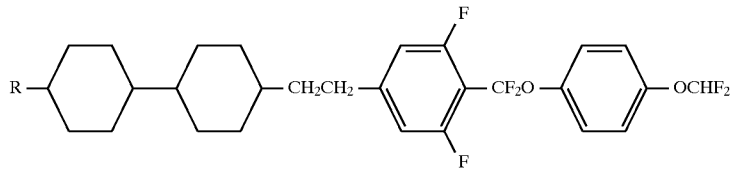 (458)
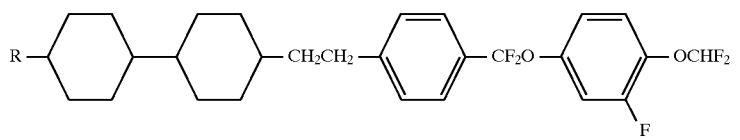 (459)
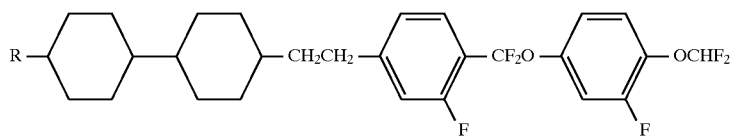 (460)
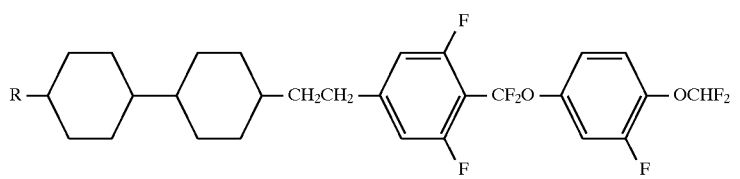 (461)
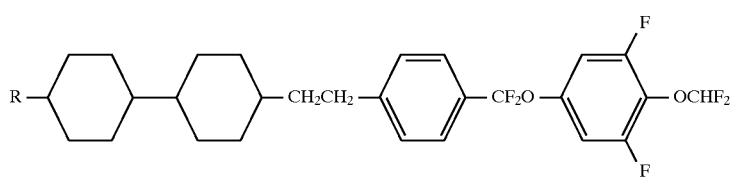 (462)
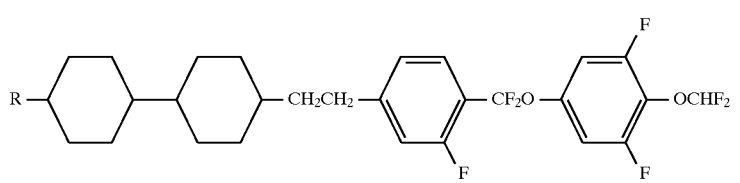 (463)
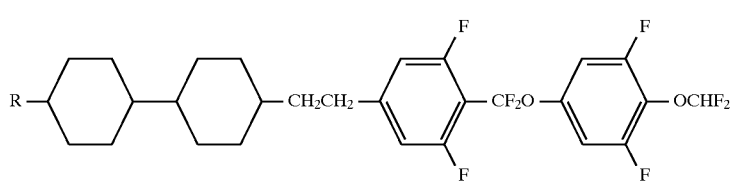 (464)
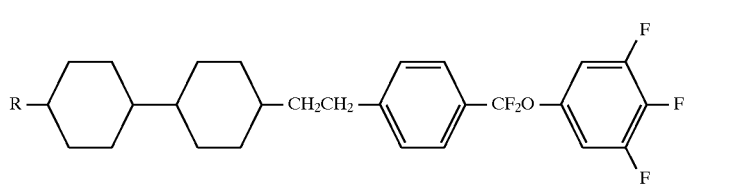 (465)

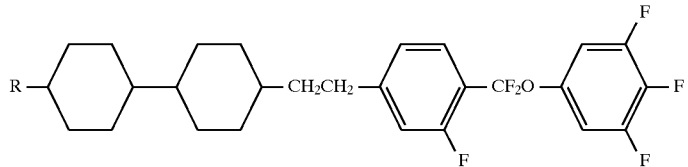
(466)
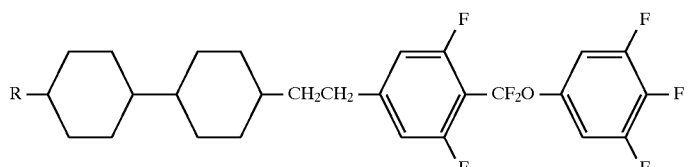
(467)
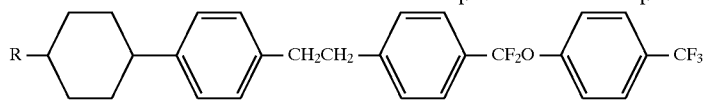
(468)
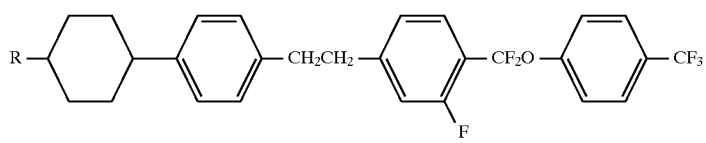
(469)
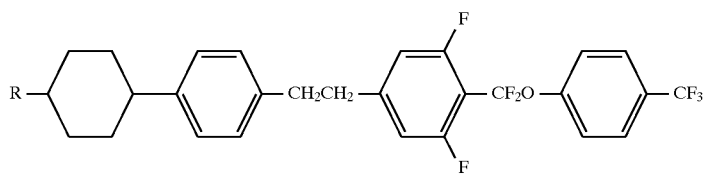
(470)
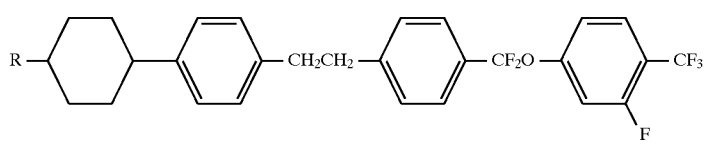
(471)
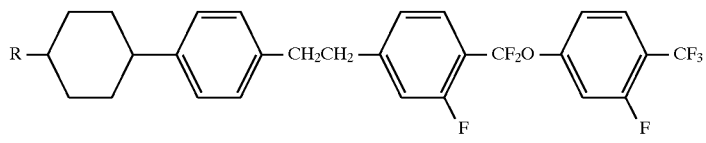
(472)
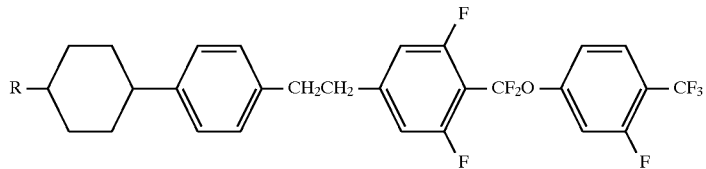
(473)
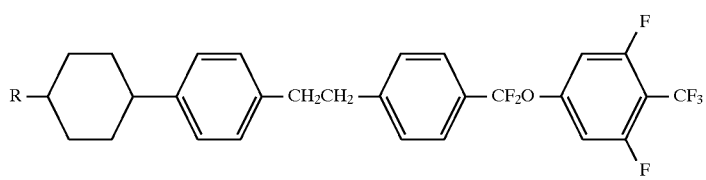
(474)
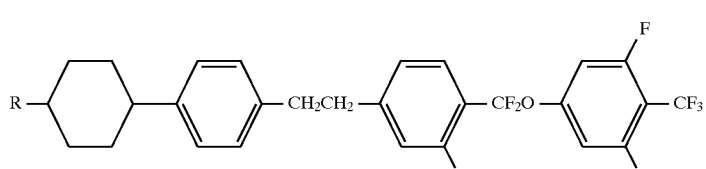
(475)

-continued
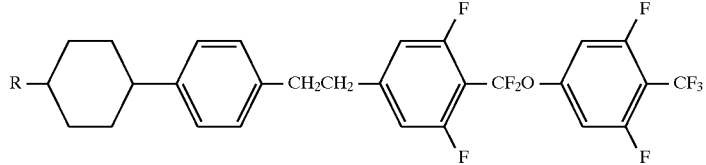 (476)
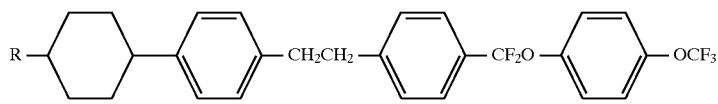 (477)
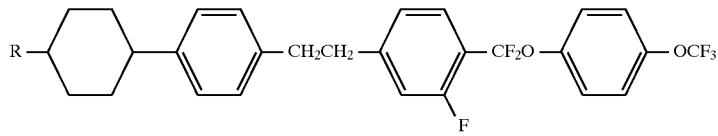 (477-a)
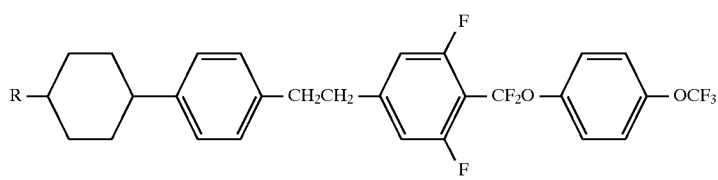 (477-b)
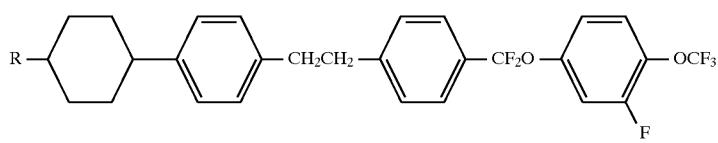 (478)
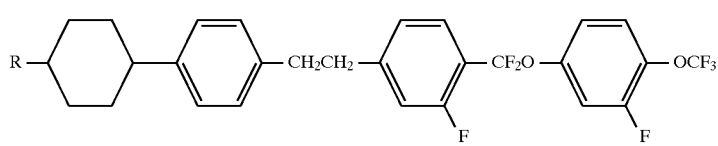 (479)
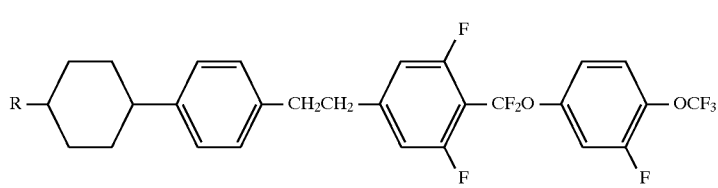 (480)
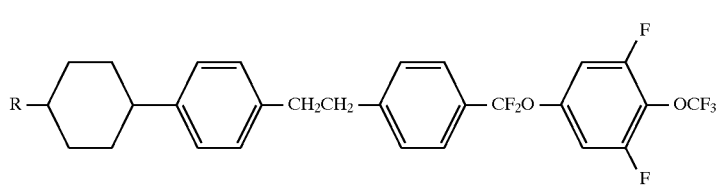 (481)
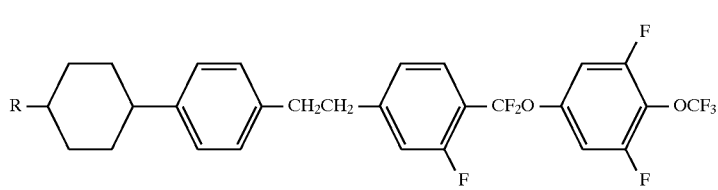 (482)
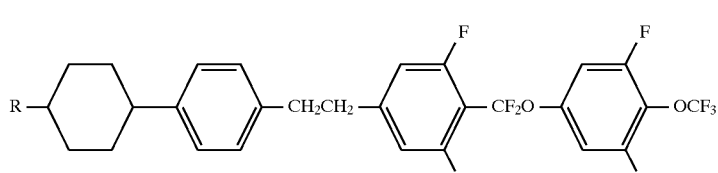 (483)

-continued
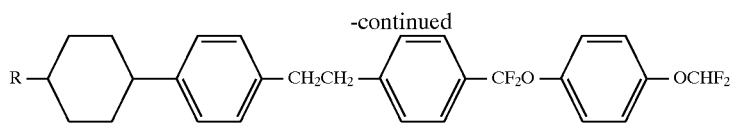 (484)
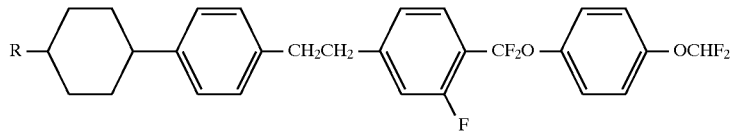 (485)
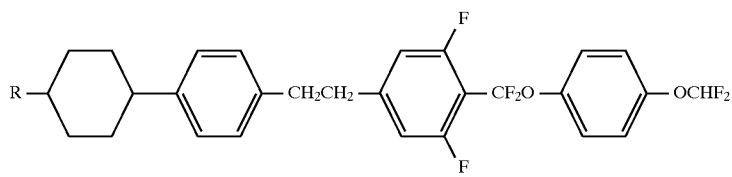 (486)
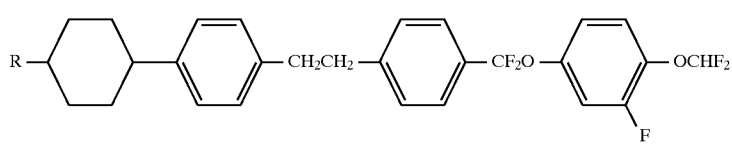 (487)
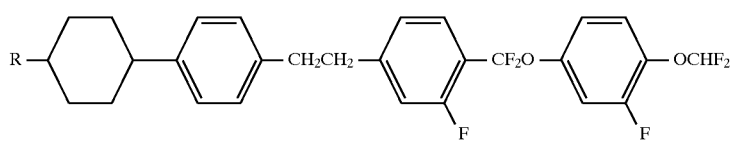 (488)
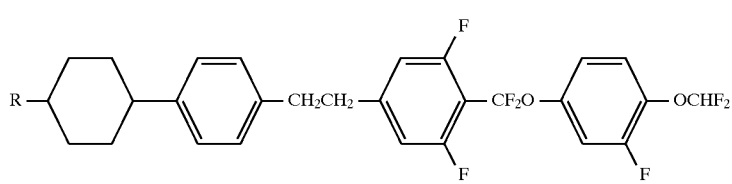 (489)
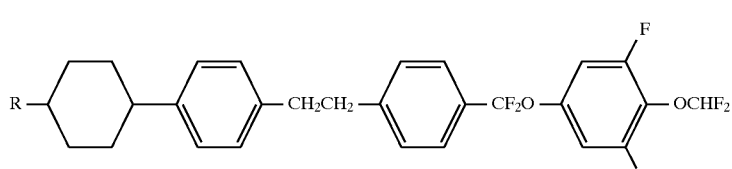 (490)
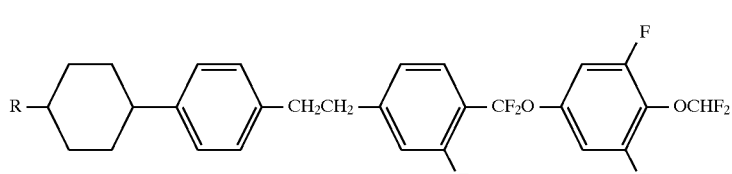 (491)
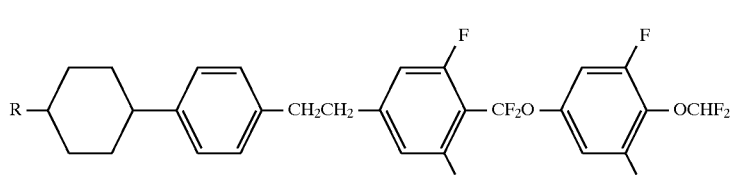 (492)
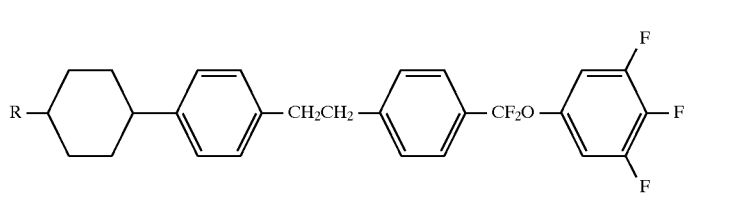 (493)

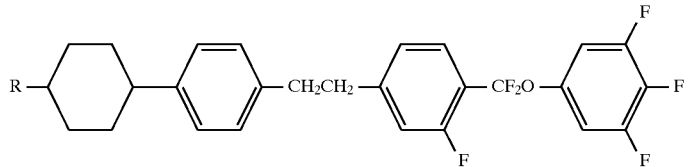
(494)
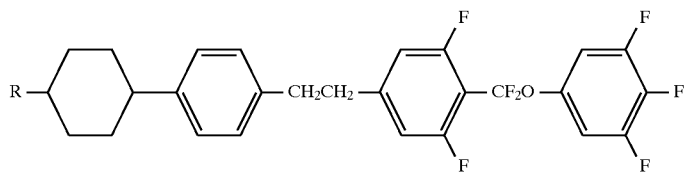
(495)
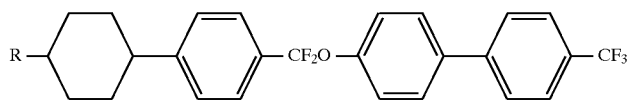
(496)
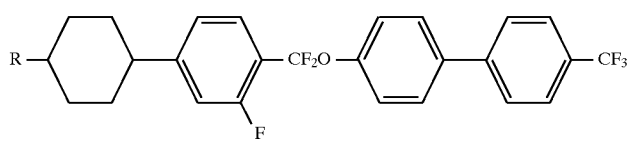
(497)
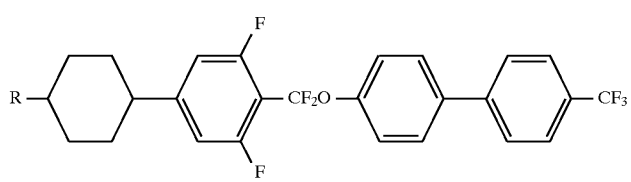
(498)
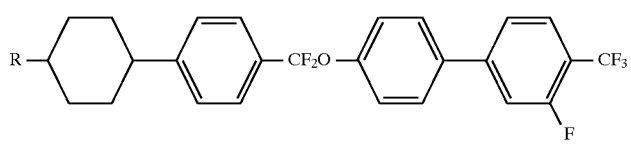
(499)
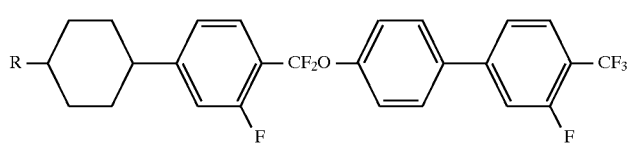
(500)
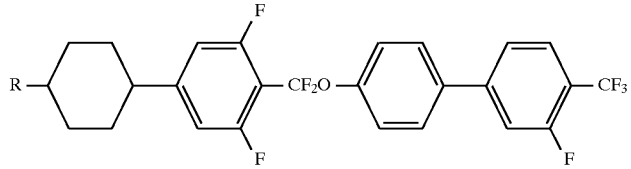
(501)
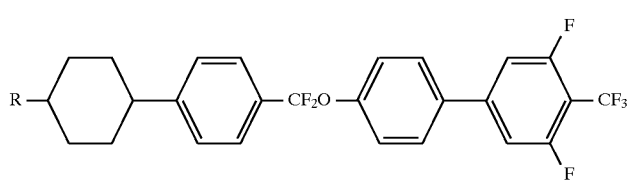
(502)
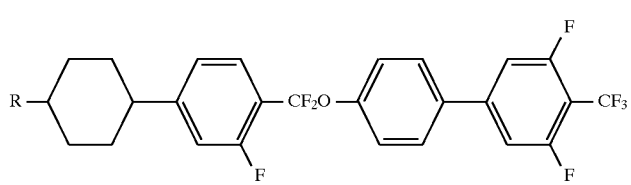
(503)

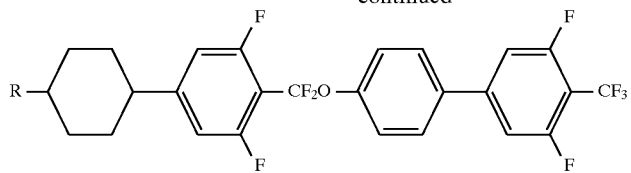 (504)
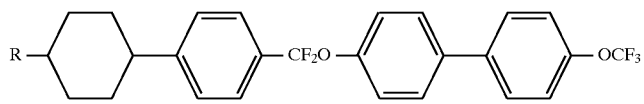 (505)
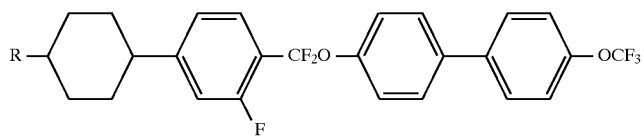 (506)
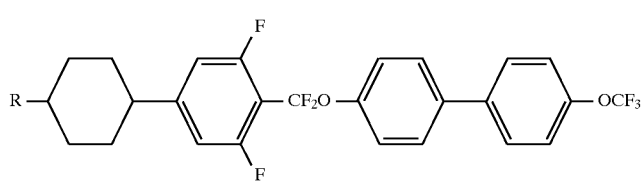 (507)
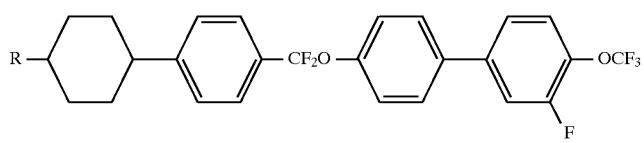 (508)
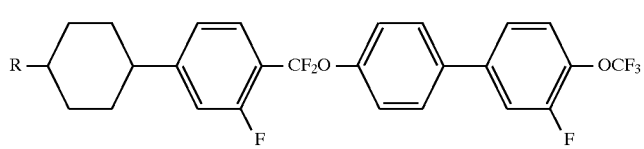 (509)
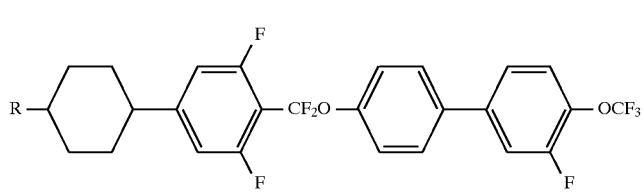 (510)
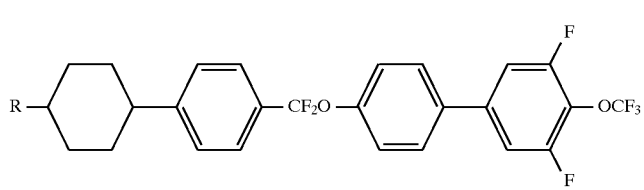 (511)
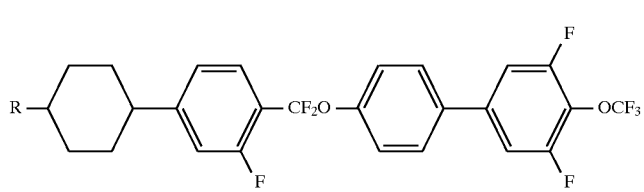 (512)
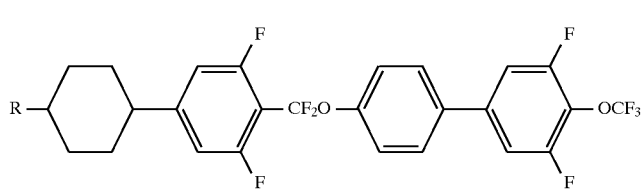 (513)

-continued
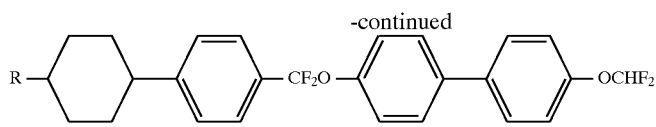 (514)
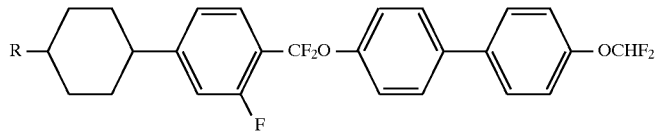 (515)
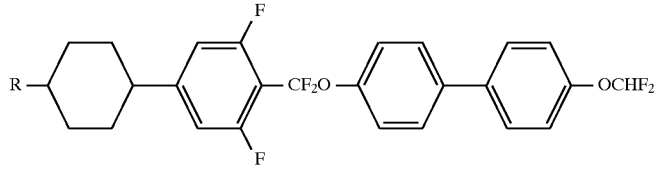 (516)
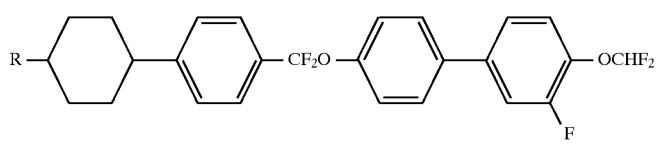 (517)
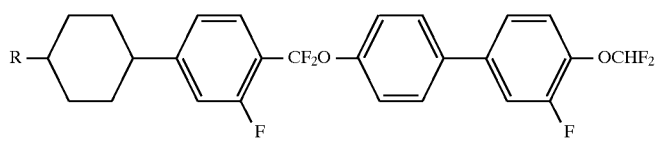 (518)
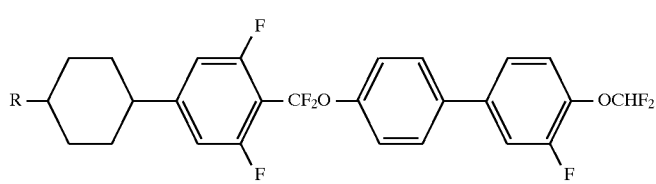 (519)
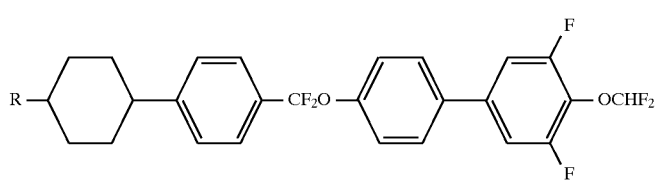 (520)
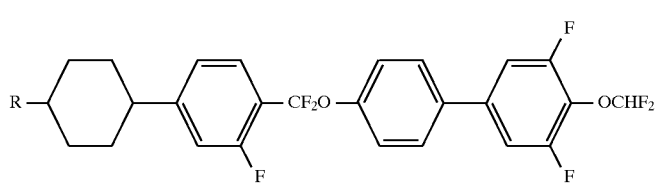 (521)
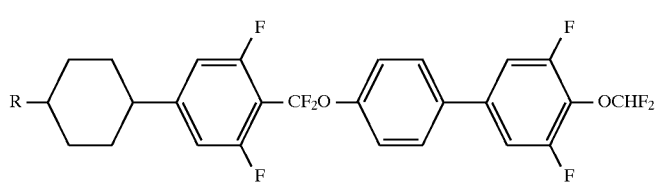 (522)
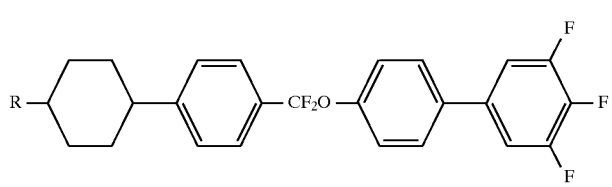 (523)

-continued
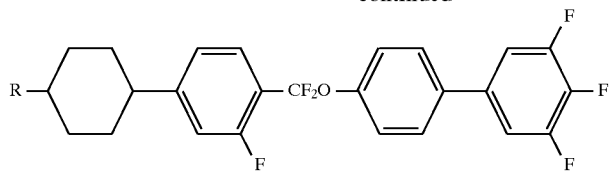
(524)
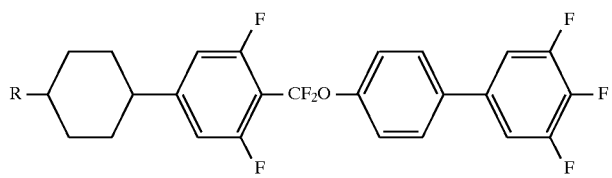
(525)
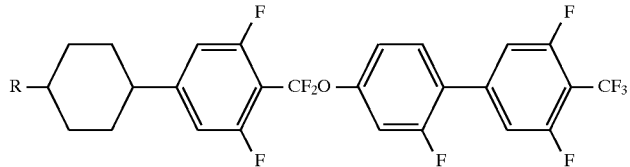
(526)
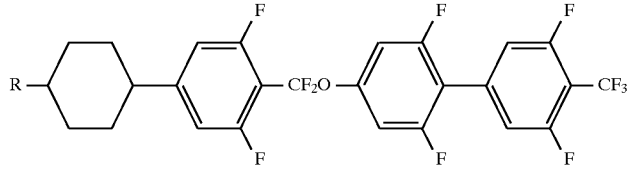
(527)
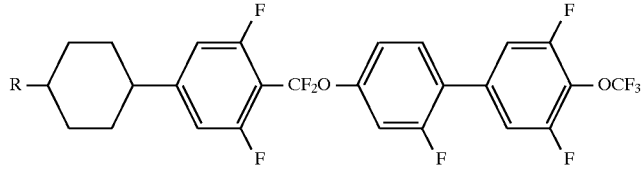
(528)
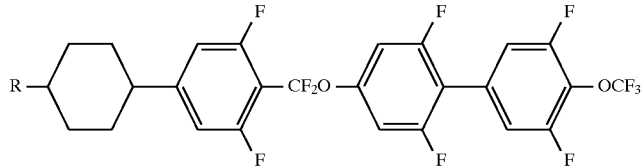
(529)
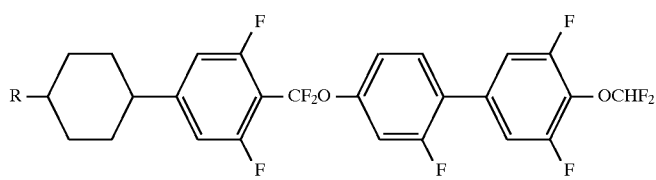
(530)
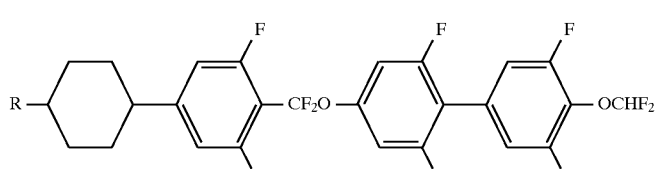
(531)
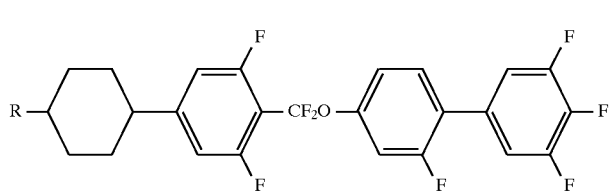
(532)

-continued
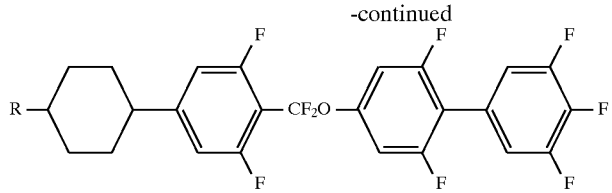 (533)
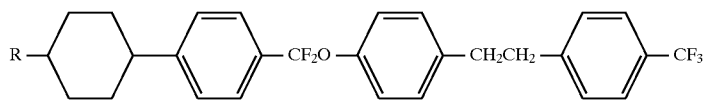 (534)
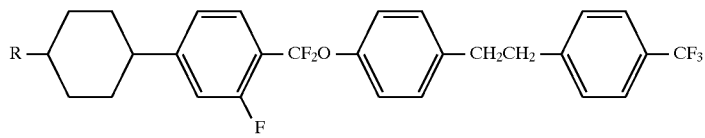 (535)
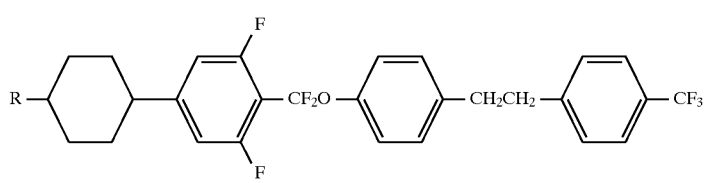 (536)
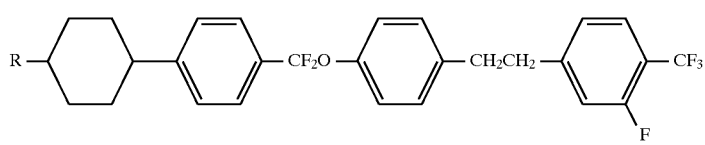 (537)
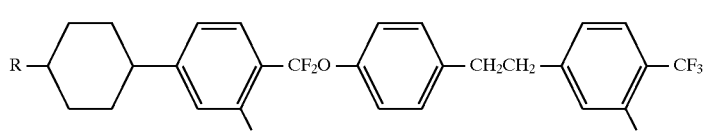 (538)
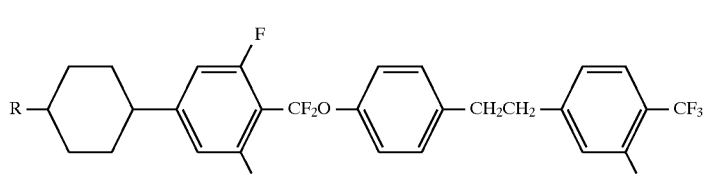 (539)
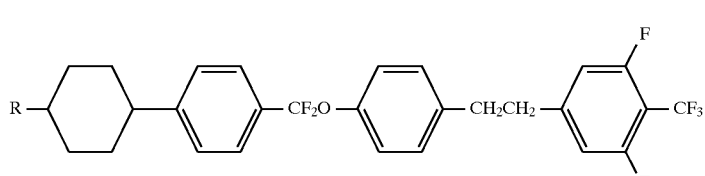 (540)
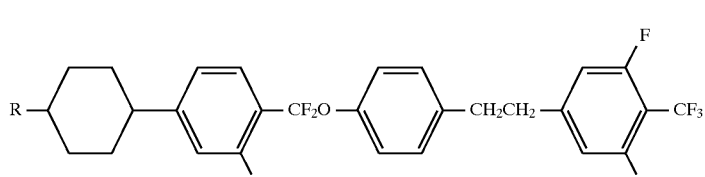 (541)
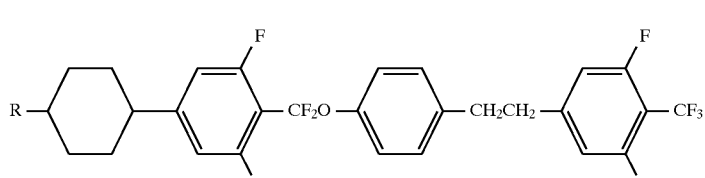 (542)

-continued
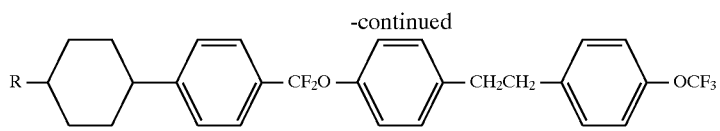 (543)
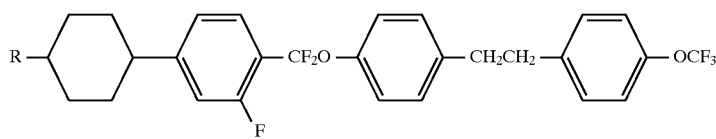 (544)
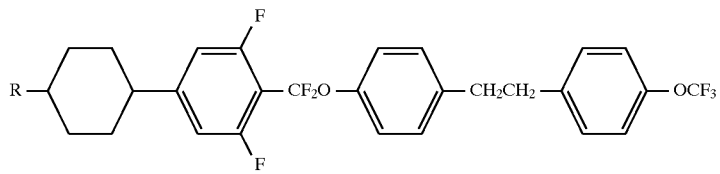 (544a)
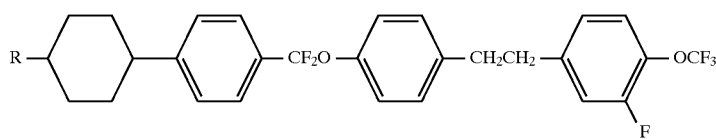 (545)
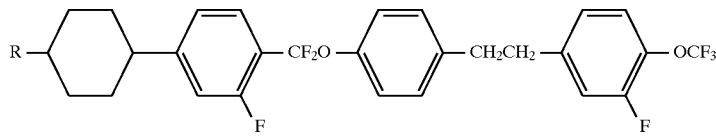 (546)
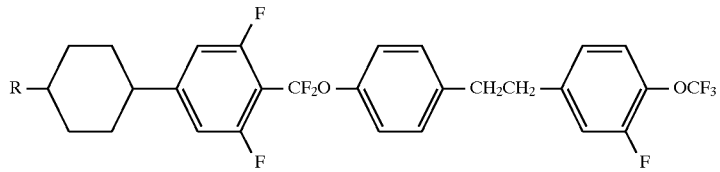 (547)
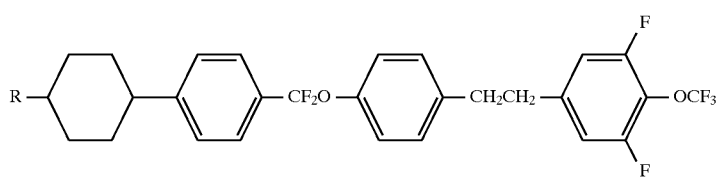 (548)
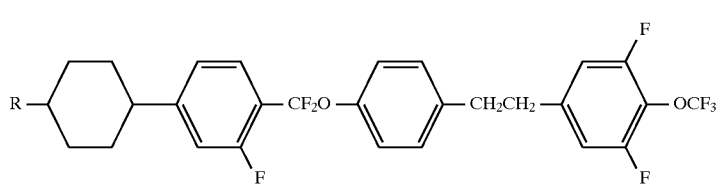 (549)
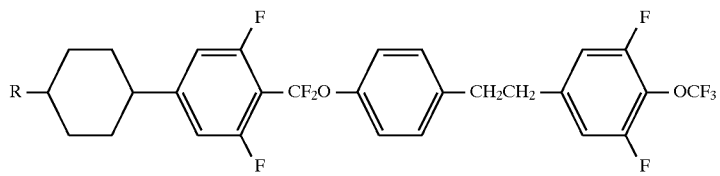 (550)
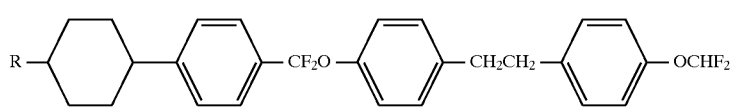 (551)

-continued
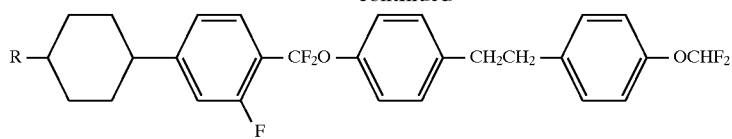 (552)
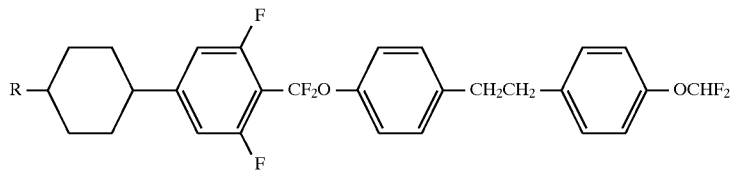 (553)
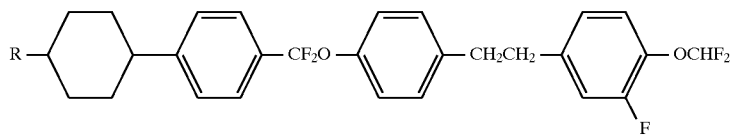 (554)
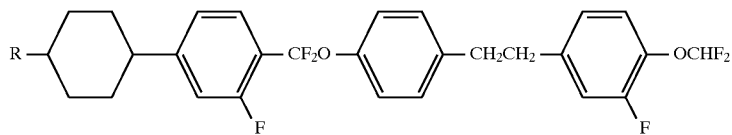 (555)
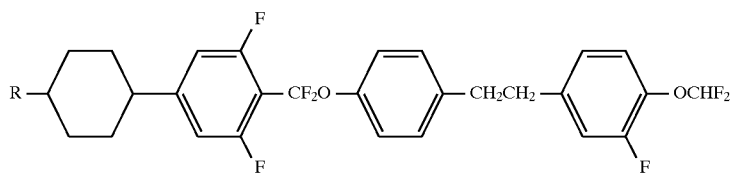 (556)
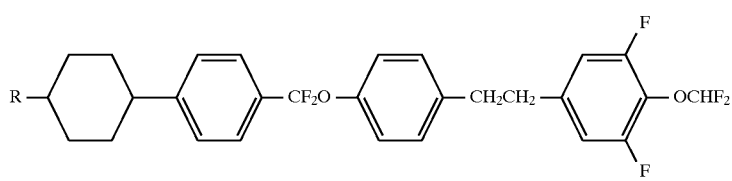 (557)
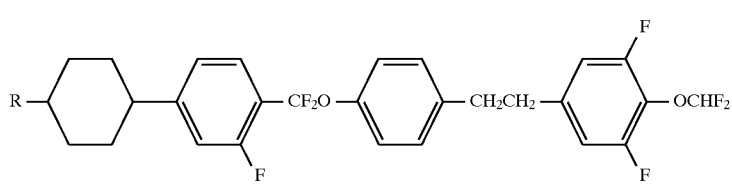 (558)
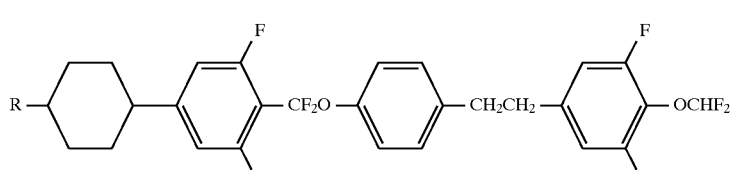 (559)
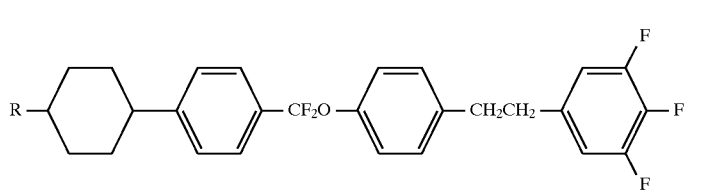 (560)

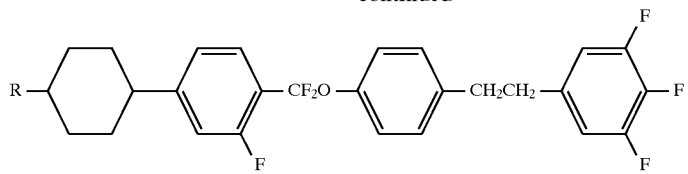
(561)
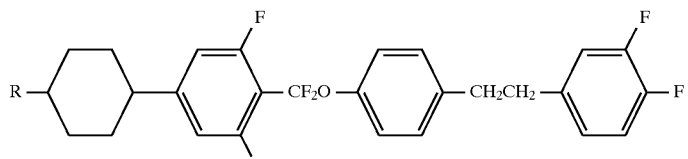
(562)
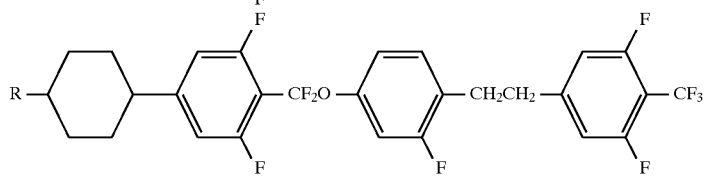
(563)
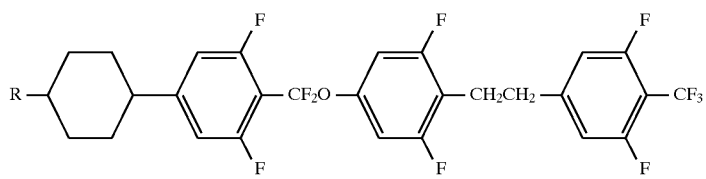
(564)
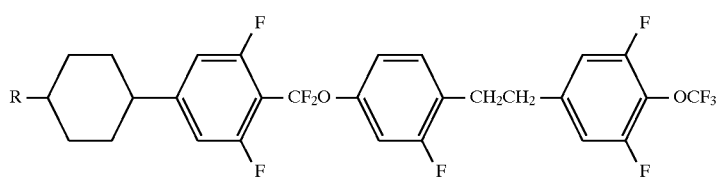
(565)
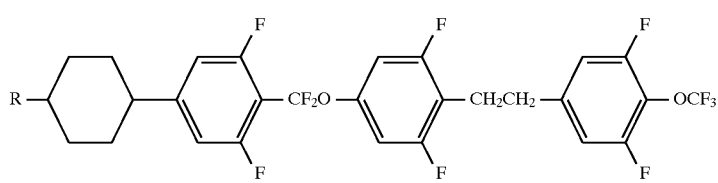
(566)
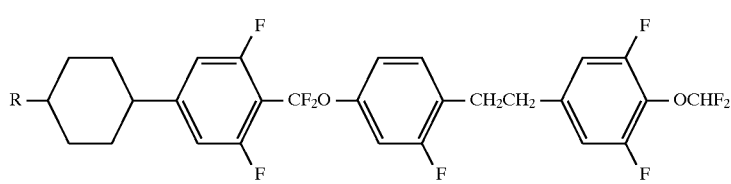
(567)
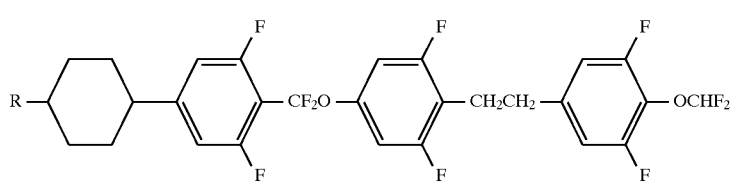
(568)
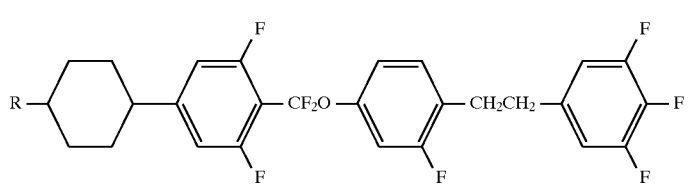
(569)

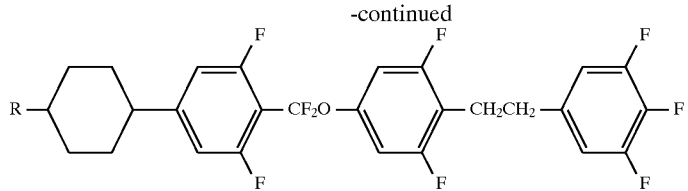 (570)
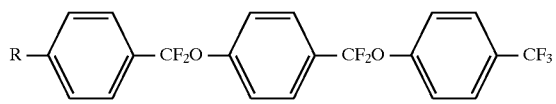 (571)
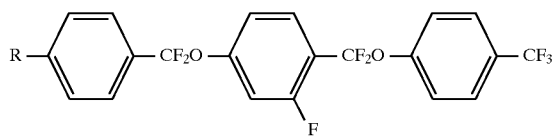 (572)
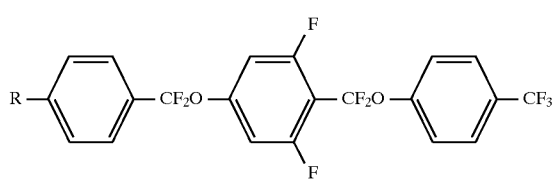 (573)
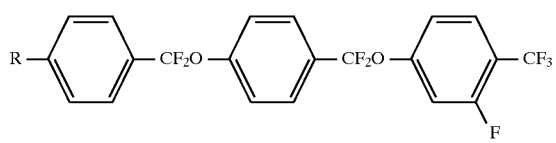 (574)
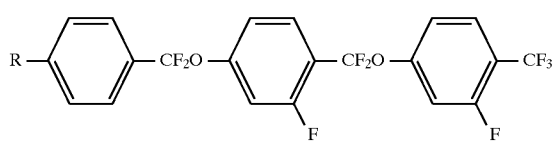 (575)
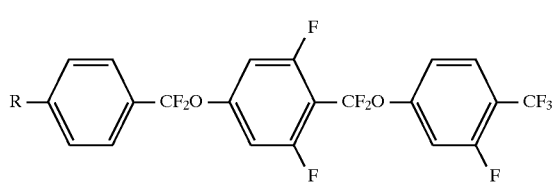 (576)
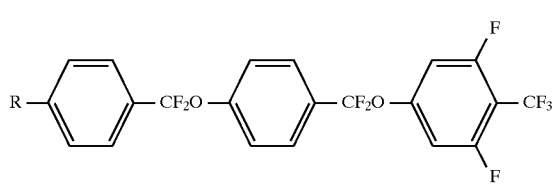 (577)
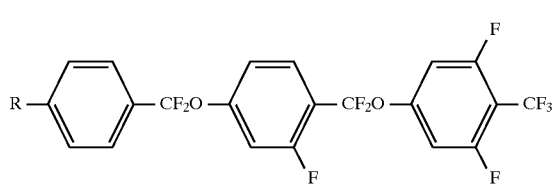 (578)
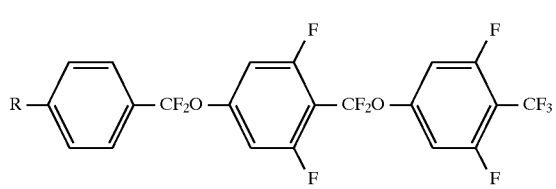 (579)

-continued
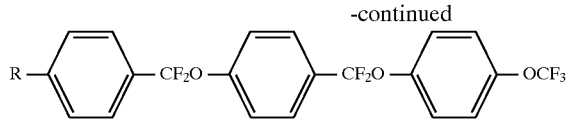 (580)
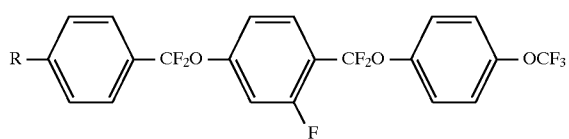 (581)
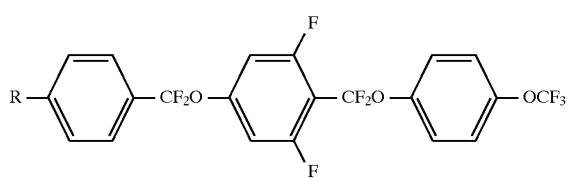 (582)
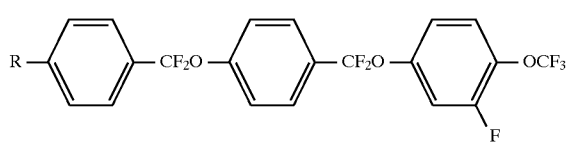 (583)
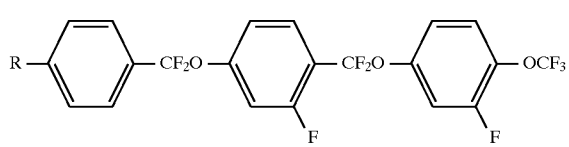 (584)
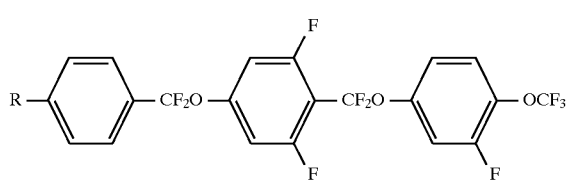 (585)
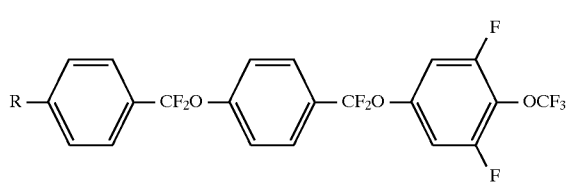 (586)
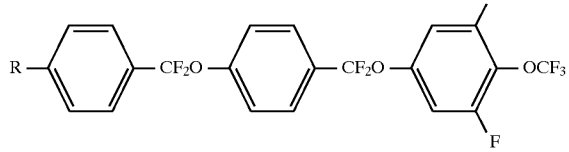 (587)
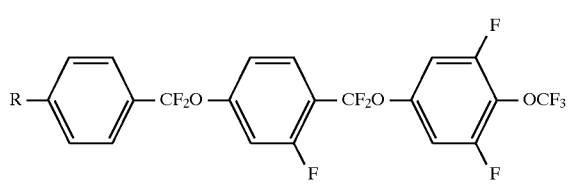 (588)
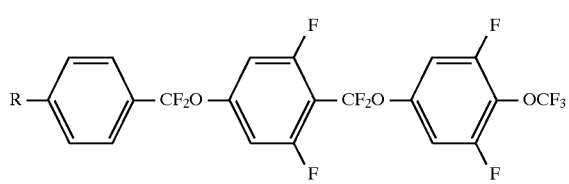 (589)

-continued
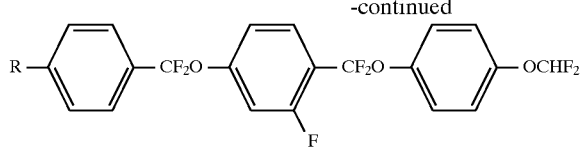 (590)
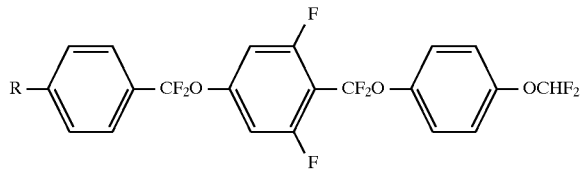 (591)
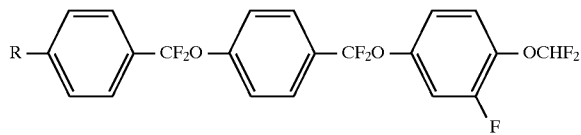 (592)
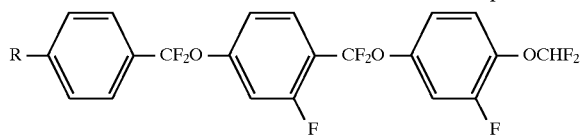 (593)
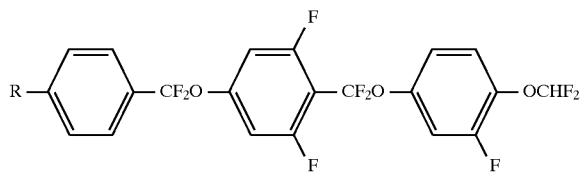 (594)
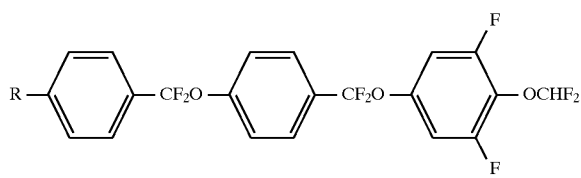 (595)
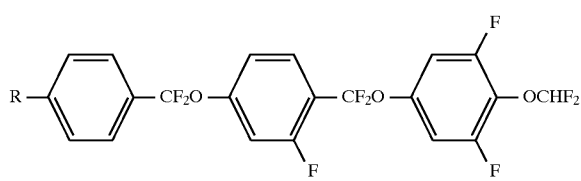 (596)
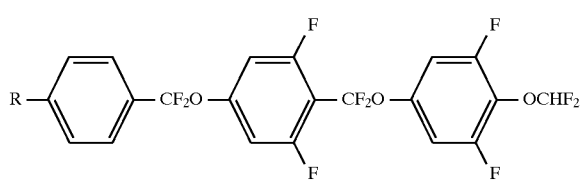 (597)
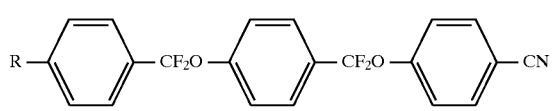 (598)
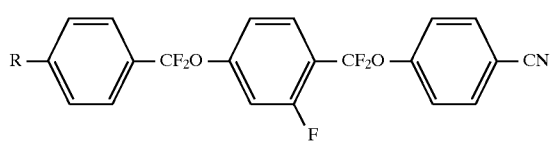 (599)

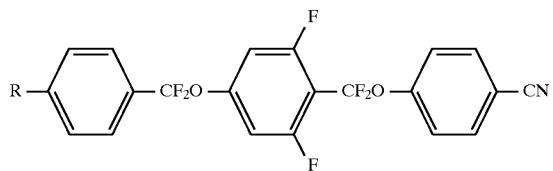
(600)
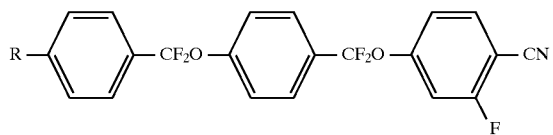
(601)
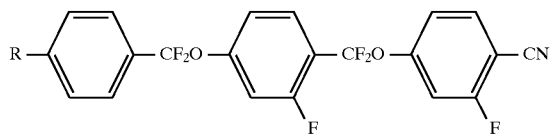
(602)
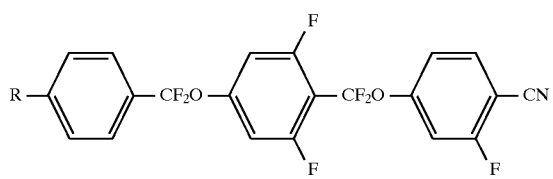
(603)
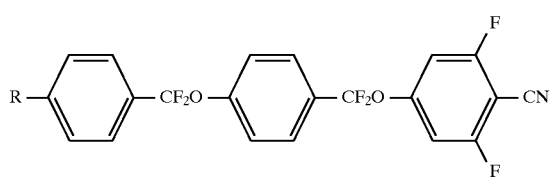
(604)
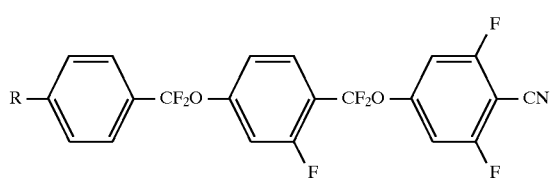
(605)
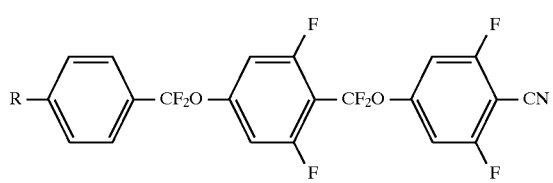
(606)
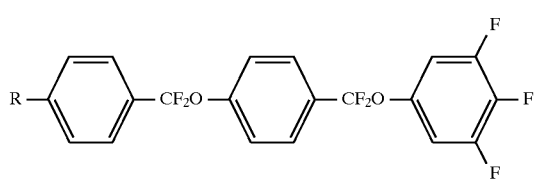
(607)
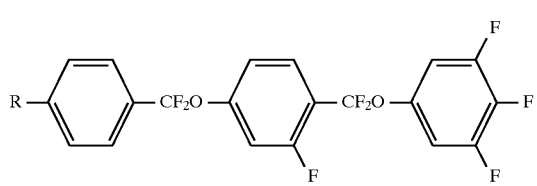
(608)

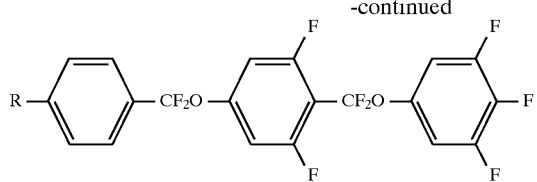
(609)
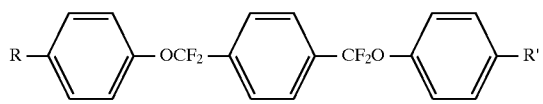
(610)
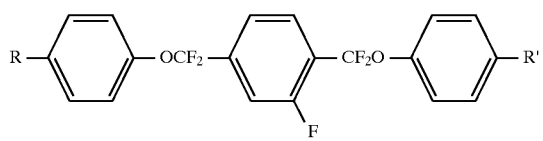
(611)
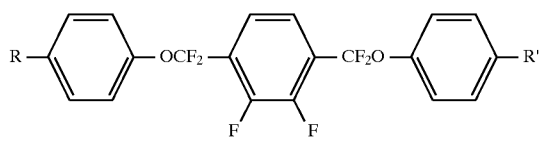
(612)
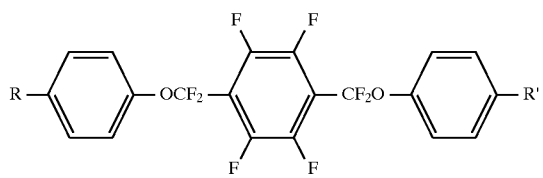
(613)
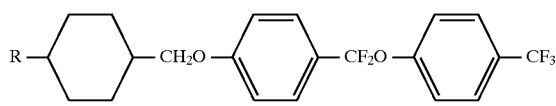
(614)
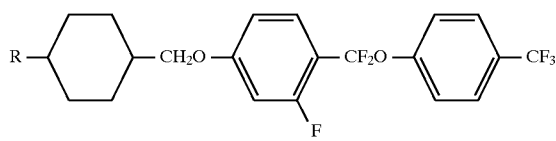
(615)
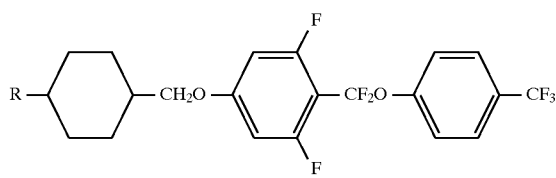
(616)
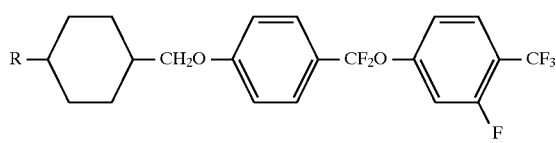
(617)
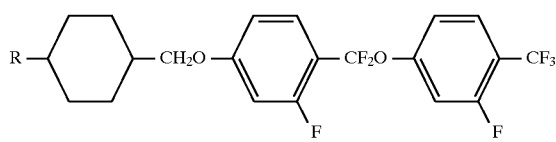
(618)
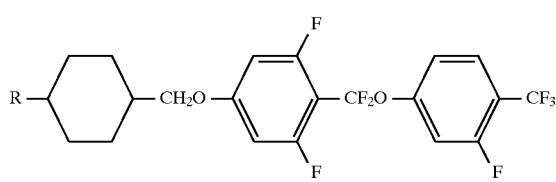
(619)

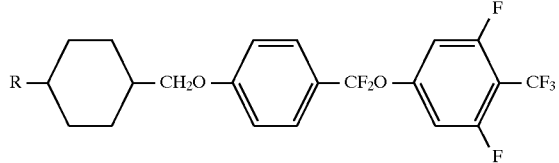
(620)
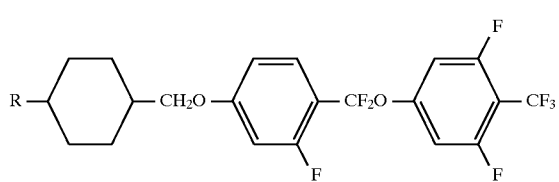
(621)
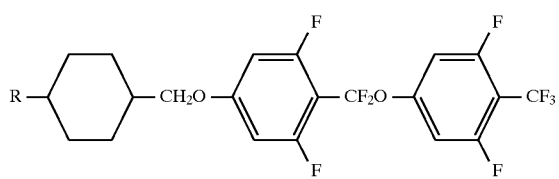
(622)
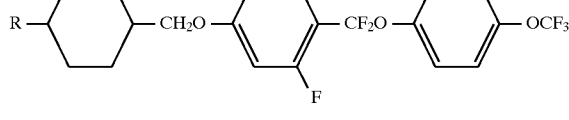
(623)
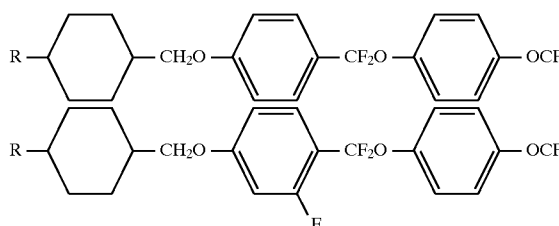
(624)
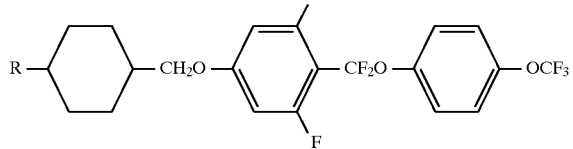
(625)
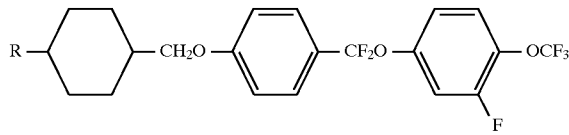
(626)
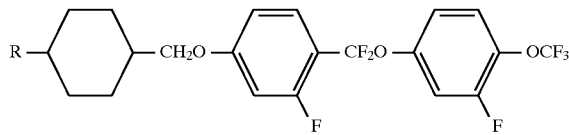
(627)
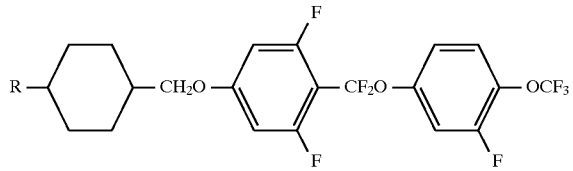
(628)
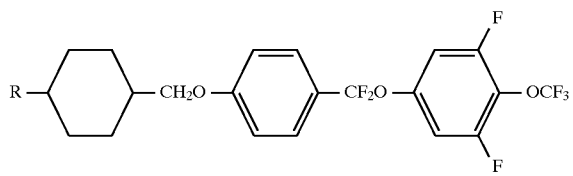
(629)

-continued
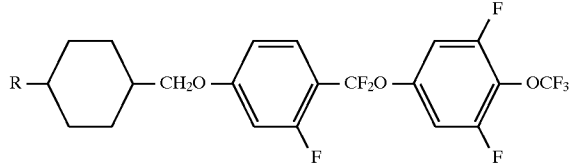
(630)
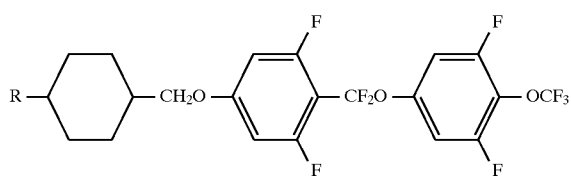
(631)
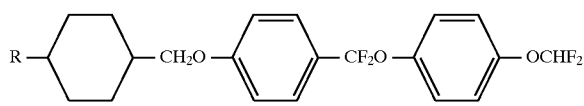
(632)
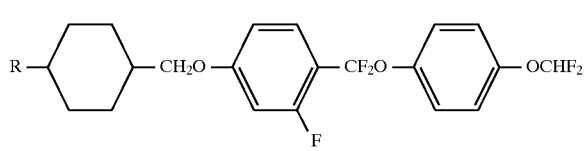
(633)
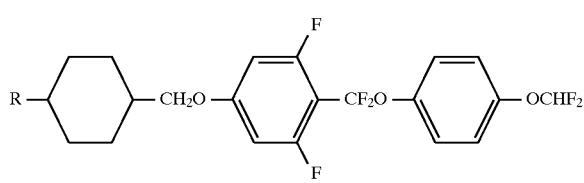
(634)
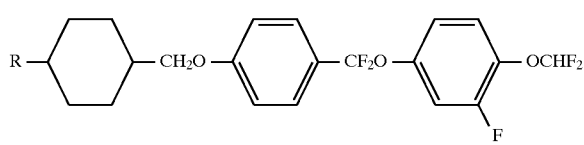
(635)
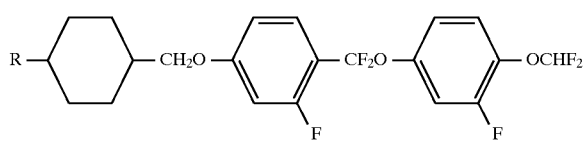
(636)
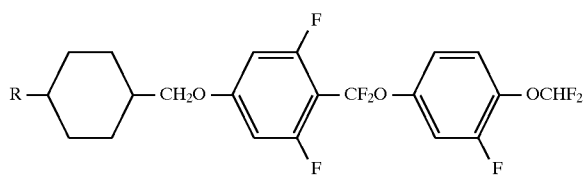
(637)
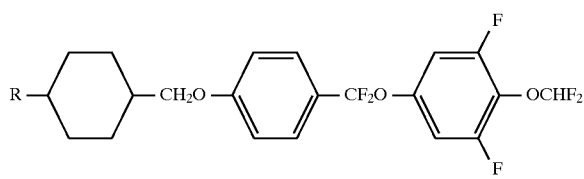
(638)
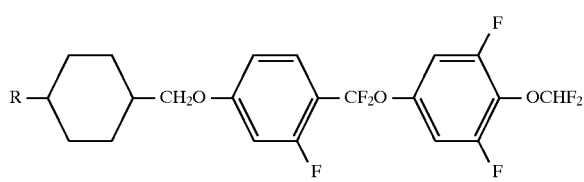
(639)

-continued
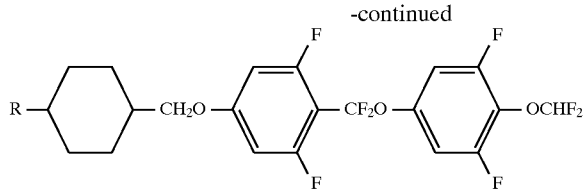
(640)
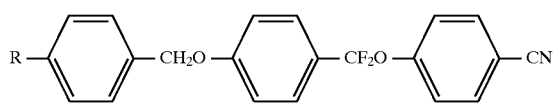
(641)
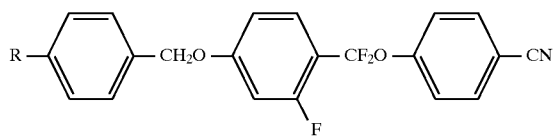
(642)
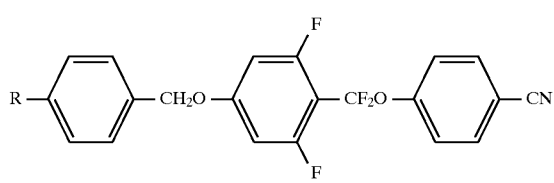
(643)
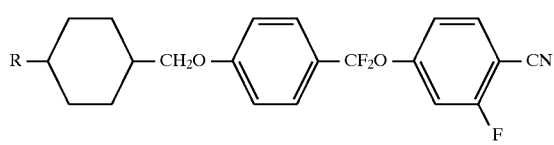
(644)
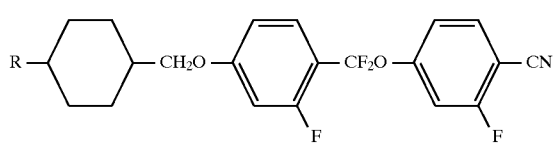
(645)
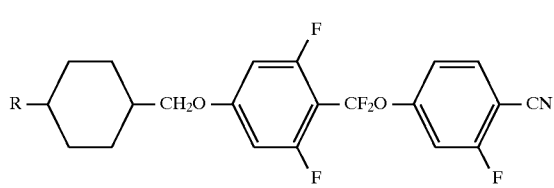
(646)
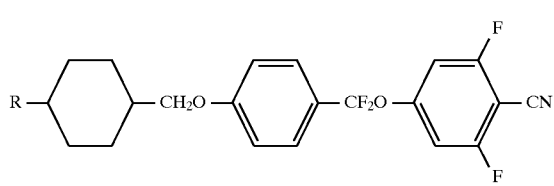
(647)
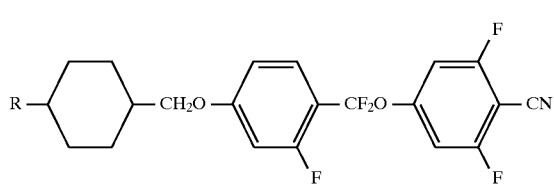
(648)
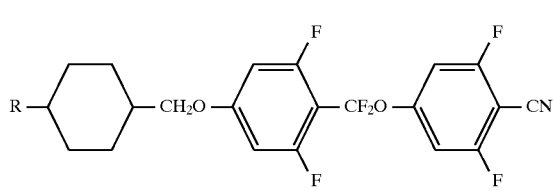
(649)

-continued
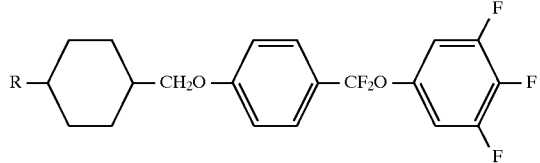
(650)
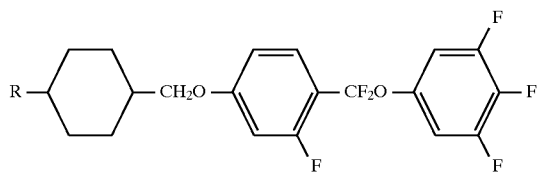
(651)
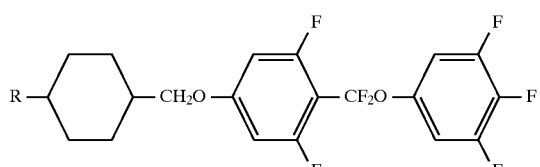
(652)
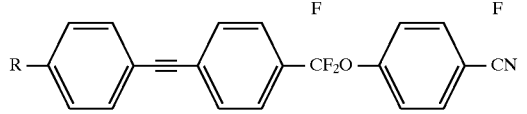
(653)
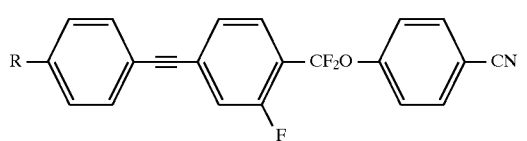
(654)
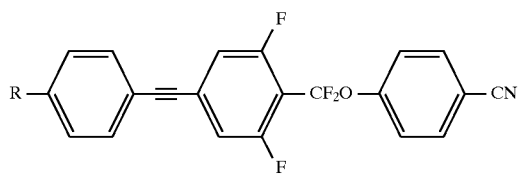
(655)
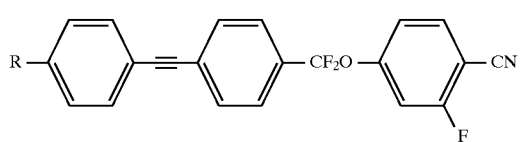
(656)
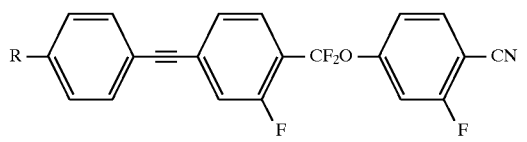
(657)
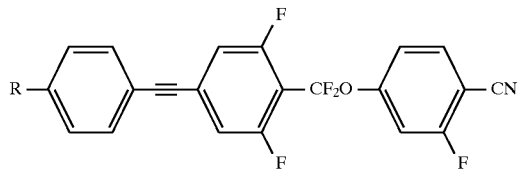
(658)
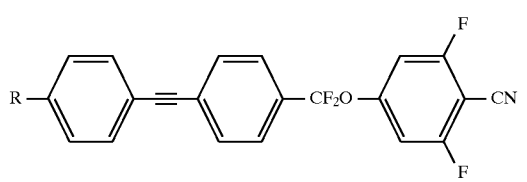
(659)

-continued

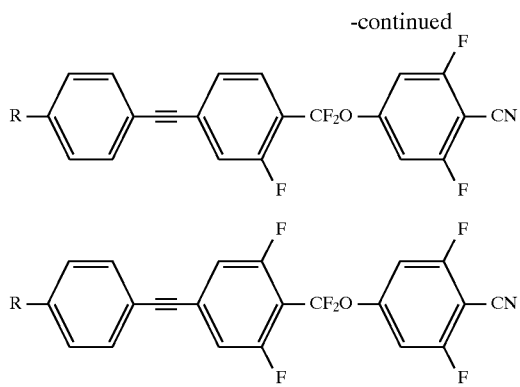

(660)

(661)

wherein R and R' represent a linear or branched alkyl group, alkenyl group, or alkoxy group having 1 to 10 carbon atoms, respectively.

These compounds (1) to (661) exhibit a large dielectric anisotropy and have a low viscosity. Particularly, the compounds having F, $CF_3$, or CN group as substituent at the terminal of the molecule exhibit extremely large dielectric anisotropy, while the compounds having $OCF_3$ or $OCHF_2$ group have a remarkably low viscosity. Further, the compounds having fluorine atom at a side position relative to the major axis of the compounds exhibit larger dielectric anisotropy and have a characteristic that they have an excellent miscibility. Compounds (571) to (613) have two —$CF_2O$— groups in the molecule and have a lower viscosity compared with compounds (67) to (103) and (143) to (320). Particularly, compounds (610) to (613) have a characteristic that they are remarkably excellent as viscosity reducing agent.

[Method for preparing the compounds]

Difluorooxymethane derivatives expressed by the general formula (I), which are the compounds of the present invention, can be preferably prepared by the steps as shown below:

As shown in equation 1 below, benzonitrile expressed by general formula (A) and used as raw material for the preparation is hydrolyzed in an alcohol solvent such as ethyl alcohol, ethylene glycol, and diethylene glycol by using, as catalyst, a base such as sodium hydroxide and potassium hydroxide, or a mineral acid such as hydrochloric acid and sulfuric acid, to lead to a carboxylic acid derivative (B). Then, the carboxylic acid derivative (B) is reacted with a phenol derivative expressed by general formula (C) according to a general esterification method, for instance, by using, as acid catalyst, a mineral acid such as hydrochloric acid and sulfuric acid, an organic acid such as p-toluene sulfonic acid or an ion exchange resin such as Amberite, or by using N,N'-dicyclohexylcarbodiimide (DCC) as catalyst, to prepare an ester derivative expressed by general formula (D). Also, the derivative of (D) can be prepared by reacting (B) with thionyl chloride to convert into an acid chloride and then reacting with (C) in the presence of a base such as pyridine. Subsequently, the ester derivative (D) is reacted with Lawesson's reagent [2,4-bis(4-methoxyphenyl)-1,3-dithia-2,4-diphosphetane-2,4-disulfide] (Bull. Soc. Chim. Belg., 87, 223, 229, 299, 525 (1978); Synthesis, 941 (1979); Tetrahedron, 35, 2433 (1979); Tetrahedron, Lett., 21, 4061 (1980)) by using benzene or toluene as solvent at an optional temperature from room temperature to the boiling point of the solvent to lead to a thioester (thione type) derivative (E). Then, the thioester derivative (thione type) (E) is reacted with diethylaminosulfur trifluoride (DAST) (Synthesis, 787 (1973)) by using dichloromethane or chloroform as solvent at an optional temperature from room temperature to the boiling point of the solvent for conducting gem-fluorination to prepare an objective difluorooxymethane derivative.

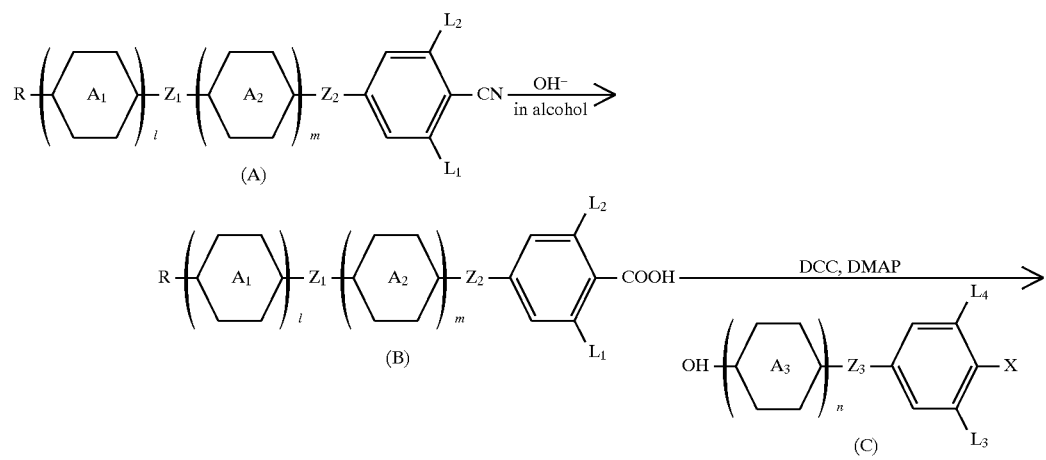

(Equation 1)

-continued

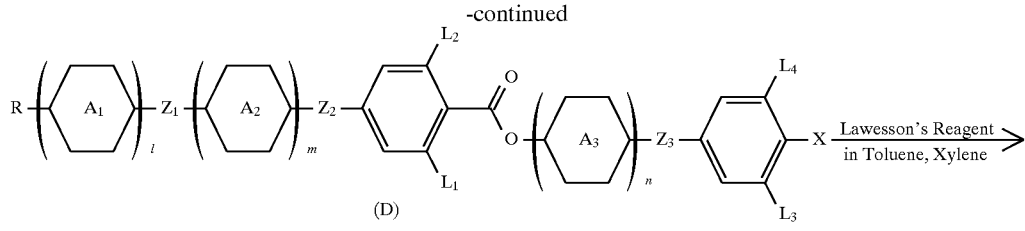

(D)

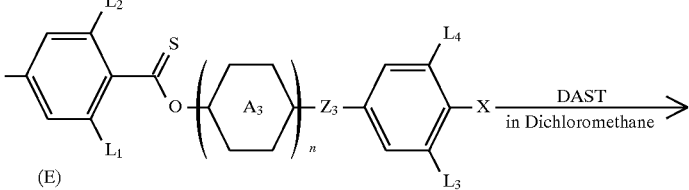

(E)

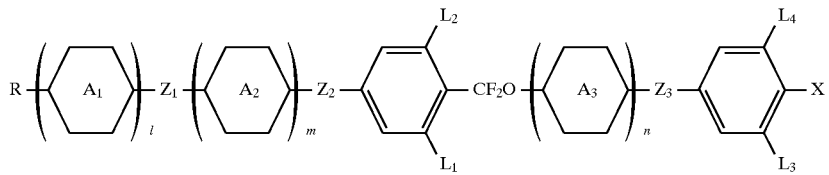

As another method, as shown in equation 2 below, a difluorooxymethane derivative can be prepared by first preparing Grignard reagent from a bromobenzene derivative (F), reacting with carbon disulfide to form a dithiocarboxylic acid derivative (G), converting it with thionyl chloride into thiocarboxylic acid chloride, reacting with a phenol derivative (C) to prepare a thioester (thione type) derivative (E), and then reacting with DAST in the same way as mentioned above.

reflux condition to convert into a thioester (thione type) derivative 3, and then reacted with DAST in dichloromethane to prepare compound (7). Besides, compounds (1) to (6) and (8) to (27) can be prepared by using a phenol having a different kind of substituent in place of 3,4,5-trifluorophenol, and further from several kinds of known benzoic acid derivatives according to the preparation procedures mentioned above.

(Equation 2)

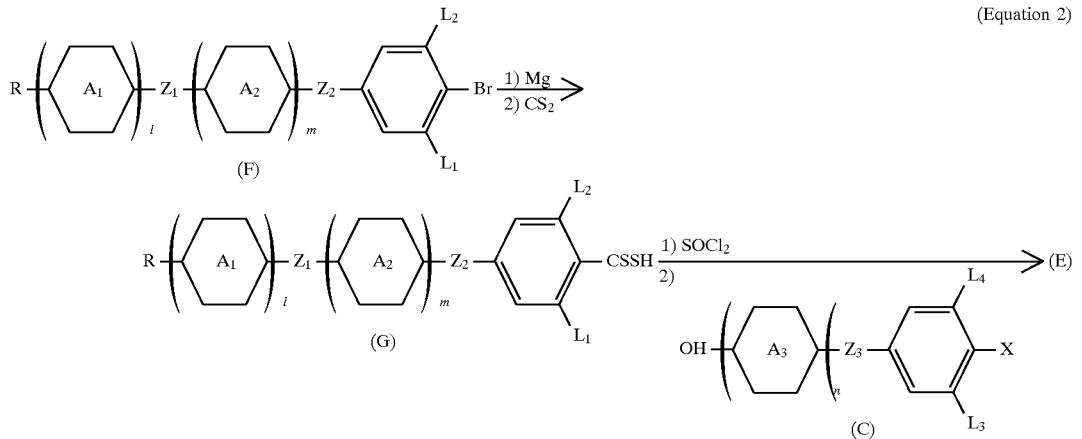

As shown in equation 3 below, for example, compound (7) among the compounds expressed by the general formula (1a) can be prepared by the method as follows:

Alkylbenzoic acid derivative 1 is subjected to an esterification with 3,4,5-trifluorophenol according to a general esterification method, for instance, by using, as acid catalyst, a mineral acid such as hydrochloric acid and sulfuric acid, an organic acid such as p-toluene sulfonic acid, or an ion exchange resin such as Amberite, or by using N,N'-dicyclohexylcarbodiimide (DCC) as catalyst to prepare 3,4,5-trifluorobenzoate derivative 2. Subsequently, the derivative 2 is reacted with Lawesson's reagent under toluene (Equation 3)

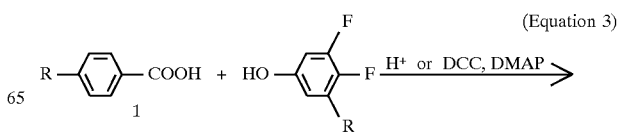

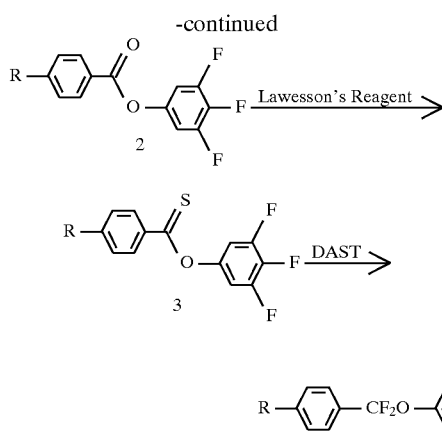
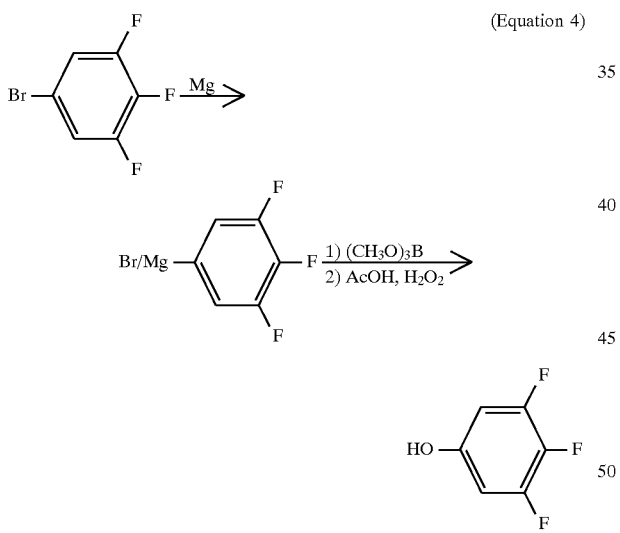

In this connection, 3,4,5-trifluorophenol which is a raw material for the preparation can be prepared by using 3,4,5-trifluorobromobenzene as starting substance. That is, as shown in equation 4 below, it can be prepared by reacting Grignard reagent prepared from 3,4,5-trifluorobromobenzene with t-butyl hydroperoxide according to the method of S. O. Lawesson et al. (J. Am. Chem. Soc. 81, 4230 (1959)) or by treating Grignard reagent prepared from 3,4,5-trifluorobromobenzene with trialkyl borate according to the method of R. L. Kidwell et al. (Org. Synth., V, 918, (1973)) to convert into a boric acid ester and then subjecting to an oxidizing treatment with hydrogen peroxide solution. In the presence of acetic acid.

As shown in equation 5 below, compound (37) among the compounds expressed by the general formula (1b) can be prepared by hydrolyzing 2-fluoro-4-(trans-4-alkylcyclohexyl)benzonitrile 4 in ethylene glycol or diethylene glycol in the presence of sodium hydroxide to convert into a benzoic acid derivative 5, subjecting to an esterification with 3,4,5-trifluorophenol according to a general esterification method, for instance, by using, as acid catalyst, a mineral acid such as hydrochloric acid and sulfuric acid, an organic acid such as p-toluene sulfonic acid, or an ion exchange resin such as Amberite, or by using N,N'-dicyclohexylcarbodiimide (DCC) as catalyst to prepare 4-trifluorobenzoate derivative 6. Subsequently, the derivative 6 is reacted with Lawesson's reagent under toluene reflux condition to convert into a thioester (thione type) derivative 7, and then reacting with DAST in dichloromethane to prepare compound (37). Besides, compounds (28) to (36) and (38) to (181) can be prepared by using phenol having a different kind of substituent in place of 3,4,5-trifluorophenol, and from several kinds of known benzoic acid derivatives according to the preparation procedures mentioned above.

As shown in equation 6 below, compound (242) among the compounds expressed by the general formula (1c) can be prepared by the following method:

That is, 4-iodobenzene is subjected to a coupling reaction with Grignard reagent prepared from 3,4,5-trifluorobromobenzene in the presence of a novel metal catalyst such as palladium chloride to convert into a biphenyl derivative 8 and then reacted with bromine in the presence of metal powder such as iron powder to prepare a bromobiphenyl derivative 9. Subsequently, Grignard reagent prepared from the derivative 9 is reacted with trimethyl borate according to the report by R. L. Kidwell et al. (Org. Synth., V, 918 (1973)), and then oxidized with hydrogen peroxide in the presence of acetic acid to prepare a phenyl phenol derivative 10. Compound (242) can be prepared by treating the derivative 10 in the same way as in the case of the preparation of compound (7). Further, other compounds (182) to (241) and (243) to (320) expressed by the general formula (1c) can be prepared from phenyl phenol derivatives prepared by using bromobenzene derivatives having a different kind of substituent in place of 3,4,5-trifulorobromobenzene.

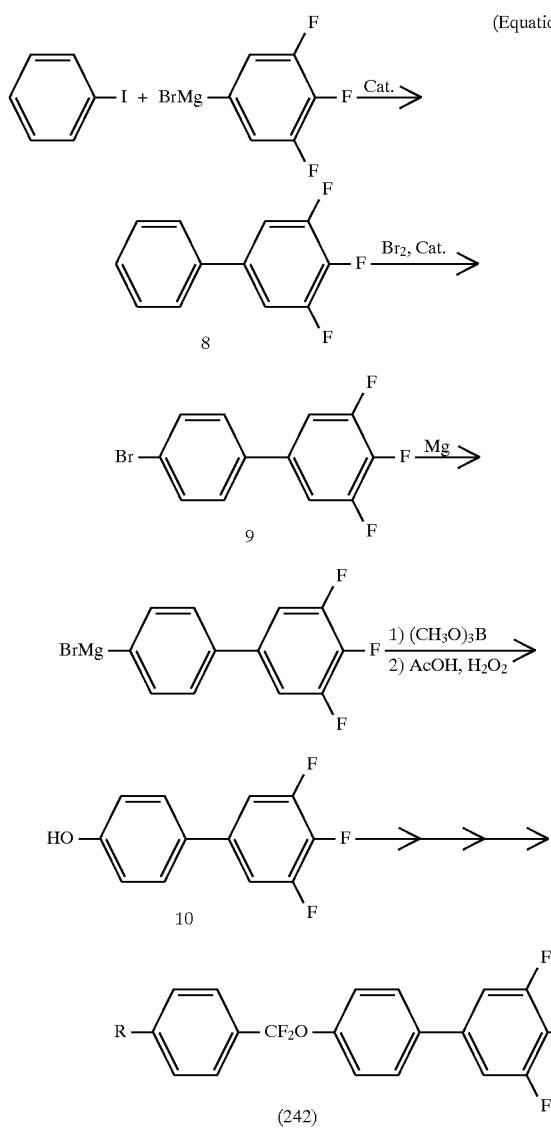

(Equation 6)

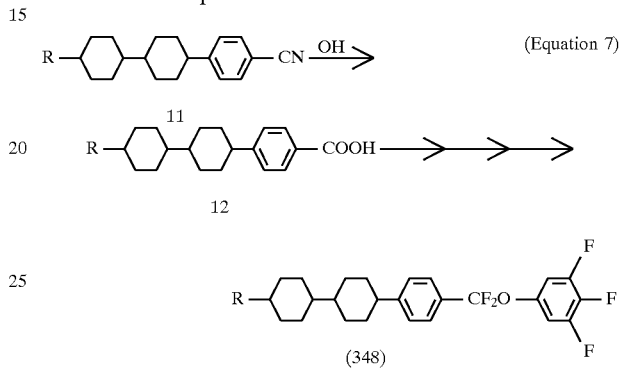

As shown in equation 7 below, for example, compound (348) among the compounds expressed by the general formula (1d) can be prepared in the same method as mentioned above by using, as raw material for the preparation, 4-[trans-4-(trans-alkylcyclohexyl) cyclohexyl]benzoic acid 12 obtained by hydrolyzing 4-[trans-4-(trans-alkylcyclohexyl)cyclohexyl]benzonitrile 11 according to a common method. Further, other compounds (321) to (347) and (349) to (495) expressed by the general formula (1d) can also be prepared by using a known carboxylic acid derivative and phenol derivative, and by selecting the combination of the reaction procedures mentioned above with other known reaction procedures.

(Equation 7)

As shown in equation 8 below, for example, compound (524) among the compounds expressed by the general formula (1e) can be prepared in the same procedures as mentioned above by using, as raw material for the preparation, 2-fluoro-4-(trans-4-alkylcyclo hexyl)benzoic acid 14 which is obtained by hydrolyzing 2-fluoro-4-(trans-4-alkylcyclohexyl)benzonitrile 13, and by using a phenylphenol derivative prepared in the same method as in the case of (1c). Further, other compounds (496) to (523) and (525) to (570) can also be prepared by using a known carboxylic acid derivative and phenol derivative and by selecting the combination of the reaction procedures mentioned above with other known reaction procedures.

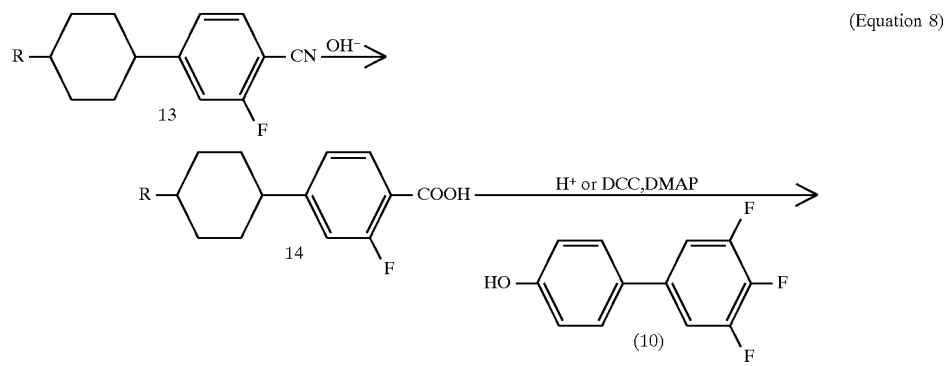

(Equation 8)

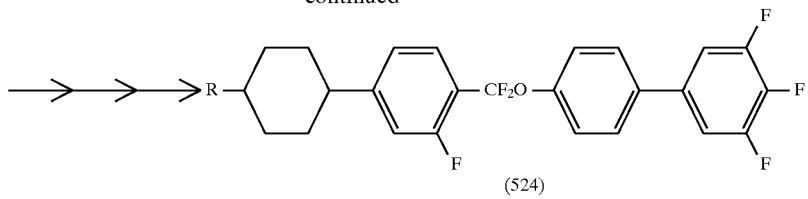

(524)

As shown in equation 9 below, for example, compound (650) can be prepared in the same method as in the case of (1b) by using, as raw material for the preparation, a carboxylic acid derivative 16 obtained by hydrolyzing (4-alkylcyclohexyl)(4-cyanophenyloxy)methane 15 according to a common method. Further, compounds (614) to (649), (651), and (652) can be prepared by using a phenol derivative having a different kind of substituent in place of 3,4,5-trifluorophenol and additionally using a different kind of fluorine substituted (4-alkylcyclo-hexyl)(4-cyanophenyloxy)methane derivative.

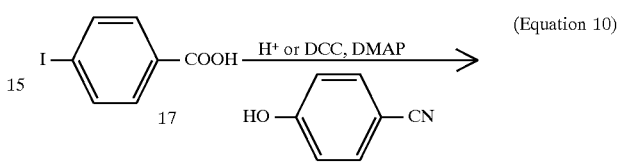

(Equation 10)

(Equation 9)

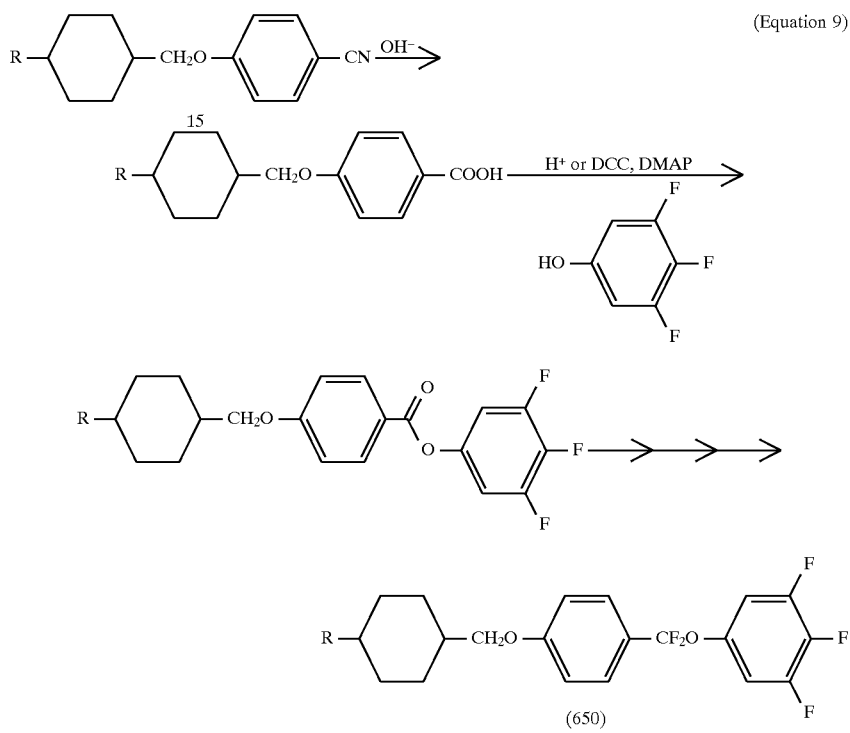

(650)

As shown in equation 10 below, for example, compound (653) can be prepared by preparing iodobenzenederivative 19 from 4-iodobenzoic acid 17 and cyanophenol in the same method as in the case of (1a), and further reacting 19 with 4-alkylphenyl acetylene in the presence of a novel metal catalyst such as platinum and palladium. Besides, compounds (654) to (661) can be prepared by using a phenol derivative having a different kind of substituent in place of 4-cyanophenol and using a different kind of known benzoic acid derivative.

-continued

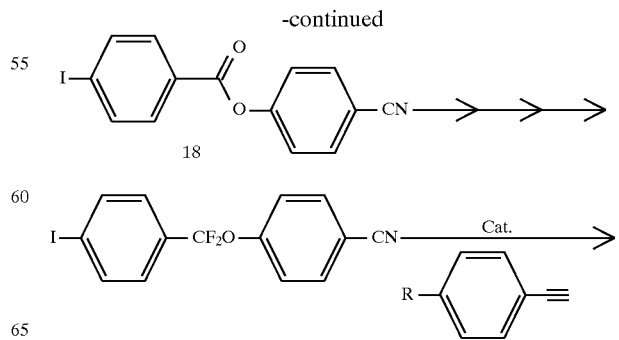

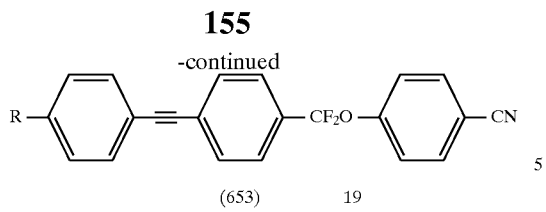

(653)

Next, the liquid crystal compositions of the present invention are explained. In the following explanation on liquid crystal compositions, difluorooxymethane derivatives of the present invention expressed by the general formula (I) are referred to as A group.

Liquid crystal compositions of the present invention may be composed only two or more compounds selected from A group. Also, the compositions may contain, as a first component, one or more compounds of A group and contain, as a second component, one or more other compounds. When the compositions contain the second component, the compound of A group is preferably contained in a ratio of 0.1 to 99% by weight.

As the second component of the liquid crystal compositions of the present invention, the compounds expressed by the general formula (II), (III), or (IV) (hereinafter, these compounds are referred to as B group) may be used. As the compounds of B group, the followings (II-1 to IX-14) can be mentioned as preferable ones:

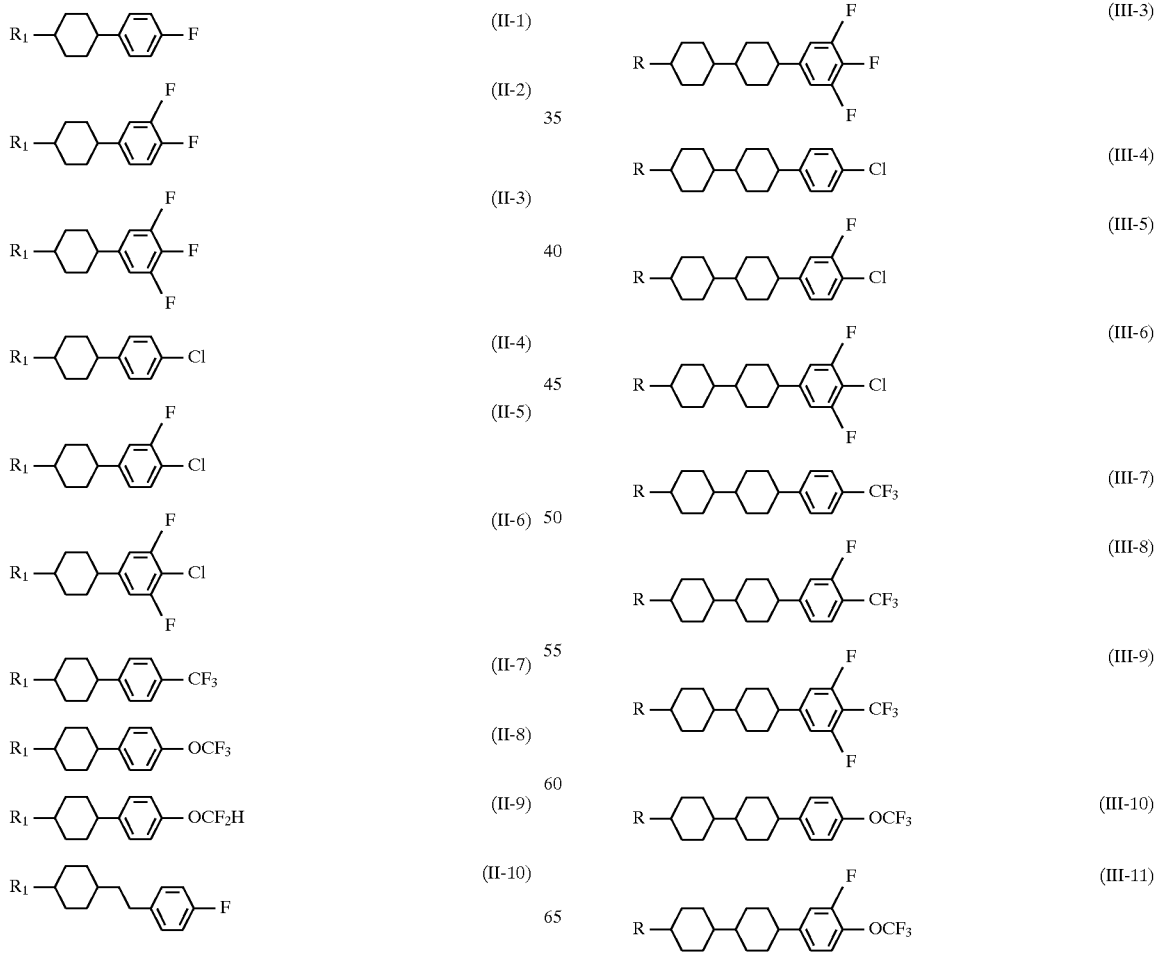

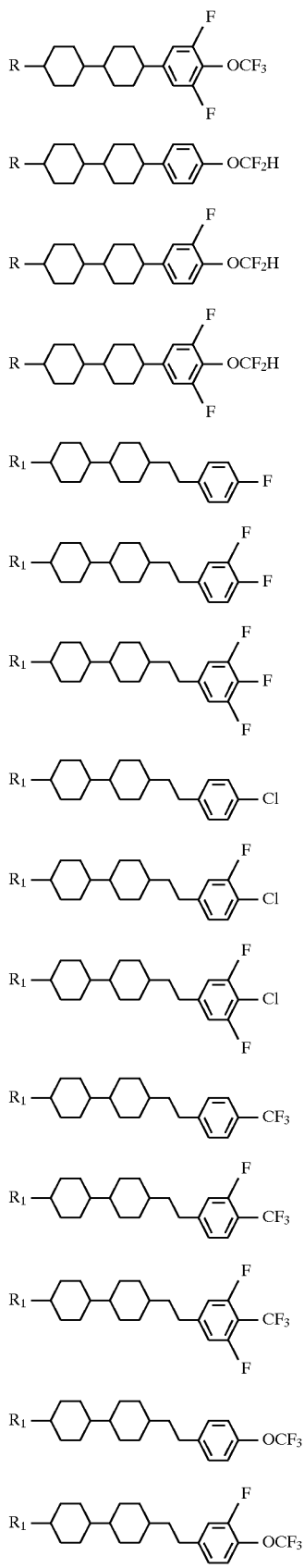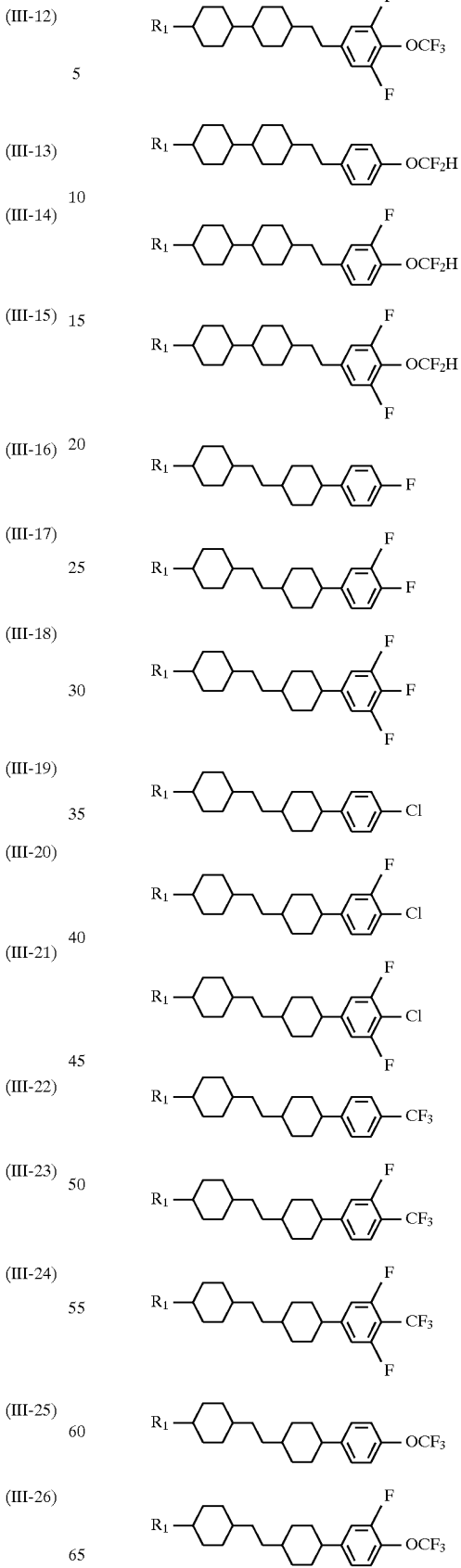

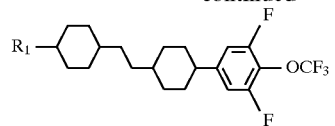 (III-42)
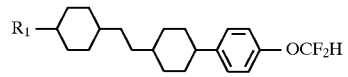 (III-43)
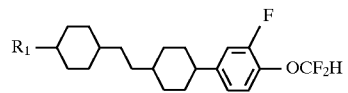 (III-44)
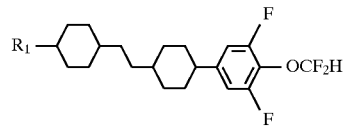 (III-45)
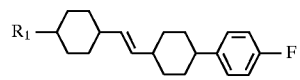 (III-46)
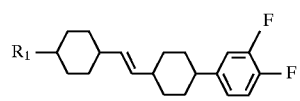 (III-47)
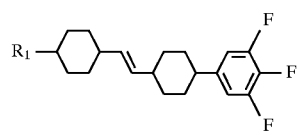 (III-48)
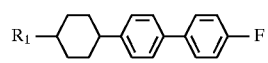 (IV-1)
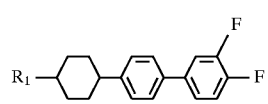 (IV-2)
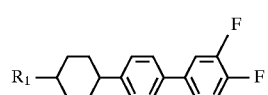 (IV-3)
 (IV-4)
 (IV-5)
 (IV-6)
 (IV-7)
 (IV-8)
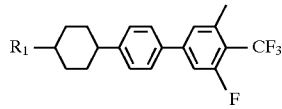 (IV-9)
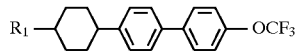 (IV-10)
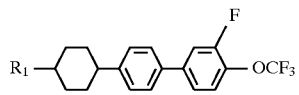 (IV-11)
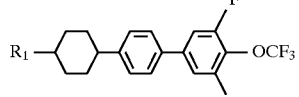 (IV-12)
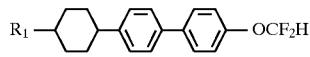 (IV-13)
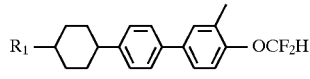 (IV-14)
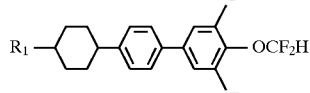 (IV-15)
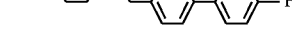 (IV-16)
 (IV-17)
 (IV-18)
 (IV-19)
 (IV-20)
 (IV-21)
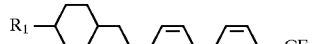 (IV-22)
 (IV-23)

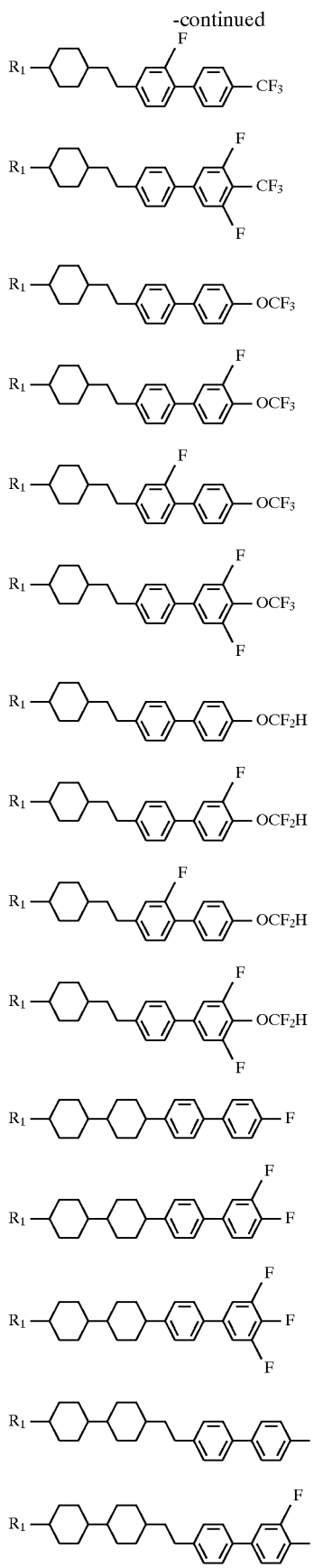

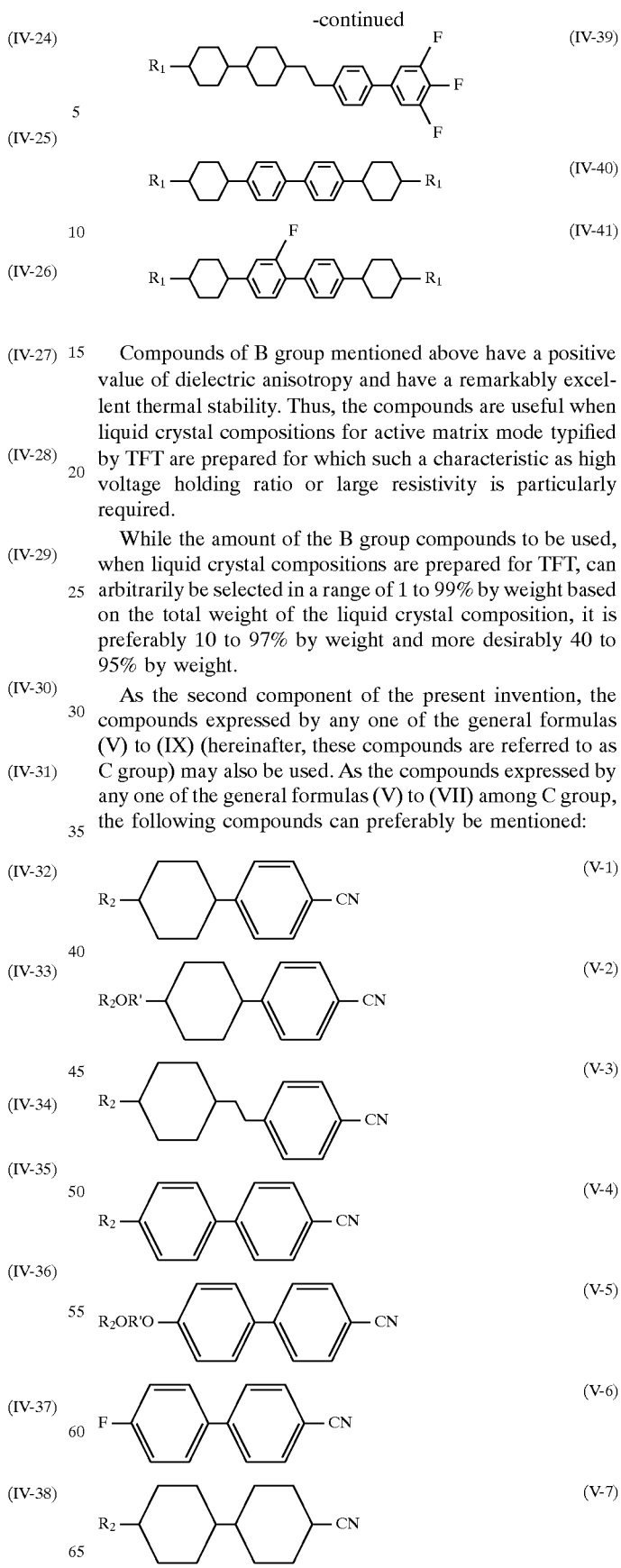

Compounds of B group mentioned above have a positive value of dielectric anisotropy and have a remarkably excellent thermal stability. Thus, the compounds are useful when liquid crystal compositions for active matrix mode typified by TFT are prepared for which such a characteristic as high voltage holding ratio or large resistivity is particularly required.

While the amount of the B group compounds to be used, when liquid crystal compositions are prepared for TFT, can arbitrarily be selected in a range of 1 to 99% by weight based on the total weight of the liquid crystal composition, it is preferably 10 to 97% by weight and more desirably 40 to 95% by weight.

As the second component of the present invention, the compounds expressed by any one of the general formulas (V) to (IX) (hereinafter, these compounds are referred to as C group) may also be used. As the compounds expressed by any one of the general formulas (V) to (VII) among C group, the following compounds can preferably be mentioned:

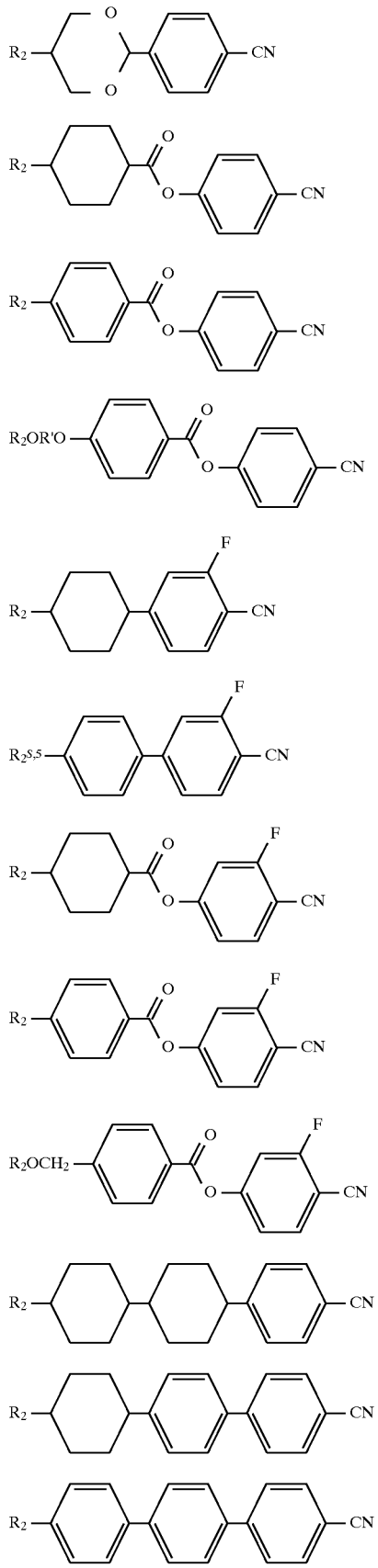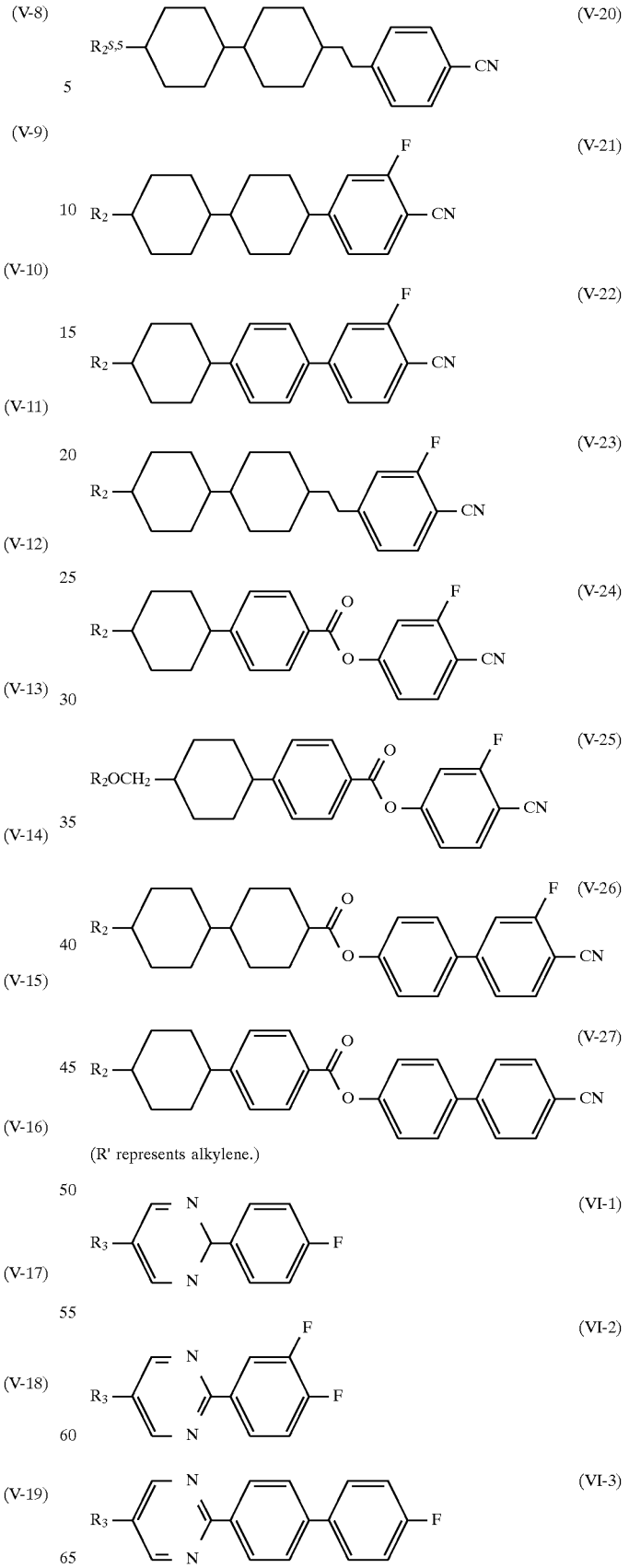
(R' represents alkylene.)

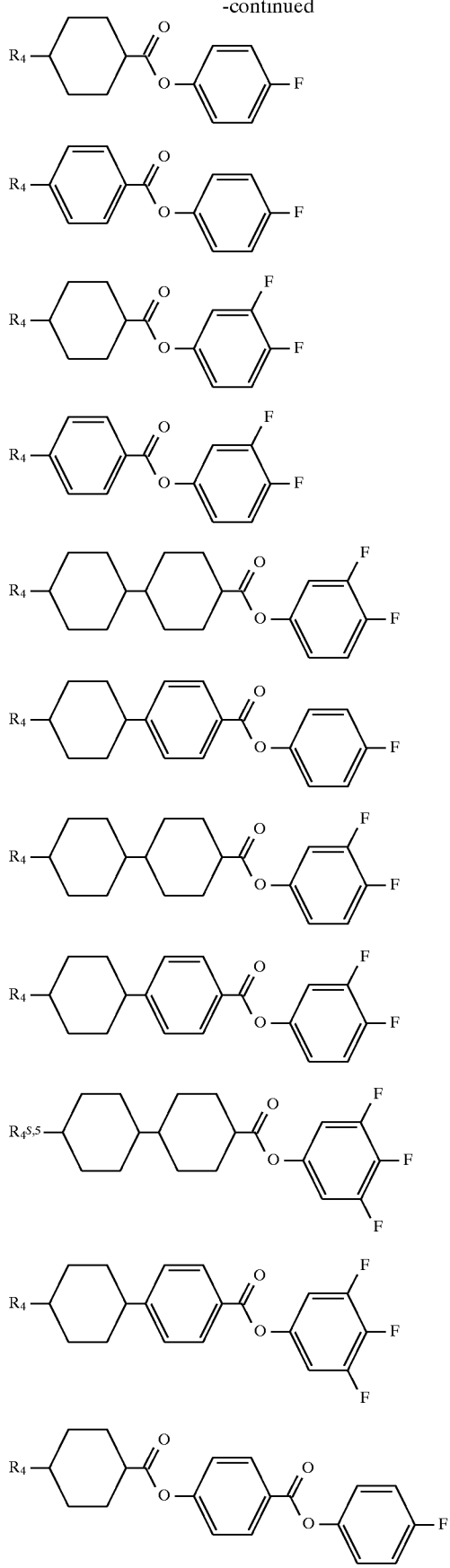

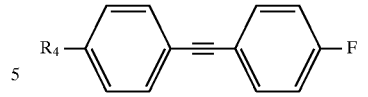
(VII-12)

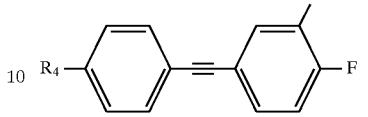
(VII-13)

Compounds expressed by the general formulas (V) to (VII) mentioned above have a large positive value of dielectric anisotropy and are used particularly for the purpose of reducing threshold voltage. They are also used for the purposes of adjusting viscosity, adjusting An, and raising clearing point to widening nematic range. Further, they are used even for the purpose of improving the steepness.

As the compounds expressed by any one of the general formulas (VIII) to (IX) among C group, the following compounds can preferably mentioned:

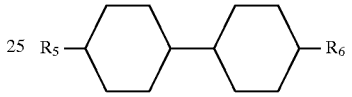
(VIII-1)

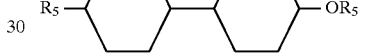
(VIII-2)

(VIII-3)

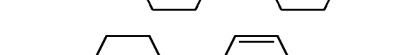
(VIII-4)

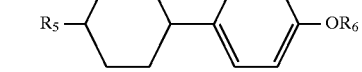
(VIII-5)

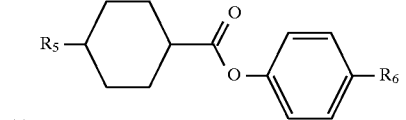
(VIII-6)

(VIII-7)

(VIII-8)

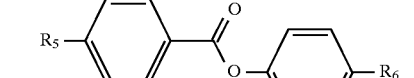

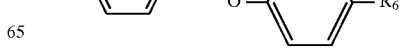
(VIII-9)

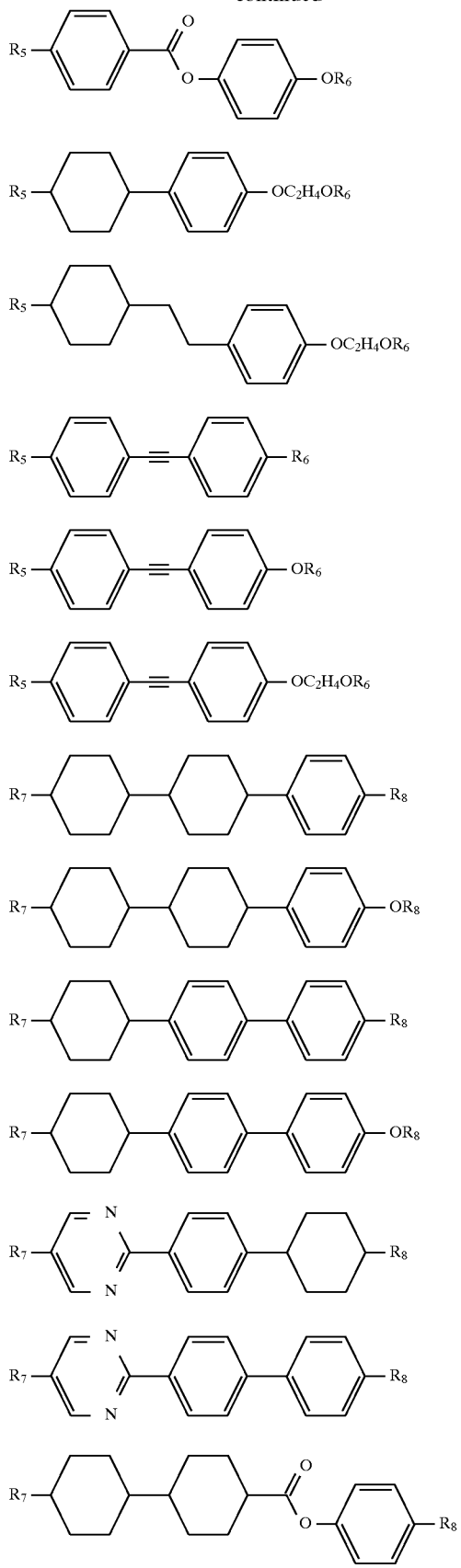
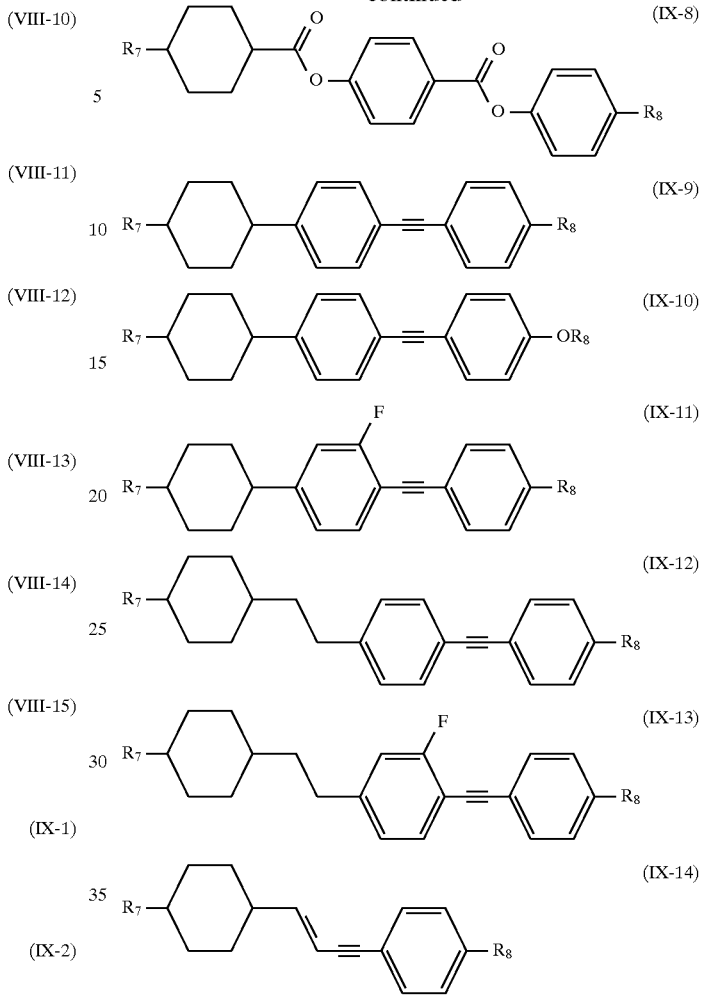

Compounds expressed by the general formulas (VIII) and (IX) mentioned above have a negative or a weak positive dielectric anisotropy. Compounds expressed by the general formula (VIII) can be used principally for the purposes of reducing viscosity and adjusting Δn. Compounds expressed by the general formula (IX) can be used for the purpose of raising clearing point to widening nematic range and for the purpose of adjusting Δn.

Compounds of C group are useful when liquid crystal compositions for super twist nematic (STN) display mode are prepared, and the compounds can be used in a range of 1 to 99% by weight and preferably 10 to 97% by weight, more desirably in a range of 40 to 95% by weight.

When liquid crystal compositions for TFT are prepared, at least one compound selected from C group may be contained in addition to the compounds of A group and the compounds of B group. Also, when liquid crystal compositions for STN or general-purpose TN are prepared, at least one compound selected from B group may be contained in addition to the compounds of A group and the compounds of C group.

Liquid crystal compositions of the present invention are prepared by conventional methods. Generally, the method is adopted in which various components are dissolved in each other at a high temperature. Also, the liquid crystal compositions of the present invention are improved, depending on the applications intended, by adding a suitable additive, and optimized. Such additives are well known in the art and described in literatures in detail. Usually, a chiral dopant or likes are added to cause a helical structure of liquid crystal to adjust a required twisting angle, and to avoid reverse-twist.

Further, the liquid crystal compositions of the present invention can be added with a dichroic dye such as merocyanine type, styryl type, azo type, azomethine type, azoxy type, quinophthalone type, anthraquinone type, and tetrazine type, and used as liquid crystal composition for guest-host (GH) mode. Alternatively, they can also be used as liquid crystal compositions for polymer dispersion type liquid crystal display devices (PDLCD) typified by NCAP which is prepared by forming a nematic liquid crystal into a micro-capsule or typified by a is polymer net work liquid crystal display device (PNLCD) which is prepared by forming a polymer of three-dimensional network structure in a liquid crystal. Also, the liquid crystal compositions of the present invention can be used as ones for electrically controlled birefringence (ECB) mode or dynamic scattering (DS) mode.

As the liquid crystal compositions of the present invention, the following composition examples 1 to 30 can be mentioned:

[Composition Example 1]

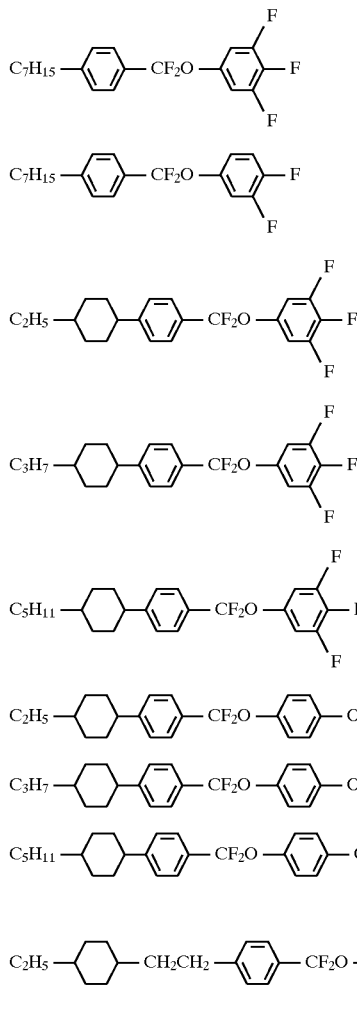

-continued
[Composition Example 1]

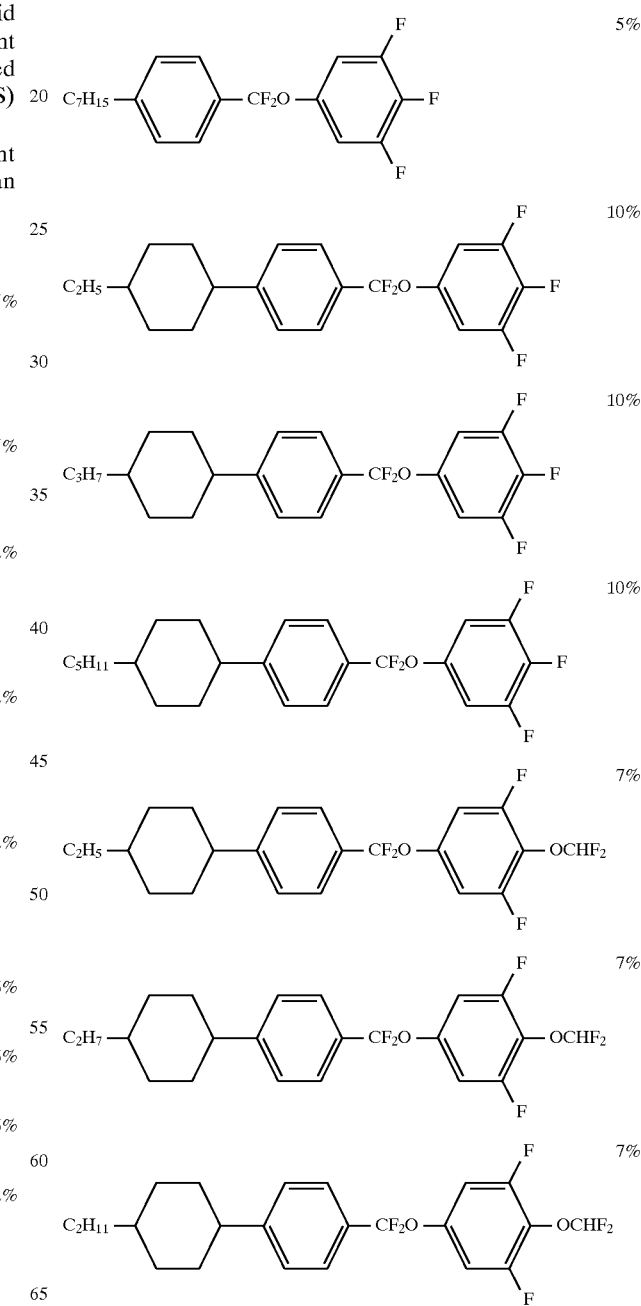

-continued
[Composition Example 2]
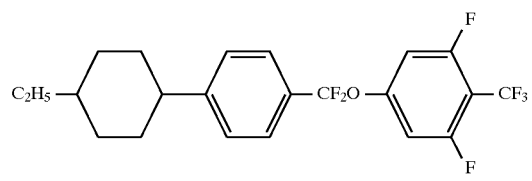 7%
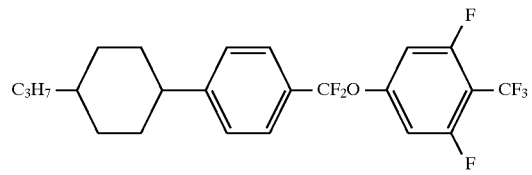 7%
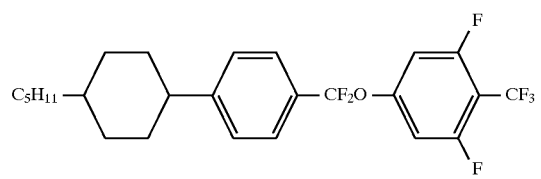 7%
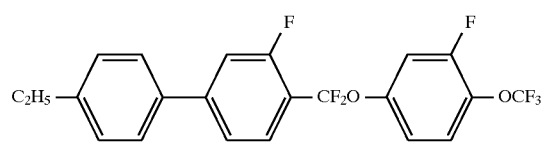 4%
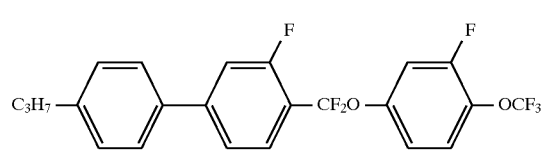 4%
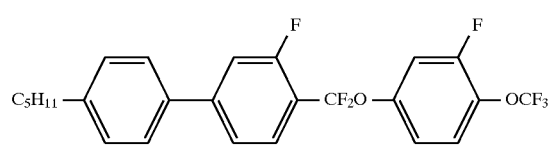 3%
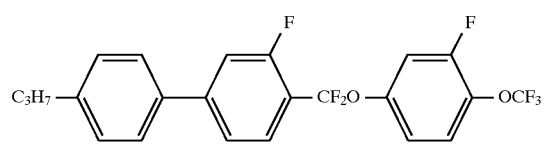 3%
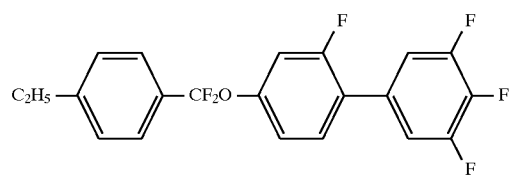 4%
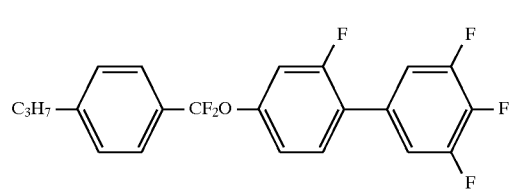 4%
-continued
[Composition Example 2]
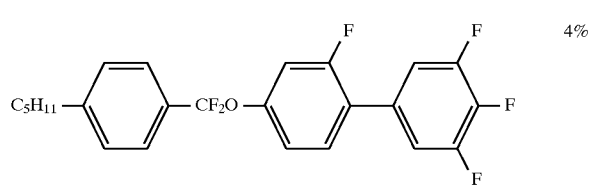 4%
[Composition Example 3]
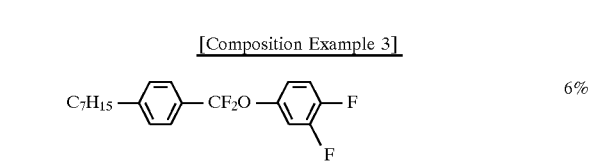 6%
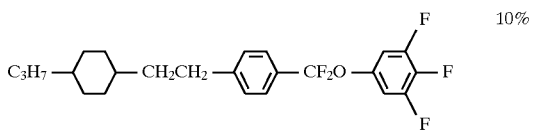 10%
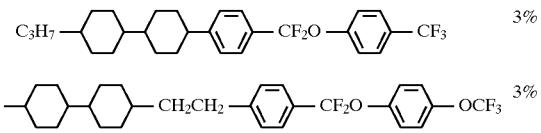 3%
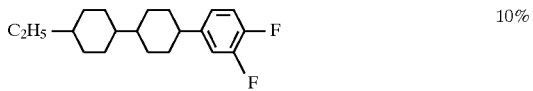 3%
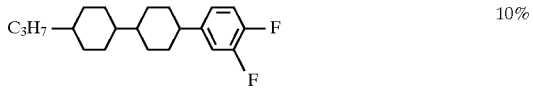 10%
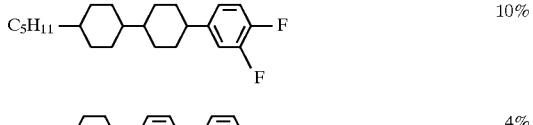 10%
 10%
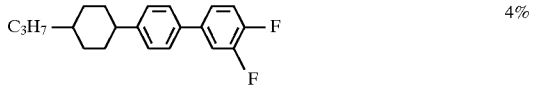 4%
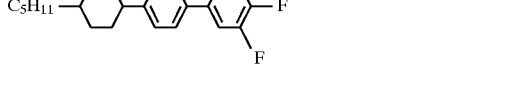 4%
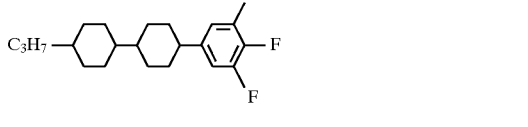 8%
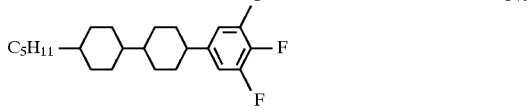 5%
 3%

[Composition Example 3] (continued)
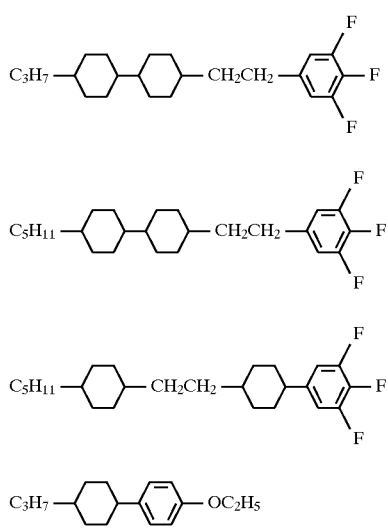
[Composition Example 4]
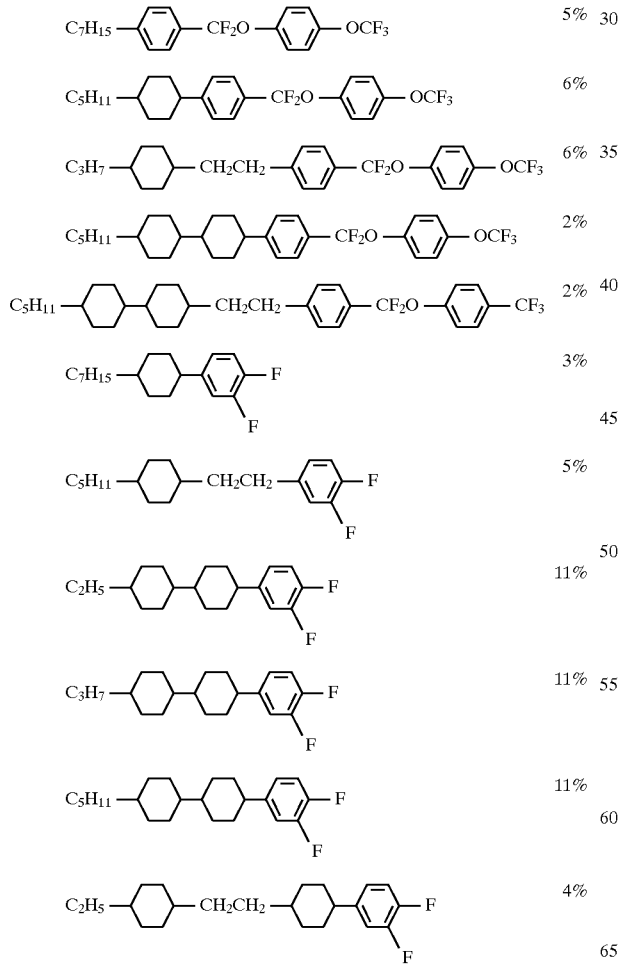
[Composition Example 4] (continued)
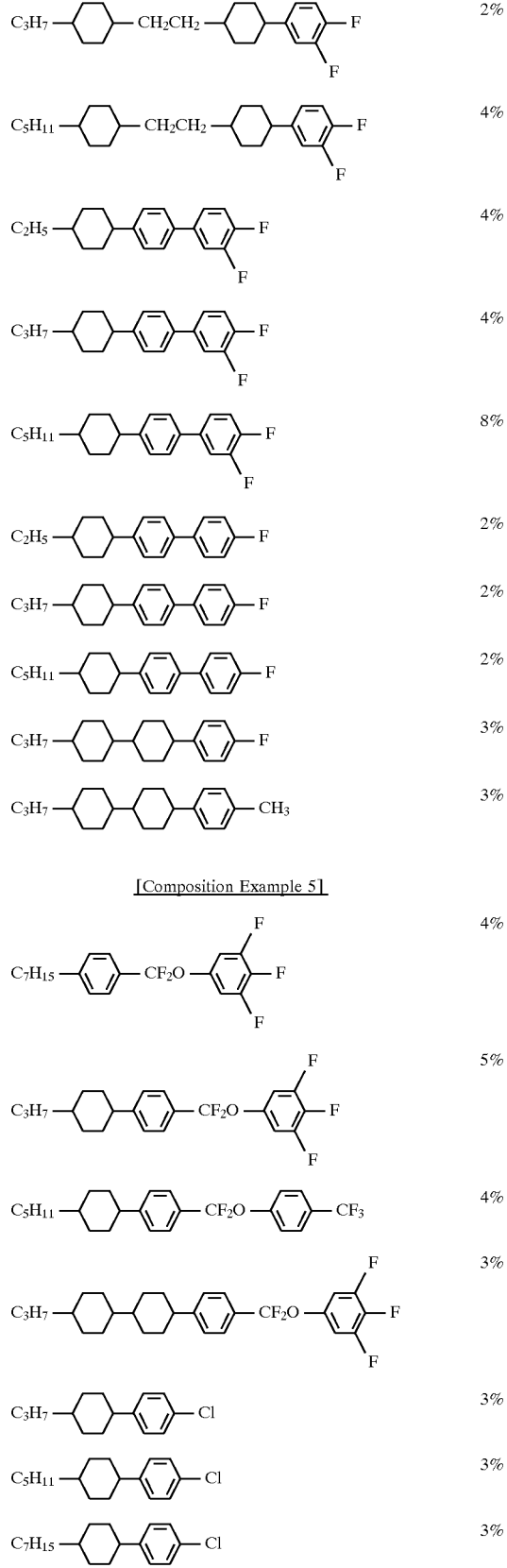
[Composition Example 5]

[Composition Example 5]

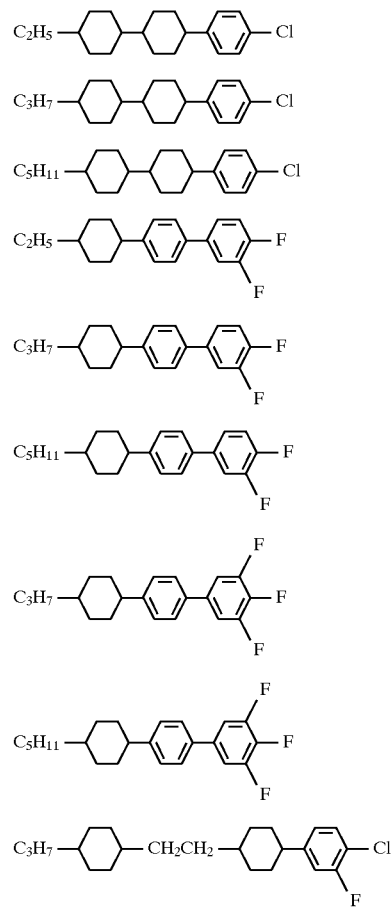

| | |
|---|---|
| C2H5-Cy-Cy-Ph-Cl | 6% |
| C3H7-Cy-Cy-Ph-Cl | 6% |
| C5H11-Cy-Cy-Ph-Cl | 6% |
| C2H5-Cy-Ph-Ph-F,F | 6% |
| C3H7-Cy-Ph-Ph-F,F | 6% |
| C5H11-Cy-Ph-Ph-F,F | 12% |
| C3H7-Cy-Ph-Ph-F,F,F | 13% |
| C5H11-Cy-Ph-Ph-F,F,F | 13% |
| C3H7-Cy-CH2CH2-Cy-Ph-Cl,F | 3% |
| C3H7-Cy-Ph(F)-C≡C-Ph-C2H5 | 2% |
| C3H7-Cy-Ph(F)-CH=CH-Ph-C2H5 | 2% |

[Composition Example 6]

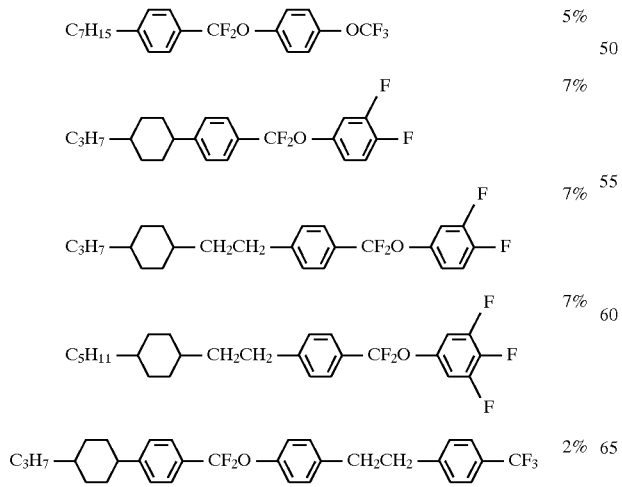

| | |
|---|---|
| C7H15-Ph-CF2O-Ph-OCF3 | 5% |
| C3H7-Cy-Ph-CF2O-Ph-F,F | 7% |
| C3H7-Cy-CH2CH2-Ph-CF2O-Ph-F,F | 7% |
| C5H11-Cy-CH2CH2-Ph-CF2O-Ph-F,F,F | 7% |
| C3H7-Cy-Ph-CF2O-Ph-CH2CH2-Ph-CF3 | 2% |

-continued
[Composition Example 6]

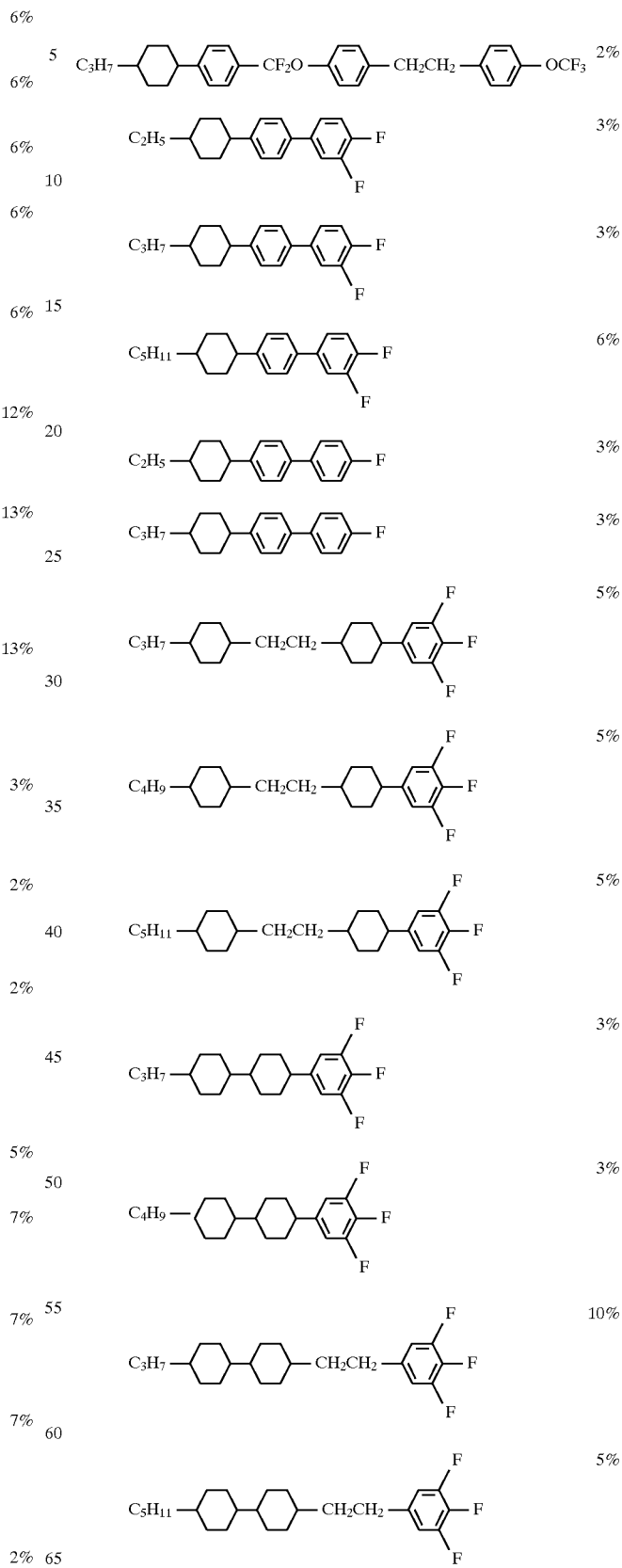

| | |
|---|---|
| C3H7-Cy-Ph-CF2O-Ph-CH2CH2-Ph-OCF3 | 2% |
| C2H5-Cy-Ph-Ph-F,F | 3% |
| C3H7-Cy-Ph-Ph-F,F | 3% |
| C5H11-Cy-Ph-Ph-F,F | 6% |
| C2H5-Cy-Ph-Ph-F | 3% |
| C3H7-Cy-Ph-Ph-F | 3% |
| C3H7-Cy-CH2CH2-Cy-Ph-F,F,F | 5% |
| C4H9-Cy-CH2CH2-Cy-Ph-F,F,F | 5% |
| C5H11-Cy-CH2CH2-Cy-Ph-F,F,F | 5% |
| C3H7-Cy-Cy-Ph-F,F,F | 3% |
| C4H9-Cy-Cy-Ph-F,F | 3% |
| C3H7-Cy-CH2CH2-Ph-F,F,F | 10% |
| C5H11-Cy-CH2CH2-Ph-F,F,F | 5% |

[Composition Example 6]
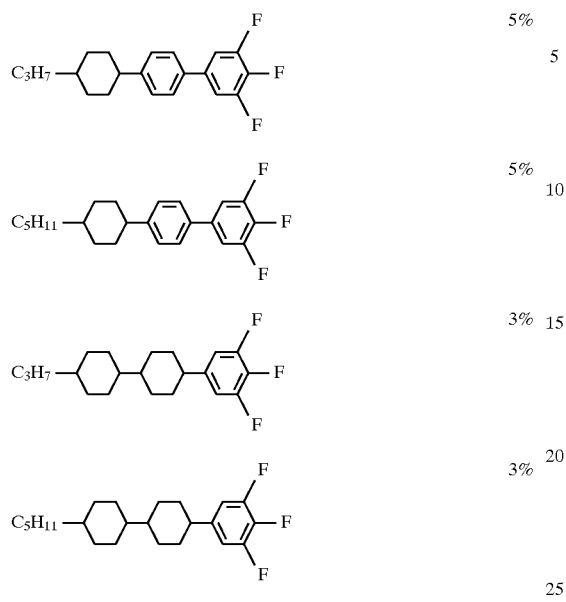
| | |
|---|---|
| | 5% |
| | 5% |
| | 3% |
| | 3% |
[Composition Example 7]
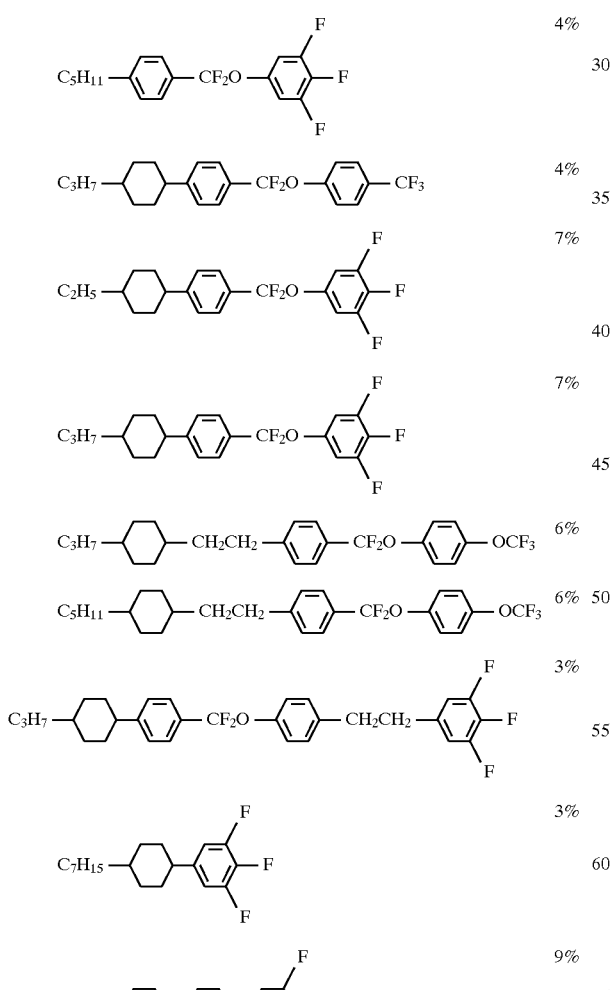
| | |
|---|---|
| | 4% |
| | 4% |
| | 7% |
| | 7% |
| | 6% |
| | 6% |
| | 3% |
| | 3% |
| | 9% |
[Composition Example 7]
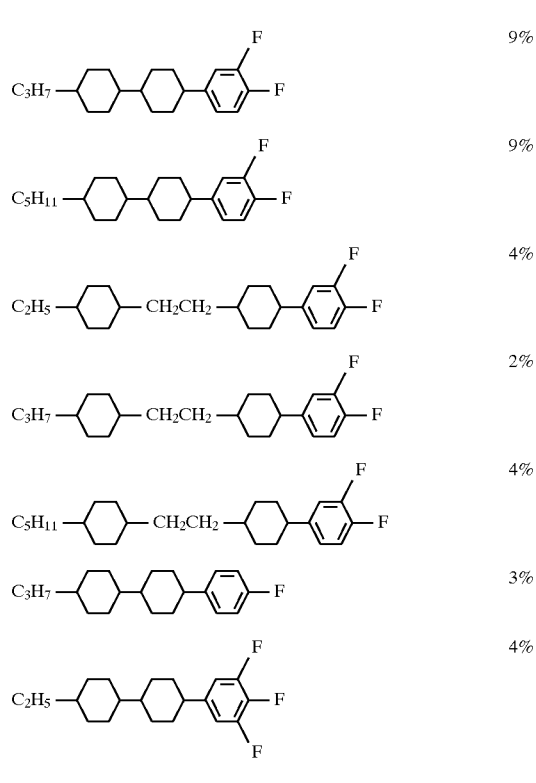
| | |
|---|---|
| | 9% |
| | 9% |
| | 4% |
| | 2% |
| | 4% |
| | 3% |
| | 4% |
| | 4% |
| | 3% |
| | 3% |
| | 3% |
| | 3% |
[Composition Example 8]
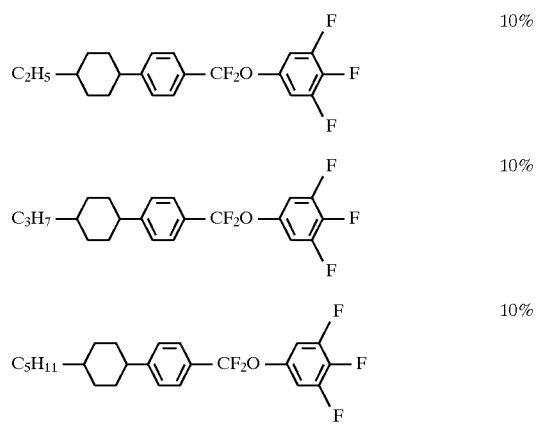
| | |
|---|---|
| | 10% |
| | 10% |
| | 10% |

[Composition Example 8]
-continued
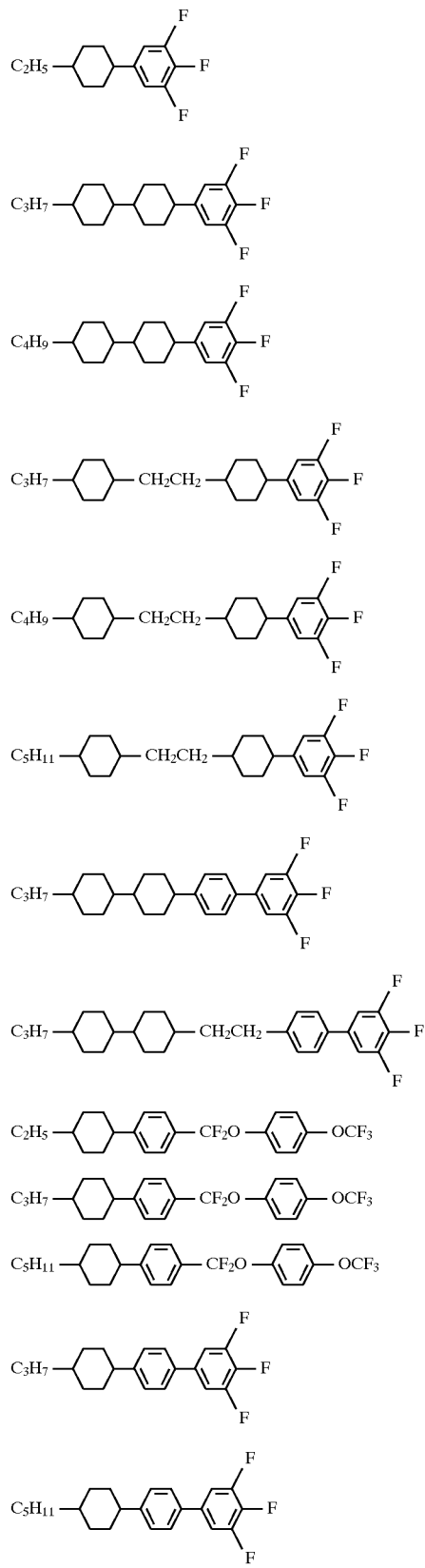
[Composition Example 8]
-continued
[Composition Example 9]
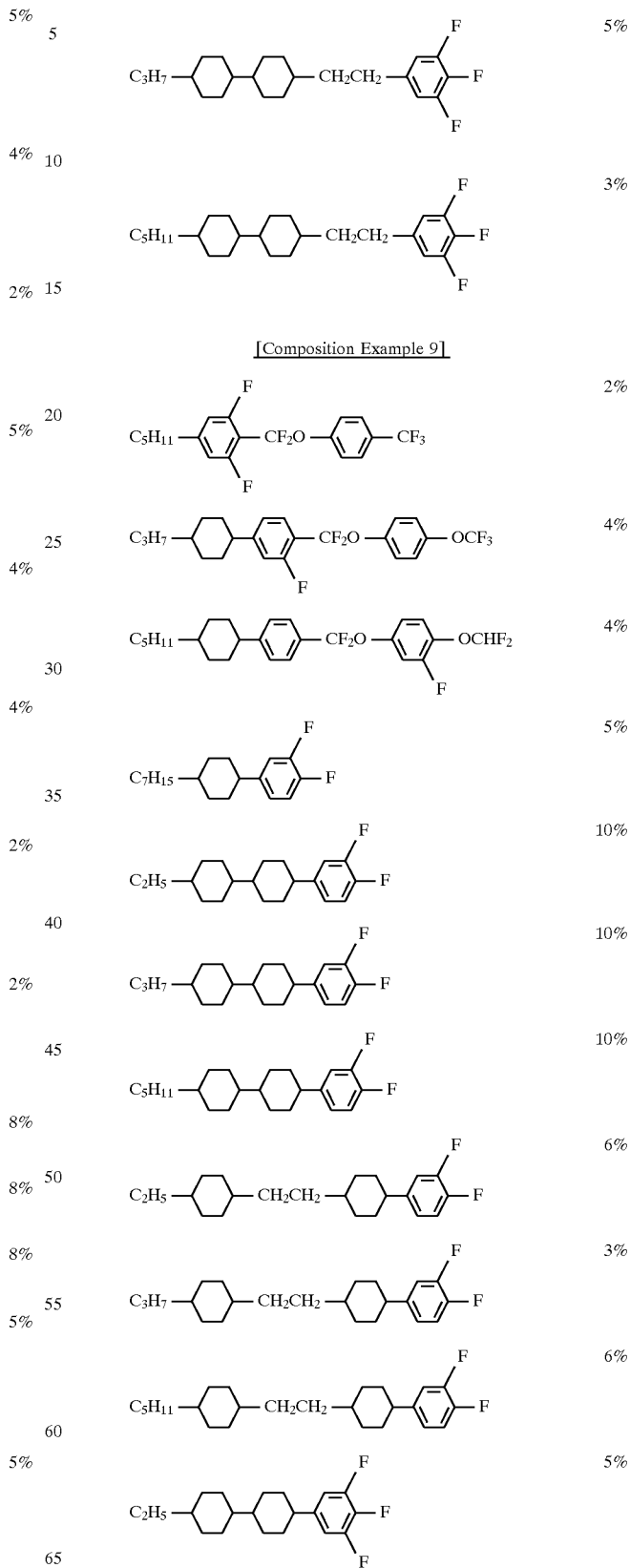

-continued
[Composition Example 9]
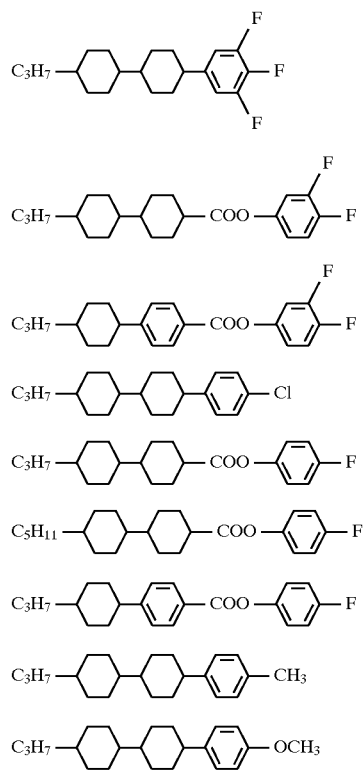
5%
5%
4%
4%
3%
3%
3%
4%
4%
[Composition Example 10]
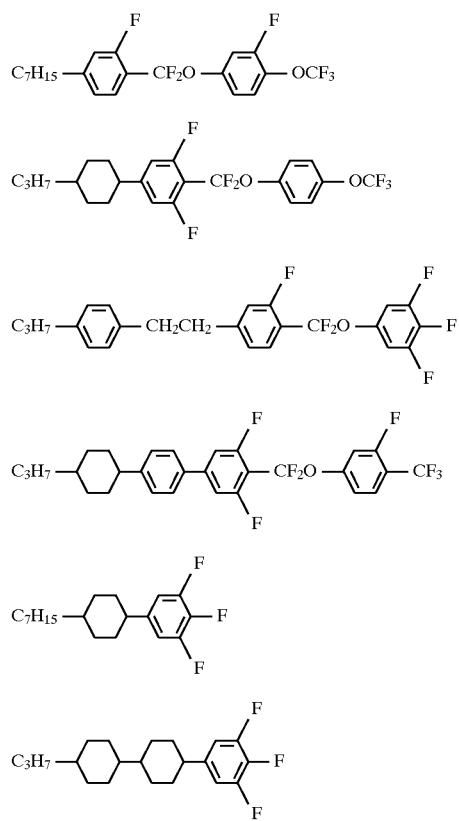
5%
7%
7%
4%
3%
5%
-continued
[Composition Example 10]
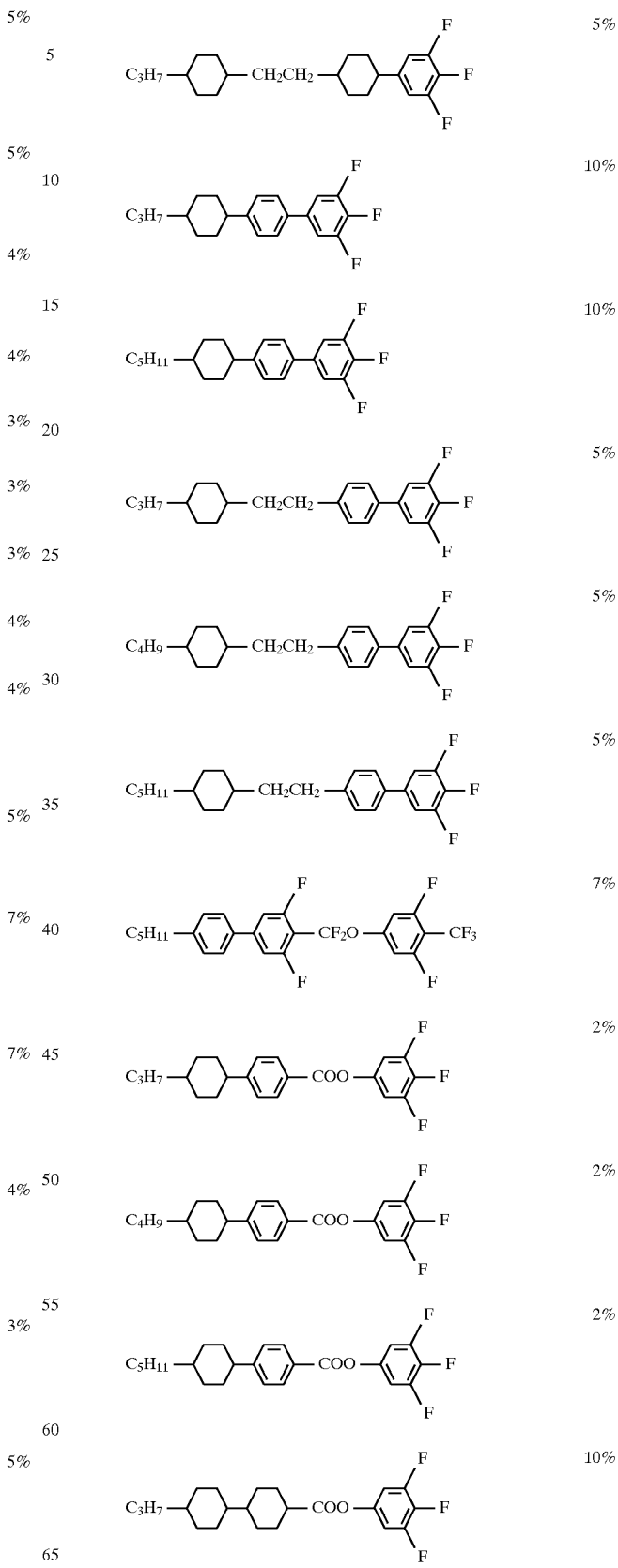
5%
10%
10%
5%
5%
5%
7%
2%
2%
2%
10%

-continued
[Composition Example 10]
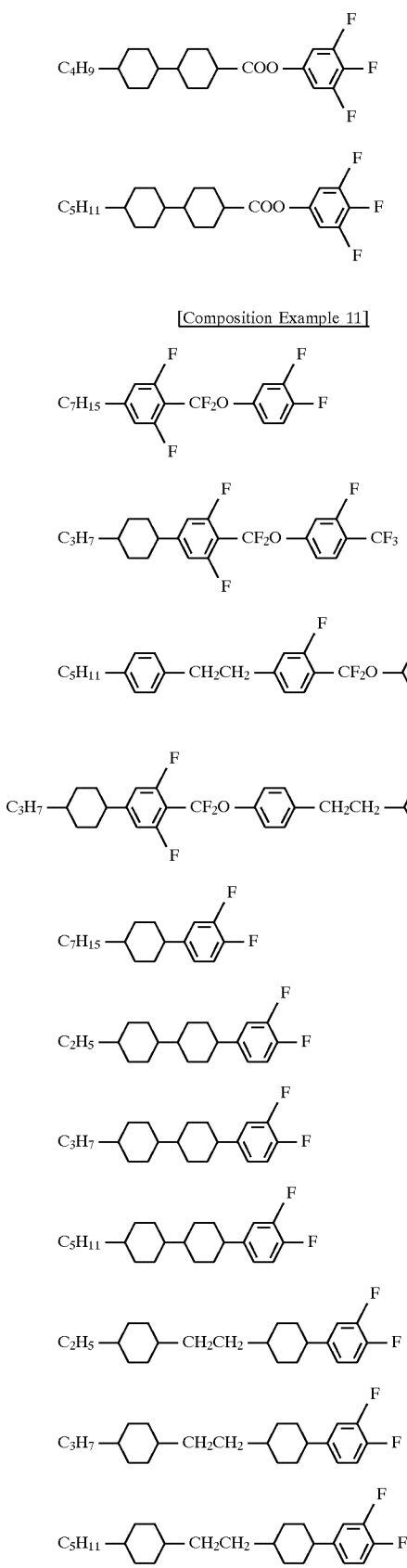
[Composition Example 11]
-continued
[Composition Example 11]
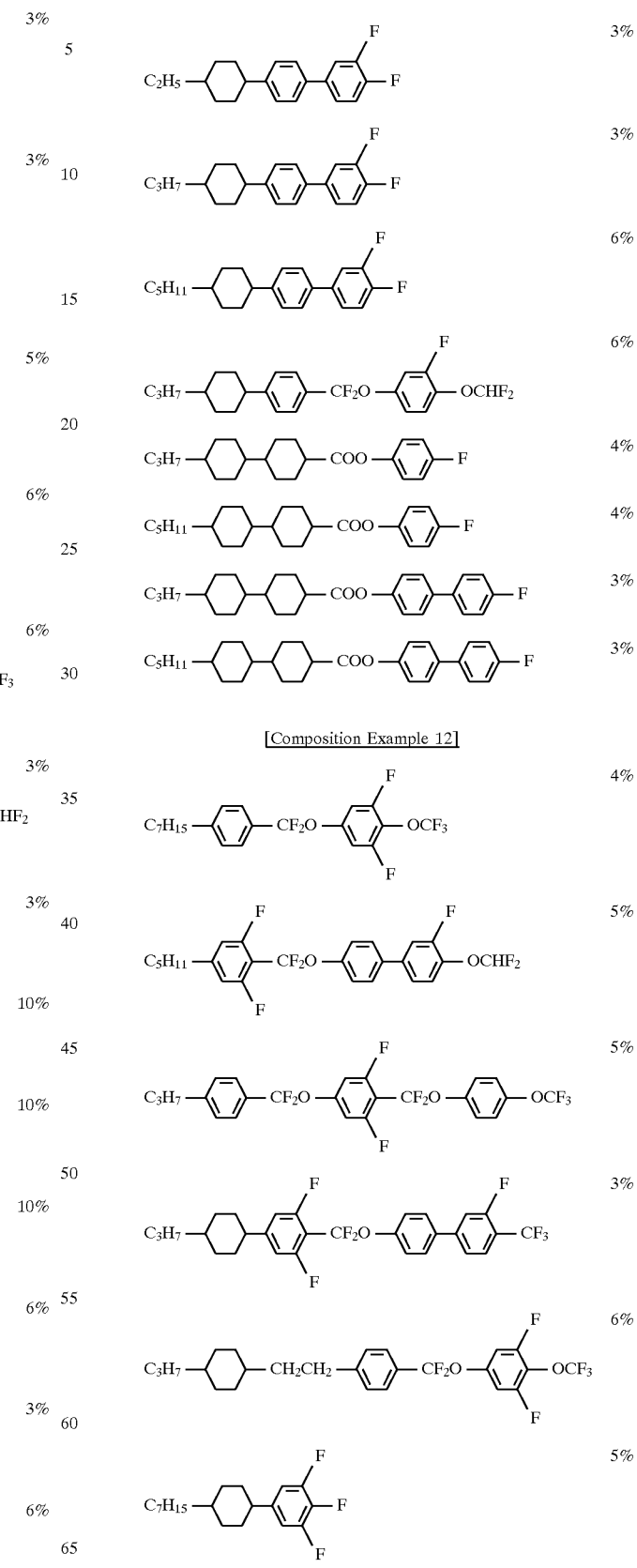
[Composition Example 12]

[Composition Example 12] (continued)
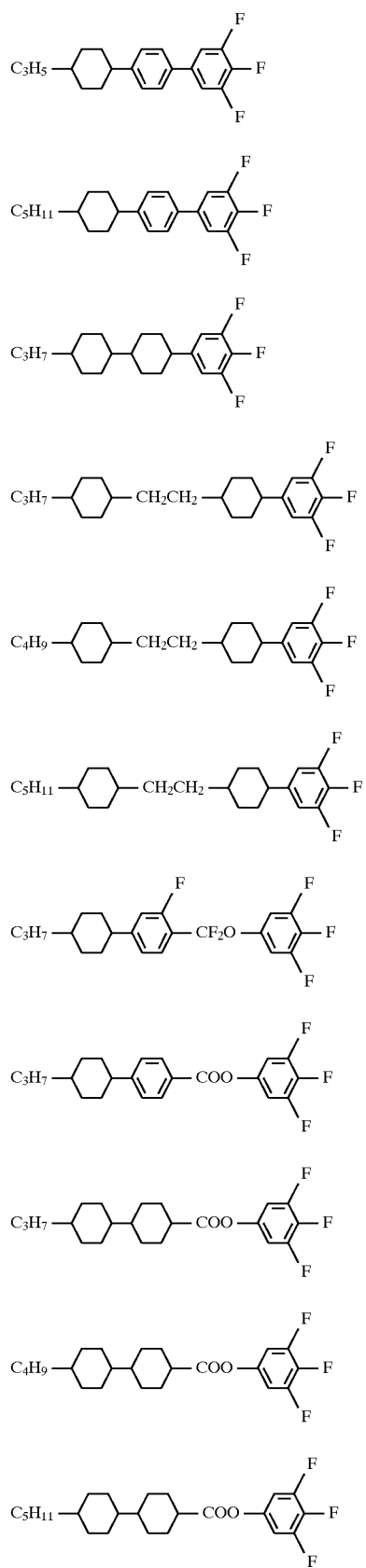
[Composition Example 13]
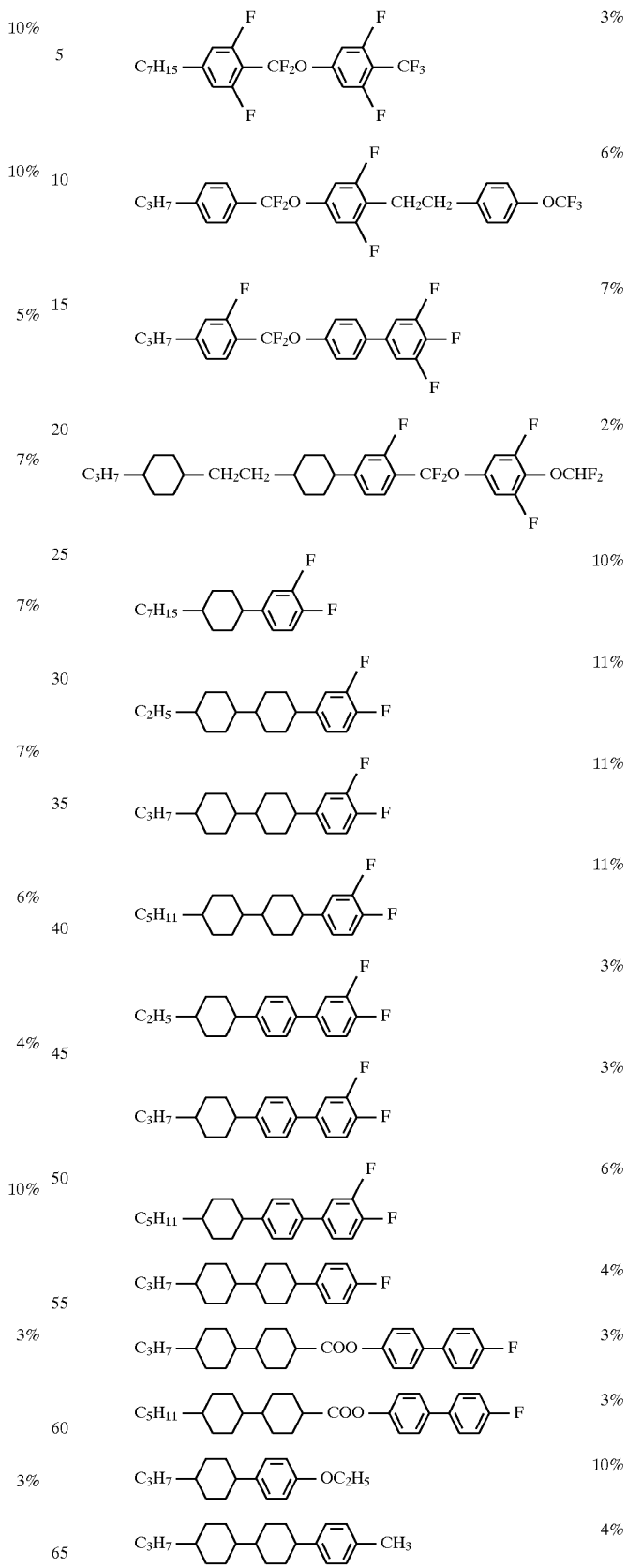

[Composition Example 13]
-continued

C₃H₇—⟨Cy⟩—⟨Cy⟩—⟨Ph⟩—C₃H₇    4%

[Composition Example 14]

C₇H₁₅—⟨Ph(2,6-F₂)⟩—CF₂O—⟨Ph⟩—OCF₃    3%

C₃H₇—⟨Cy⟩—⟨Ph(2,6-F₂)⟩—CF₂O—⟨Ph(2,6-F₂)⟩—OCHF₂    6%

C₃H₇—⟨Cy⟩—⟨Ph⟩—⟨Ph(2-F)⟩—CF₂O—⟨Ph(2,3,5-F₃)⟩    3%

C₃H₇—⟨Ph⟩—OCF₂—⟨Ph⟩—CF₂O—⟨Ph⟩—C₂H₅    4%

C₃H₇—⟨Cy⟩—⟨Ph⟩—Cl    10%

C₅H₁₁—⟨Cy⟩—⟨Ph⟩—Cl    3%

C₇H₁₅—⟨Cy⟩—⟨Ph(3,4,5-F₃)⟩    3%

C₃H₇—⟨Cy⟩—⟨Cy⟩—⟨Ph(3,4,5-F₃)⟩    10%

C₃H₇—⟨Cy⟩—⟨Ph⟩—⟨Ph(3,4,5-F₃)⟩    5%

C₅H₁₁—⟨Cy⟩—⟨Ph⟩—⟨Ph(3,4,5-F₃)⟩    5%

C₂H₅—⟨Cy⟩—⟨Cy⟩—⟨Ph⟩—Cl    7%

C₄H₉—⟨Cy⟩—⟨Cy⟩—⟨Ph⟩—Cl    10%

C₅H₁₁—⟨Cy⟩—⟨Cy⟩—⟨Ph⟩—Cl    8%

[Composition Example 14]
-continued

C₅H₁₁—⟨Cy⟩—⟨Cy⟩—CH₂CH₂—⟨Ph⟩—⟨Ph(3,4,5-F₃)⟩    3%

C₃H₇—⟨Ph⟩—CF₂O—⟨Ph(2-F)⟩—CF₂O—⟨Ph(3,4,5-F₃)⟩    5%

C₅H₁₁—⟨Ph(2-F)⟩—CF₂O—⟨Ph⟩—⟨Ph(2-F)⟩—OCF₃    6%

C₃H₇—⟨Cy⟩—⟨Cy⟩—C₄H₉    9%

[Composition Example 15]

C₂H₅—⟨Cy⟩—⟨Ph⟩—CF₂O—⟨Ph(2-F)⟩—CN    6%

C₃H₇—⟨Cy⟩—⟨Ph⟩—CF₂O—⟨Ph(2-F)⟩—CN    6%

C₅H₁₁—⟨Cy⟩—⟨Ph⟩—CF₂O—⟨Ph(2-F)⟩—CN    6%

C₃H₇OH₂C—⟨Ph⟩—COO—⟨Ph(2-F)⟩—CN    5%

C₂H₅—⟨Cy⟩—⟨Ph⟩—CN    5%

C₃H₇—⟨Cy⟩—⟨Ph⟩—CN    15%

C₂H₅—⟨Cy⟩—⟨Cy⟩—⟨Ph⟩—CN    5%

C₃H₇—⟨Cy⟩—⟨Cy⟩—⟨Ph⟩—CN    5%

-continued
[Composition Example 15]
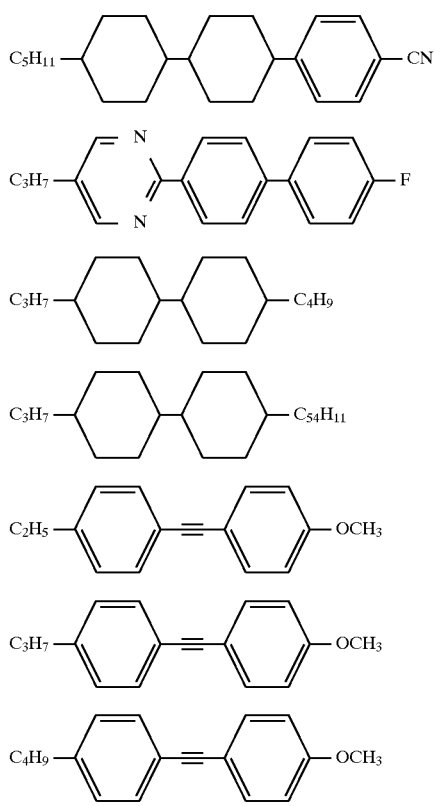
5%
5%
10%
3%
3%
3%
3%
-continued
[Composition Example 15]
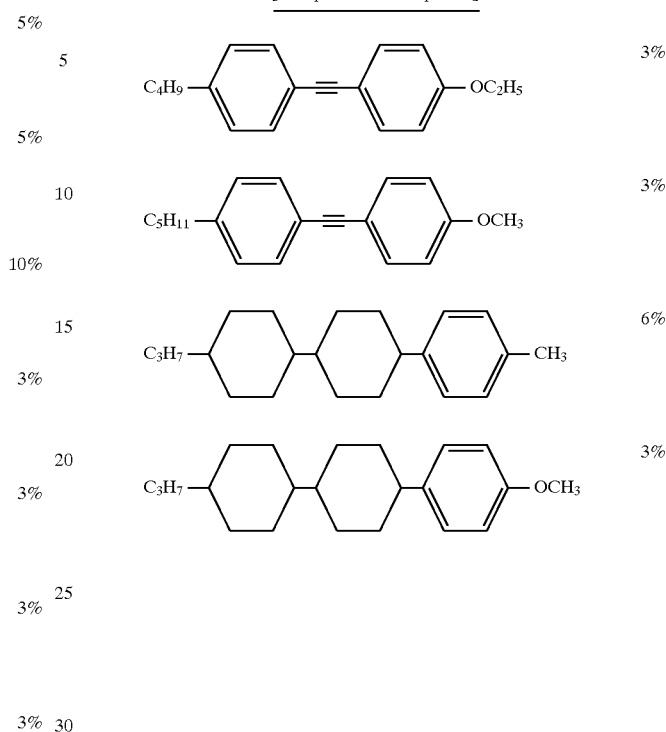
3%
3%
6%
3%
[Composition Example 16]
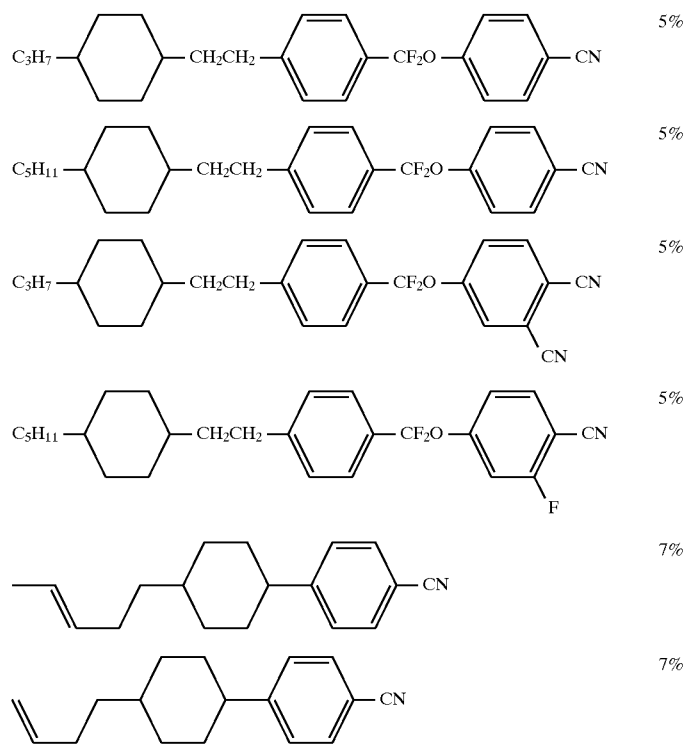
5%
5%
5%
5%
7%
7%

-continued
[Composition Example 16]
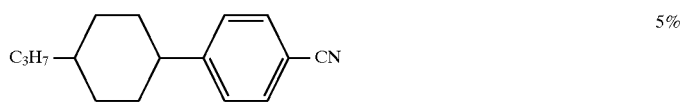
5%
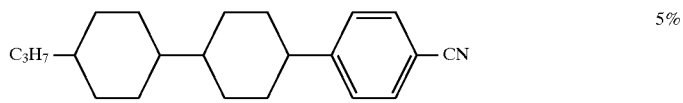
5%
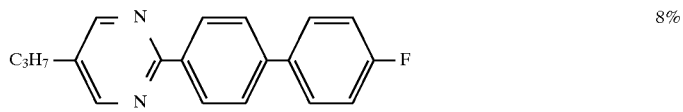
8%
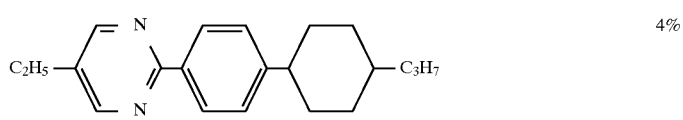
4%
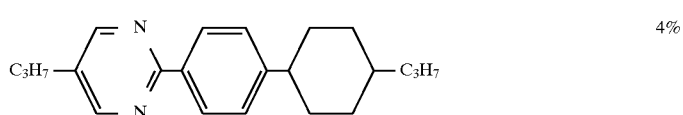
4%
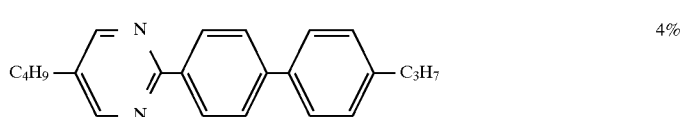
4%
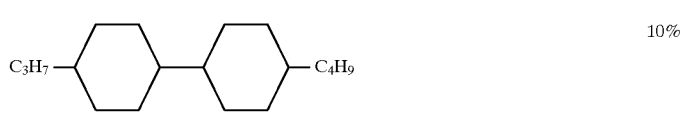
10%
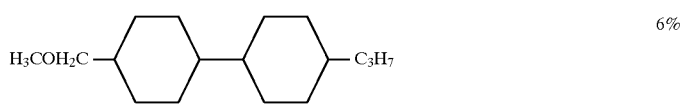
6%
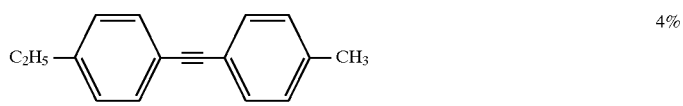
4%
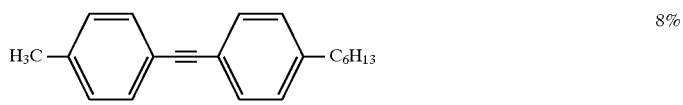
8%
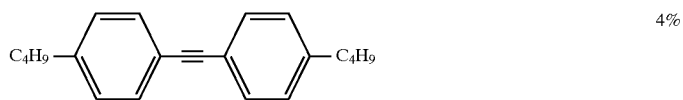
4%
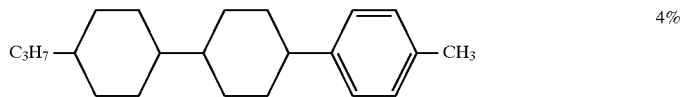
4%
[Composition Example 17]
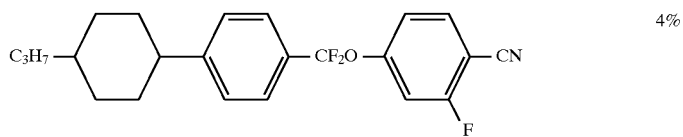
4%

-continued
[Composition Example 17]
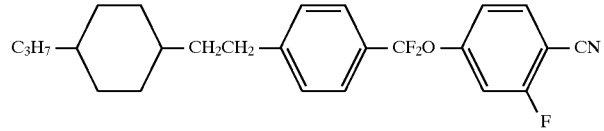 4%
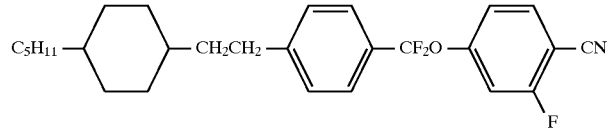 4%
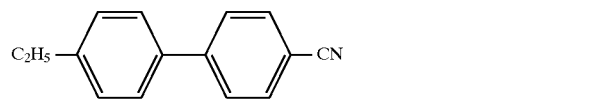 7%
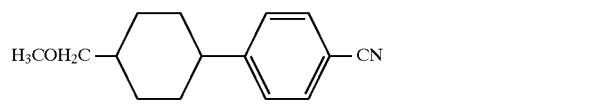 8%
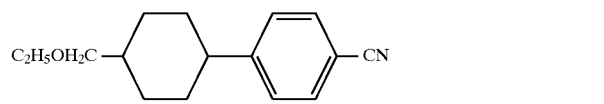 7%
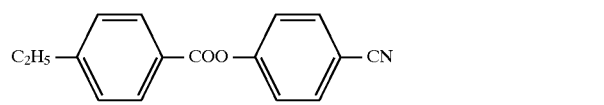 4%
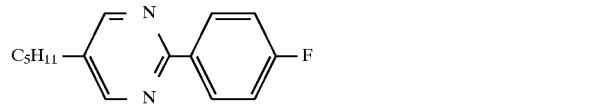 5%
 5%
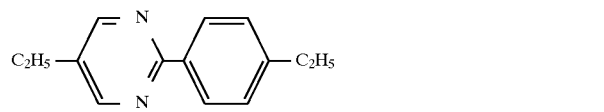 3%
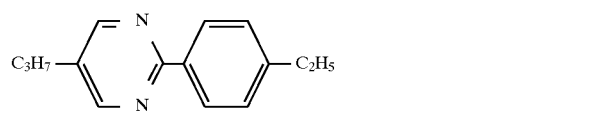 3%
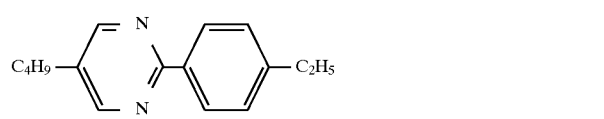 3%
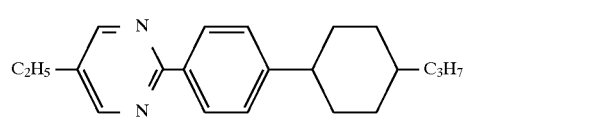 5%
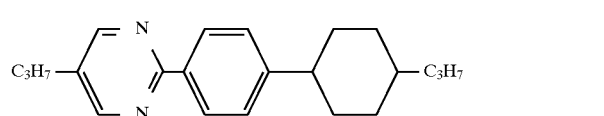 5%

-continued
[Composition Example 17]
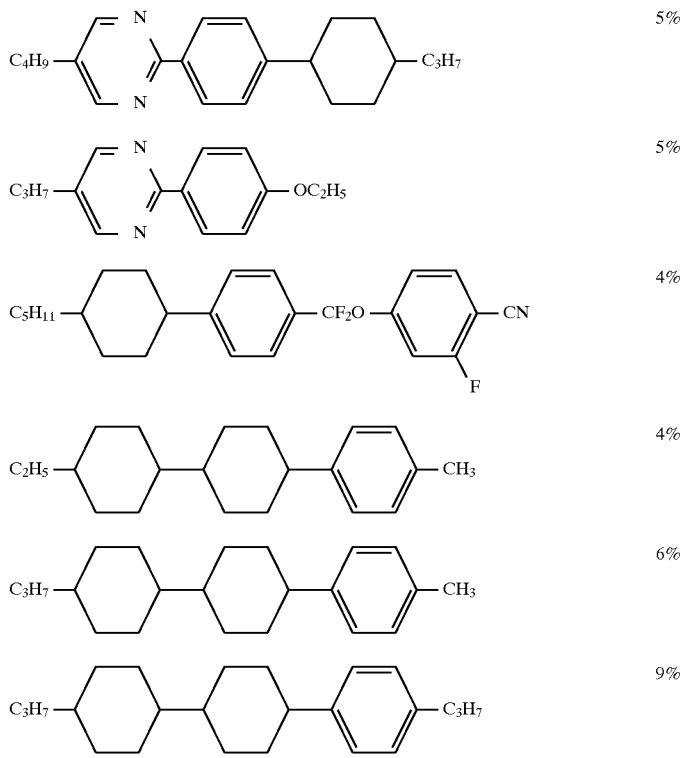
| | |
|---|---|
| | 5% |
| | 5% |
| | 4% |
| | 4% |
| | 6% |
| | 9% |
[Composition Example 18]
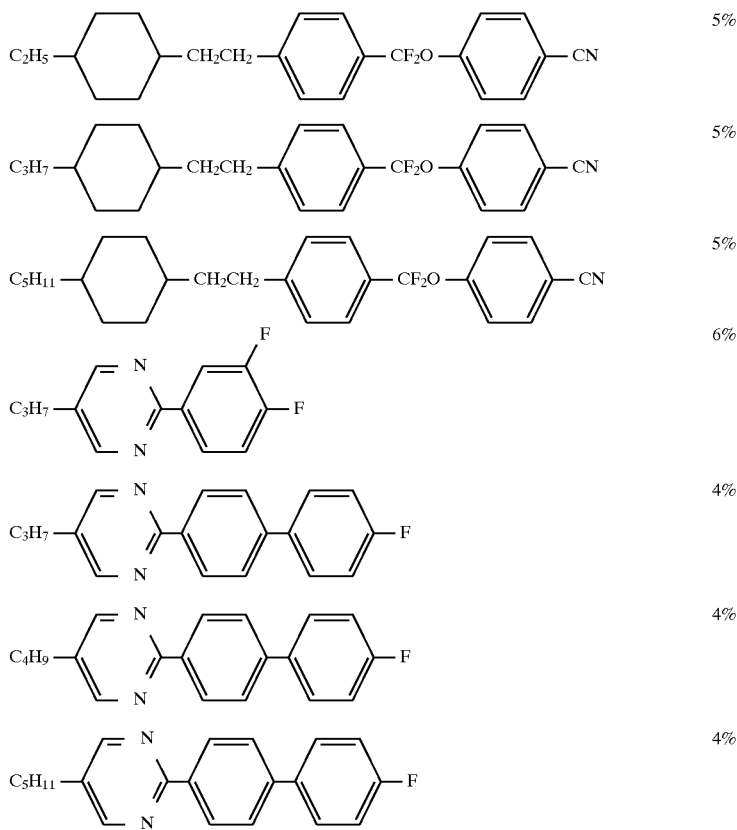
| | |
|---|---|
| | 5% |
| | 5% |
| | 5% |
| | 6% |
| | 4% |
| | 4% |
| | 4% |

-continued
[Composition Example 18]
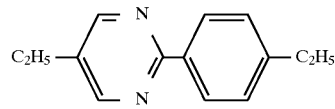 6%
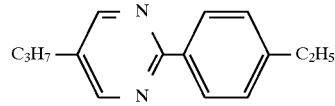 6%
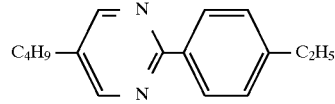 6%
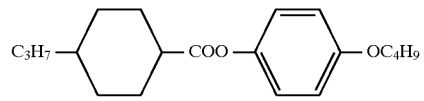 6%
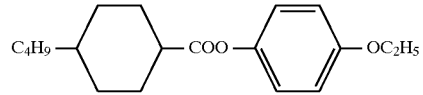 6%
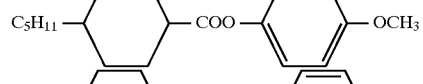 6%
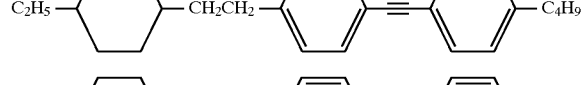 4%
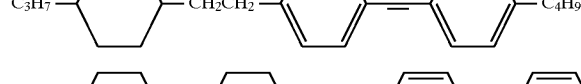 4%
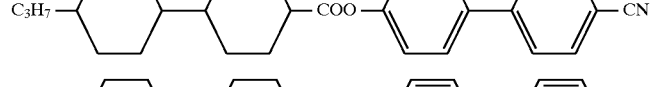 3%
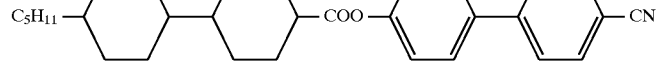 3%
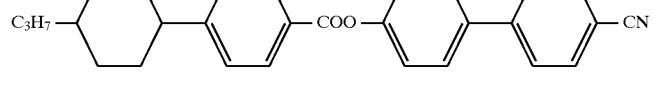 3%
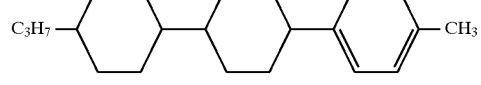 7%
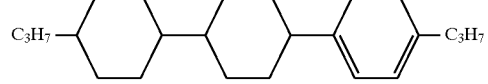 7%
[Composition Example 19]
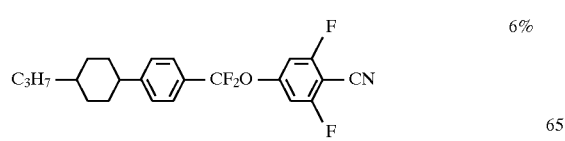 6%
-continued
[Composition Example 19]
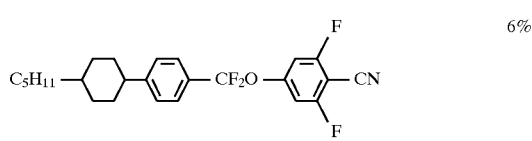 6%

-continued
[Composition Example 19]
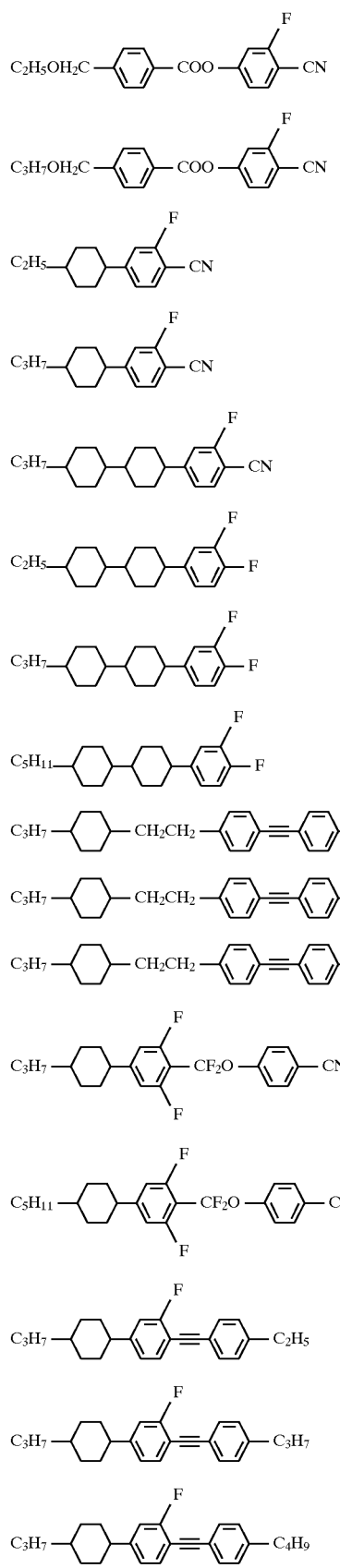
[Composition Example 19]
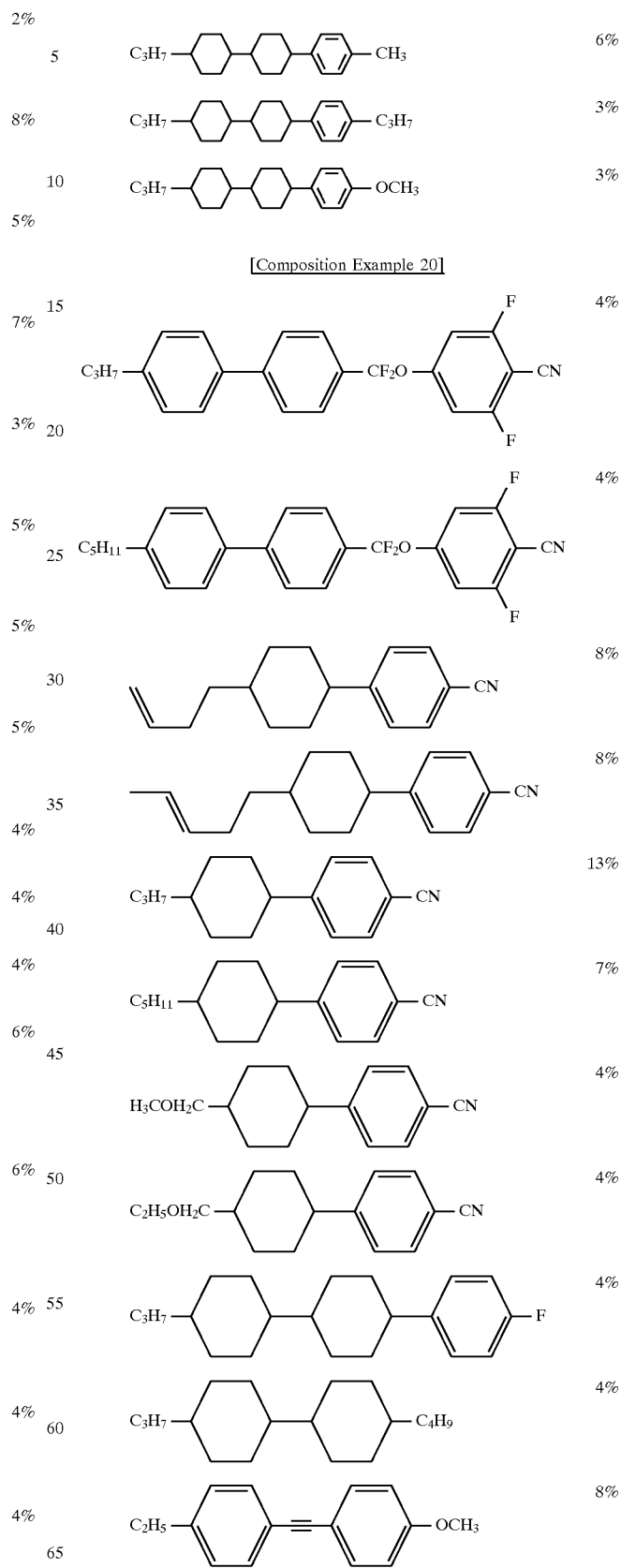
[Composition Example 20]

[Composition Example 20]

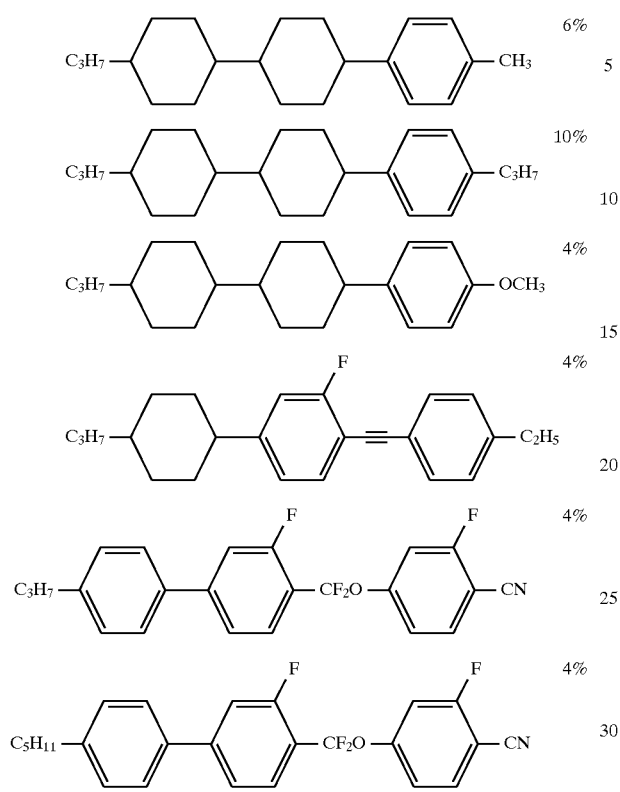

| | |
|---|---|
| C3H7–⬡–⬡–⌬–CH3 | 6% |
| C3H7–⬡–⬡–⌬–C3H7 | 10% |
| C3H7–⬡–⬡–⌬–OCH3 | 4% |
| C3H7–⬡–⌬(F)–C≡C–⌬–C2H5 | 4% |
| C3H7–⌬–⌬(F)–CF2O–⌬(F)–CN | 4% |
| C5H11–⌬–⌬(F)–CF2O–⌬(F)–CN | 4% |

[Composition Example 21]

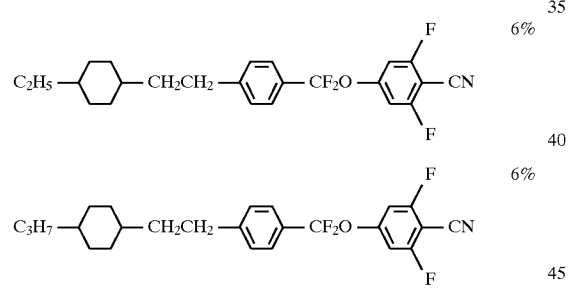

| | |
|---|---|
| C2H5–⬡–CH2CH2–⌬–CF2O–⌬(F,F)–CN | 6% |
| C3H7–⬡–CH2CH2–⌬–CF2O–⌬(F,F)–CN | 6% |

[Composition Example 21] -continued

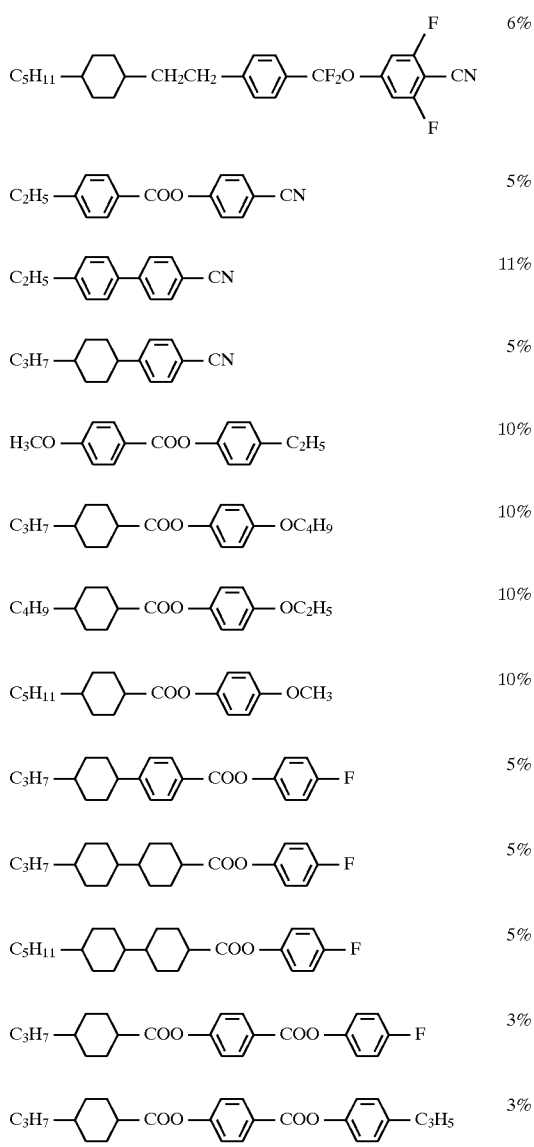

| | |
|---|---|
| C5H11–⬡–CH2CH2–⌬–CF2O–⌬(F,F)–CN | 6% |
| C2H5–⌬–COO–⌬–CN | 5% |
| C2H5–⌬–⌬–CN | 11% |
| C3H7–⬡–⌬–CN | 5% |
| H3CO–⌬–COO–⌬–C2H5 | 10% |
| C3H7–⬡–COO–⌬–OC4H9 | 10% |
| C4H9–⬡–COO–⌬–OC2H5 | 10% |
| C5H11–⬡–COO–⌬–OCH3 | 10% |
| C3H7–⬡–⌬–COO–⌬–F | 5% |
| C3H7–⬡–⬡–COO–⌬–F | 5% |
| C5H11–⬡–⬡–COO–⌬–F | 5% |
| C3H7–⬡–COO–⌬–COO–⌬–F | 3% |
| C3H7–⬡–COO–⌬–COO–⌬–C3H5 | 3% |

[Composition Example 22]

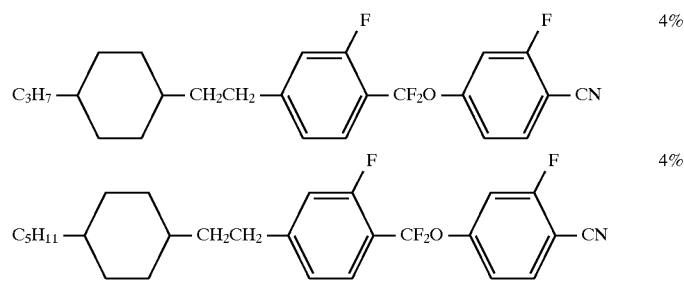

| | |
|---|---|
| C3H7–⬡–CH2CH2–⌬(F)–CF2O–⌬(F)–CN | 4% |
| C5H11–⬡–CH2CH2–⌬(F)–CF2O–⌬(F)–CN | 4% |

-continued
[Composition Example 22]
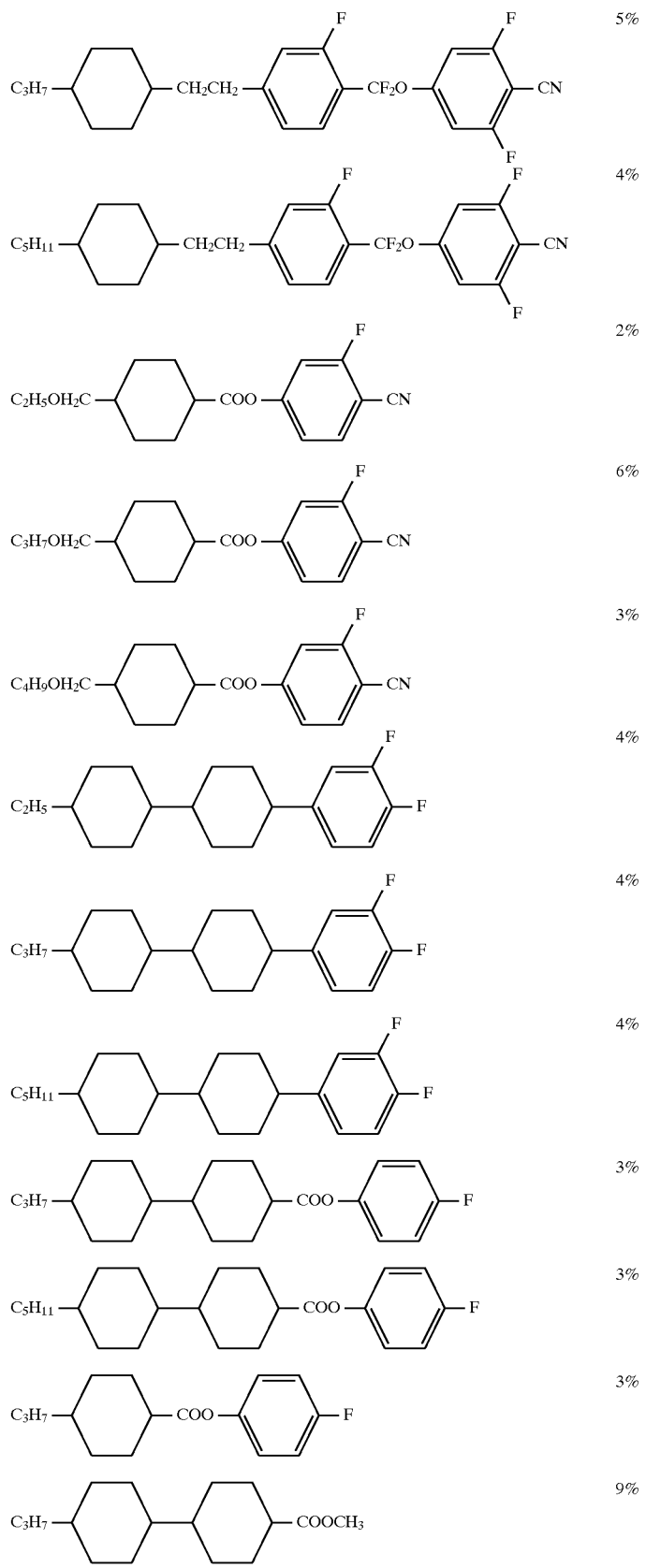

[Composition Example 22] (continued)

| Structure | % |
|---|---|
| C₃H₇–(Cy)–COO–(Ph)–OC₄H₉ | 4% |
| C₄H₉–(Cy)–COO–(Ph)–C₃H₇ | 4% |
| C₄H₉–(Cy)–COO–(Ph)–C₄H₉ | 4% |
| C₂H₅–(Pyrimidine)–(Ph)–(Cy)–C₃H₇ | 5% |
| C₃H₇–(Pyrimidine)–(Ph)–(Cy)–C₃H₇ | 5% |
| C₄H₉–(Pyrimidine)–(Ph)–(Cy)–C₃H₇ | 5% |
| C₃H₇–(Cy)–(Ph)–OC₂H₅ | 10% |
| C₃H₇–(Cy)–(Cy)–(Ph)–CH₃ | 5% |

[Composition Example 23]

| Structure | % |
|---|---|
| C₂H₅–(2,6-diF-Ph)–CF₂O–(Ph)–(3-F-Ph)–CN | 5% |
| C₃H₇–(2,6-diF-Ph)–CF₂O–(Ph)–(3-F-Ph)–CN | 5% |
| C₅H₁₁–(2,6-diF-Ph)–CF₂O–(Ph)–(3-F-Ph)–CN | 5% |
| C₃H₇–CH₂–(dioxane)–(Ph)–CN | 4% |
| C₄H₉–CH₂–(dioxane)–(Ph)–CN | 4% |
| H₃COH₂C–(Cy)–(Ph)–CN | 5% |
| C₂H₅–(Pyrimidine)–(Ph)–C₂H₅ | 9% |
| C₃H₇–(Pyrimidine)–(Ph)–C₂H₅ | 9% |

[Composition Example 23]
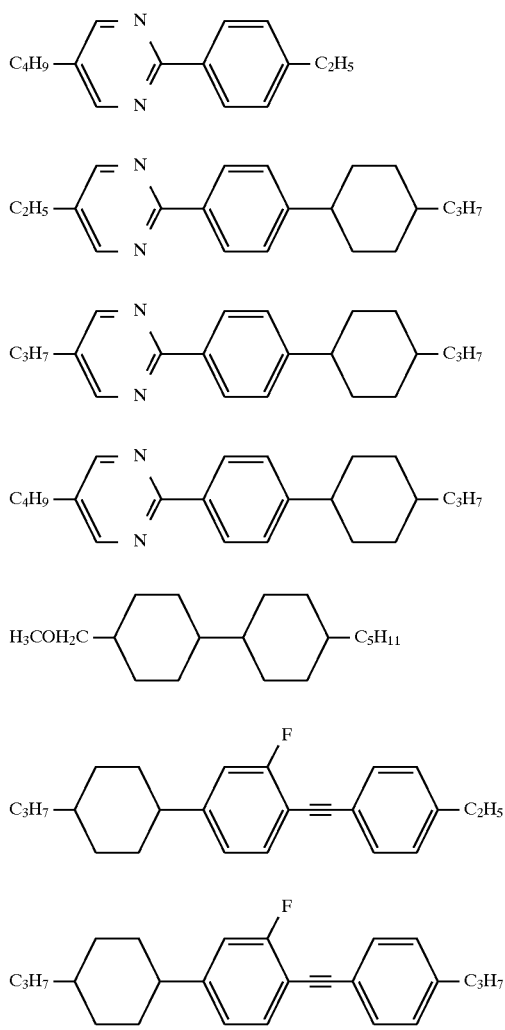
9%
7%
6%
6%
8%
6%
6%
6%
[Composition Example 24]
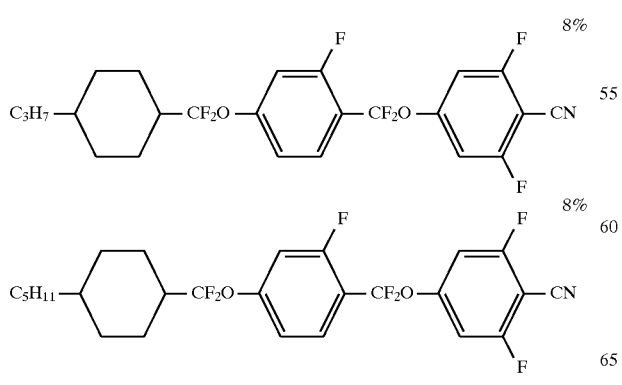
8%
8%
[Composition Example 24]
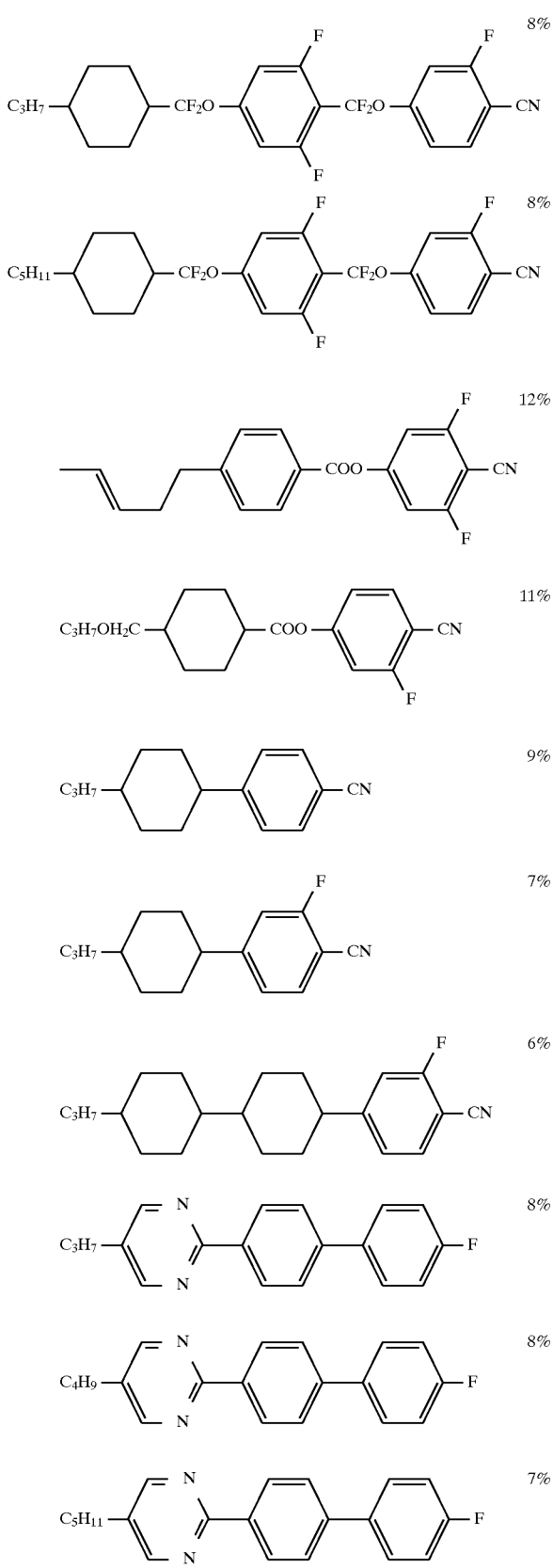
8%
8%
12%
11%
9%
7%
6%
8%
8%
7%

[Composition Example 25]
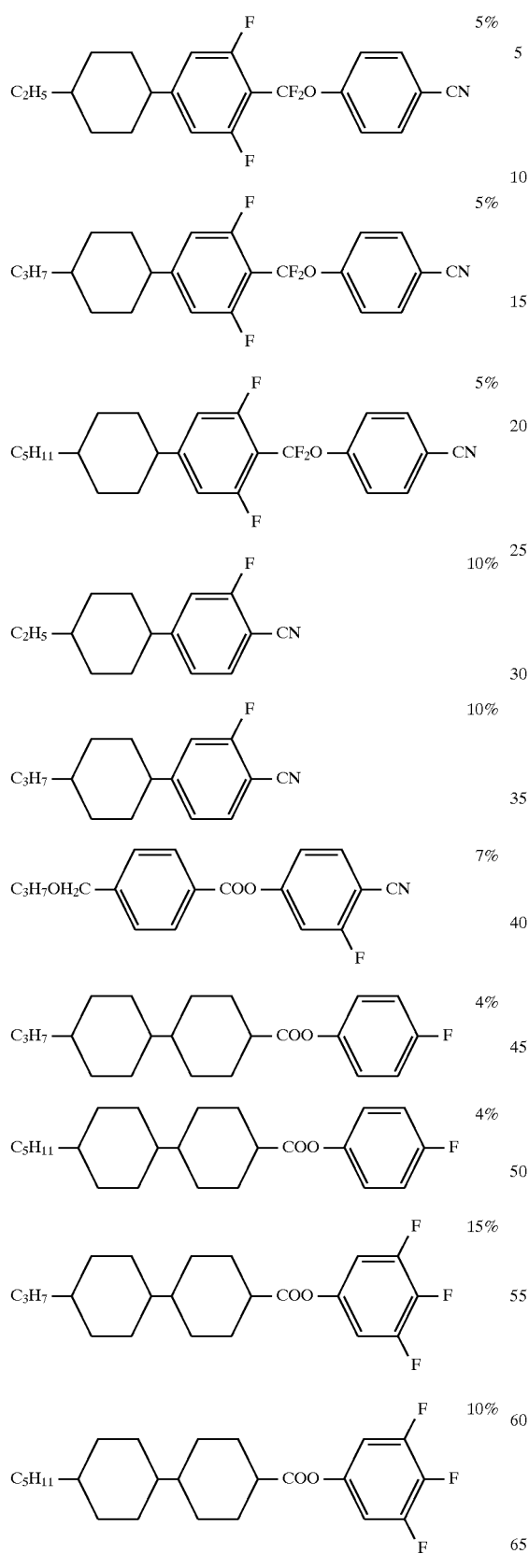
[Composition Example 25]
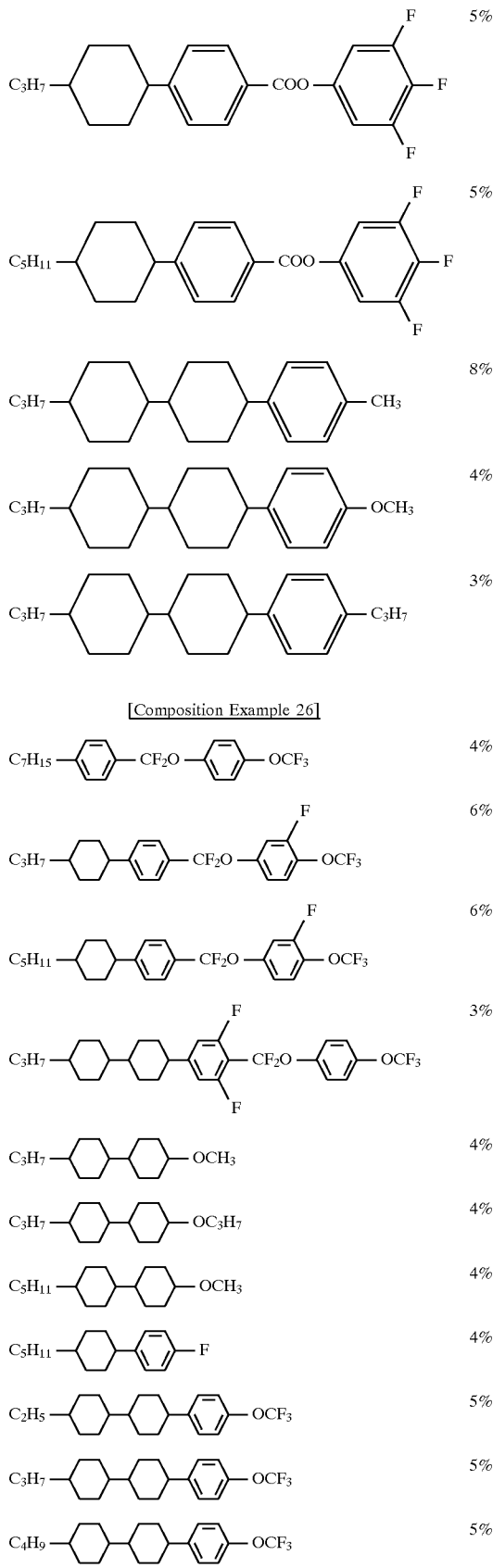
[Composition Example 26]

[Composition Example 26]

| Structure | % |
|---|---|
| C₅H₁₁–Cy–Cy–Ph–OCF₃ | 5% |
| C₃H₇–Cy–Cy–CH₂CH₂–Ph(3,4-F₂) | 5% |
| C₅H₁₁–Cy–Cy–CH₂CH₂–Ph(3,4-F₂) | 5% |
| C₃H₇–Cy–Cy–Ph(2,6-F₂)–OCHF₂ | 10% |
| C₃H₇–Cy–Cy–COO–Ph(3,4-F₂) | 5% |
| C₅H₁₁–Cy–Ph–Ph(3,4-F₂) | 4% |
| C₅H₁₁–Cy–Ph–Ph(3-F)–C₂H₅ | 4% |
| C₃H₇–Cy–Ph–Ph–OCHF₂ | 6% |
| C₅H₁₁–Cy–Ph–Ph–OCHF₂ | 6% |

[Composition Example 27]

| Structure | % |
|---|---|
| C₇H₁₅–Ph(3-F)–CF₂O–Ph(4-F) | 3% |
| C₃H₇–Ph–CF₂O–Ph(3-F)–CF₂O–Ph–OCHF₂ | 7% |
| C₅H₁₁–Ph–CF₂O–Ph(3-F)–CF₂O–Ph–OCHF₂ | 7% |
| C₃H₇–Cy–Ph–CH₂CH₂–Ph(3-F)–CF₂O–Ph(3,5-F₂)–CF₃ | 3% |
| C₅H₁₁–Cy–Ph–F | 8% |
| C₆H₁₃–Cy–Ph–F | 8% |
| C₇H₁₅–Cy–Ph–F | 8% |

[Composition Example 27] (continued)

| Structure | % |
|---|---|
| C₂H₅–Cy–Cy–Ph–OCF₃ | 6% |
| C₃H₇–Cy–Cy–Ph–OCF₃ | 6% |
| C₄H₉–Cy–Cy–Ph–OCF₃ | 6% |
| C₅H₁₁–Cy–Cy–Ph–OCF₃ | 6% |
| C₃H₇–Cy–Cy–CH₂CH₂–Ph–OCF₃ | 5% |
| C₅H₁₁–Cy–Cy–CH₂CH₂–Ph–OCF₃ | 5% |
| C₃H₇–Cy–Ph–Ph(3,4-F₂) | 8% |
| C₅H₁₁–Cy–Ph–Ph(3,4-F₂) | 8% |
| C₃H₇–Cy–Ph(2-F)–Ph–Cy–C₃H₇ | 3% |
| C₅H₁₁–Cy–Ph(2-F)–Ph–Cy–C₃H₇ | 3% |

[Composition Example 28]

| Structure | % |
|---|---|
| C₇H₁₅–Ph–CF₂O–Ph(3,4,5-F₃) | 4% |
| C₃H₇–Ph–CF₂O–Ph–CF₂O–Ph(3,4,5-F₃) | 7% |
| C₅H₁₁–Ph–CF₂O–Ph–CF₂O–Ph(3,4,5-F₃) | 7% |
| C₃H₇–Cy–CH₂CH₂–Cy–Ph(3-F)–CF₂O–Ph(3,4,5-F₃) | 3% |
| C₅H₁₁–Cy–Ph–F | 8% |
| C₇H₁₅–Cy–Ph–F | 8% |

[Composition Example 28]
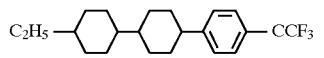 5%
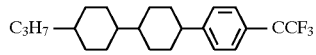 5%
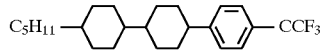 5%
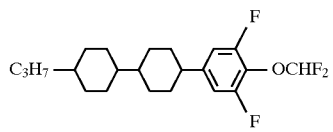 15%
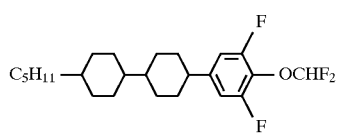 15%
[Composition Example 28]
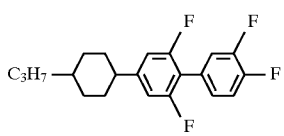 6%
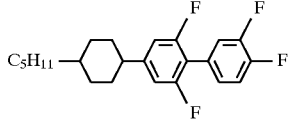 6%
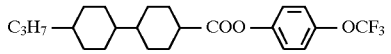 3%
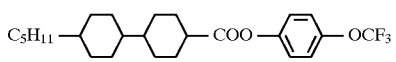 3%
[Composition Example 29]
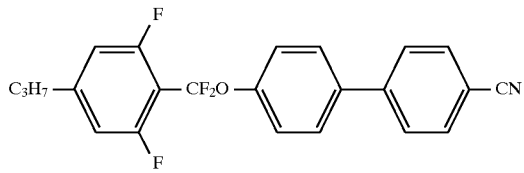 6%
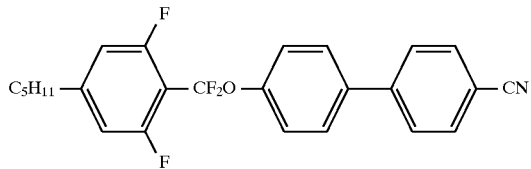 6%
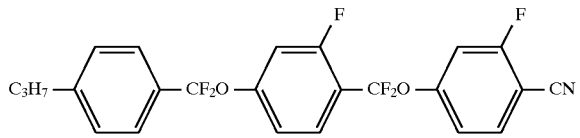 6%
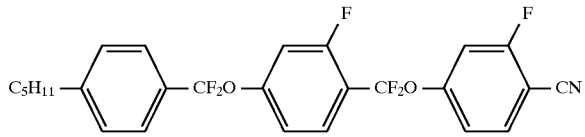 7%
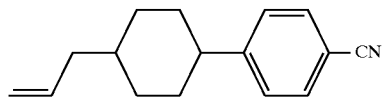 3%
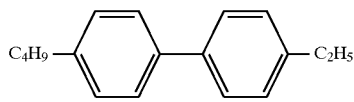 3%

-continued
[Composition Example 29]
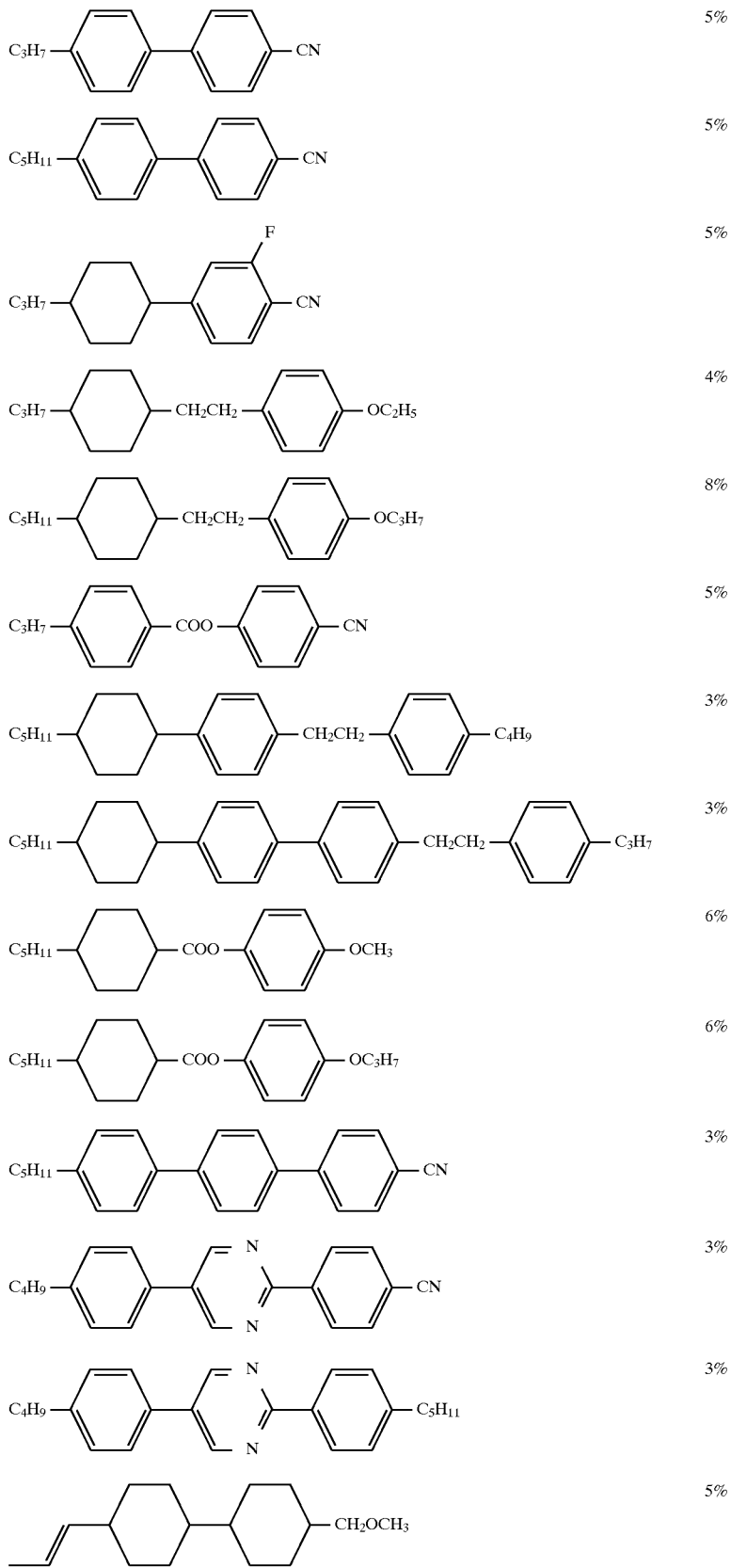
5%
5%
5%
4%
8%
5%
3%
3%
6%
6%
3%
3%
3%
5%

-continued
[Composition Example 29]

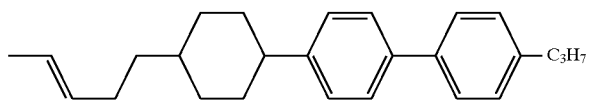

[Composition Example 30]

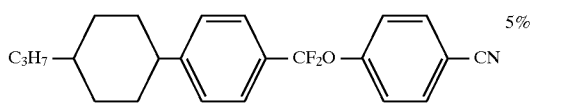 5%

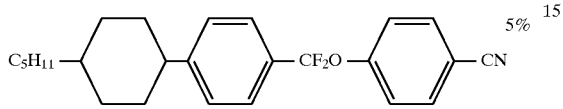 5%

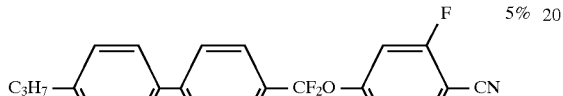 5%

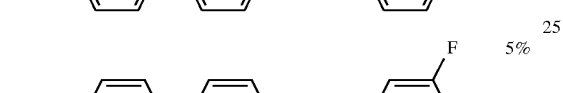 5%

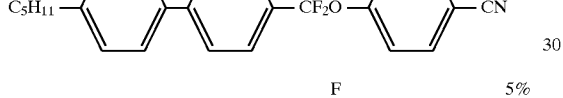 5%

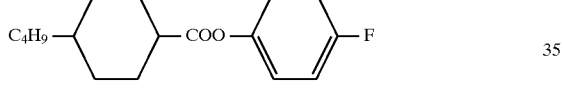 5%

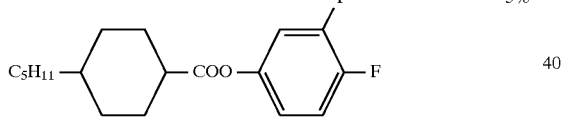 4%

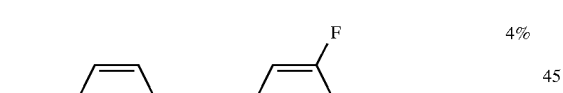 4%

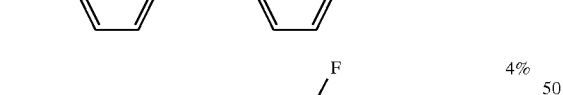 6%

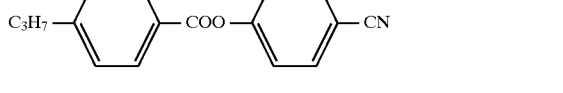 6%

-continued
[Composition Example 30]

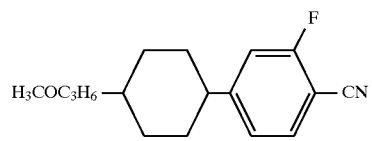 5%

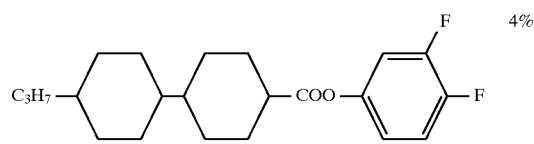 6%

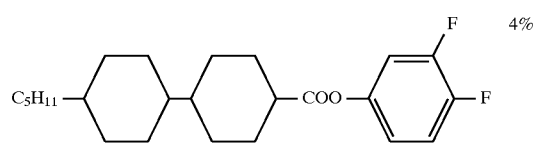 4%

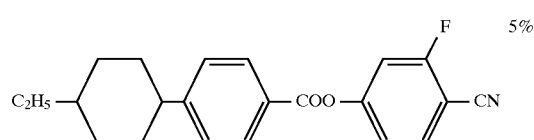 4%

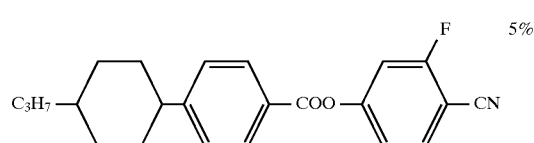 5%

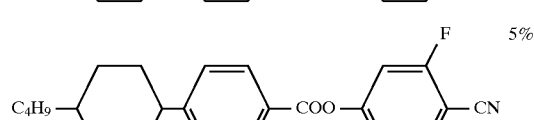 5%

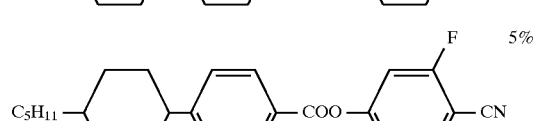 5%

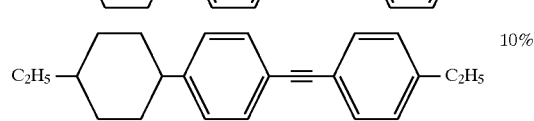 5%

 10%

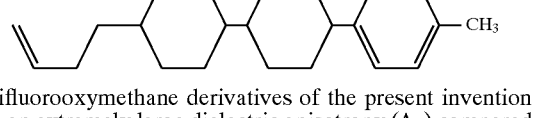 3%

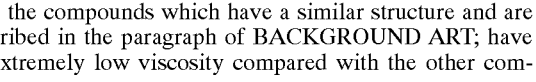 3%

Difluorooxymethane derivatives of the present invention have an extremely large dielectric anisotropy (Δε) compared with the compounds which have a similar structure and are described in the paragraph of BACKGROUND ART; have an extremely low viscosity compared with the other compounds having the same substituent at the terminal of the molecule; and have excellent characteristics as liquid crystalline compounds for low voltages in various modes including active matrix mode and STN mode. Further, the difluorooxymethane derivatives of the present invention are excellent in miscibility with many other liquid crystalline compounds, that is, with existing liquid crystalline compounds including fluorine type compounds as well as ester type, Schiff base type, biphenyl type, phenylcyclohexane type, bicyclohexane type, and heterocyclic type compounds. Also, the derivatives have a characteristic that they are excellent in miscibility particularly at low temperatures. Besides, it is possible to considerably reduce driving voltage (threshold voltage) by adding the compound of the present invention as a component of liquid crystal compositions while suppressing the increase in viscosity.

Methods for preparing and using the compounds of the present invention are illustrated in more detail below with reference to Examples. However, it should be understood that the present invention is by no means restricted by such specific Examples. In each of the Examples, Cr represents crystal, N does nematic phase, S does smectic phase, Iso represents iostropic liquid, and the unit of every phase transition temperature is °C.

EXAMPLE 1

Preparation of difluoro-(4-propylphenyl)-(3,4,5-trifluorophe nyloxy)methane (Compound expressed by the formula (I) wherein R=$C_3H_7$, l, m, and n are 0, $Z_1$, $Z_2$, and $Z_3$ are covalent bond, $L_1$=$L_2$=H, $L_3$=$L_4$=F, and X=F)

In a 500 ml three neck distillation flask provided with a stirrer, thermometer, dropping funnel, and nitrogen gas introducing pipe, 15.0 g (91.4 mmol) of 4-propyl benzoic acid, 22.6 g (109.7 mmol) of dicyclohexylcarbodiimide (hereinafter abbreviated as DCC), and 0.43 g (3.3 mmol) of 4-dimethylaminopyridine (hereinafter abbreviated as DMAP) were dissolved in 200 ml of dichloromethane under nitrogen gas atmosphere, and then 16.2 g (109.7 mmol) of 3,4,5-trifluorophenol was added dropwise to the solution in 5 min while stirring at room temperature. After the dropping, the solution was stirred for 18 hours at room temperature. Then, 100 ml of water was added to the reaction solution to terminate the reaction. After dichloromethane insoluble matter was filtered off, the dichloromethane layer was separated and the water layer was further extracted with 100 ml of dichloromethane. Extracted layers were mixed and washed with 100 ml×2 ("×2" means "repeated twice", the same rule applies hereinafter) of water, 100 ml of saturated aqueous solution of sodium hydrogencarbonate, and 100 ml×2 of water in turn, dried over anhydrous magnesium sulfate, and then concentrated under a reduced pressure to obtain 25.8 g of reaction product. Reaction product was purified by a column chromatography using silica gel as filler and using toluene as developing solvent to obtain 22.8 g of colorless crystal product. This product was 3,4,5-trifluoro-(4-propylphenyl)benzoate.

Subsequently, in a 1000 ml egg-plant type flask provided with a nitrogen gas introducing pipe and cooling pipe, 22.8 g (77.6 mmol) of 3,4,5-trifluoro-(4-propylphenyl)benzoate obtained by the procedures mentioned above and 62.8 g (155.2 mmol) of 2,4-bis(methoxyphenyl)-1,3-dithia-2,4-diphosphetane-2,4-disulfide (hereinafter abbreviated as Lawesson's reagent) were dissolved in 400 ml of toluene, and the solution was refluxed while stirring under nitrogen gas stream for 60 hours. After the reaction solution was cooled down to room temperature, 200 ml of water was added, the toluene layer was separated, and then the water layer was further extracted with 150 ml of toluene. Organic layers were mixed, washed with 200 ml×2 of water, 100 ml of saturated aqueous solution of sodium hydrogencarbonate, 100 ml of 10% aqueous solution of sodium hydrogensulfite, and 200 ml×2 of water in turn, dried over anhydrous magnesium sulfate, and then concentrated under a reduced pressure to obtain 23.9 g of brown crystalline mixture. Reaction product was purified by a column chromatography using silica gel as filler and using heptane as developing solvent, and then recrystallized from heptane to obtain 5.4 g of yellow needle-like crystal product. This product was 4-propylphenyl carbothio acid-O-3,4,5-trifluorophenyl.

Subsequently, the thioncarboxylic acid ester derivative was subjected to a gem-fluorination. That is, in a 100 ml egg-plant type flask provided with a nitrogen gas introducing pipe, 5.4 g (17.4 mmol) of 4-propylphenyl carbothio acid-O-3,4,5-trifluorophenyl was dissolved in 50 ml of dichloromethane, and then 8.4 g (52.2 mmol) of diethylaminosulfur trifluoride (hereinafter abbreviated as DAST) was added to the solution and then the solution was stirred at room temperature for 28 hours. Reaction solution was added with 50 ml of water, the dichloromethane layer was separated, and the water layer was further extracted with 50 ml of dichloromethane. Extracted layers were mixed, washed with 50 ml×2 of water, 30 ml of saturated aqueous solution of sodium hydrogencarbonate, and 50 ml×2 of water in turn, dried over anhydrous magnesium sulfate, and then concentrated under a reduced pressure to obtain 4.5 g of light yellow oily product. Reaction product was purified by a column chromatography using silica gel as filler and using heptane as developing solvent, and then recrystallized from heptane to obtain 1.2 g of colorless needle-like crystal product. This product was difluoro-(4-propylphenyl)-(3,4,5-trifluorophenyloxy) methane.

Following compounds can be prepared according to the preparation method mentioned above by using 4-alkylbenzoic acids having a different alkyl chain in place of 4-propylbenzoic acid:

Difluoro-(4-methylphenyl)-(3,4,5-trifluorophenyloxy) methane
Difluoro-(4-ethylphenyl)-(3,4,5-trifluorophenyloxy) methane
Difluoro-(4-butylphenyl)-(3,4,5-trifluorophenyloxy) methane
Difluoro-(4-pentylphenyl)-(3,4,5-trifluorophenyloxy) methane
Difluoro-(4-hexylphenyl)-(3,4,5-trifluorophenyloxy) methane
Difluoro-(4-heptylphenyl)-(3,4,5-trifluorophenyloxy) methane
Difluoro-(4-octylphenyl)-(3,4,5-trifluorophenyloxy) methane
Difluoro-(4-nonylphenyl)-(3,4,5-trifluorophenyloxy) methane
Difluoro-(4-decylphenyl)-(3,4,5-trifluorophenyloxy) methane Also, the following compounds can be prepared according to the preparation method mentioned above by using several known phenol derivatives in place of 3,4,5-trifluorophenol:

Difluoro-(4-ethylphenyl)-(4-trifluoromethylphenyloxy) methane
Difluoro-(4-propylphenyl)-(4-trifluoromethylphenyloxy) methane
Difluoro-(4-butylphenyl)-(4-trifluoromethylphenyloxy) methane
Difluoro-(4-pentylphenyl)-(4-trifluoromethylphenyloxy) methane Difluoro-(4-ethylphenyl)-(4-difluoromethoxyphenyloxy) methane
Difluoro-(4-propylphenyl)-(4-difluoromethoxyphenyloxy) methane
Difluoro-(4-butylphenyl)-(4-difluoromethoxyphenyloxy) methane
Difluoro-(4-pentylphenyl)-(4-difluoromethoxyphenyloxy) methane
Difluoro-(4-ethylphenyl)-(4-trifluoromethoxyphenyloxy) methane
Difluoro-(4-propylphenyl)-(4-trifluoromethoxyphenyloxy) methane
Cr 12.1 Iso
Difluoro-(4-butylphenyl)-(4-trifluoromethoxyphenyloxy) methane
Difluoro-(4-pentylphenyl)-(4-trifluoromethoxyphenyloxy) methane
Difluoro-(4-ethylphenyl)-(3-fluoro-4-trifluoromethylphenyloxy)methane
Difluoro-(4-propylphenyl)-(3-fluoro-4-trifluoromethylphenyloxy) methane
Difluoro-(4-butylphenyl)-(3-fluoro-4-trifluoromethylphenyloxy)methane
Difluoro-(4-pentylphenyl)-(3-fluoro-4-trifluoromethylphenyloxy) methane
Difluoro-(4-ethylphenyl)-(3,5-difluoro-4-trifluoromethylphenyloxy)methane
Difluoro-(4-propylphenyl)-(3,5-difluoro-4-trifluoromethylphenyloxy)methane
Difluoro-(4-butylphenyl)-(3,5-difluoro-4-trifluoromethylphenyloxy)methane
Difluoro-(4-pentylphenyl)-(3,5-difluoro-4-trifluoromethylphenyloxy)methane
Difluoro-(4-ethylphenyl)-(3-fluoro-4-trifluoromethoxyphenyloxy)methane
Difluoro-(4-propylphenyl)-(3-fluoro-4-trifluoromethoxyphenyloxy) methane
Difluoro-(4-butylphenyl)-(3-fluoro-4-trifluoromethoxyphenyloxy)methane
Difluoro-(4-pentylphenyl)-(3-fluoro-4-trifluoromethoxyphenyloxy) methane
Difluoro-(4-ethylphenyl)-(3,5-difluoro-4-trifluoromethoxyphenyloxy)methane
Difluoro-(4-propylphenyl)-(3,5-difluoro-4-trifluoromethoxyphenyloxy)methane
Difluoro-(4-butylphenyl)-(3,5-difluoro-4-trifluoromethoxyphenyloxy)methane
Difluoro-(4-pentylphenyl)-(3,5-difluoro-4-trifluoromethoxyphenyloxy)methane
Difluoro-(4-ethylphenyl)-(3-fluoro-4-difluoromethoxyphenyloxy)methane
Difluoro-(4-propylphenyl)-(3-fluoro-4-difluoromethoxyphenyloxy)methane
Difluoro-(4-butylphenyl)-(3-fluoro-4-difluoromethoxyphenyloxy)methane
Difluoro-(4-pentylphenyl)-(3-fluoro-4-difluoromethoxyphenyloxy)methane
Difluoro-(4-ethylphenyl)-(3,5-difluoro-4-difluoromethoxyphenyloxy)methane
Difluoro-(4-propylphenyl)-(3,5-difluoro-4-difluoromethoxyphenyloxy)methane
Difluoro-(4-butylphenyl)-(3,5-difluoro-4-difluoromethoxyphenyloxy)methane
Difluoro-(4-pentylphenyl)-(3,5-difluoro-4-difluoromethoxyphenyloxy)methane
Difluoro-(2-fluoro-4-ethylphenyl)-(3,5-difluoro-4-trifluoromethylphenyloxy)methane
Difluoro-(2-fluoro-4-propylphenyl)-(3,5-difluoro-4-trifluoromethylphenyloxy)methane
Difluoro-(2-fluoro-4-butylphenyl)-(3,5-difluoro-4-trifluoromethylphenyloxy)methane
Difluoro-(2-fluoro-4-pentylphenyl)-(3,5-difluoro-4-trifluoromethylphenyloxy)methane
Difluoro-(2-fluoro-4-ethylphenyl)-(3,5-difluoro-4-trifluoromethoxyphenyloxy)methane
Difluoro-(2-fluoro-4-propylphenyl)-(3,5-difluoro-4-trifluoromethoxyphenyloxy)methane
Difluoro-(2-fluoro-4-butylphenyl)-(3,5-difluoro-4-trifluoromethoxyphenyloxy)methane
Difluoro-(2-fluoro-4-pentylphenyl)-(3,5-difluoro-4-trifluoromethoxyphenyloxy)methane
Difluoro-(2-fluoro-4-ethylphenyl)-(3,5-difluoro-4-difluoromethoxyphenyloxy)methane
Difluoro-(2-fluoro-4-propylphenyl)-(3,5-difluoro-4-difluoromethoxyphenyloxy)methane
Difluoro-(2-fluoro-4-butylphenyl)-(3,5-difluoro-4-difluoromethoxyphenyloxy)methane
Difluoro-(2-fluoro-4-pentylphenyl)-(3,5-difluoro-4-difluoromethoxyphenyloxy)methane
Difluoro-(2-fluoro-4-ethylphenyl)-(3,4,5-trifluorophenyloxy)methane
Difluoro-(2-fluoro-4-propylphenyl)-(3,4,5-trifluorophenyloxy)methane
Difluoro-(2-fluoro-4-butylphenyl)-(3,4,5-trifluorophenyloxy)methane
Difluoro-(2-fluoro-4-pentylphenyl)-(3,4,5-trifluorophenyloxy)methane
Difluoro-(2,6-difluoro-4-ethylphenyl)-(3,5-difluoro-4-trifluoromethylphenyloxy)methane
Difluoro-(2,6-difluoro-4-propylphenyl)-(3,5-difluoro-4-trifluoromethylphenyloxy)methane
Difluoro-(2,6-difluoro-4-butylphenyl)-(3,5-difluoro-4-trifluoromethylphenyloxy)methane
Difluoro-(2,6-difluoro-4-pentylphenyl)-(3,5-difluoro-4-trifluoromethylphenyloxy)methane
Difluoro-(2,6-difluoro-4-ethylphenyl)-(3,5-difluoro-4-trifluoromethoxyphenyloxy)methane
Difluoro-(2,6-difluoro-4-propylphenyl)-(3,5-difluoro-4-trifluoromethoxyphenyloxy)methane
Difluoro-(2,6-difluoro-4-butylphenyl)-(3,5-difluoro-4-trifluoromethoxyphenyloxy)methane
Difluoro-(2,6-difluoro-4-pentylphenyl)-(3,5-difluoro-4-trifluoromethoxyphenyloxy)methane
Difluoro-(2,6-difluoro-4-ethylphenyl)-(3,5-difluoro-4-difluoromethoxyphenyloxy)methane
Difluoro-(2,6-difluoro-4-propylphenyl)-(3,5-difluoro-4-difluoromethoxyphenyloxy)methane
Difluoro-(2,6-difluoro-4-butylphenyl)-(3,5-difluoro-4-difluoromethoxyphenyloxy)methane
Difluoro-(2,6-difluoro-4-pentylphenyl)-(3,5-difluoro-4-difluoromethoxyphenyloxy)methane
Difluoro-(2,6-difluoro-4-ethylphenyl)-(3,4,5-trifluorophenyloxy)methane
Difluoro-(2,6-difluoro-4-propylphenyl)-(3,4,5-trifluorophenyloxy)methane
Difluoro-(2,6-difluoro-4-butylphenyl)-(3,4,5-trifluorophenyloxy)methane
Difluoro-(2,6-difluoro-4-pentylphenyl)-(3,4,5-trifluorophenyloxy)methane

EXAMPLE 2

Preparation of difluoro-[4-(trans-4-propylcyclohexyl)phenyl]-(3,4,5-trifluorophenyloxy)methane (Compound expressed by the formula (I) wherein R=$C_3H_7$, l=1, m and n are 0, ring $A_1$ is trans-1,4-cyclohexylene group, $Z_1$, $Z_2$, and $Z_3$ are covalent bond, $L_1=L_2=H$, $L_3=L_4=F$, and $X=F$)

In a 500 ml three neck distillation flask provided with a stirrer, thermometer, dropping funnel, and nitrogen gas introducing pipe, 15.0 g (60.9 mmol) of 4-(trans-4-propylcyclohexyl)benzoic acid, 15.1 g (73.1 mmol) of DCC, and 0.3 g (2.2 mmol) of DMAP were dissolved in 250 ml of dichloromethane under nitrogen gas atmosphere, and then 10.8 g (73. mmol) of 3,4,5-trifluorophenol was added dropwise in 3 min while stirring at room temperature. After the dropping, the solution was stirred for 10 hours at room temperature. Then, 100 ml of water was added to the reaction solution. After dichloromethane insoluble matter was filtered off, the dichloromethane layer was separated, the water layer was further extracted with 200 ml of dichloromethane. Extracted layers were mixed and washed with 100 ml×2 of water, 100 ml of saturated aqueous solution of sodium hydrogencarbonate, and 100 ml×2 of water in turn, dried over anhydrous magnesium sulfate, and then concentrated under a reduced pressure to obtain 23.8 g of reaction product. Reaction product was purified by a column chromatography using silica gel as filler and using toluene as developing solvent, and then recrystallized from a mixed solvent of heptane-ethanol to obtain 13.2 g of colorless crystal product. This product was 3,4,5-trifluoro-[4-(trans-4-propylcyclohexyl)phenyl]benzoate.

Subsequently, in a 1000 ml egg-plant type flask provided with a nitrogen gas introducing pipe and cooling pipe, 13.2 g (35.2 mmol) of 3,4,5-trifluoro-[4-(trans-4-propylcyclohexyl) phenyl]benzoate obtained by the procedures mentioned above and 28.5 g (70.4 mmol) of Lawesson's reagent were dissolved in 500 ml of toluene, and the solution was refluxed while stirring under nitrogen gas stream for 60 hours. After the reaction solution was cooled down to room temperature, 200 ml of water was added, the toluene layer was separated, and then the water layer was further extracted with 150 ml of toluene. Organic layers were mixed, washed with 200 ml×2 of water, 100 ml of saturated aqueous solution of sodium hydrogencarbonate, 100 ml of 10% aqueous solution of sodium hydrogensulfite, and 200 ml×2 of water in turn, dried over anhydrous magnesium sulfate, and then concentrated under a reduced pressure to obtain 13.8 g of brown crystalline mixture. Reaction product was purified by a column chromatography using silica gel as filler and using heptane as developing solvent, and then recrystallized from heptane to obtain 4.7 g of yellow needle-like crystal product having a phase transition point of Cr 127.7°–128.2° C. Iso. This product was 4-(trans-4-propylcyclohexyl)phenylcarbothio acid-O-3,4,5-trifluorophenyl.

$^1$H-NMR (CDCl$_3$; δ ppm) 0.8–2.0(16H,m), 2.57(1H,m), 6.78(2H,m), 7.29(2H,d,J=8,2 Hz), and 8.23(2H d,J=8,2 Hz).

Subsequently, in a 1000 ml egg-plant type flask provided with a nitrogen gas introducing pipe, 4.7 g (12.1 mmol) of 4-(trans-4-propylcyclohexyl)phenylcarbothio acid-O-3,4,5-trifluoro phenyl was dissolved in 50 ml of dichloromethane at room temperature, and then 5.9 g (36.2 mmol) of DAST was added to the solution and the solution was stirred at room temperature for 34 hours. Reaction solution was added with 50 ml of water, the dichloromethane layer was separated, and the water layer was further extracted with 50 ml of dichloromethane. Extracted layers were mixed, washed with 50 ml×2 of water, 30 ml of saturated aqueous solution of sodium hydrogencarbonate, and 50 ml×2 of water in turn, dried over anhydrous magnesium sulfate, and then concentrated under a reduced pressure to obtain 4.3 g of colorless crystal product. Reaction product was purified by a column chromatography using silica gel as filler and using heptane as developing solvent, and then recrystallized from heptane to obtain 1.5 g of colorless needle-like crystal product (phase transition point: Cr 70.5–71.4 Iso). This product was difluoro-[4-(trans-4-propylcyclohexyl)phenyl]-(3,4,5-trifluorophenyloxy)methane.

$^1$H-NMR (CDCl$_3$; δ ppm) 0.8–2.10(16H,m), 2.60(1H,m), 6.96(2H,m), 7.32(2H,d,J=8,6 Hz), and 7.62(2H,d,J=8,6 Hz).
$^{19}$F-NMR (CDCl$_3$; δ ppm) −66.754 (2F,s,—C$\underline{F}_2$O—), −133.521(2F,d), −164.754(1F,t) GC-MS (CI) m/z251 (100%), 379(M$^+$+1-HF,34), and 125(27).

Following compounds can be prepared according to the preparation method mentioned above by using 4-(trans-4-alkylcyclohexyl)benzoic acids having a different alkyl chain in place of 4-(trans-4-propylcyclohexyl)benzoic acid:

Difluoro-[4-(trans-4-methylcyclohexyl)phenyl]-(3,4,5-trifluorophenyloxy)methane

Difluoro-[4-(trans-4-ethylcyclohexyl)phenyl]-(3,4,5-trifluorophenyloxy)methane

Difluoro-[4-(trans-4-butylcyclohexyl)phenyl]-(3,4,5-trifluorophenyloxy)methane

Difluoro-[4-(trans-4-pentylcyclohexyl)phenyl]-(3,4,5-trifluorophenyloxy)methane
Cr 62.6–63.0 Iso Difluoro-[4-(trans-4-hexylcyclohexyl)phenyl]-(3,4,5-trifluorophenyloxy)methane Difluoro-[4-(trans-4-heptylcyclohexyl)phenyl]-(3,4,5-trifluorophenyloxy)methane Difluoro-[4-(trans-4-octylcyclohexyl)phenyl]-(3,4,5-trifluorophenyloxy)methane Difluoro-[4-(trans-4-nonylcyclohexyl)phenyl]-(3,4,5-trifluorophenyloxy)methane Difluoro-[4-(trans-4-decylcyclohexyl)phenyl]-(3,4,5-trifluorophenyloxy)methane Following compounds can be prepared according to the preparation method mentioned above by using several known phenol derivatives in place of 3,4,5-trifluorophenol:

Difluoro-[4-(trans-4-ethylcyclohexyl)phenyl]-(3,4-difluorophenyloxy)methane

Difluoro-[4-(trans-4-propylcyclohexyl)phenyl]-(3,4-difluorophenyloxy)methane

Difluoro-[4-(trans-4-pentylcyclohexyl)phenyl]-(3,4-difluorophenyloxy)methane
Cr 42.9–43.4N 66.2–67.5 Iso Difluoro-[4-(trans-4-ethylcyclohexyl)phenyl]-(4-trifluoromethylphenyloxy)methane Difluoro-[4-(trans-4-propylcyclohexyl)phenyl]-(4-trifluoromethylphenyloxy)methane Difluoro-[4-(trans-4-butylcyclohexyl)phenyl]-(4-trifluoromethylphenyloxy)methane Difluoro-[4-(trans-4-pentylcyclohexyl)phenyl]-(4-trifluoromethylphenyloxy)methane
Cr 79.6–79.9 Iso Difluoro-[4-(trans-4-ethylcyclohexyl)phenyl]-(4-difluoromethoxyphenyloxy)methane Difluoro-[4-(trans-4-propylcyclohexyl)phenyl]-(4-difluoromethoxyphenyloxy)methane Difluoro-[4-(trans-4-butylcyclohexyl)phenyl]-(4-difluoromethoxyphenyloxy)methane Difluoro-[4-(trans-4-pentylcyclohexyl)phenyl]-(4-difluoromethoxyphenyloxy)methane Difluoro-[4-(trans-4-ethylcyclohexyl)phenyl]-(4-trifluoromethoxyphenyloxy)methane Difluoro-[4-(trans-4-propylcyclohexyl)phenyl]-(4-trifluoromethoxyphenyloxy)methane
Cr 57.3–58.2 S$_B$ 70.9–72.0N 83.1–83.5 Iso Difluoro-[4-(trans-4-butylcyclohexyl)phenyl]-(4-trifluoromethoxyphenyloxy)methane Difluoro-[4-(trans-4-pentylcyclohexyl)phenyl]-(4-trifluoromethoxyphenyloxy)methane
Cr 68.1–68.3 SB 80.5–80.8N 90.2–90.4 Iso
Difluoro-[4-(trans-4-ethylcyclohexyl)phenyl]-(4-cyanophenyloxy) methane
Difluoro-[4-(trans-4-propylcyclohexyl)phenyl]-(4-cyanophenyloxy) methane
Difluoro-[4-(trans-4-butylcyclohexyl)phenyl]-(4-cyanophenyloxy) methane
Difluoro-[4-(trans-4-pentylcyclohexyl)phenyl]-(4-cyanophenyloxy) methane
Difluoro-[4-(trans-4-ethylcyclohexyl)phenyl]-(3-fluoro-4-trifluoromethoxyphenyloxy)methane
Difluoro-[4-(trans-4-propylcyclohexyl)phenyl]-(3-fluoro-4-trifluoromethoxyphenyloxy)methane
Difluoro-[4-(trans-4-butylcyclohexyl)phenyl]-(3-fluoro-4-trifluoromethoxyphenyloxy)methane
Difluoro-[4-(trans-4-pentylcyclohexyl)phenyl]-(3-fluoro-4-trifluoromethoxyphenyloxy)methane
Cr 35.9–36.3N 61.1–61.3 Iso
Difluoro-[4-(trans-4-ethylcyclohexyl)phenyl]-(3-fluoro-4-trifluoromethylphenyloxy)methane
Difluoro-[4-(trans-4-propylcyclohexyl)phenyl]-(3-fluoro-4-trifluoromethylphenyloxy)methane
Difluoro-[4-(trans-4-butylcyclohexyl)phenyl]-(3-fluoro-4-trifluoromethylphenyloxy)methane
Difluoro-[4-(trans-4-pentylcyclohexyl)phenyl]-(3-fluoro-4-trifluoromethylphenyloxy)methane
Difluoro-[4-(trans-4-ethylcyclohexyl)phenyl]-(3-fluoro-4-difluoromethoxyphenyloxy)methane
Difluoro-[4-(trans-4-propylcyclohexyl)phenyl]-(3-fluoro-4-difluoromethoxyphenyloxy)methane
Difluoro-[4-(trans-4-butylcyclohexyl)phenyl]-(3-fluoro-4-difluoromethoxyphenyloxy)methane
Difluoro-[4-(trans-4-pentylcyclohexyl)phenyl]-(3-fluoro-4-difluoromethoxyphenyloxy)methane
Difluoro-[4-(trans-4-ethylcyclohexyl)phenyl]-(3-fluoro-4-cyanophenyloxy)methane
Difluoro-[4-(trans-4-propylcyclohexyl)phenyl]-(3-fluoro-4-cyanophenyloxy)methane
Cr 65.4–66.3N 104.9–105.4 Iso
Difluoro-[4-(trans-4-butylcyclohexyl)phenyl]-(3-fluoro-4-cyanophenyloxy)methane
Difluoro-[4-(trans-4-pentylcyclohexyl)phenyl]-(3-fluoro-4-cyanophenyloxy)methane
Difluoro-[4-(trans-4-ethylcyclohexyl)phenyl]-(3,5-difluoro-4-trifluoromethoxyphenyloxy)methane
Difluoro-[4-(trans-4-propylcyclohexyl)phenyl]-(3,5-difluoro-4-trifluoromethoxyphenyloxy)methane
Difluoro-[4-(trans-4-butylcyclohexyl)phenyl]-(3,5-difluoro-4-trifluoromethoxyphenyloxy)methane
Difluoro-[4-(trans-4-pentylcyclohexyl)phenyl]-(3,5-difluoro-4-trifluoromethoxyphenyloxy)methane
Difluoro-[4-(trans-4-ethylcyclohexyl)phenyl]-(3,5-difluoro-4-trifluoromethylphenyloxy)methane
Difluoro-[4-(trans-4-propylcyclohexyl)phenyl]-(3,5-difluoro-4-trifluoromethylphenyloxy)methane
Difluoro-[4-(trans-4-butylcyclohexyl)phenyl]-(3,5-difluoro-4-trifluoromethylphenyloxy)methane
Difluoro-[4-(trans-4-pentylcyclohexyl)phenyl]-(3,5-difluoro-4-trifluoromethylphenyloxy)methane
Cr 56.9–57.5 Iso
Difluoro-[4-(trans-4-ethylcyclohexyl)phenyl]-(3,5-difluoro-4-difluoromethoxyphenyloxy)methane
Difluoro-[4-(trans-4-propylcyclohexyl)phenyl]-(3,5-difluoro-4-difluoromethoxyphenyloxy)methane
Difluoro-[4-(trans-4-butylcyclohexyl)phenyl]-(3,5-difluoro-4-difluoromethoxyphenyloxy)methane
Difluoro-[4-(trans-4-pentylcyclohexyl)phenyl]-(3,5-difluoro-4-difluoromethoxyphenyloxy)methane
Difluoro-[4-(trans-4-ethylcyclohexyl)phenyl]-(3,5-difluoro-4-cyanophenyloxy)methane
Difluoro-[4-(trans-4-propylcyclohexyl)phenyl]-(3,5-difluoro-4-cyanophenyloxy)methane
Difluoro-[4-(trans-4-butylcyclohexyl)phenyl]-(3,5-difluoro-4-cyanophenyloxy)methane
Difluoro-[4-(trans-4-pentylcyclohexyl)phenyl]-(3,5-difluoro-4-cyanophenyloxy)methane

EXAMPLE 3

Preparation of difluoro-[2-fluoro-4-(trans-4-propylcyclohexyl)phenyl]-(4-trifluoromethoxyphenyloxy) methane (Compound expressed by the formula (I) wherein $R=C_3H_7$, $l=1$, m and n are 0, ring $A_1$ is trans-1,4-cyclohexylene group, $Z_1$, $Z_2$, and $Z_3$ are covalent bond, $L_1=F$, $L_2=L_3=L_4=H$, and $X=OCF_3$)

In a 500 ml three neck distillation flask provided with a stirrer, thermometer, dropping funnel, and nitrogen gas introducing pipe, 1.8 g (75.8 mmol) of magnesium turnings and 50 ml of diethyl ether were added under nitrogen gas atmosphere and then a solution of 25 g (72.2 mmol) of 2-fuloro-4-(trans-4-propylcyclohexyl)iodobenzene in 50 ml of diethyl ether was added dropwise while stirring under reflux condition in 40 min. Reaction solution was further refluxed on a hot water bath for 1 hour to age. Subsequently, the reaction solution was cooled down with ice to lower than 10° C., 7.5 g (987 mmol) of carbon disulfide was added dropwise while keeping the temperature at lower than 10° C., raised up to room temperature, and then further stirred at room temperature for 3 hours. Reaction solution was cooled again down with ice to lower than 10° C. and added dropwise with 50 ml of 2N aqueous solution of hydrochloric acid to terminate the reaction. From the reaction solution, the diethyl ether layer was separated and then the water layer was further extracted with 200 ml of diethyl ether. The organic layers were mixed, washed with 200 ml of water twice, dried over anhydrous magnesium sulfate, and then concentrated to obtain 19.7 g of dark purplish red solid of dithiocarboxylic acid derivative.

Subsequently, in a 300 ml egg-plant type flask provided with a cooling pipe, 19.7 g of dithiocarboxylic acid derivative obtained by the procedures mentioned above was dissolved in 150 ml of diethyl ether, and then 25.8 g (217.0 mmol) of thionyl chloride was added dropwise to the solution while stirring at room temperature in 15 min. After the dropping, reflux was conducted on a hot water bath for 8 hours. After the reaction solution was heated to distill off diethyl ether, the solution was concentrated under a reduced pressure with an aspirator to obtain 18.4 g of thio acid chloride derivative. Subsequently, in a 500 ml three neck distillation flask provided with a stirrer, thermometer, dropping funnel, and nitrogen gas introducing pipe, 6.4 g (36.1 mmol) of 4-trifluoromethoxyphenol and 5.7 g (72.2 mmol) of pyridine were dissolved in 50 ml of toluene under nitrogen gas atmosphere, added dropwise with 18.4 g of the thio acid chloride derivative obtained by the procedures mentioned above at room temperature while stirring in 20 min. Then, the internal temperature on the hot water bath was heated to 60° C. and stirred for 3 hours. After cooled down to room temperature, the reaction solution was added dropwise with 300 ml of water and 30 ml of 2N aqueous solution of hydrochloric acid to terminate the reaction, the toluene layer was separated, and the water layer was further extracted with 200 ml of toluene. The extracted layer was washed with 200 ml×2 of water, 100 ml of 2N aqueous solution of sodium hydroxide, and 200 ml×3 of water in turn, dried over anhydrous magnesium sulfate, and then concentrated under a reduced pressure to obtain 14.9 g of reddish brown crystalline reaction product. Reaction product was purified by a column chromatography using silica gel as filler and using heptane/toluene mixed solvent as developing solvent, and then recrystallized from heptane to obtain 6.7 g of yellow needle-like crystal product. This product was 2-fluoro-4-(trans-4-propylcyclohexyl)phenycarbothio acid-O-4-trifluoromethoxyphenyl.

In a 100 ml egg-plant type flask provided with a nitrogen gas introducing pipe, 6.7 g (15.2 mmol) of 2-fluoro-4-(trans-4-propylcyclohexyl)phenylcarbothio acid-O-4-trifluoromethoxyphenyl was dissolved in 50 ml of dichloromethane at room temperature, and then 4.9 g (30.4 mmol) of DAST was added to the solution and the solution was stirred at room temperature for 28 hours. Reaction solution was added with 50 ml of water, the dichloromethane layer was separated, and the water layer was further extracted with 50 ml of dichloromethane. Extracted layers were mixed, washed with 50 ml×2 of water, 40 ml of saturated aqueous solution of sodium hydrogencarbonate, and 50 ml×2 of water in turn, dried over anhydrous magnesium sulfate, and then concentrated under a reduced pressure to obtain 3.2 g of colorless crystalline reaction product. Reaction product was purified by a column chromatography using silica gel as filler and using heptane as developing solvent, and then recrystallized from heptane to obtain 1.9 g of colorless needle-like crystal product. This product was difluoro-[2-fluoro-4-(trans-4-propylcyclohexyl)phenyl]-(4-trifluoromethoxyphenyloxy)methane.

Following compounds can be prepared according to the preparation method mentioned above by using 2-fluoro-4-(trans-4-alkylcyclohexyl)iodobenzenes having a different alkyl chain in place of 2-fluoro-4-(trans-4-propylcyclohexyl)iodobenzene:

Difluoro-[2-fluoro-4-(trans-4-methylcyclohexyl)phenyl]-(4-trifluoromethoxyphenyloxy)methane
Difluoro-[2-fluoro-4-(trans-4-ethylcyclohexyl)phenyl]-(4-trifluoromethoxyphenyloxy)methane
Difluoro-[2-fluoro-4-(trans-4-butylcyclohexyl)phenyl]-(4-trifluoromethoxyphenyloxy)methane Difluoro-[2-fluoro-4-(trans-4-pentylcyclohexyl)phenyl]-(4-trifluoromethoxyphenyloxy)methane
Difluoro-[2-fluoro-4-(trans-4-hexylcyclohexyl)phenyl]-(4-trifluoromethoxyphenyloxy)methane
Difluoro-[2-fluoro-4-(trans-4-heptylcyclohexyl)phenyl]-(4-trifluoromethoxyphenyloxy)methane
Difluoro-[2-fluoro-4-(trans-4-octylcyclohexyl)phenyl]-(4-trifluoromethoxyphenyloxy)methane
Difluoro-[2-fluoro-4-(trans-4-nonylcyclohexyl)phenyl]-(4-trifluoromethoxyphenyloxy)methane
Difluoro-[2-fluoro-4-(trans-4-decylcyclohexyl)phenyl]-(4-trifluoromethoxyphenyloxy)methane Also, the following compounds can be prepared according to the preparation method mentioned above by using several known phenol derivatives in place of 4-trifluoromethoxyphenol:

Difluoro-[2-fluoro-4-(trans-4-ethylcyclohexyl)phenyl]-(3,5-difluoro-4-trifluoromethoxyphenyloxy)methane
Difluoro-[2-fluoro-4-(trans-4-propylcyclohexyl)phenyl]-(3,5-difluoro-4-trifluoromethoxyphenyloxy)methane
Difluoro-[2-fluoro-4-(trans-4-butylcyclohexyl)phenyl]-(3,5-difluoro-4-trifluoromethoxyphenyloxy)methane
Difluoro-[2-fluoro-4-(trans-4-pentylcyclohexyl)phenyl]-(3,5-difluoro-4-trifluoromethoxyphenyloxy)methane
Difluoro-[2-fluoro-4-(trans-4-ethylcyclohexyl)phenyl]-(3,5-difluoro-4-trifluoromethylphenyloxy)methane
Difluoro-[2-fluoro-4-(trans-4-propylcyclohexyl)phenyl]-(3,5-difluoro-4-trifluoromethylphenyloxy)methane
Difluoro-[2-fluoro-4-(trans-4-butylcyclohexyl)phenyl]-(3,5-difluoro-4-trifluoromethylphenyloxy)methane
Difluoro-[2-fluoro-4-(trans-4-pentylcyclohexyl)phenyl]-(3,5-difluoro-4-trifluoromethylphenyloxy)methane
Difluoro-[2-fluoro-4-(trans-4-ethylcyclohexyl)phenyl]-(3,5-difluoro-4-difluoromethoxyphenyloxy)methane
Difluoro-[2-fluoro-4-(trans-4-propylcyclohexyl)phenyl]-(3,5-difluoro-4-difluoromethoxyphenyloxy)methane
Difluoro-[2-fluoro-4-(trans-4-butylcyclohexyl)phenyl]-(3,5-difluoro-4-difluoromethoxyphenyloxy)methane
Difluoro-[2-fluoro-4-(trans-4-pentylcyclohexyl)phenyl]-(3,5-difluoro-4-difluoromethoxyphenyloxy)methane
Difluoro-[2-fluoro-4-(trans-4-ethylcyclohexyl)phenyl]-(3,4,5-trifluorophenyloxy)methane
Difluoro-[2-fluoro-4-(trans-4-propylcyclohexyl)phenyl]-(3,4,5-trifluorophenyloxy)methane
Difluoro-[2-fluoro-4-(trans-4-butylcyclohexyl)phenyl]-(3,4,5-trifluorophenyloxy)methane
Difluoro-[2-fluoro-4-(trans-4-pentylcyclohexyl)phenyl]-(3,4,5-trifluorophenyloxy)methane
Difluoro-[2-fluoro-4-(trans-4-ethylcyclohexyl)phenyl]-(3,5-difluoro-4-cyanophenyloxy)methane
Difluoro-[2-fluoro-4-(trans-4-propylcyclohexyl)phenyl]-(3,5-difluoro-4-cyanophenyloxy)methane
Difluoro-[2-fluoro-4-(trans-4-butylcyclohexyl)phenyl]-(3,5-difluoro-4-cyanophenyloxy)methane
Difluoro-[2-fluoro-4-(trans-4-pentylcyclohexyl)phenyl]-(3,5-difluoro-4-cyanophenyloxy)methane
Difluoro-[2,6-difluoro-4-(trans-4-ethylcyclohexyl)phenyl]-(3,5-difluoro-4-trifluoromethoxyphenyloxy)methane
Difluoro-[2,6-difluoro-4-(trans-4-propylcyclohexyl)phenyl]-(3,5-difluoro-4-trifluoromethoxyphenyloxy)methane
Difluoro-[2,6-difluoro-4-(trans-4-butylcyclohexyl)phenyl]-(3,5-difluoro-4-trifluoromethoxyphenyloxy)methane
Difluoro-[2,6-difluoro-4-(trans-4-pentylcyclohexyl)phenyl]-(3,5-difluoro-4-trifluoromethoxyphenyloxy)methane
Difluoro-[2,6-difluoro-4-(trans-4-ethylcyclohexyl)phenyl]-(3,5-difluoro-4-trifluoromethylphenyloxy)methane
Difluoro-[2,6-difluoro-4-(trans-4-propylcyclohexyl)phenyl]-(3,5-difluoro-4-trifluoromethylphenyloxy) methane
Difluoro-[2,6-difluoro-4-(trans-4-butylcyclohexyl)phenyl]-(3,5-difluoro-4-trifluoromethylphenyloxy)methane
Difluoro-[2,6-difluoro-4-(trans-4-pentylcyclohexyl)phenyl]-(3,5-difluoro-4-trifluoromethylphenyloxy) methane
Difluoro-[2,6-difluoro-4-(trans-4-ethylcyclohexyl)phenyl]-(3,5-difluoro-4-difluoromethoxyphenyloxy)methane
Difluoro-[2,6-difluoro-4-(trans-4-propylcyclohexyl)phenyl]-(3,5-difluoro-4-difluoromethoxyphenyloxy) methane
Difluoro-[2,6-difluoro-4-(trans-4-butylcyclohexyl)phenyl]-(3,5-difluoro-4-difluoromethoxyphenyloxy)methane
Difluoro-[2,6-difluoro-4-(trans-4-pentylcyclohexyl)phenyl]-(3,5-difluoro-4-difluoromethoxyphenyloxy) methane
Difluoro-[2,6-difluoro-4-(trans-4-ethylcyclohexyl)phenyl]-(3,4,5-trifluorophenyloxy)methane
Difluoro-[2,6-difluoro-4-(trans-4-propylcyclohexyl)phenyl]-(3,4,5-trifluorophenyloxy) methane
Difluoro-[2,6-difluoro-4-(trans-4-butylcyclohexyl)phenyl]-(3,4,5-trifluorophenyloxy)methane
Difluoro-[2,6-difluoro-4-(trans-4-pentylcyclohexyl)phenyl]-(3,4,5-trifluorophenyloxy) methane Difluoro-[2,6-difluoro-4-(trans-4-ethylcyclohexyl)phenyl]-(3,5-difluoro-4-cyanophenyloxy)methane
Difluoro-[2,6-difluoro-4-(trans-4-propylcyclohexyl)phenyl]-(3,5-difluoro-4-cyanophenyloxy)methane
Difluoro-[2,6-difluoro-4-(trans-4-butylcyclohexyl)phenyl]-(3,5-difluoro-4-cyanophenyloxy)methane
Difluoro-[2,6-difluoro-4-(trans-4-pentylcyclohexyl)phenyl]-(3,5-difluoro-4-cyanophenyloxy) methane

EXAMPLE 4

Preparation of difluoro-{4-[2-(trans-4-propylcyclohexyl)ethyl]phenyl}-(3,4,5-trifluorophenyloxy)methane (Compound expressed by the formula (I) wherein R=$C_3H_7$, l=1, m and n are 0, ring $A_1$ is trans-1,4-cyclohexylene group, $Z_1$ is —$CH_2CH_2$—, $Z_2$ and $Z_3$ are covalent bond, $L_1$=$L_2$=H, $L_3$=$L_4$=F, and X=F)

In a 500 ml three neck distillation flask provided with a stirrer, thermometer, dropping funnel, and nitrogen gas introducing pipe, 15.0 g (54.7 mmol) of 4-[2-(trans-4-propylcyclohexyl)ethyl]benzoic acid, 13.5 g (65.6 mmol) of DCC, and 0.25 g (1.9 mmol) of DMAP were dissolved in 250 ml of dichloromethane under nitrogen gas atmosphere, and then 9.7 g (65.6 mmol) of 3,4,5-trifluorophenol was added dropwise to the solution in 3 min while stirring at room temperature. After the dropping, the solution was stirred for 15 hours at room temperature. Then, 100 ml of water was added to the reaction solution. After dichloromethane insoluble matter was filtered off, the dichloromethane layer was separated, and the water layer was further extracted with 200 ml of dichloromethane. Extracted layers were mixed and washed with 100 ml×2 of water, 100 ml of saturated aqueous solution of sodium hydrogencarbonate, and 100 ml×2 of water in turn, dried over anhydrous magnesium sulfate, and then concentrated under a reduced pressure to obtain 22.5 g of reaction product. Reaction product was purified by a column chromatography using silica gel as filler and using toluene as developing solvent, and then recrystallized from a mixed solvent of heptane-ethanol to obtain 12.9 g of colorless crystal product. This product was 3,4,5-trifluoro-{4-[2-(trans-4-propylcyclohexyl)ethyl]phenyl} benzoate.

Subsequently, in a 1000 ml egg-plant type flask provided with a nitrogen gas introducing pipe and cooling pipe, 12.9 g (31.9 mmol) of 3,4,5-trifluoro-{4-[2-(trans-4-propylcyclohexyl) ethyl]phenyl} benzoate obtained by the procedures mentioned above and 25.8 g (63.9 mmol) of Lawesson's reagent were dissolved in 500 ml of toluene, and the solution was refluxed while stirring under nitrogen gas stream for 65 hours. After the reaction solution was cooled down to room temperature, 200 ml of water was added, the toluene layer was separated, and then the water layer was further extracted with 150 ml of toluene. Organic layers were mixed, washed with 200 ml×2 of water, 100 ml of saturated aqueous solution of sodium hydrogencarbonate, 100 ml of 10% aqueous solution of sodium hydrogensulfite, and 200 ml×2 of water in turn, dried over anhydrous magnesium sulfate, and then concentrated under a reduced pressure to obtain 13.3 g of brown crystalline mixture. Reaction product was purified by a column chromatography using silica gel as filler and using heptane as developing solvent, and then recrystallized from heptane to obtain 4.5 g of yellow needle-like crystal product. This product was 4-[2-(trans-4-propylcyclohexyl) ethyl]phenylcarbothio acid-O-3,4,5-trifluorophenyl.

Cr 95.5–97.6 Iso $^1$H-NMR (CDCl$_3$; δ ppm) 0.7–1.9(19H,m), 2.70(2H,m), 6.80(2H,m), 7.25(2H,d,J=8,3 Hz), and 8.21(2H d,J=8,3 Hz).

Subsequently, in a 1000 ml egg-plant type flask provided with a nitrogen gas introducing pipe, 4.5 g (10.8 mmol) of 4-[2-(trans-4-propylcyclohexyl)ethyl]phenylcarbothio acid-O-3,4,5-trifluorophenyl was dissolved in 50 ml of dichloromethane at room temperature, and then 5.3 g (32.6 mmol) of DAST was added to the solution and then the solution was stirred at room temperature for 40 hours. Reaction solution was added with 50 ml of water, the dichloromethane layer was separated, and the water layer was further extracted with 50 ml of dichloromethane. Extracted layers were mixed, washed with 50 ml×2 of water, 30 ml of saturated aqueous solution of sodium hydrogencarbonate, and 50 ml×2 of water in turn, dried over anhydrous magnesium sulfate, and then concentrated under a reduced pressure to obtain 3.9 g of colorless crystal product. Reaction product was purified by a column chromatography using silica gel as filler and using heptane as developing solvent, and then recrystallized from heptane to obtain 1.5 g of colorless needle-like crystal product. This product was difluoro-{4-[2-(trans-4-propylcyclohexyl)ethyl]phenyl}-(3,4,5-trifluorophenyloxy) methane.

Cr 36.8–37.5 (NI 23.5–23.7) Iso $^1$H-NMR (CDCl$_3$; δ ppm) 0.7–2.0(19H,m), 2.68(2H,m), 6.93(2H,m), 7.27(2H,d,J=8,4 Hz), and 7.58(2H,d,J=8,4 Hz).

The following compounds can be prepared according to the preparation method mentioned above by using 4-[2-(trans-4-alkylcyclohexyl)ethyl]benzoic acids having a different alkyl chain in place of 4-[2-(trans-4-propylcyclohexyl)ethyl]benzoic acid:

Difluoro-{4-[2-(trans-4-methylcyclohexyl)ethyl]phenyl}-(3,4,5-trifluorophenyloxy)methane
Difluoro-{4-[2-(trans-4-ethylcyclohexyl)ethyl]phenyl}-(3,4,5-trifluorophenyloxy)methane
Difluoro-{4-[2-(trans-4-butylcyclohexyl)ethyl]phenyl}-(3,4,5-trifluorophenyloxy)methane
Difluoro-{4-[2-(trans-4-pentylcyclohexyl)ethyl]phenyl}-(3,4,5-trifluorophenyloxy)methane
Difluoro-{4-[2-(trans-4-hexylcyclohexyl)ethyl]phenyl}-(3,4,5-trifluorophenyloxy)methane
Difluoro-{4-[2-(trans-4-heptylcyclohexyl)ethyl]phenyl}-(3,4,5-trifluorophenyloxy)methane
Difluoro-{4-[2-(trans-4-octylcyclohexyl)ethyl]phenyl}-(3,4,5-trifluorophenyloxy)methane
Difluoro-{4-[2-(trans-4-nonylcyclohexyl)ethyl]phenyl}-(3,4,5-trifluorophenyloxy)methane
Difluoro-{4-[2-(trans-4-decylcyclohexyl)ethyl]phenyl}-(3,4,5-trifluorophenyloxy)methane Also, the following compounds can be prepared according to the preparation method by using several known phenol derivatives in place of 3,4,5-trifluorophenol:

Difluoro-{4-[2-(trans-4-ethylcyclohexyl)ethyl]phenyl}-(4-trifluoromethylphenyloxy)methane
Difluoro-{4-[2-(trans-4-propylcyclohexyl)ethyl]phenyl}-(4-trifluoromethylphenyloxy)methane
Difluoro-{4-[2-(trans-4-butylcyclohexyl)ethyl]phenyl}-(4-trifluoromethylphenyloxy)methane
Difluoro-{4-[2-(trans-4-pentylcyclohexyl)ethyl]phenyl}-(4-trifluoromethylphenyloxy)methane
Difluoro-{4-[2-(trans-4-ethylcyclohexyl)ethyl]phenyl}-(4-difluoromethoxyphenyloxy)methane
Difluoro-{4-[2-(trans-4-propylcyclohexyl)ethyl]phenyl}-(4-difluoromethoxyphenyloxy)methane
Difluoro-{4-[2-(trans-4-butylcyclohexyl)ethyl]phenyl}-(4-difluoromethoxyphenyloxy)methane
Difluoro-{4-[2-(trans-4-pentylcyclohexyl)ethyl]phenyl}-(4-difluoromethoxyphenyloxy)methane
Difluoro-{4-[2-(trans-4-ethylcyclohexyl)ethyl]phenyl}-(4-trifluoromethoxyphenyloxy)methane Difluoro-{4-[2-(trans-4-propylcyclohexyl)ethyl]phenyl}-(4-trifluoromethoxyphenyloxy)methane
Cr 60.2–60.9N 72.6–73.2 Iso
Difluoro-{4-[2-(trans-4-butylcyclohexyl)ethyl]phenyl}-(4-trifluoromethoxyphenyloxy)methane
Difluoro-{4-[2-(trans-4-pentylcyclohexyl)ethyl]phenyl}-(4-trifluoromethoxyphenyloxy)methane
Difluoro-{4-[2-(trans-4-ethylcyclohexyl)ethyl]phenyl}-(4-cyanophenyloxy)methane
Difluoro-{4-[2-(trans-4-propylcyclohexyl)ethyl]phenyl}-(4-cyanophenyloxy)methane
Difluoro-{4-[2-(trans-4-butylcyclohexyl)ethyl]phenyl}-(4-cyanophenyloxy)methane
Difluoro-{4-[2-(trans-4-pentylcyclohexyl)ethyl]phenyl}-(4-cyanophenyloxy)methane
Difluoro-{4-[2-(trans-4-ethylcyclohexyl)ethyl]phenyl}-(3-fluoro-4-trifluoromethoxyphenyloxy)methane
Difluoro-{4-[2-(trans-4-propylcyclohexyl)ethyl]phenyl}-(3-fluoro-4-trifluoromethoxyphenyloxy)methane
Cr 30.8–31.3N 76.9–77.7 Iso
Difluoro-{4-[2-(trans-4-butylcyclohexyl)ethyl]phenyl}-(3-fluoro-4-trifluoromethoxyphenyloxy)methane
Difluoro-{4-[2-(trans-4-pentylcyclohexyl)ethyl]phenyl}-(3-fluoro-4-trifluoromethoxyphenyloxy)methane
Difluoro-{4-[2-(trans-4-ethylcyclohexyl)ethyl]phenyl}-(3-fluoro-4-trifluoromethylphenyloxy)methane
Difluoro-{4-[2-(trans-4-propylcyclohexyl)ethyl]phenyl}-(3-fluoro-4-trifluoromethylphenyloxy)methane
Difluoro-{4-[2-(trans-4-butylcyclohexyl)ethyl]phenyl}-(3-fluoro-4-trifluoromethylphenyloxy)methane
Difluoro-{4-[2-(trans-4-pentylcyclohexyl)ethyl]phenyl}-(3-fluoro-4-trifluoromethylphenyloxy)methane
Difluoro-{4-[2-(trans-4-ethylcyclohexyl)ethyl]phenyl}-(3-fluoro-4-difluoromethoxyphenyloxy)methane
Difluoro-{4-[2-(trans-4-propylcyclohexyl)ethyl]phenyl}-(3-fluoro-4-difluoromethoxyphenyloxy)methane
Difluoro-{4-[2-(trans-4-butylcyclohexyl)ethyl]phenyl}-(3-fluoro-4-difluoromethoxyphenyloxy)methane
Difluoro-{4-[2-(trans-4-pentylcyclohexyl)ethyl]phenyl}-(3-fluoro-4-difluoromethoxyphenyloxy)methane
Difluoro-{4-[2-(trans-4-ethylcyclohexyl)ethyl]phenyl}-(3-fluoro-4-cyanophenyloxy)methane
Difluoro-{4-[2-(trans-4-propylcyclohexyl)ethyl]phenyl}-(3-fluoro-4-cyanophenyloxy)methane
Difluoro-{4-[2-(trans-4-butylcyclohexyl)ethyl]phenyl}-(3-fluoro-4-cyanophenyloxy)methane
Difluoro-{4-[2-(trans-4-pentylcyclohexyl)ethyl]phenyl}-(3-fluoro-4-cyanophenyloxy)methane
Difluoro-{4-[2-(trans-4-ethylcyclohexyl)ethyl]phenyl}-(3,5-difluoro-4-trifluoromethoxyphenyloxy)methane
Difluoro-{4-[2-(trans-4-propylcyclohexyl)ethyl]phenyl}-(3,5-difluoro-4-trifluoromethoxyphenyloxy)methane
Difluoro-{4-[2-(trans-4-butylcyclohexyl)ethyl]phenyl}-(3,5-difluoro-4-trifluoromethoxyphenyloxy)methane
Difluoro-{4-[2-(trans-4-pentylcyclohexyl)ethyl]phenyl}-(3,5-difluoro-4-trifluoromethoxyphenyloxy)methane
Difluoro-{4-[2-(trans-4-ethylcyclohexyl)ethyl]phenyl}-(3,5-difluoro-4-trifluoromethylphenyloxy)methane
Difluoro-{4-[2-(trans-4-propylcyclohexyl)ethyl]phenyl}-(3,5-difluoro-4-trifluoromethylphenyloxy)methane
Difluoro-{4-[2-(trans-4-butylcyclohexyl)ethyl]phenyl}-(3,5-difluoro-4-trifluoromethylphenyloxy)methane
Difluoro-{4-[2-(trans-4-pentylcyclohexyl)ethyl]phenyl}-(3,5-difluoro-4-trifluoromethylphenyloxy)methane
Difluoro-{4-[2-(trans-4-ethylcyclohexyl)ethyl]phenyl}-(3,5-difluoro-4-difluoromethoxyphenyloxy)methane
Difluoro-{4-[2-(trans-4-propylcyclohexyl)ethyl]phenyl}-(3,5-difluoro-4-difluoromethoxyphenyloxy)methane
Difluoro-{4-[2-(trans-4-butylcyclohexyl)ethyl]phenyl}-(3,5-difluoro-4-difluoromethoxyphenyloxy)methane
Difluoro-{4-[2-(trans-4-pentylcyclohexyl)ethyl]phenyl}-(3,5-difluoro-4-difluoromethoxyphenyloxy)methane
Difluoro-{4-[2-(trans-4-ethylcyclohexyl)ethyl]phenyl}-(3,5-difluoro-4-cyanophenyloxy)methane
Difluoro-{4-[2-(trans-4-propylcyclohexyl)ethyl]phenyl}-(3,5-difluoro-4-cyanophenyloxy)methane
Difluoro-{4-[2-(trans-4-butylcyclohexyl)ethyl]phenyl}-(3,5-difluoro-4-cyanophenyloxy)methane
Difluoro-{4-[2-(trans-4-pentylcyclohexyl)ethyl]phenyl}-(3,5-difluoro-4-cyanophenyloxy)methane
Difluoro-{2-fluoro-4-[2-(trans-4-ethylcyclohexyl)ethyl]phenyl}-(3,5-difluoro-4-trifluoromethoxyphenyloxy)methane
Difluoro-{2-fluoro-4-[2-(trans-4-propylcyclohexyl)ethyl]phenyl}-(3,5-difluoro-4-trifluoromethoxyphenyloxy)methane
Difluoro-{2-fluoro-4-[2-(trans-4-butylcyclohexyl)ethyl]phenyl}-(3,5-difluoro-4-trifluoromethoxyphenyloxy)methane
Difluoro-{2-fluoro-4-[2-(trans-4-pentylcyclohexyl)ethyl]phenyl}-(3,5-difluoro-4-trifluoromethoxyphenyloxy)methane
Difluoro-{2-fluoro-4-[2-(trans-4-ethylcyclohexyl)ethyl]phenyl}-(3,5-difluoro-4-trifluoromethylphenyloxy)methane
Difluoro-{2-fluoro-4-[2-(trans-4-propylcyclohexyl)ethyl]phenyl}-(3,5-difluoro-4-trifluoromethylphenyloxy)methane
Difluoro-{2-fluoro-4-[2-(trans-4-butylcyclohexyl)ethyl]phenyl}-(3,5-difluoro-4-trifluoromethylphenyloxy)methane
Difluoro-{2-fluoro-4-[2-(trans-4-pentylcyclohexyl)ethyl]phenyl}-(3,5-difluoro-4-trifluoromethylphenyloxy)methane
Difluoro-{2-fluoro-4-[2-(trans-4-ethylcyclohexyl)ethyl]phenyl}-(3,5-difluoro-4-difluoromethoxyphenyloxy)methane
Difluoro-{2-fluoro-4-[2-(trans-4-propylcyclohexyl)ethyl]phenyl}-(3,5-difluoro-4-difluoromethoxyphenyloxy)methane
Difluoro-{2-fluoro-4-[2-(trans-4-butylcyclohexyl)ethyl]phenyl}-(3,5-difluoro-4-difluoromethoxyphenyloxy)methane
Difluoro-{2-fluoro-4-[2-(trans-4-pentylcyclohexyl)ethyl]phenyl}-(3,5-difluoro-4-difluoromethoxyphenyloxy)methane
Difluoro-{2-fluoro-4-[2-(trans-4-ethylcyclohexyl)ethyl]phenyl}-(3,4,5-trifluorophenyloxy)methane
Difluoro-{2-fluoro-4-[2-(trans-4-propylcyclohexyl)ethyl]phenyl}-(3,4,5-trifluorophenyloxy)methane
Difluoro-{2-fluoro-4-[2-(trans-4-butylcyclohexyl)ethyl]phenyl}-(3,4,5-trifluorophenyloxy)methane
Difluoro-{2-fluoro-4-[2-(trans-4-pentylcyclohexyl)ethyl]phenyl}-(3,4,5-trifluorophenyloxy)methane
Difluoro-{2-fluoro-4-[2-(trans-4-ethylcyclohexyl)ethyl]phenyl}-(3,5-difluoro-4-cyanophenyloxy)methane
Difluoro-{2-fluoro-4-[2-(trans-4-propylcyclohexyl)ethyl]phenyl}-(3,5-difluoro-4-cyanophenyloxy)methane
Difluoro-{2-fluoro-4-[2-(trans-4-butylcyclohexyl)ethyl]phenyl}-(3,5-difluoro-4-cyanophenyloxy)methane
Difluoro-{2-fluoro-4-[2-(trans-4-pentylcyclohexyl)ethyl]phenyl}-(3,5-difluoro-4-cyanophenyloxy)methane
Difluoro-{2,6-difluoro-4-[2-(trans-4-ethylcyclohexyl)ethyl]phenyl}-(3,5-difluoro-4-trifluoromethoxyphenyloxy)methane Difluoro-{2,6-difluoro-4-[2-(trans-4-propylcyclohexyl) ethyl]phenyl)-(3,5-difluoro-4-trifluoromethoxyphenyloxy)methane Difluoro-{2,6-difluoro-4-[2-(trans-4-butylcyclohexyl) ethyl]phenyl}-(3,5-difluoro-4-trifluoromethoxyphenyloxy)methane Difluoro-{2,6-difluoro-4-[2-(trans-4-pentylcyclohexyl) ethyl]phenyl}-(3,5-difluoro-4-trifluoromethoxyphenyloxy)methane Difluoro-{2,6-difluoro-4-[2-(trans-4-ethylcyclohexyl) ethyl] phenyl}-(3,5-difluoro-4-trifluoromethylphenyloxy) methane Difluoro-{2,6-difluoro-4-[2-(trans-4-propylcyclohexyl) ethyl]phenyl}-(3,5-difluoro-4-trifluoromethylphenyloxy) methane Difluoro-{2,6-difluoro-4-[2-(trans-4-butylcyclohexyl) ethyl]phenyl}-(3,5-difluoro-4-trifluoromethylphenyloxy) methane Difluoro-{2,6-difluoro-4-[2-(trans-4-pentylcyclohexyl) ethyl]phenyl}-(3,5-difluoro-4-trifluoromethylphenyloxy) methane Difluoro-{2,6-difluoro-4-[2-(trans-4-ethylcyclohexyl) ethyl] phenyl}-(3,5-difluoro-4-difluoromethoxyphenyloxy) methane Difluoro-{2,6-difluoro-4-[2-(trans-4-propylcyclohexyl) ethyl]phenyl}-(3,5-difluoro-4-difluoromethoxyphenyloxy)methane Difluoro-{2,6-difluoro-4-[2-(trans-4-butylcyclohexyl) ethyl]phenyl}-(3,5-difluoro-4-difluoromethoxyphenyloxy)methane Difluoro-{2,6-difluoro-4-[2-(trans-4-pentylcyclohexyl) ethyl]phenyl}-(3,5-difluoro-4-difluoromethoxyphenyloxy)methane Difluoro-{2 6-difluoro-4-[2-(trans-4-ethylcyclohexyl) ethyl] phenyl}-(3,4,5-trifluorophenyloxy)methane Difluoro-{2,6-difluoro-4-[2-(trans-4-propylcyclohexyl) ethyl]phenyl}-(3,4,5-trifluorophenyloxy)methane Difluoro-{2,6-difluoro-4-[2-(trans-4-butylcyclohexyl) ethyl]phenyl}-(3,4,5-trifluorophenyloxy)methane Difluoro-{2,6-difluoro-4-[2-(trans-4-pentylcyclohexyl) ethyl]phenyl}-(3,4,5-trifluorophenyloxy)methane Difluoro-{2,6-difluoro-4-[2-(trans-4-ethylcyclohexyl) ethyl] phenyl}-(3,5-difluoro-4-cyanophenyloxy)methane Difluoro-{2,6-difluoro-4-[2-(trans-4-propylcyclohexyl) ethyl]phenyl}-(3,5-difluoro-4-cyanophenyloxy)methane Difluoro-{2,6-difluoro-4-[2-(trans-4-butylcyclohexyl) ethyl]phenyl}-(3,5-difluoro-4-cyanophenyloxy)methane Difluoro-{2,6-difluoro-4-[2-(trans-4-pentylcyclohexyl) ethyl]phenyl}-(3,5-difluoro-4-cyanophenyloxy)methane

EXAMPLE 5

Preparation of difluoro-{4-[trans-4-(3-butenyl) cyclohexyl]phenyl}-(3,4,5-trifluorophenyloxy)methane (Compound expressed by the formula (I) wherein R is 3-butenyl group, l=1, m and n are 0, ring $A_1$ is trans-1,4-cyclohexylene group, $Z_1$, $Z_2$ and $Z_3$ are covalent bond, $L_1=L_2=H$, $L_3=L_4=F$, and $X=F$)

Preparation of the compound includes four steps of hydrolysis of a benzonitrile derivative, preparation of an ester intermediate, thionesterification, and gem-fluorination. Each of the steps is illustrated in detail below.

In a 1000 ml three neck distillation flask provided with a stirrer and thermometer, 20.0 g (83.6 mmol) of 4-[trans-4-(3-butenyl)cyclohexyl]benzonitrile and 11.7 g (208.9 mmol) of potassium hydroxide were dissolved in 500 ml of ethylene glycol, and the solution was heated while stirring and while keeping internal temperature at 150° C. for 10 hours. After cooled down to room temperature, 300 ml of water and 300 ml of 6N aqueous solution of hydrochloric acid were added to the solution, and the precipitated insoluble matter was filtered to separate. Separated precipitate was sufficiently washed with water and then recrystallized from a mixed solvent of toluene-heptane to obtain 16.5 g of colorless crystal product. This product was 4-[trans-4-(3-butenyl) cyclohexyl]benzoic acid. Subsequently, this benzoic acid derivative was reacted with a phenol derivative to esterify. That is, in a 500 ml three neck distillation flask provided with a stirrer, thermometer, dropping funnel, and nitrogen gas introducing pipe, 16.5 g (63.8 mmol) of 4-[trans-4-(3-butenyl)cyclohexyl]benzoic acid obtained by the procedures mentioned above, 15.8 g (76.6 mmol) of DCC, and 0.28 g (2.3 mmol) of DMAP were dissolved in 250 ml of dichloromethane, and then 11.3 g (76.6 mmol) of 3,4,5-trifluorophenol was added dropwise to the solution in 3 min while stirring at room temperature. After the dropping, the solution was stirred at room temperature for 13 hours. Reaction solution was added with 100 ml of water, dichloromethane insoluble matter was filtered off, the dichloromethane layer was separated, and then the water was further extracted with 200 ml of dichloromethane. Extracted layers were mixed, washed with 100 ml×2 of water, 100 ml of saturated aqueous solution of sodium hydrogencarbonate, and 100 ml×2 of water in turn, dried over anhydrous magnesium sulfate, and then concentrated under a reduced pressure to obtain 25.1 g of reaction product. Reaction product was purified by a column chromatography using silica gel as filler and using toluene as developing solvent, and further recrystallized from a mixed solvent of heptane-ethanol to obtain 16.6 g of colorless crystal product. This product was 3,4,5-trifluoro-{4-[trans-4-(3-butenyl) cyclohexyl)phenyl} benzoate.

Subsequently, in a 1000 ml egg-plant type flask provided with a nitrogen gas introducing pipe and cooling pipe, 16.6 g (42.8 mmol) of 3,4,5-trifluoro-{4-[trans-4-(3-butenyl) cyclohexyl)phenyl} benzoate obtained by the procedures mentioned above and 34.6 g (85.6 mmol) of Lawesson's reagent were dissolved in 500 ml of toluene, and the solution was refluxed while stirring under nitrogen gas stream for 55 hours. After the reaction solution was cooled down to room temperature, 200 ml of water was added, the toluene layer was separated, and then the water layer was further extracted with 150 ml of toluene. Organic layers were mixed, washed with 200 ml×2 of water, 100 ml of saturated aqueous solution of sodium hydrogencarbonate, 100 ml of 10% aqueous solution of sodium hydrogensulfite, and 200 ml×2 of water in turn, dried over anhydrous magnesium sulfate, and then concentrated under a reduced pressure to obtain 17.6 g of brown crystalline product. Reaction product was purified by a column chromatography using silica gel as filler and using heptane as developing solvent, and then recrystallized from heptane to obtain 4.5 g of yellow needle-like crystal product. This product was 4-[trans-4-(3-butenyl) cyclohexyl]phenylcarbothio acid-O-3,4,5-trifluorophenyl.

In a 100 ml egg-plant type flask provided with a nitrogen gas introducing pipe, 4.5 g (11.3 mmol) of 4-[trans-4-(3-butenyl)cyclohexyl]phenylcarbothio acid-O-3,4,5-trifluorophenyl was dissolved in 50 ml of dichloromethane at room temperature, and then 5.5 g (33.8 mmol) of DAST was added to the solution and the solution was stirred at room temperature for 40 hours. Reaction solution was added with 50 ml of water, the dichloromethane layer was separated, and the water layer was further extracted with 50 ml of dichloromethane. Extracted layers were mixed, washed with 50 ml×2 of water, 30 ml of saturated aqueous solution of sodium hydrogencarbonate, and 50 ml×2 of water in turn, dried over anhydrous magnesium sulfate, and then concentrated under a reduced pressure to obtain 3.8 g of colorless crystal product. Reaction product was purified by a column chromatography using silica gel as filler and using heptane as developing solvent, and then recrystallized from ethanol to obtain 1.1 g of colorless needle-like crystal product. This product was difluoro-{4-[trans-4-(3-butenyl)cyclohexyl]phenyl}-(3,4,5-trifluorophenyloxy)methane.

The following compounds can be prepared according to the preparation method mentioned above by using 4-[trans-4-alkenylcyclohexyl)benzoic acids having a different chain length and different position of double bond in place of 4-[trans-4-(3-butenyl)cyclohexyl]benzoic acid:

Difluoro-{4-[trans-4-[(Z)-1-butenyl]cyclohexyl]phenyl}-(3,4,5-trifluorophenyloxy)methane
Difluoro-{4-[trans-4-[(Z)-2-butenyl]cyclohexyl]phenyl}-(3,4,5-trifluorophenyloxy)methane
Difluoro-{4-[trans-4-[(Z)-1-pentenyl]cyclohexyl]phenyl}-(3,4,5-trifluorophenyloxy)methane
Difluoro-{4-[trans-4-[(Z)-2-pentenyl]cyclohexyl]phenyl}-(3,4,5-trifluorophenyloxy)methane
Difluoro-{4-[trans-4-[(Z)-3-pentenyl]cyclohexyl]phenyl}-(3,4,5-trifluorophenyloxy)methane
Difluoro-{4-[trans-4-(4-pentenyl)cyclohexyl]phenyl}-(3,4,5-trifluorophenyloxy)methane Also, the following compounds can be prepared according to the preparation method mentioned above by using several known phenol derivatives in place of 3,4,5-trifluorophenol:

Difluoro-{4-[trans-4-[(Z)-1-butenyl]cyclohexyl]phenyl}-(4-cyanophenyloxy)methane
Difluoro-{4-[trans-4-[(Z)-2-butenyl]cyclohexyl]phenyl}-(4-cyanophenyloxy)methane
Difluoro-{4-[trans-4-(3-butenyl)cyclohexyl]phenyl}-(4-cyanophenyloxy)methane
Difluoro-{4-[trans-4-[(Z)-1-pentenyl]cyclohexyl]phenyl}-(4-cyanophenyloxy)methane
Difluoro-{4-[trans-4-[(Z)-2-pentenyl]cyclohexyl]phenyl}-(4-cyanophenyloxy)methane
Difluoro-{4-[trans-4-[(Z)-3-pentenyl]cyclohexyl]phenyl}-(4-cyanophenyloxy)methane
Difluoro-{4-[trans-4-(4-pentenyl)cyclohexyl]phenyl}-(4-cyanophenyloxy)methane
Difluoro-{4-[trans-4-[(Z)-1-butenyl]cyclohexyl]phenyl}-(3-fluoro-4-cyanophenyloxy)methane
Difluoro-{4-[trans-4-[(Z)-2-butenyl]cyclohexyl]phenyl}-(3-fluoro-4-cyanophenyloxy)methane
Difluoro-{4-[trans-4-(3-butenyl)cyclohexyl]phenyl}-(3-fluoro-4-cyanophenyloxy)methane
Difluoro-{4-[trans-4-[(Z)-1-pentenyl]cyclohexyl]phenyl}-(3-fluoro-4-cyanophenyloxy)methane
Difluoro-{4-[trans-4-[(Z)-2-pentenyl]cyclohexyl]phenyl}-(3-fluoro-4-cyanophenyloxy)methane
Difluoro-{4-[trans-4-[(Z)-3-pentenyl]cyclohexyl]phenyl}-(3-fluoro-4-cyanophenyloxy)methane
Difluoro-{4-[trans-4-(4-pentenyl)cyclohexyl]phenyl}-(3-fluoro-4-cyanophenyloxy)methane
Difluoro-{4-[trans-4-[(Z)-1-butenyl]cyclohexyl]phenyl}-(3,5-difluoro-4-cyanophenyloxy)methane
Difluoro-{4-[trans-4-[(Z)-2-butenyl]cyclohexyl]phenyl}-(3,5-difluoro-4-cyanophenyloxy)methane
Difluoro-{4-[trans-4-(3-butenyl)cyclohexyl]phenyl}-(3,5-difluoro-4-cyanophenyloxy)methane
Difluoro-{4-[trans-4-[(Z)-1-pentenyl]cyclohexyl]phenyl}-(3,5-difluoro-4-cyanophenyloxy)methane
Difluoro-{4-[trans-4-[(z)-2-pentenyl]cyclohexyl]phenyl}-(3,5-difluoro-4-cyanophenyloxy)methane
Difluoro-{4-[trans-4-[(Z)-3-pentenyl]cyclohexyl]phenyl}-(3,5-difluoro-4-cyanophenyloxy)methane
Difluoro-{4-[trans-4-(4-pentenyl)cyclohexyl]phenyl}-(3,5-difluoro-4-cyanophenyloxy)methane
Difluoro-{2-fluoro-4-[trans-4-[(Z)-1-butenyl]cyclohexyl]phenyl}-(3,5-difluoro-4-cyanophenyloxy)methane
Difluoro-{2-fluoro-4-[trans-4-[(Z)-2-butenyl]cyclohexyl]phenyl}-(3,5-difluoro-4-cyanophenyloxy)methane
Difluoro-{2-fluoro-4-[trans-4-(3-butenyl)cyclohexyl]phenyl}-(3,5-difluoro-4-cyanophenyloxy)methane
Difluoro-{2-fluoro-4-[trans-4-[(Z)-1-pentenyl]cyclohexyl]phenyl}-(3,5-difluoro-4-cyanophenyloxy)methane
Difluoro-{2-fluoro-4-[trans-4-[(Z)-2-pentenyl]cyclohexyl]phenyl}-(3,5-difluoro-4-cyanophenyloxy)methane
Difluoro-{2-fluoro-4-[trans-4-[(Z)-3-pentenyl]cyclohexyl]phenyl)-(3,5-difluoro-4-cyanophenyloxy)methane
Difluoro-{2-fluoro-4-[trans-4-(4-pentenyl)cyclohexyl]phenyl}-(3,5-difluoro-4-cyanophenyloxy)methane
Difluoro-{2,6-difluoro-4-[trans-4-[(Z)-1-butenyl]cyclohexyl]phenyl}-(3,5-difluoro-4-cyanophenyloxy)methane
Difluoro-{2,6-difluoro-4-[trans-4-[(Z)-2-butenyl]cyclohexyl]phenyl}-(3,5-difluoro-4-cyanophenyloxy)methane
Difluoro-{2,6-difluoro-4-[trans-4-(3-butenyl)cyclohexyl]phenyl}-(3,5-difluoro-4-cyanophenyloxy)methane
Difluoro-{2,6-difluoro-4-[trans-4-[(Z)-1-pentenyl]cyclohexyl]phenyl}-(3,5-difluoro-4-cyanophenyloxy)methane
Difluoro-{2,6-difluoro-4-[trans-4-[(Z)- 2-pentenyl]cyclohexyl]phenyl}-(3,5-difluoro-4-cyanophenyloxy)methane
Difluoro-{2,6-difluoro-4-[trans-4-[(Z)-3-pentenyl]cyclohexyl]phenyl}-(3,5-difluoro-4-cyanophenyloxy)methane
Difluoro-{2,6-difluoro-4-[trans-4-(4-pentenyl)cyclohexyl]phenyl}-(3,5-difluoro-4-cyanophenyloxy)methane

EXAMPLE 6

Preparation of difluoro-(4-propylphenyl)-[4-(3',4',5'-trifluorobiphenyl)oxy]methane (Compound expressed by the formula (I) wherein R=$C_3H_7$, l=m=0, n=1, ring $A_3$ is 1,4-phenylene group, $Z_1$, $Z_2$ and $Z_3$ are covalent bond, $L_1$=$L_2$=H, $L_3$=$L_4$=F, and X=F)

1) Preparation of 4-(3,4,5-trifluorophenyl)phenol

By the following procedures, 4-(3,4,5-trifluorophenyl)phenol was prepared which is a raw material for the preparation of the subject compounds of this Example. That is, in a 1000 ml three neck distillation flask provided with a stirrer, thermometer, nitrogen gas introducing pipe, dropping funnel, and cooling pipe, 7.9 g (324.2 mmol) of magnesium turnings were added, and then a solution of 65.2 g (308.8 mmol) of 3,4,5-trifluorobromobe nzene in 80 ml of tetrahydrofuran (hereinafter abbreviated as THF) was added dropwise in 50 min so that the internal temperature was maintained at 50° C. After completion of the dropping, the solution was stirred on a hot water bath while keeping the same temperature for 1 hour for ageing to prepare a Grignard reagent. Then, in a 1000 ml three neck distillation flask provided with a stirrer, thermometer, nitrogen gas introducing pipe, dropping funnel, and a cooling pipe, separately provided for, 35.0 g (171.6 mmol) of iodobenzene, 1.64 g (9.3 mmol) of palladium chloride, and 300 ml of THF were added under nitrogen gas atmosphere, and added dropwise with the Grignard reagent prepared by the procedures mentioned above in 50 min while refluxing. After the dropping, the solution was further refluxed for 3 hours, cooled down to room temperature, and then added with 200 ml of water to terminate the reaction. After insoluble matter was filtered off the reaction solution, the solution was extracted with 300 ml×2 of toluene. Extracted layer was washed with 300 ml×3 of water, dried over anhydrous magnesium sulfate, and then concentrated under a reduced pressure to obtain 38. 4 g of dark brown solid. Concentration residue was purified by a chromatography using silica gel as a filler and using heptane as developing solvent, and then recrystallized from a mixed solvent of heptane-ethanol to obtain 19.0 g of colorless crystal product. This product was 3,4,5-trifluorobiphenyl. Subsequently, the biphenyl derivative was subjected to bromination. That is, in a 100 ml three neck distillation flask provided with a stirrer, thermometer, nitrogen gas introducing pipe, and dropping funnel, 19.0 g (91.5 mmol) of the 3,4,5-trifluorobiphenyl prepared by the procedures mentioned above was dissolved in 200 ml of dichoromethane, and the solution was cooled down to −5° C. while stirring, added with 0.26 g (4.6 mmol) of iron powder, and then added dropwise with 8.8 g (109.8 mmol) of bromine in 15 min so that the temperature of −5° to 0° C. was maintained. After the dropping, the solution was further stirred for 1 hour while maintaining the same temperature. Reaction solution was added with 200 ml of water to terminate the reaction, and then extracted with 250 ml×2 of toluene. Extracted layer was washed with 200 ml×4 of water, dried over anhydrous magnesium sulfate, and concentrated under a reduced pressure to obtain 25.1 g of brown oily product. Concentration residue was purified by a chromatography using silica gel as filler and using heptane as developing solvent, and recrystallized from a mixed solvent of heptane-ethanol to obtain 16.6 of colorless crystal product. This product was 4-bromo-3',4',5'-trifluorobiphenyl.

With reference to the report by R. L. Kidwell et al. (Org. Synth., V, 918 (1973)), the bromobiphenyl derivative obtained by the procedures mentioned above was led to a phenylphenol derivative by the following procedures. That is, in a 300 ml three neck distillation flask provided with a stirrer, thermometer, nitrogen gas introducing pipe, and dropping funnel, 1.5 g (60.9 mmol) of magnesium turnings were added, and a solution of 16.6 g (58.0 mmol) of 4-bromo-3',4',5'-trifluorobiphenyl in 30 ml of THF was added dropwise in 25 min so that the internal temperature was maintained at 50° C. After completion of the dropping, the solution was stirred on a hot water bath for 1 hour while keeping the same temperature for ageing to prepare a Grignard reagent. Then, the reaction solution was cooled with dry ice-acetone coolant down to −20° C., added dropwise with 7.2 g of trimethyl borate, and stirred at the same temperature for 30 min. The solution was added with 20 3.5 g (58.0 mmol) of acetic acid at the same temperature, raised up to 20° C., and added dropwise with 7.9 g (69.6 mmol) of 30% aqueous solution of hydrogen peroxide in 10 min so that temperature of 25° C. was maintained. Reaction solution was cooled again with the coolant down to −30° C. and added dropwise with 50 ml of 20% aqueous solution of sodium thiosulfate in 10 min to terminate the reaction. Reaction solution was extracted with 150 ml×3 of ethyl acetate, washed with 200 ml×2 of saturated brine, dried over anhydrous magnesium sulfate, and then concentrated under a reduced pressure to obtain 14.5 g of brown solid product. Concentrated residue was recrystallized from a mixed solvent of heptane-toluene to obtain 10.9 g of colorless crystal product. This product was 4-(3,4,5-trifluorophenyl)phenol.

2) Preparation of difluoro-(4-propylphenyl)-[4-(3',4',5'-trifluo robiphenyl)oxy]methane In a 500 ml three neck distillation flask provided with a stirrer, thermometer, dropping funnel, and nitrogen gas introducing pipe, 6.7 g (40.7 mmol) of 4-propylbenzoic acid, 10.1 g (48.8 mmol) of DCC, and 0.18 g (1.5 mmol) of DMAP were dissolved in 150 ml of dichloromethane, and then a solution of 10.9 g (48.8 mmol) of 4-(3,4,5-trifluorophenyl)phenol in 50 ml of dichloromethane was added dropwise at room temperature in 20 min while stirring. After the dropping, the solution was stirred at room temperature for 17 hours. After the reaction solution was added with 100 ml of water, the dichloromethane insoluble matter was filtered off, the dichloromethane layer was separated, and the water layer was extracted with 200 ml of dichoromethane. Extracted layers were mixed, washed with 100 ml×2 of water, 100 ml of saturated aqueous solution of sodium hydrogencarbonate, and 100 ml×2 of water in turn, dried over anhydrous magnesium sulfate, and then concentrated under a reduced pressure to obtain 15.3 g of reaction product. The reaction product was purified by a chromatograhy using silica gel as filler and using toluene as developing solvent, and further recrystallized from a mixed solvent of heptane-ethanol to obtain 10.5 g of colorless crystal product. This product was 4-(3',4',5'-trifluoro)biphenyl-(4-propyl)benzoate.

Subsequently, in a 1000 ml egg-plant type flask provided with a nitrogen gas introducing pipe and cooling pipe, 10.5 g (28.5 mmol) of 4-(3',4',5'-trifluoro)biphenyl-(4-propyl)benzoate obtained by the procedures mentioned above and 23.0 g (56.9 mmol) of Lawesson's reagent were dissolved in 350 ml of toluene, and the solution was refluxed while stirring under nitrogen gas stream for 60 hours. After the reaction solution was cooled down to room temperature, 200 ml of water was added, the toluene layer was separated, and then the water layer was further extracted with 150 ml of toluene. Organic layers were mixed, washed with 200 ml×2 of water, 100 ml of saturated aqueous solution of sodium hydrogencarbonate, 100 ml of 10% aqueous solution of sodium hydrogensulfite, and 200 ml×2 of water in turn, dried over anhydrous magnesium sulfate, and then concentrated under a reduced pressure to obtain 10.5 g of brown crystalline mixture. Concentrated product was purified by a column chromatography using silica gel as filler and using heptane as developing solvent, and then recrystallized from heptane to obtain 6.3 g of yellow needle-like crystal product. This product was 4-propylphenylcarbothio acid-O-4-(3',4',5'-trifluoro)biphenyl.

In a 100 ml egg-plant type flask provided with a nitrogen gas introducing pipe, 6.3 g (16.3 mmol) of 4-propylphenylcarbothio acid-O-4-(3',4',5'-trifluoro)biphenyl was dissolved in 50 ml of dichloromethane at room temperature, and then 7.9 g (48.9 mmol) of DAST was added to the solution and the solution was stirred at room temperature for 30 hours. Reaction solution was added with 50 ml of water, the dichloromethane layer was separated, and the water layer was further extracted with 50 ml of dichloromethane. Extracted layers were mixed, washed with 50 ml×2 of water, 30 ml of saturated aqueous solution of sodium hydrogencarbonate, and 50 ml×2 of water in turn, dried over anhydrous magnesium sulfate, and then concentrated under a reduced pressure to obtain 5.9 g of colorless crystal product. Reaction product was purified by a column chromatography using silica gel as filler and using heptane as developing solvent, and then recrystallized from heptane to obtain colorless needle-like crystal product. This product was difluoro-(4-propylphenyl)-[4-(3',4',5'-trifluorobiphenyl)oxy]methane.

Following compounds can be prepared according to the preparation method mentioned above by using 4-alkylbenzoic acids having a different alkyl chain in place of 4-propylbenzoic acid:

Difluoro-(4-methylphenyl)-[4-(3',4',5'-trifluorobiphenyl) oxy]methane
Difluoro-(4-ethylphenyl)-[4-(3',4',5'-trifluorobiphenyl) oxy]methane
Difluoro-(4-butylphenyl)-[4-(3',4',5'-trifluorobiphenyl) oxy]methane
Difluoro-(4-pentylphenyl)-[4-(3',4',5'-trifluorobiphenyl) oxy]methane
Difluoro-(4-hexylphenyl)-[4-(3',4',5'-trifluorobiphenyl) oxy]methane
Difluoro-(4-heptylphenyl)-[4-(3',4',5'-trifluorobiphenyl) oxy]methane
Difluoro-(4-octylphenyl)-[4-(3',4',5'-trifluorobiphenyl) oxy]methane
Difluoro-(4-nonylphenyl)-[4-(3',4',5'-trifluorobiphenyl) oxy]methane
Difluoro-(4-decylphenyl)-[4-(3',4',5'-trifluorobiphenyl) oxy]methane Also, the following compounds can be prepared according to the preparation method mentioned above by using several known phenol derivatives in place of 4-(3,4,5-trifluorophenyl)phenol:

Difluoro-(4-ethylphenyl)-[4-(4'-difluoromethoxybiphenyl) oxy]methane
Difluoro-(4-propylphenyl)-[4-(4'-difluoromethoxybiphenyl) oxy]methane
Difluoro-(4-butylphenyl)-[4-(4'-difluoromethoxybiphenyl) oxy]methane
Difluoro-(4-pentylphenyl)-[4-(4'-difluoromethoxybiphenyl) oxy]methane
Difluoro-(4-ethylphenyl)-[4-(4'-trifluoromethylbiphenyl) oxy]methane
Difluoro-(4-propylphenyl)-[4-(4'-trifluoromethylbiphenyl) oxy]methane
Difluoro-(4-butylphenyl)-[4-(4'-trifluoromethylbiphenyl) oxy]methane
Difluoro-(4-pentylphenyl)-[4-(4'-trifluoromethylbiphenyl) oxy]methane
Difluoro-(4-ethylphenyl)-[4-(4'-trifluoromethoxybiphenyl) oxy]methane
Difluoro-(4-propylphenyl)-[4-(4'-trifluoromethoxybiphenyl) oxy]methane
Difluoro-(4-butylphenyl)-[4-(4'-trifluoromethoxybiphenyl) oxy]methane
Difluoro-(4-pentylphenyl)-[4-(4'-trifluoromethoxybiphenyl) oxy]methane
Difluoro-(4-ethylphenyl)-[4-(4'-cyanobiphenyl)oxy] methane
Difluoro-(4-propylphenyl)-[4-(4'-cyanobiphenyl)oxy] methane
Difluoro-(4-butylphenyl)-[4-(4'-cyanobiphenyl)oxy] methane
Difluoro-(4-pentylphenyl)-[4-(4'-cyanobiphenyl)oxy] methane
Difluoro-(4-ethylphenyl)-[4-(3'-fluoro-4'-trifluoromethoxybiphenyl)oxy]methane
Difluoro-(4-propylphenyl)-[4-(3'-fluoro-4'-trifluoromethoxybiphenyl)oxy]methane
Difluoro-(4-butylphenyl)-[4-(3'-fluoro-4'-trifluoromethoxybiphenyl)oxy]methane
Difluoro-(4-pentylphenyl)-[4-(3'-fluoro-4'-trifluoromethoxybiphenyl)oxy]methane
Difluoro-(4-ethylphenyl)-[4-(3'-fluoro-4'-difluoromethoxybiphenyl)oxy]methane
Difluoro-(4-propylphenyl)-[4-(3'-fluoro-4'-difluoromethoxybiphenyl)oxy]methane
Difluoro-(4-butylphenyl)-[4-(3'-fluoro-4'-difluoromethoxybiphenyl)oxy]methane
Difluoro-(4-pentylphenyl)-[4-(3'-fluoro-4'-difluoromethoxybiphenyl)oxy]methane
Difluoro-(4-ethylphenyl)-[4-(3'-fluoro-4'-trifluoromethylbiphenyl)oxy]methane
Difluoro-(4-propylphenyl)-[4-(3'-fluoro-4'-trifluoromethylbiphenyl)oxy]methane
Difluoro-(4-butylphenyl)-[4-(3-fluoro-4'-trifluoromethylbiphenyl)oxy]methane
Difluoro-(4-pentylphenyl)-[4-(3'-fluoro-4'-trifluoromethylbiphenyl)oxy]methane
Difluoro-(4-ethylphenyl)-[4-(3'-fluoro-4'-cyanobiphenyl) oxy]methane
Difluoro-(4-propylphenyl)-[4-(3'-fluoro-4'-cyanobiphenyl) oxy]methane
Difluoro-(4-butylphenyl)-[4-(3'-fluoro-4'-cyanobiphenyl) oxy]methane
Difluoro-(4-pentylphenyl)-[4-(3'-fluoro-4'-cyanobiphenyl) oxy]methane
Difluoro-(4-ethylphenyl)-[4-(3',5'-difluoro-4'-trifluoromethoxybiphenyl)oxy]methane
Difluoro-(4-propylphenyl)-[4-(3',5'-difluoro-4'-trifluoromethoxybiphenyl)oxy]methane
Difluoro-(4-butylphenyl)-[4-(3',5'-difluoro-4'-trifluoromethoxybiphenyl)oxy]methane
Difluoro-(4-pentylphenyl)-[4-(3',5'-difluoro-4'-trifluoromethoxybiphenyl)oxy]methane
Difluoro-(4-ethylphenyl)-[4-(3',5'-difluoro-4'-difluoromethoxybiphenyl)oxy]methane
Difluoro-(4-propylphenyl)-[4-(3',5'-difluoro-4'-difluoromethoxybiphenyl)oxy]methane
Difluoro-(4-butylphenyl)-[4-(3',5'-difluoro-4'-difluoromethoxybiphenyl)oxy]methane
Difluoro-(4-pentylphenyl)-[4-(3',5'-difluoro-4'-difluoromethoxybiphenyl)oxy]methane
Difluoro-(4-ethylphenyl)-[4-(3',5'-difluoro-4'-trifluoromethylbiphenyl)oxy]methane
Difluoro-(4-propylphenyl)-[4-(3',5'-difluoro-4'-trifluoromethylbiphenyl)oxy]methane
Difluoro-(4-butylphenyl)-[4-(3',5-difluoro-4'-trifluoromethylbiphenyl)oxy]methane
Difluoro-(4-pentylphenyl)-[4-(3',5'-difluoro-4'-trifluoromethylbiphenyl)oxy]methane
Difluoro-(4-ethylphenyl)-[4-(3',5'-difluoro-4'-cyanobiphenyl)oxy]methane
Difluoro-(4-propylphenyl)-[4-(3',5'-difluoro-4'-cyanobiphenyl)oxy]methane
Difluoro-(4-butylphenyl)-[4-(3',5'-difluoro-4'-cyanobiphenyl)oxy]methane
Difluoro-(4-pentylphenyl)-[4-(3',5'-difluoro-4'-cyanobiphenyl)oxy]methane
Difluoro-(2-fluoro-4-ethylphenyl)-[4-(3',5'-difluoro-4'-trifluoromethoxybiphenyl)oxy]methane
Difluoro-(2-fluoro-4-propylphenyl)-[4-(3',5'-difluoro-4'-trifluoromethoxybiphenyl)oxy]methane
Difluoro-(2-fluoro-4-butylphenyl)-[4-(3',5'-difluoro-4'-trifluoromethoxybiphenyl]oxy)methane
Difluoro-(2-fluoro-4-pentylphenyl)-[4-(3',5'-difluoro-4'-trifluoromethoxybiphenyl)oxy]methane
Difluoro-(2-fluoro-4-ethylphenyl)-[4-(3',5'-difluoro-4'-difluoromethoxybiphenyl)oxy]methane
Difluoro-(2-fluoro-4-propylphenyl)-[4-(3',5'-difluoro-4'-difluoromethoxybiphenyl)oxy]methane
Difluoro-(2-fluoro-4-butylphenyl)-[4-(3',5'-difluoro-4'-difluoromethoxybiphenyl)oxy]methane
Difluoro-(2-fluoro-4-pentylphenyl)-[4-(3',5'-difluoro-4'-difluoromethoxybiphenyl)oxy]methane
Difluoro-(2-fluoro-4-ethylphenyl)-[4-(3',5'-difluoro-4'-trifluoromethylbiphenyl)oxy]methane Difluoro-(2-fluoro-4-propylphenyl)-[4-(3',5'-difluoro-4'-trifluoromethylbiphenyl)oxy]methane
Difluoro-(2-fluoro-4-butylphenyl)-[4-(3',5'-difluoro-4'-trifluoromethylbiphenyl)oxy]methane
Difluoro-(2-fluoro-4-pentylphenyl)-[4-(3',5'-difluoro-4'-trifluoromethylbiphenyl)oxy]methane
Difluoro-(2-fluoro-4-ethylphenyl)-[4-(3',4',5'-trifluorobiphenyl)oxy]methane
Difluoro-(2-fluoro-4-propylphenyl)-[4-(3',4',5'-trifluorobiphenyl)oxy]methane
Difluoro-(2-fluoro-4-butylphenyl)-[4-(3',4',5'-trifluorobiphenyl)oxy]methane
Difluoro-(2-fluoro-4-pentylphenyl)-[4-(3',4',5'-trifluorobiphenyl)oxy]methane
Difluoro-(2-fluoro-4-ethylphenyl)-[4-(3',5'-difluoro-4'-cyanobiphenyl)oxy]methane
Difluoro-(2-fluoro-4-propylphenyl)-[4-(3',5'-difluoro-4'-cyanobiphenyl)oxy]methane
Difluoro-(2-fluoro-4-butylphenyl)-[4-(3',5'-difluoro-4'-cyanobiphenyl)oxy]methane
Difluoro-(2-fluoro-4-pentylphenyl)-[4-(3',5'-difluoro-4'-cyanobiphenyl)oxy]methane
Difluoro-(2,6-difluoro-4-ethylphenyl)-[4-(3',5'-difluoro-4'-trifluoromethoxybiphenyl)oxy]methane
Difluoro-(2,6-difluoro-4-propylphenyl)-[4-(3',5'-difluoro-4'-trifluoromethoxybiphenyl)oxy]methane
Difluoro-(2,6-difluoro-4-butylphenyl)-[4-(3',5'-difluoro-4'-trifluoromethoxybiphenyl)oxy]methane
Difluoro-(2,6-difluoro-4-pentylphenyl)-[4-(3',5'-difluoro-4'-trifluoromethoxybiphenyl)oxy)methane
Difluoro-(2,6-difluoro-4-ethylphenyl)-[4-(3',5'-difluoro-4'-difluoromethoxybiphenyl)oxy]methane
Difluoro-(2,6-difluoro-4-propylphenyl)-[4-(3',5'-difluoro-4'-difluoromethoxybiphenyl)oxy]methane
Difluoro-(2,6-difluoro-4-butylphenyl)-[4-(3',5'-difluoro-4'-difluoromethoxybiphenyl)oxy]methane
Difluoro-(2,6-difluoro-4-pentylphenyl)-[4-(3',5'-difluoro-4'-difluoromethoxybiphenyl)oxy]methane
Difluoro-(2,6-difluoro-4-ethylphenyl)-[4-(3',5'-difluoro-4'-trifluoromethylbiphenyl)oxy]methane
Difluoro-(2,6-difluoro-4-propylphenyl)-[4-(3',5'-difluoro-4'-trifluoromethylbiphenyl)oxy]methane
Difluoro-(2,6-difluoro-4-butylphenyl)-[4-(3',5'-difluoro-4'-trifluoromethylbiphenyl)oxy]methane
Difluoro-(2,6-difluoro-4-pentylphenyl)-[4-(3',5'-difluoro-4'-trifluoromethylbiphenyl)oxy]methane
Difluoro-(2,6-difluoro-4-ethylphenyl)-[4-(3',4',5'-trifluorobiphenyl)oxy]methane
Difluoro-(2,6-difluoro-4-propylphenyl)-[4-(3',4',5'-trifluorobiphenyl)oxy]methane Difluoro-(2,6-difluoro-4-butylphenyl)-[4-(3',4',5'-trifluorobiphenyl)oxy]methane
Difluoro-(2,6-difluoro-4-pentylphenyl)-[4-(3',4',5'-trifluorobiphenyl)oxy]methane
Difluoro-(2,6-difluoro-4-ethylphenyl)-[4-(3',5'-difluoro-4'-cyanobiphenyl)oxy]methane
Difluoro-(2,6-difluoro-4-propylphenyl)-[4-(3',5'-difluoro-4'-cyanobiphenyl)oxy]methane
Difluoro-(2,6-difluoro-4-butylphenyl)-[4-(3',5'-difluoro-4'-cyanobiphenyl)oxy]methane
Difluoro-(2,6-difluoro-4-pentylphenyl)-[4-(3',5'-difluoro-4'-cyanobiphenyl)oxy]methane

EXAMPLE 7

Preparation of difluoro-(4-propylphenyl)-{4-[2-(3,4,5-trifuorophenyl)ethyl]phenyloxy} methane (Compound expressed by the formula (I) wherein R=$C_3H_7$, l=m=0, n=1, ring $A_3$ is 1, 4-phenylene group, $Z_1$ and $Z_2$ are covalent bond, $Z_3$=—$CH_2CH_2$—, $L_1$=$L_2$=H, $L_3$=$L_4$=F, and X=F) 1) Preparation of 4-[2-(3,4,5-trifluorophenyl)ethyl]phenol By the following procedures, 4-[2-(4-trifluoromethoxyphenyl) ethyl]phenol was prepared which is a raw material for the preparation of the subject compounds of this Example. That is, in a 300 ml three neck distillation flask provided with a stirrer, thermometer, nitrogen gas introducing pipe, dropping funnel, and cooling pipe, 2.7 g (108.9 mmol) of magnesium turnings were added, and then a solution of 21.8 g (103.7 mmol) of 3,4,5-trifluorobromobenzene in 30 ml of THF was added dropwise in 25 min so that the internal temperature was maintained at 50° C. After completion of the dropping, the solution was stirred on a hot water bath while keeping the same temperature for 1 hour for ageing to prepare a Grignard reagent. Then, in a 500 ml three neck distillation flask provided with a stirrer, thermometer, nitrogen gas introducing pipe, dropping funnel, and a cooling pipe, separately provided for, 13.4 g (86.4 mmol) of phenyl acetic acid chloride was dissolved in 200 ml of THF. Solution was cooled down to 0° C. while stirring, added with 1.1 g (3.1 mmol) of iron (III) acetyl acetonate, and added further with the Grignard reagent prepared by the procedures mentioned above in 40 min while maintaining 0° C. After completion of the dropping, the solution was further stirred at the same temperature for 1 hour and then 100 ml of 6N aqueous solution of hydrochloric acid was added to terminate the reaction. Reaction solution was extracted with 200 ml×2 of toluene, washed with 200 ml×2 of water, 100 ml of saturated aqueous solution of sodium hydrogencarbonate, and 200 ml×2 of water in turn, dried over anhydrous magnesium sulfate, and then concentrated under a reduced pressure to obtain 23.4 g of reaction product. The reaction product was purified by a reduced-pressure distillation to obtain 18.3 g of colorless oily product. Subsequently, the reaction product was dissolved in 150 ml of toluene in a 1 liter autoclave, added with 1.0 g of 5%-Pd/C, and then subjected to a reduction with hydrogen at a temperature of 90 to 100° C. under a hydrogen pressure of 100 Kg/$cm^2$ for 13 hours. From the reaction solution, catalyst was filtered off, and the solution was concentrated under a reduced pressure to obtain 17.2 g of reaction product. The reaction product was purified by a chromatography to obtain 15.3 g of colorless crystal product. This product was 4-[2-(3,4,5-trifluo rophenyl)ethyl] benzene. By treating the 4-[2-(3,4,5-trifluoroph enyl)ethyl] benzene by the same procedures as shown in Example 5, 1) mentioned above, 10.8 g (43.1 mmol) of 4-[2-(3,4,5-trifluorophenyl)ethyl]phenol was prepared.

2) Preparation of difluoro-(4-propylphenyl)-{4-[2-(3,4,5-trifluorophenyl)ethyl]phenyloxy} methane In a 500 ml three neck distillation flask provided with a stirrer, thermometer, dropping funnel, and nitrogen gas introducing pipe, 5.9 g (35.9 mmol) of 4-propylbenzoic acid, 8.5 g (43.1 mmol) of DCC, and 0.15 g (1.2 mmol) of DMAP were dissolved in 150 ml of dichloromethane, and then a solution of 10.8 g (43.1 mmol) of 4-[2-(3,4,5-trifluorophenyl)ethyl]phenol in 50 ml of dichloromethane was added dropwise at room temperature in 15 min while stirring. After the dropping, the solution was stirred at room temperature for 20 hours. After the reaction solution was added with 100 ml of water, the dichloromethane insoluble matter was filtered off, the dichloromethane layer was separated, and the water layer was further extracted with 200 ml of dichoromethane. Extracted layers were mixed, washed with 100 ml×2 of water, 100 ml of saturated aqueous solution of sodium hydrogencarbonate, and 100 ml×2 of water in turn, dried over anhydrous magnesium sulfate, and then concentrated under a reduced pressure to obtain 14.8 g of reaction product. The reaction product was purified by a chromatograhy using silica gel as filler and using toluene as developing solvent, and further recrystallized from a mixed solvent of heptane-ethanol to obtain 11.4 g of colorless crystal product. This product was 4-[2-(3,4,5-trifluorophenyl) ethyl]phenyl-(4-propyl)benzoate.

Subsequently, in a 1000 ml egg-plant type flask provided with a nitrogen gas introducing pipe and cooling pipe, 11.4 g (28.7 mmol) of 4-[2-(3,4,5-trifluorophenyl)ethyl]phenyl-(4-propyl)benzoate obtained by the procedures mentioned above and 23.2 g (57.4 mmol) of Lawesson's reagent were dissolved in 350 ml of toluene, and the solution was refluxed while stirring under nitrogen gas stream for 60 hours. After the reaction solution was cooled down to room temperature, 200 ml of water was added, the toluene layer was separated, and then the water layer was further extracted with 150 ml of toluene. Organic layers were mixed, washed with 200 ml×2 of water, 100 ml of 10% aqueous solution of sodium hydrogencarbonate, 100 ml of 10% aqueous solution of sodium hydrogensulfite, and 200 ml×2 of water in turn, dried over anhydrous magnesium sulfate, and then concentrated under a reduced pressure to obtain 11.4 g of brown crystalline mixture. The reaction product was purified by a column chromatography using silica gel as filler and using heptane as developing solvent, and then recrystallized from heptane to obtain 5.5 g of yellow needle-like crystal product. This product was 4-propylphenylcarbothio acid-O-4-[2-(3,4,5-trifluorophenyl)ethyl]phenyl.

In a 100 ml egg-plant type flask provided with a nitrogen gas introducing pipe, 5.5 g (13.3 mmol) of 4-propylphenylcarbothio acid-O-4-[2-(3,4,5-trifluorophenyl)ethyl]phenyl was dissolved in 50 ml of dichloromethane at room temperature, and then 6.4 g (39.8 mmol) of DAST was added to the solution and the solution was stirred at room temperature for 30 hours. Reaction solution was added with 50 ml of water, the dichloromethane layer was separated, and the water layer was further extracted with 50 ml of dichloromethane. Extracted layers were mixed, washed with 50 ml×2 of water, 30 ml of saturated aqueous solution of sodium hydrogencarbonate, and 50 ml×2 of water in turn, dried over anhydrous magnesium sulfate, and then concentrated under a reduced pressure to obtain 5.5 g of colorless crystal product. Reaction product was purified by a column chromatography using silica gel as filler and using heptane as developing solvent, and then recrystallized from heptane to obtain 1.1 g of colorless needle-like crystal product. This product was difluoro-(4-propylphenyl)-{4-[2-(3,4,5-trifluorophenyl)ethyl]phenyloxy} methane.

Following compounds can be prepared according to the preparation method by using 4-alkylbenzoic acids having a different alkyl chain in place of 4-propylbenzoic acid:

Difluoro-(4-methylphenyl)-{4-[2-(3,4,5-trifluorophenyl)ethyl]phenyloxy} methane
Difluoro-(4-ethylphenyl)-{4-[2-(3,4,5-trifluorophenyl)ethyl]phenyloxy} methane
Difluoro-(4-butylphenyl)-{4-[2-(3,4,5-trifluorophenyl)ethyl]phenyloxy} methane
Difluoro-(4-pentylphenyl)-{4-[2-(3,4,5-trifluorophenyl)ethyl]phenyloxy} methane
Difluoro-(4-hexylphenyl)-{4-[2-(3,4,5-trifluorophenyl)ethyl]phenyloxy} methane
Difluoro-(4-heptylphenyl)-{4-[2-(3,4,5-trifluorophenyl)ethyl]phenyloxy} methane
Difluoro-(4-octylphenyl)-{4-[2-(3,4,5-trifluorophenyl)ethyl]phenyloxy} methane
Difluoro-(4-nonylphenyl)-{4-[2-(3,4,5-trifluorophenyl)ethyl]phenyloxy} methane
Difluoro-(4-decylphenyl)-{4-[2-(3,4,5-trifluorophenyl)ethyl]phenyloxy} methane Also, the following compounds can be prepared according to the preparation method mentioned above by using several phenol derivatives which can be prepared by the procedures in 1) above in place of 4-[2-(3,4,5-trifluorophenyl)ethyl]phenol:

Difluoro-(4-ethylphenyl)-{4-[2-(4-difluoromethoxyphenyl)ethyl]phenyloxy} methane
Difluoro-(4-propylphenyl)-{4-[2-(4-difluoromethoxyphenyl) ethyl]phenyloxy} methane
Difluoro-(4-butylphenyl)-{4-[2-(4-difluoromethoxyphenyl)ethyl]phenyloxy} methane
Difluoro-(4-pentylphenyl)-{4-[2-(4-difluoromethoxyphenyl) ethyl]phenyloxy} methane
Difluoro-(4-ethylphenyl)-{4-[2-(4-trifluoromethylphenyl)ethyl]phenyloxy} methane
Difluoro-(4-propylphenyl)-{4-[2-(4-trifluoromethylphenyl)ethyl]phenyloxy} methane
Difluoro-(4-butylphenyl)-{4-[2-(4-trifluoromethylphenyl)ethyl]phenyloxy} methane
Difluoro-(4-pentylphenyl)-{4-[2-(4-trifluoromethylphenyl)ethyl]phenyloxy} methane
Difluoro-(4-ethylphenyl)-{4-[2-(4-trifluoromethoxyphenyl)ethyl]phenyloxy} methane
Difluoro-(4-propylphenyl)-{4-[2-(4-trifluoromethoxyphenyl)ethyl]phenyloxy} methane
Difluoro-(4-butylphenyl)-{4-[2-(4-trifluoromethoxyphenyl)ethyl]phenyloxy} methane
Difluoro-(4-pentylphenyl)-{4-[2-(4-trifluoromethoxyphenyl)ethyl] phenyloxy} methane
Difluoro-(4-ethylphenyl)-{4-[2-(4-cyanophenyl)ethyl] phenyloxy} methane
Difluoro-(4-propylphenyl)-{4-[2-(4-cyanophenyl)ethyl] phenyloxy} methane
Difluoro-(4-butylphenyl)-{4-[2-(4-cyanophenyl)ethyl] phenyloxy} methane
Difluoro-(4-pentylphenyl)-{4-[2-(4-cyanophenyl)ethyl] phenyloxy} methane
Difluoro-(4-ethylphenyl)-{4-[2-(3-fluoro-4-trifluoromethoxyphenyl)ethyl]phenyloxy} methane
Difluoro-(4-propylphenyl)-{4-[2-(3-fluoro-4-trifluoromethoxyphenyl)ethyl]phenyloxy} methane
Difluoro-(4-butylphenyl)-{4-[2-(3-fluoro-4-trifluoromethoxyphenyl)ethyl]phenyloxy} methane
Difluoro-(4-pentylphenyl)-{4-[2-(3-fluoro-4-trifluoromethoxyphenyl)ethyl]phenyloxy} methane
Difluoro-(4-ethylphenyl)-{4-[2-(3-fluoro-4-difluoromethoxyphenyl)ethyl]phenyloxy} methane
Difluoro-(4-propylphenyl)-{4-[2-(3-fluoro-4-difluoromethoxyphenyl)ethyl]phenyloxy} methane
Difluoro-(4-butylphenyl)-{4-[2-(3-fluoro-4-difluoromethoxyphenyl)ethyl]phenyloxy} methane
Difluoro-(4-pentylphenyl)-{4-[2-(3-fluoro-4-difluoromethoxyphenyl)ethyl]phenyloxy} methane
Difluoro-(4-ethylphenyl)-{4-[2-(3-fluoro-4-trifluoromethylphenyl)ethyl]phenyloxy} methane
Difluoro-(4-propylphenyl)-{4-[2-(3-fluoro-4-trifluoromethylphenyl)ethyl]phenyloxy} methane
Difluoro-(4-butylphenyl)-{4-[2-(3-fluoro-4-trifluoromethylphenyl)ethyl]phenyloxy} methane
Difluoro-(4-pentylphenyl)-{4-[2-(3-fluoro-4-trifluoromethylphenyl)ethyl]phenyloxy} methane
Difluoro-(4-ethylphenyl)-{4-[2-(3-fluoro-4-cyanophenyl)ethyl]phenyloxy} methane Difluoro-(4-propylphenyl)-{4-[2-(3-fluoro-4-cyanophenyl)ethyl]phenyloxy} methane
Difluoro-(4-butylphenyl)-{4-[2-(3-fluoro-4-cyanophenyl)ethyl]phenyloxy} methane
Difluoro-(4-pentylphenyl)-{4-[2-(3-fluoro-4-cyanophenyl)ethyl]phenyloxy} methane
Difluoro-(4-ethylphenyl)-{4-[2-(3,5-difluoro-4-trifluoromethoxyphenyl)ethyl]phenyloxy} methane
Difluoro-(4-propylphenyl)-{4-[2-(3,5-difluoro-4-trifluoromethoxyphenyl)ethyl]phenyloxy} methane
Difluoro-(4-butylphenyl)-{4-[2-(3,5-difluoro-4-trifluoromethoxyphenyl)ethyl]phenyloxy} methane
Difluoro-(4-pentylphenyl)-{4-[2-(3,5-difluoro-4-trifluoromethoxyphenyl)ethyl]phenyloxy} methane
Difluoro-(4-ethylphenyl)-{4-[2-(3,5-difluoro-4-difluoromethoxyphenyl)ethyl]phenyloxy} methane
Difluoro-(4-propylphenyl)-{4-[2-(3,5-difluoro-4-difluoromethoxyphenyl)ethyl]phenyloxy} methane
Difluoro-(4-butylphenyl)-(4-[2-(3,5-difluoro-4-difluoromethoxyphenyl)ethyl]phenyloxy} methane
Difluoro-(4-pentylphenyl)-{4-[2-(3,5-difluoro-4-difluoromethoxyphenyl)ethyl]phenyloxy} methane
Difluoro-(4-ethylphenyl)-{4-[2-(3,5-difluoro-4-trifluoromethylphenyl)ethyl]phenyloxy} methane
Difluoro-(4-propylphenyl)-{4-[2-(3,5-difluoro-4-trifluoromethylphenyl)ethyl]phenyloxy} methane
Difluoro-(4-butylphenyl)-{4-[2-(3,5-difluoro-4-trifluoromethylphenyl)ethyl]phenyloxy} methane
Difluoro-(4-pentylphenyl)-{4-(2-(3,5-difluoro-4-trifluoromethylphenyl)ethyl]phenyloxy} methane
Difluoro-(4-ethylphenyl)-{4-[2-(3,5-difluoro-4-cyanophenyl)ethyl]phenyloxy} methane
Difluoro-(4-propylphenyl)-{4-[2-(3,5-difluoro-4-cyanophenyl)ethyl]phenyloxy} methane
Difluoro-(4-butylphenyl)-{4-[2-(3,5-difluoro-4-cyanophenyl)ethyl]phenyloxy} methane
Difluoro-(4-pentylphenyl)-{4-[2-(3,5-difluoro-4-cyanophenyl)ethyl]phenyloxy} methane
Difluoro-(2-fluoro-4-ethylphenyl)-{4-[2-(3,5-difluoro-4-trifluoromethoxyphenyl)ethyl]phenyloxy} methane
Difluoro-(2-fluoro-4-propylphenyl)-{4-[2-(3,5-difluoro-4-trifluoromethoxyphenyl)ethyl]phenyloxy} methane
Difluoro-(2-fluoro-4-butylphenyl)-{4-[2-(3,5-difluoro-4-trifluoromethoxyphenyl)ethyl]phenyloxy} methane
Difluoro-(2-fluoro-4-pentylphenyl)-{4-[2-(3,5-difluoro-4-trifluoromethoxyphenyl)ethyl]phenyloxy} methane
Difluoro-(2-fluoro-4-ethylphenyl)-{4-[2-(3,5-difluoro-4-difluoromethoxyphenyl)ethyl]phenyloxy} methane
Difluoro-(2-fluoro-4-propylphenyl)-{4-[2-(3,5-difluoro-4-difluoromethoxyphenyl)ethyl]phenyloxy} methane
Difluoro-(2-fluoro-4-butylphenyl)-{4-[2-(3,5-difluoro-4-difluoromethoxyphenyl)ethyl]phenyloxy} methane
Difluoro-(2-fluoro-4-pentylphenyl)-{4-[2-(3,5-difluoro-4-difluoromethoxyphenyl)ethyl]phenyloxy} methane
Difluoro-(2-fluoro-4-ethylphenyl)-{4-[2-(3,5-difluoro-4-trifluoromethylphenyl)ethyl]phenyloxy} methane
Difluoro-(2-fluoro-4-propylphenyl)-{4-[2-(3,5-difluoro-4-trifluoromethylphenyl)ethyl]phenyloxy} methane
Difluoro-(2-fluoro-4-butylphenyl)-{4-[2-(3,5-difluoro-4-trifluoromethylphenyl)ethyl]phenyloxy} methane
Difluoro-(2-fluoro-4-pentylphenyl)-{4-[2-(3,5-difluoro-4-trifluoromethylphenyl)ethyl]phenyloxy} methane
Difluoro-(2-fluoro-4-ethylphenyl)-{4-[2-(3,4,5-trifluorophenyl)ethyl]phenyloxy} methane
Difluoro-(2-fluoro-4-propylphenyl)-{4-[2-(3,4,5-trifluorophenyl)ethyl]phenyloxy} methane
Difluoro-(2-fluoro-4-butylphenyl)-{4-[2-(3,4,5-trifluorophenyl)ethyl]phenyloxy} methane
Difluoro-(2-fluoro-4-pentylphenyl)-{4-[2-(3,4,5-trifluorophenyl)ethyl]phenyloxy} methane
Difluoro-(2-fluoro-4-ethylphenyl)-{4-[2-(3,5-difluoro-4-cyanophenyl)ethyl]phenyloxy} methane
Difluoro-(2-fluoro-4-propylphenyl)-{4-[2-(3,5-difluoro-4-cyanophenyl)ethyl]phenyloxy} methane
Difluoro-(2-fluoro-4-butylphenyl)-{4-[2-(3,5-difluoro-4-cyanophenyl)ethyl]phenyloxy} methane
Difluoro-(2-fluoro-4-pentylphenyl)-{4-[2-(3,5-difluoro-4-cyanophenyl)ethyl]phenyloxy} methane
Difluoro-(2,6-difluoro-4-ethylphenyl)-(4-[2-(3,5-difluoro-4-trifluoromethoxyphenyl)ethyl]phenyloxy} methane
Difluoro-(2,6-difluoro-4-propylphenyl)-{4-[2-(3,5-difluoro-4-trifluoromethoxyphenyl)ethyl]phenyloxy} methane
Difluoro-(2,6-difluoro-4-butylphenyl)-{4-[2-(3,5-difluoro-4-trifluoromethoxyphenyl)ethyl]phenyloxy} methane
Difluoro-(2,6-difluoro-4-pentylphenyl)-{4-[2-(3,5-difluoro-4-trifluoromethoxyphenyl)ethyl]phenyloxy} methane
Difluoro-(2,6-difluoro-4-ethylphenyl)-{4-[2-(3,5-difluoro-4-difluoromethoxyphenyl)ethyl]phenyloxy} methane
Difluoro-(2,6-difluoro-4-propylphenyl)-{4-[2-(3,5-difluoro-4-difluoromethoxyphenyl)ethyl]phenyloxy} methane
Difluoro-(2,6-difluoro-4-butylphenyl)-{4-[2-(3,5-difluoro-4-difluoromethoxyphenyl)ethyl]phenyloxy} methane
Difluoro-(2,6-difluoro-4-pentylphenyl)-{4-[2-(3,5-difluoro-4-difluoromethoxyphenyl)ethyl]phenyloxy} methane
Difluoro-(2,6-difluoro-4-ethylphenyl)-{4-[2-(3,5-difluoro-4-trifluoromethylphenyl)ethyl]phenyloxy} methane
Difluoro-(2,6-difluoro-4-propylphenyl)-{4-[2-(3,5-difluoro-4-trifluoromethylphenyl)ethyl]phenyloxy} methane
Difluoro-(2,6-difluoro-4-butylphenyl)-{4-[2-(3,5-difluoro-4-trifluoromethylphenyl)ethyl]phenyloxy} methane
Difluoro-(2,6-difluoro-4-pentylphenyl)-{4-[2-(3,5-difluoro-4-trifluoromethylphenyl)ethyl]phenyloxy} methane
Difluoro-(2,6-difluoro-4-ethylphenyl)-{4-[2-(3,4,5-trifluorophenyl)ethyl]phenyloxy} methane
Difluoro-(2,6-difluoro-4-propylphenyl)-{4-[2-(3,4,5-trifluorophenyl)ethyl]phenyloxy} methane
Difluoro-(2,6-difluoro-4-butylphenyl)-{4-[2-(3,4,5-trifluorophenyl)ethyl]phenyloxy} methane
Difluoro-(2,6-difluoro-4-pentylphenyl)-{4-[2-(3,4,5-trifluorophenyl)ethyl]phenyloxy} methane
Difluoro-(2,6-difluoro-4-ethylphenyl)-{4-[2-(3,5-difluoro-4-cyanophenyl)ethyl]phenyloxy} methane
Difluoro-(2,6-difluoro-4-propylphenyl)-{4-[2-(3,5-difluoro-4-cyanophenyl)ethyl]phenyloxy} methane
Difluoro-(2,6-difluoro-4-butylphenyl)-{4-[2-(3,5-difluoro-4-cyanophenyl)ethyl]phenyloxy} methane
Difluoro-(2,6-difluoro-4-pentylphenyl)-{4-[2-(3,5-difluoro-4-cyanophenyl)ethyl]phenyloxy} methane

EXAMPLE 8

Preparation of difluoro-(4-propylphenyl)-{4-[difluoro-(4-trifuoromethoxyphenyloxy)methyl]phenyloxy} methane (Compound expressed by the formula (I) wherein R=$C_3H_7$, l=1, m=n=0, ring $A_1$ is 1,4-phenylene group, $Z_1$=—$CF_2O$—, $Z_2$ and $Z_3$ are covalent bond, $L_1$, $L_2$, L3, and $L_4$ are hydrogen atom, and X=$OCF_3$)

1) Preparation of 4-[difluoro-(4-propylphenyl)methyloxy]benzoic acid

By the following procedures, 4-[difluoro-(4-propylphenyl) methyloxy]benzoic acid was prepared which is a raw material for the preparation of the subject compounds of this Example.

It was prepared by using difluoro-(4-propylphenyl)-(4-cyanophenyloxy)methane (prepared in Example 1) as a raw material for the preparation and subjecting it to a hydrolysis. That is, in a 500 ml three neck distillation flask provided with a stirrer, thermometer, and cooling pipe, 15.0 g (52.2 mmol) of difluoro-(4-propylphenyl)-(4-cyanophenyloxy) methane and 7.3 g (130.5 mmol) of potassium hydroxide were dissolved in 200 ml of ethylene glycol and the solution was heated at 150° C. for 10 hours while stirring. Reaction solution was cooled down to room temperature and added with 100 ml of water and 50 ml of 6N aqueous solution of hydrochloric acid. Precipitated insoluble matter was filtered off, and the precipitate was washed with water, dried under a reduced pressure, and further recrystallized from a mixed solvent of toluene-heptane to obtain 14.3 g of colorless crystal product. This product was 4-[difluo ro-(4-propylphenyl)methyloxy]benzoic acid.

2) Preparation of difluoro-(4-propylphenyl)-{4-[difluoro-(4-trifluoromethoxyphenyloxy)methyl]phenyloxy} methane In a 500 ml three neck distillation flask provided with a stirrer, thermometer, dropping funnel, and nitrogen gas introducing pipe, 14.3 g (46.5 mmol) of 4-[difluoro(4-propylphenyl)methyloxy]benzoic acid, 11.5 g (55.7 mmol) of DCC, and 0.2 g (1.7 mmol) of DMAP were dissolved in 250 ml of dichloromethane, and then 9.9 g (55.7 mmol) of (4-trifluoromethoxy)phenol was added to the solution while stirring at room temperature in 5 min, and then stirred at room temperature for 20 hours. After the reaction solution was added with 100 ml of water, dichoromethane insoluble matter was filtered off, the dichloromethane layer was separated, and the water layer was further extracted with 200 ml of dichloromethane. Extracted layers were mixed, washed with 100 ml×2 of water, 100 ml of saturated aqueous solution of sodium hydrogencarbonate, and 100 ml×2 of water in turn, dried over anhydrous magnesium sulfate, and then concentrated under a reduced pressure to obtain 25.4 g of reaction product. The reaction product was purified by a chromatograhy using silica gel as filler and using toluene as developing solvent, and further recrystallized from a mixed solvent of heptane-ethanol to obtain 21.8 g of colorless crystal product. This product was 4-trifluoromethoxyphenyl-{4-[difluoro-(4-propylphenyl)methyloxy)benzoate.

Subsequently, in a 1000 ml egg-plant type flask provided with a nitrogen gas introducing pipe and cooling pipe, 21.8 g (46.8 mmol) of 4-trifluoromethoxyphenyl-{4-[difluoro-(4-propylphenyl)methyloxy)benzoate obtained by the procedures mentioned above and 37.8 g (93.6 mmol) of Lawesson's reagent were dissolved in 350 ml of toluene, and the solution was refluxed while stirring under nitrogen gas stream for 60 hours. After the reaction solution was cooled down to room temperature, 200 ml of water was added, the toluene layer was separated, and the water layer was further extracted with 150 ml of toluene. Organic layers were mixed, washed with 200 ml×2 of water, 100 ml of saturated aqueous solution of sodium hydrogencarbonate, 100 ml of 10% aqueous solution of sodium hydrogensulfite, and 200 ml×2 of water in turn, dried over anhydrous magnesium sulfate, and then concentrated under a reduced pressure to obtain 21.9 g of brown crystalline product. Concentrated product was purified by a column chromatography using silica gel as filler and using heptane as developing solvent, and then recrystallized from heptane to obtain 8.9 g of yellow needle-like crystal product. This product was 4-(difluoro-(4-propylphe nyl)methyloxy]phenylcarbothio acid-O-(4-trifluoromethoxy)phenyl.

In a 100 ml egg-plant type flask provided with a nitrogen gas introducing pipe, 8.9 g (18.4 mmol) of 4-[difluoro-(4-propylphenyl)methyloxy]phenylcarbothio acid-O-(4-trifluoromethoxy)phenyl was dissolved in 50 ml of dichloromethane at room temperature, and then 8.9 g (55.3 mmol) of DAST was added to the solution and the solution was stirred at room temperature for 30 hours. Reaction solution was added with 50 ml of water, the dichloromethane layer was separated, and the water layer was further extracted with 50 ml of dichloromethane. Extracted layers were mixed, washed with 50 ml×2 of water, 30 ml of saturated aqueous solution of sodium hydrogencarbonate, and 50 ml×2 of water in turn, dried over anhydrous magnesium sulfate, and then concentrated under a reduced pressure to obtain 8.5 g of colorless crystal product. Reaction product was purified by a column chromatography using silica gel as filler and using heptane as developing solvent, and then recrystallized from heptane to obtain 1.9 g of colorless needle-like crystal product. This product was difluoro-(4-propylphenyl)-{4-[difluoro(4-trifluoromethoxyphenyloxy)methyl]phenyloxy} methane.

Following compounds can be prepared according to the preparation method mentioned above by using 4-[difluoro (4-alkylphenyl)methyloxy]benzoic acid having a different alkyl chain in place of 4-[difluoro(4-propylphenyl) methyloxy]benzoic acid:

Difluoro-(4-methylphenyl)-{4-[difluoro-(4-trifluoromethoxyphenyloxy)methyl]phenyloxy} methane Difluoro-(4-ethylphenyl)-{4-[difluoro-(4-trifluoromethoxyphenyloxy)methyl]phenyloxy} methane Difluoro-(4-butylphenyl)-{4-[difluoro-(4-trifluoromethoxyphenyloxy)methyl]phenyloxy} methane Difluoro-(4-pentylphenyl)-{4-[difluoro-(4-trifluoromethoxyphenyloxy)methyl]phenyloxy} methane Difluoro-(4-hexylphenyl)-{4-[difluoro-(4-trifluoromethoxyphenyloxy)methyl]phenyloxy} methane Difluoro-(4-heptylphenyl)-{4-[difluoro-(4-trifluoromethoxyphenyloxy)methyl]phenyloxy} methane Difluoro-(4-octylphenyl)-{4-[difluoro-(4-trifluoromethoxyphenyloxy)methyl]phenyloxy} methane Difluoro-(4-nonylphenyl)-{4-[difluoro-(4-trifluoromethoxyphenyloxy)methyl]phenyloxy} methane Difluoro-(4-decylphenyl)-{4-[difluoro-(4-trifluoromethoxyphenyloxy)methyl]phenyloxy} methane Also, the following compounds can be prepared according to the preparation method mentioned above by using several known phenol derivatives in place of (4-trifluoromethoxy)phenol:

Difluoro-(4-ethylphenyl)-{4-[difluoro-(4-difluoromethoxyphenyloxy)methyl]phenyloxy} methane Difluoro-(4-propylphenyl)-{4-[difluoro-(4-difluoromethoxyphenyloxy)methyl]phenyloxy} methane Difluoro-(4-butylphenyl)-{4-[difluoro-(4-difluoromethoxyphenyloxy)methyl]phenyloxy} methane Difluoro-(4-pentylphenyl)-{4-[difluoro-(4-difluoromethoxyphenyloxy)methyl]phenyloxy} methane Difluoro-(4-ethylphenyl)-{4-[difluoro-(4-trifluoromethylphenyloxy)methyl]phenyloxy} methane Difluoro-(4-propylphenyl)-{4-[difluoro-(4-trifluoromethylphenyloxy)methyl]phenyloxy} methane Difluoro-(4-butylphenyl)-{4-[difluoro-(4-trifluoromethylphenyloxy)methyl]phenyloxy} methane Difluoro-(4-pentylphenyl)-{4-[difluoro-(4-trifluoromethylphenyloxy)methyl]phenyloxy} methane Difluoro-(4-ethylphenyl)-{4-[difluoro-(3,4,5-trifluorophenyloxy) methyl]phenyloxy} methane Difluoro-(4-propylphenyl)-{4-[difluoro-(3,4,5-trifluorophenyloxy)methyl]phenyloxy} methane Difluoro-(4-butylphenyl)-{4-[difluoro-(3,4,5-trifluorophenyloxy) methyl]phenyloxy} methane Difluoro-(4-pentylphenyl)-{4-[difluoro-(3,4,5-trifluorophenyloxy)methyl]phenyloxy} methane
Difluoro-(4-ethylphenyl)-{4-[difluoro-(4-cyanophenyloxy)methyl]phenyloxy} methane
Difluoro-(4-propylphenyl)-{4-[difluoro-(4-cyanophenyloxy)methyl]phenyloxy} methane
Difluoro-(4-butylphenyl)-{4-[difluoro-(4-cyanophenyloxy)methyl]phenyloxy} methane
Difluoro-(4-pentylphenyl)-{4-[difluoro-(4-cyanophenyloxy)methyl]phenyloxy} methane
Difluoro-(4-ethylphenyl)-{4-[difluoro-(3-fluoro-4-trifluoromethoxyphenyloxy)methyl]phenyloxy} methane
Difluoro-(4-propylphenyl)-{4-[difluoro-(3-fluoro-4-trifluoromethoxyphenyloxy)methyl]phenyloxy} methane
Difluoro-(4-butylphenyl)-{4-[difluoro-(3-fluoro-4-trifluoromethoxyphenyloxy)methyl]phenyloxy} methane
Difluoro-(4-pentylphenyl)-{4-[difluoro-(3-fluoro-4-trifluoromethoxyphenyloxy)methyl]phenyloxy)} methane
Difluoro-(4-ethylphenyl)-{4-[difluoro-(3-fluoro-4-difluoromethoxyphenyloxy)methyl]phenyloxy} methane
Difluoro-(4-propylphenyl)-{4-[difluoro-(3-fluoro-4-difluoromethoxyphenyloxy)methyl]phenyloxy} methane
Difluoro-(4-butylphenyl)-{4-[difluoro-(3-fluoro-4-difluoromethoxyphenyloxy)methyl]phenyloxy} methane
Difluoro-(4-pentylphenyl)-{4-[difluoro-(3-fluoro-4-difluoromethoxyphenyloxy)methyl]phenyloxy} methane
Difluoro-(4-ethylphenyl)-{4-[difluoro-(3-fluoro-4-trifluoromethylphenyloxy)methyl]phenyloxy} methane
Difluoro-(4-propylphenyl)-{4-[difluoro-(3-fluoro-4-trifluoromethylphenyloxy)methyl]phenyloxy} methane
Difluoro-(4-butylphenyl)-{4-[difluoro-(3-fluoro-4-trifluoromethylphenyloxy)methyl]phenyloxy} methane
Difluoro-(4-pentylphenyl)-{4-[difluoro-(3-fluoro-4-trifluoromethylphenyloxy)methyl]phenyloxy} methane
Difluoro-(4-ethylphenyl)-{4-[difluoro-(3-fluoro-4-cyanophenyloxy)methyl]phenyloxy} methane
Difluoro-(4-propylphenyl)-{4-[difluoro-(3-fluoro-4-cyanophenyloxy)methyl]phenyloxy} methane
Difluoro-(4-butylphenyl)-{4-[difluoro-(3-fluoro-4-cyanophenyloxy)methyl]phenyloxy} methane
Difluoro-(4-pentylphenyl)-{4-[difluoro-(3-fluoro-4-cyanophenyloxy)methyl]phenyloxy} methane
Difluoro-(4-ethylphenyl)-{4-[difluoro-(3,5-difluoro-4-trifluoromethoxyphenyloxy)methyl]phenyloxy} methane
Difluoro-(4-propylphenyl)-{4-[difluoro-(3,5-difluoro-4-trifluoromethoxyphenyloxy)methyl]phenyloxy} methane
Difluoro-(4-butylphenyl)-{4-[difluoro-(3,5-difluoro-4-trifluoromethoxyphenyloxy)methyl]phenyloxy} methane
Difluoro-(4-pentylphenyl)-{4-[difluoro-(3,5-difluoro-4-trifluoromethoxyphenyloxy)methyl]phenyloxy} methane
Difluoro-(4-ethylphenyl)-{4-[difluoro-(3,5-difluoro-4-difluoromethoxyphenyloxy)methyl]phenyloxy} methane
Difluoro-(4-propylphenyl)-{4-[difluoro-(3,5-difluoro-4-difluoromethoxyphenyloxy)methyl]phenyloxy} methane
Difluoro-(4-butylphenyl)-{4-[difluoro-(3,5-difluoro-4-difluoromethoxyphenyloxy)methyl]phenyloxy} methane
Difluoro-(4-pentylphenyl)-{4-[difluoro-(3,5-difluoro-4-difluoromethoxyphenyloxy)methyl]phenyloxy} methane
Difluoro-(4-ethylphenyl)-{4-[difluoro-(3,5-difluoro-4-trifluoromethylphenyloxy)methyl]phenyloxy} methane
Difluoro-(4-propylphenyl)-{4-[difluoro-(3,5-difluoro-4-trifluoromethylphenyloxy)methyl]phenyloxy} methane
Difluoro-(4-butylphenyl)-{4-[difluoro-(3,5-difluoro-4-trifluoromethylphenyloxy)methyl]phenyloxy} methane
Difluoro-(4-pentylphenyl)-{4-[difluoro-(3,5-difluoro-4-trifluoromethylphenyloxy)methyl]phenyloxy} methane
Difluoro-(4-ethylphenyl)-{4-[difluoro-(3,5-difluoro-4-cyanophenyloxy)methyl]phenyloxy} methane
Difluoro-(4-propylphenyl)-{4-[difluoro-(3,5-difluoro-4-cyanophenyloxy)methyl]phenyloxy} methane
Difluoro-(4-butylphenyl)-{4-[difluoro-(3,5-difluoro-4-cyanophenyloxy)methyl]phenyloxy} methane
Difluoro-(4-pentylphenyl)-{4-[difluoro-(3,5-difluoro-4-cyanophenyloxy)methyl]phenyloxy} methane
Difluoro-(2-fluoro-4-ethylphenyl)-{4-[difluoro-(3,5-difluoro-4-trifluoromethoxyphenyloxy)methyl]phenyloxy} methane
Difluoro-(2-fluoro-4-propylphenyl)-{4-[difluoro-(3,5-difluoro-4-trifluoromethoxyphenyloxy)methyl]phenyloxy} methane
Difluoro-(2-fluoro-4-butylphenyl)-{4-[difluoro-(3,5-difluoro-4-trifluoromethoxyphenyloxy)methyl]phenyloxy} methane
Difluoro-(2-fluoro-4-pentylphenyl)-{4-[difluoro-(3,5-difluoro-4-trifluoromethoxyphenyloxy)methyl]phenyloxy} methane
Difluoro-(2-fluoro-4-ethylphenyl)-{4-[difluoro-(3,5-difluoro-4-difluoromethoxyphenyloxy)methyl]phenyloxy} methane
Difluoro-(2-fluoro-4-propylphenyl)-{4-[difluoro-(3,5-difluoro-4-difluoromethoxyphenyloxy)methyl]phenyloxy} methane
Difluoro-(2-fluoro-4-butylphenyl)-{4-[difluoro-(3,5-difluoro-4-difluoromethoxyphenyloxy)methyl]phenyloxy} methane
Difluoro-(2-fluoro-4-pentylphenyl)-{4-[difluoro-(3,5-difluoro-4-difluoromethoxyphenyloxy)methyl]phenyloxy} methane
Difluoro-(2-fluoro-4-ethylphenyl)-{4-[difluoro-(3,5-difluoro-4-trifluoromethylphenyloxy)methyl]phenyloxy} methane
Difluoro-(2-fluoro-4-propylphenyl)-{4-[difluoro-(3,5-difluoro-4-trifluoromethylphenyloxy)methyl]phenyloxy} methane
Difluoro-(2-fluoro-4-butylphenyl)-{4-[difluoro-(3,5-difluoro-4-trifluoromethylphenyloxy)methyl]phenyloxy} methane
Difluoro-(2-fluoro-4-pentylphenyl)-{4-[difluoro-(3,5-difluoro-4-trifluoromethylphenyloxy)methyl]phenyloxy} methane
Difluoro-(2-fluoro-4-ethylphenyl)-{4-[difluoro-(3,4,5-trifluorophenyloxy)methyl]phenyloxy} methane
Difluoro-(2-fluoro-4-propylphenyl)-{4-[difluoro-(3,4,5-trifluorophenyloxy)methyl]phenyloxy} methane
Difluoro-(2-fluoro-4-butylphenyl)-{4-[difluoro-(3,4,5-trifluorophenyloxy)methyl]phenyloxy} methane
Difluoro-(2-fluoro-4-pentylphenyl)-{4-[difluoro-(3,4,5-trifluorophenyloxy)methyl]phenyloxy} methane
Difluoro-(2-fluoro-4-ethylphenyl)-{4-[difluoro-(3,5-difluoro-4-cyanophenyloxy)methyl]phenyloxy} methane
Difluoro-(2-fluoro-4-propylphenyl)-{4-[difluoro-(3,5-difluoro-4-cyanophenyloxy)methyl]phenyloxy} methane
Difluoro-(2-fluoro-4-butylphenyl)-{4-[difluoro-(3,5-difluoro-4-cyanophenyloxy)methyl]phenyloxy} methane
Difluoro-(2-fluoro-4-pentylphenyl)-{4-[difluoro-(3,5-difluoro-4-cyanophenyloxy)methyl]phenyloxy} methane
Difluoro-(2,6-difluoro-4-ethylphenyl)-{4-[difluoro-(3,5-difluoro-4-trifluoromethoxyphenyloxy)methyl]phenyloxy} methane
Difluoro-(2,6-difluoro-4-propylphenyl)-{4-[difluoro-(3,5-difluoro-4-trifluoromethoxyphenyloxy)methyl]phenyloxy} methane
Difluoro-(2,6-difluoro-4-butylphenyl)-{4-[difluoro-(3,5-difluoro-4-trifluoromethoxyphenyloxy)methyl]phenyloxy} methane Difluoro-(2,6-difluoro-4-pentylphenyl)-{4-(difluoro-(3,5-difluoro-4-trifluoromethoxyphenyloxy)methyl]phenyloxy} methane Difluoro-(2,6-difluoro-4-ethylphenyl)-{4-(difluoro-(3,5-difluoro-4-difluoromethoxyphenyloxy)methyl]phenyloxy} methane Difluoro-(2,6-difluoro-4-propylphenyl)-{4-[difluoro-(3,5-difluoro-4-difluoromethoxyphenyloxy)methyl]phenyloxy} methane Difluoro-(2,6-difluoro-4-butylphenyl)-{4-[difluoro-(3,5-difluoro-4-difluoromethoxyphenyloxy)methyl]phenyloxy} methane Difluoro-(2,6-difluoro-4-pentylphenyl)-{4-[difluoro-(3,5-difluoro-4-difluoromethoxyphenyloxy)methyl]phenyloxy} methane Difluoro-(2,6-difluoro-4-ethylphenyl)-{4-[difluoro-(3,5-difluoro-4-trifluoromethylphenyloxy)methyl]phenyloxyl methane Difluoro-(2,6-difluoro-4-propylphenyl)-{4-[difluoro-(3,5-difluoro-4-trifluoromethylphenyloxy)methyl]phenyloxy} methane Difluoro-(2,6-difluoro-4-butylphenyl)-{4-(difluoro-(3,5-difluoro-4-trifluoromethylphenyloxy)methyl]phenyloxy} methane Difluoro-(2,6-difluoro-4-pentylphenyl)-{4-[difluoro-(3,5-difluoro-4-trifluoromethylphenyloxy)methyl]phenyloxy} methane Difluoro-(2,6-difluoro-4-ethylphenyl)-{4-[difluoro-(3,4,5-trifluorophenyloxy)methyl]phenyloxy} methane Difluoro-(2,6-difluoro-4-propylphenyl)-{4-[difluoro-(3,4,5-trifluorophenyloxy)methyl]phenyloxy} methane Difluoro-(2,6-difluoro-4-butylphenyl)-{4-[difluoro-(3,4,5-trifluorophenyloxy)methyl]phenyloxy} methane Difluoro-(2,6-difluoro-4-pentylphenyl)-{4-[difluoro-(3,4,5-trifluorophenyloxy)methyl]phenyloxy} methane Difluoro-(2,6-difluoro-4-ethylphenyl)-{4-[difluoro-(3,5-difluoro-4-cyanophenyloxy)methyl]phenyloxy} methane Difluoro-(2,6-difluoro-4-propylphenyl)-{4-[difluoro-(3,5-difluoro-4-cyanophenyloxy)methyl]phenyloxy} methane Difluoro-(2,6-difluoro-4-butylphenyl)-{4-[difluoro-(3,5-difluoro-4-cyanophenyloxy)methyl]phenyloxy} methane Difluoro-(2,6-difluoro-4-pentylphenyl)-{4-[difluoro-(3,5-difluoro-4-cyanophenyloxy)methyl]phenyloxy} methane Difluoro-(2,6-difluoro-4-ethylphenyl)-{4-[difluoro-(4-ethylphenyloxy)methyl]pentyloxy} methane Difluoro-(2,6-difluoro-4-ethylphenyl)-{4-[difluoro-(4-propylphenyloxy)methyl]pentyloxy} methane Difluoro-(2,6-difluoro-4-ethylphenyl)-{4-[difluoro-(4-butylphenyloxy)methyl]pentyloxy} methane Difluoro-(2,6-difluoro-4-ethylphenyl)-{4-[difluoro-(4-pentylphenyloxy)methyl]pentyloxy} methane Difluoro-(2,6-difluoro-4-ethylphenyl)-{4-[difluoro-(4-hexylphenyloxy)methyl]pentyloxy} methane Difluoro-(2,6-difluoro-4-propylphenyl)-{4-[difluoro-(4-ethylphenyloxy)methyl]phenyloxy} methane Difluoro-(2,6-difluoro-4-propylphenyl)-{4-[difluoro-(4-propylphenyloxy)methyl]phenyloxy} methane Difluoro-(2,6-difluoro-4-propylphenyl)-{4-[difluoro-(4-butylphenyloxy)methyl]phenyloxy} methane Difluoro-(2,6-difluoro-4-propylphenyl)-{4-[difluoro-(4-pentylphenyloxy)methyl]phenyloxy} methane Difluoro-(2,6-difluoro-4-propylphenyl)-{4-[difluoro-(4-hexylphenyloxy)methyl]phenyloxy} methane Difluoro-(2,6-difluoro-4-butylphenyl)-{4-[difluoro-(4-ethylphenyloxy)methyl]phenyloxy} methane Difluoro-(2,6-difluoro-4-butylphenyl)-{4-[difluoro-(4-propylphenyloxy)methyl]phenyloxy} methane Difluoro-(2,6-difluoro-4-butylphenyl)-{4-[difluoro-(4-butylphenyloxy)methyl]phenyloxy} methane Difluoro-(2,6-difluoro-4-butylphenyl)-{4-[difluoro-(4-pentylphenyloxy)methyl]phenyloxy} methane Difluoro-(2,6-difluoro-4-butylphenyl)-{4-[difluoro-(4-hexylphenyloxy)methyl]phenyloxy} methane Difluoro-(2,6-difluoro-4-pentylphenyl)-{4-[difluoro-(4-ethylphenyloxy)methyl]phenyloxy} methane Difluoro-(2,6-difluoro-4-pentylphenyl)-{4-[difluoro-(4-propylphenyloxy)methyl]phenyloxy} methane Difluoro-(2,6-difluoro-4-pentylphenyl)-{4-[difluoro-(4-butylphenyloxy)methyl]phenyloxy} methane Difluoro-(2,6-difluoro-4-pentylphenyl)-{4-[difluoro-(4-pentylphenyloxy)methyl]phenyloxy} methane Difluoro-(2,6-difluoro-4-pentylphenyl)-{4-[difluoro-(4-hexylphenyloxy)methyl]phenyloxy} methane Difluoro-(2,6-difluoro-4-hexylphenyl)-{4-[difluoro-(4-ethylphenyloxy)methyl]phenyloxy} methane Difluoro-(2,6-difluoro-4-hexylphenyl)-{4-[difluoro-(4-propylphenyloxy)methyl]phenyloxy} methane Difluoro-(2,6-difluoro-4-hexylphenyl)-{4-[difluoro-(4-butylphenyloxy)methyl]phenyloxy} methane Difluoro-(2,6-difluoro-4-hexylphenyl)-{4-[difluoro-(4-pentylphenyloxy)methyl]phenyloxy} methane Difluoro-(2,6-difluoro-4-hexylphenyl)-{4-[difluoro-(4-hexylphenyloxy)methyl]phenyloxy} methane

EXAMPLE 9

Preparation of difluoro-(4-propylphenyloxy)-{4-[difluoro-(4-pentylphenyloxy)methyl]phenyl} methane (Compound expressed by the formula (I) wherein $R=C_3H_7$, $l=1$, $m=n=0$, ring $A_1$ is 1,4-phenylene group, $Z_1=$—$OCF_2$—, $Z_2$ and $Z_3$ are covalent bond, $L_1$, $L_2$, $L_3$, and $L_4$ are hydrogen atom, and $X=C_5H_{11}$.)

In a 1000 ml three neck distillation flask provided with a stirrer, dropping funnel, thermometer, and cooling pipe, 25.0 g (166.5 mmol) of 4-forlmylbenzoic acid, 41.2 g (199.8 mmol) of DCC, and 0.73 g (5.9 mmol) of DMAP were dissolved in 300 ml of dichloromethane at room temperature, and then a solution of 27.2 g (199.8 mmol) of 4-propylphenol in 100 ml of dichloromethane was added dropwise in 40 min while stirring. After the dropping, the solution was stirred for 10 hours. Reaction solution was added with 200 ml of water, and dichloromethane insoluble matter was filtered off, the dichloromethane layer was separated, and the water layer was further extracted with 300 ml of dichloromethane. Extracted layers were mixed, washed with 300 ml×2 of water, 200 ml of saturated aqueous solution of sodium hydrogencarbonate, and 300 ml×2 of water in turn, dried over anhydrous magnesium sulfate, and then concentrated under a reduced pressure to obtain 42.1 g of reaction product. This product was 4-propylphenyl-(4-formyl)benzoate. This 4-propylphenyl-(4-formyl)benzoate which was used for next preparation step as it is.

In a 1000 ml three neck distillation flask provided with a stirrer, dropping funnel, and thermometer, 42.1 g of 4-propylphenyl-(4-formyl)benzoate obtained by the procedures mentioned above was dissolved in 450 ml of acetone, and the solution was cooled down with a coolant to O.C. Then, 58.8 ml (470.7 mmol) of 8M solution of Jones reagent (K. Bowden, I. M. Heilbron, E. R. Jones, et al., J. Chem. Soc., 1946, 39) was added dropwise in 30 min so that the solution was maintained at the same temperature. After the dropping, the solution was stirred for 4 hours and then added with 300 m of water to terminate the reaction. Reaction solution was extracted with 250 ml×2 of diethyl ether, and the extracted layer was further washed with 250 ml×3 of water, dried over anhydrous magnesium sulfate, and then concentrated under a reduced pressure to obtain 43.1 g of brown crystal product. Concentrated product was recrystallized from toluene to obtain 35.2 g of colorless crystal product. This product was 4-propylphenyl(carboxy) benzoate.

In a 1000 ml three neck distillation flack provided with a stirrer, dropping funnel, thermometer, and cooling pipe, 35.2 g (123.9 mmol) of 4-propylphenyl-(4-carboxy)benzoate, 30.7 g (148.7 mmol) of DCC and 0.55 g (4.5 mmol) of DMAP were dissolved in 500 ml of dichloromethane at room temperature, and then a solution of 24.4 g (148.7 mmol) of 4-pentylphenol in 100 ml of dichloromethane was added dropwise at room temperature in 30 min while stirring. After the dropping, the reaction solution was stirred for 10 hours and added with 200 ml of water to terminate the reaction. From the reaction solution, dichloromethane insoluble matter was filtered off, the dichloromethane layer was separated, and the water layer was further extracted with 300 m of dichloromethane. Extracted layers were mixed, and washed with 300 ml×2 of water, 200 ml of saturated aqueous solution of sodium hydrogencarbonate, and 300 ml×2 of water in turn, dried over anhydrous magnesium sulfate, and then concentrated under a reduced pressure to obtain 50.2 g of reaction product. Reaction product was purified by a column chromatography using silica gel as filler and using a mixed solvent of toluene-ethyl acetate as developing solvent, and further recrystallized from a mixed solvent of heptane-ethanol to obtain 36.8 g of colorless crystal product. This product was terephthalic acid-(4-propylphenyl)-(4-pentylphenyl).

Subsequently, in a 1000 ml egg-plant type flask provided with a nitrogen gas introducing pipe and cooling pipe, 36.8 g (85.5 mmol) of terephthalic acid-(4-propylphenyl)-(4-pentylphenyl) obtained by the procedures mentioned above and 138.3 g (341.9 mmol) of Lawesson's reagent were dissolved in 600 ml of toluene, and the reflux was conducted under nitrogen gas stream for 60 hours while stirring. Reaction solution was cooled down to room temperature and added with 200 ml of water. Toluene layer was separated and the water layer was further extracted with 400 ml of toluene. Organic layers were mixed, washed with 300 ml×2 of water, 300 ml of saturated aqueous solution of sodium hydrogencarbonate, 300 ml of 10% aqueous solution of sodium hydrogensulfite, and 300 ml×2 of water in turn, dried over anhydrous magnesium sulfate, and then concentrated under a reduced pressure to obtain 38.7 g of brown crystalline mixture. The reaction product was purified by a column chromatography using silica gel as filler and using a mixed solvent of heptane-toluene as developing solvent, and then recrystallized from heptane to obtain 19.8 g of yellow needle-like crystal of a derivative of dithiocaroxylic acid ester.

In a 200 ml egg-plant type flask provided with a nitrogen gas introducing pipe, 19.8 g (42.7 mmol) of the derivative of dithiocarboxyic acid ester obtained by the procedures mentioned above was dissolved in 100 ml of dichoromethane at room temperature, and then the solution was added with 20.7 g (128.3 mmol) of DAST and stirred at room temperature for 30 hours. Reaction solution was added with 100 ml of water, the dichloromethane layer was separated, and the water layer was further extracted with 150 ml of dichloromethane. Extracted layers were mixed, and washed with 100 ml×2 of water, 100 ml of saturated aqueous solution of sodium hydrogencarbonate, and 100 ml×2 of water in turn, dried over anhydrous magnesium sulfate, and then concentrated under a reduced pressure to obtain 18.9 g of brown crystal product. Reaction product was purified by a column chromatography using silica gel as filler and using heptane as developing solvent, and then recrystallized from heptane to obtain 9.1 g of colorless needle-like crystal product. This product was difluoro-(4-propylphenyloxy)-{4-[difluoro(4-pentylphenyloxy)methyl]phenyl} methane.

Following compounds can be prepared according to the preparation method mentioned above by using phenol derivatives having a different alkyl chain in place of 4-propylphenol or 4-pentylphenol:

Difluoro-(4-methylphenyloxy)-{4-[difluoro-(4-methylphenyloxy)methyl]phenyl} methane
Difluoro-(4-methylphenyloxy)-{4-[difluoro-(4-ethylphenyloxy) methyl]phenyl} methane
Difluoro-(4-methylphenyloxy)-{4-[difluoro-(4-propylphenyloxy)methyl]phenyl} methane
Difluoro-(4-methylphenyloxy)-{4-[difluoro-(4-butylphenyloxy)methyl]phenyl} methane
Difluoro-(4-methylphenyloxy)-{4-[difluoro-(4-pentylphenyloxy)methyl]phenyl} methane
Difluoro-(4-methylphenyloxy)-{4-[difluoro-(4-hexylphenyle oxy)methyl]phenyl} methane
Difluoro-(4-methylphenyloxy)-{4-[difluoro-(4-heptylphenyloxy)methyl]phenyl} methane
Difluoro-(4-methylphenyloxy)-{4-[difluoro-(4-octylphenyloxy)methyl]phenyl} methane
Difluoro-(4-methylphenyloxy)-{4-[difluoro-(4-nonylphenyloxy)methyl]phenyl} methane
Difluoro-(4-methylphenyloxy)-{4-[difluoro-(4-decylphenyloxy)methyl]phenyl} methane
Difluoro-(4-ethylphenyloxy)-{4-[difluoro-(4-ethylphenyloxy)methyl]phenyl} methane
Difluoro-(4-ethylphenyloxy)-{4-[difluoro-(4-propylphenyloxy)methyl]phenyl} methane
Difluoro-(4-ethylphenyloxy)-{4-[difluoro-(4-butylphenyloxy)methyl]phenyl} methane
Difluoro-(4-ethylphenyloxy)-{4-[difluoro-(4-pentylphenyloxy)methyl]phenyl} methane
Difluoro-(4-ethylphenyloxy)-{4-[difluoro-(4-hexylphenyloxy)methyl]phenyl} methane
Difluoro-(4-ethylphenyloxy)-{4-[difluoro-(4-heptylphenyloxy)methyl]phenyl} methane
Difluoro-(4-ethylphenyloxy)-{4-[difluoro-(4-octylphenyloxy)methyl]phenyl} methane
Difluoro-(4-ethylphenyloxy)-{4-[difluoro-(4-nonylphenyloxy)methyl]phenyl} methane
Difluoro-(4-ethylphenyloxy)-{4-[difluoro-(4-decylphenyloxy)methyl]phenyl} methane
Difluoro-(4-propylphenyloxy)-{4-[difluoro-(4-propylphenyloxy)methyl]phenyl} methane
Difluoro-(4-propylphenyloxy)-{4-[difluoro-(4-butylphenyloxy)methyl]phenyl} methane
Difluoro-(4-propylphenyloxy)-(4-[difluoro-(4-hexylphenyloxy)methyl]phenyl} methane
Difluoro-(4-propylphenyloxy)-{4-[difluoro-(4-heptylphenyloxy)methyl]phenyl} methane
Difluoro-(4-propylphenyloxy)-{4-[difluoro-(4-octylphenyloxy)methyl]phenyl} methane
Difluoro-(4-propylphenyloxy)-{4-[difluoro-(4-nonylphenyloxy)methyl]phenyl} methane
Difluoro-(4-propylphenyloxy)-{4-[difluoro-(4-decylphenyloxy)methyl]phenyl} methane
Difluoro-(4-butylphenyloxy)-{4-[difluoro-(4-butylphenyloxy)methyl]phenyl} methane
Difluoro-(4-butylphenyloxy)-{4-[difluoro-(4-pentylphenyloxy)methyl]phenyl} methane
Difluoro-(4-butylphenyloxy)-{4-[difluoro-(4-hexylphenyloxy)methyl]phenyl} methane Difluoro-(4-butylphenyloxy)-{4-[difluoro-(4-heptylphenyloxy)methyl]phenyl} methane
Difluoro-(4-butylphenyloxy)-{4-[difluoro-(4-octylphenyloxy)methyl]phenyl} methane
Difluoro-(4-butylphenyloxy)-{4-[difluoro-(4-nonylphenyloxy)methyl]phenyl} methane
Difluoro-(4-butylphenyloxy)-{4-[difluoro-(4-decylphenyloxy)methyl]phenyl} methane
Difluoro-(4-pentylphenyloxy)-{4-[difluoro-(4-pentylphenyloxy)methyl]phenyl} methane
Difluoro-(4-pentylphenyloxy)-{4-[difluoro-(4-hexylphenyloxy)methyl]phenyl} methane
Difluoro-(4-pentylphenyloxy)-{4-[difluoro-(4-heptylphenyloxy)methyl]phenyl} methane
Difluoro-(4-pentylphenyloxy)-{4-[difluoro-(4-octylphenyloxy)methyl]phenyl} methane
Difluoro-(4-pentylphenyloxy)-{4-[difluoro-(4-nonylphenyloxy)methyl]phenyl} methane
Difluoro-(4-pentylphenyloxy)-{4-[difluoro-(4-decylphenyloxy)methyl]phenyl} methane
Difluoro-(4-hexylphenyloxy)-{4-[difluoro-(4-hexylphenyloxy)methyl]phenyl} methane
Difluoro-(4-hexylphenyloxy)-{4-[difluoro-(4-heptylphenyloxy)methyl]phenyl} methane
Difluoro-(4-hexylphenyloxy)-{4-[difluoro-(4-octylphenyloxy)methyl]phenyl} methane
Difluoro-(4-hexylphenyloxy)-{4-[difluoro-(4-nonylphenyloxy)methyl]phenyl} methane
Difluoro-(4-hexylphenyloxy)-{4-[difluoro-(4-decylphenyloxy)methyl]phenyl} methane
Difluoro-(4-heptylphenyloxy)-{4-[difluoro-(4-heptylphenyloxy)methyl]phenyl} methane
Difluoro-(4-heptylphenyloxy)-{4-[difluoro-(4-octylphenyloxy)methyl]phenyl} methane
Difluoro-(4-heptylphenyloxy)-{4-[difluoro-(4-nonylphenyloxy)methyl]phenyl} methane
Difluoro-(4-heptylphenyloxy)-{4-[difluoro-(4-decylphenyloxy)methyl]phenyl} methane
Difluoro-(4-octylphenyloxy)-{4-[difluoro-(4-octylphenyloxy)methyl]phenyl} methane
Difluoro-(4-octylphenyloxy)-{4-[difluoro-(4-nonylphenyloxy)methyl]phenyl} methane
Difluoro-(4-octylphenyloxy)-{4-[difluoro-(4-decylphenyloxy)methyl]phenyl} methane
Difluoro-(4-nonylphenyloxy)-{4-[difluoro-(4-nonylphenyloxy)methyl]phenyl} methane
Difluoro-(4-nonylphenyloxy)-{4-[difluoro-(4-decylphenyloxy)methyl]phenyl} methane
Difluoro-(4-decylphenyloxy)-{4-[difluoro-(4-decylphenyloxy)methyl]phenyl} methane

EXAMPLE 10

Preparation of difluoro-(3,4,5-trifluorophenyloxy)-{4-[trans-4-(trans-4-propylcyclohexyl)cyclohexyl]phenyl} methane (Compound expressed by the formula (I) wherein R=$C_3H_7$, l=m=1, n=0, both rings $A_1$ and $A_2$ are trans-1,4-cyclohexylene group, $Z_1$, $Z_2$ and $Z_3$ are covalent bond, $L_1$=$L_2$=H, $L_3$=$L_4$=F, and X=F.)

In a 500 ml three neck distillation flask provided with a stirrer, thermometer, dropping funnel, and nitrogen gas introducing pipe, 15.0 g (45.7 mmol) of 4-[trans-4-(trans-4-propylcyclohexyl)cyclohexyl]benzoic acid, 11.3 g (54.8 mmol) of DCC, and 0.2 g (1.6 mmol) of DMAP were dissolved in 250 ml of dichloromethane under nitrogen gas atmosphere, and then 8.1 g (54.8 mmol) of 3,4,5-trifluorophenol was added dropwise to the solution at room temperature in 3 min while stirring. After the dropping, the solution was stirred at room temperature for 10 hours. Reaction solution was added with 100 ml of water, and dichloromethane insoluble matter was filtered off, the dichloromethane layer was separated, and the water layer was further extracted with 200 ml of dichloromethane. Extracted layers were mixed, washed with 100 ml×2 of water, 100 ml of saturated aqueous solution of sodium hydrogencarbonate, and 100 ml×2 of water in turn, dried over anhydrous magnesium sulfate, and then concentrated under a reduced pressure to obtain 21.9 g of reaction product. Reaction product was purified by a column chromatography using silica gel as filler and using toluene as developing solvent, and further recrystallized from a mixed solvent of heptane-ethanol to obtain 16.5 g of colorless crystal product. This product was 3,4,5-trifluorophenyl-4-[4-trans(trans-4-propylcyclohexyl)cyclohexyl]benzoate.

Subsequently, in a 1000 ml egg-plant type flask provided with a nitrogen gas introducing pipe and cooling pipe, 16.5 g (33.9 mmol) of the 3,4,5-trifluorophenyl-4-[4-trans-(trans-4-propylcyclohexyl)cyclohexyl]benzoate obtained by the procedures mentioned above and 27.5 g (67.9 mmol) of Lawesson reagent were dissolved in 500 ml of toluene, and the solution was refluxed while stirring under nitrogen gas stream for 60 hours. After the reaction solution was cooled down to room temperature, 200 ml of water was added to the reaction solution, the toluene layer was separated, and then the water layer was further extracted with 150 ml of toluene. Organic layers were mixed, washed with 200 ml×2 of water, 100 ml of saturated sodium hydrogencarbonate, 100 ml of 10% aqueous solution of sodium hydrogensulfite, and 200 ml×2 of water in turn, dried over anhydrous magnesium sulfate, and then concentrated under a reduced pressure to obtain 15.4 g of brown crystalline mixture. Reaction product was purified by a column chromatography using silica gel as filler and using heptane as developing solvent, and then recrystallized from heptane to obtain 6.4 g of yellow needle-like crystal product. This product was 4-[trans-4-(trans-4-propylcyclohexyl)cyclohexyl]phenylcarbothio acid-O-3,4,5-trifluorophenyl.

In a 100 ml egg-plant type flask provided with a nitrogen gas introducing pipe, 6.4 g (13.5 mmol) of 4-[trans-4-(trans-4-propylcyclohexyl)cyclohexyl]phenylcarbothio acid-O-3,4,5-trifluo rophenyl was dissolved in 50 ml of dichloromethane at room temperature, and then 6.5 g (40.5 mmol) of DAST was added to the solution and the solution was stirred at room temperature for 40 hours. Reaction solution was added with 50 ml of water, the dichloromethane layer was separated, and the water layer was further extracted with 50 ml of dichloromethane. Extracted layers were mixed, washed with 50 ml×2 of water, 30 ml of saturated aqueous solution of sodium hydrogencarbonate, and 50 ml×2 of water in turn, dried over anhydrous magnesium sulfate, and then concentrated under a reduced pressure to obtain 6.4 g of brown crystal product. Reaction product was purified by a column chromatography using silica gel as filler and using heptane as developing solvent, and then recrystallized from heptane to obtain 1.3 g of colorless needle-like crystal product. This product was difluoro-(3,4,5-trifluorophenyloxy)-{4-[trans-4-(trans-4-propylcyclohexyl) cyclohexyl]phenyl} methane.

Following compounds can be prepared according to the preparation method mentioned above by using 4-[trans-4-(trans-4-alkylcyclohexyl)cyclohexyl]benzoic acids having a different alkyl chain in place of 4-[trans-4-(trans-4-propylcyclohexyl) cyclohexyl]benzoic acid:

Difluoro-(3,4,5-trifluorophenyloxy)-{4-[trans-4-(trans-4-ethylcyclohexyl)cyclohexyl]phenyl} methane Difluoro-(3,4,5-trifluorophenyloxy)-{4-[trans-4-(trans-4-butylcyclohexyl)cyclohexyl]phenyl} methane
Difluoro-(3,4,5-trifluorophenyloxy)-{4-[trans-4-(trans-4-pentylcyclohexyl)cyclohexyl]phenyl} methane
Difluoro-(3,4,5-trifluorophenyloxy)-{4-[trans-4-(trans-4-hexylcyclohexyl)cyclohexyl]phenyl} methane
Difluoro-(3,4,5-trifluorophenyloxy)-{4-[trans-4-(trans-4-heptylcyclohexyl)cyclohexyl]phenyl} methane
Difluoro-(3,4,5-trifluorophenyloxy)-{4-[trans-4-(trans-4-octylcyclohexyl)cyclohexyl]phenyl} methane
Difluoro-(3,4,5-trifluorophenyloxy)-{4-[trans-4-(trans-4-nonylcyclohexyl)cyclohexyl]phenyl} methane
Difluoro-(3,4,5-trifluorophenyloxy)-{4-[trans-4-(trans-4-decylcyclohexyl)cyclohexyl]phenyl} methane Following compounds can be prepared according to the preparation method mentioned above by selectively using several known benzoic acid derivatives and several known phenol derivatives, including the compounds preparation examples of which are described in detail in the Examples mentioned above, in place of 4-[trans-4-(trans-4-propylcyclohexyl)cyclohexyl] benzoic acid or 3,4,5-trifluorophenol:

Difluoro-(4-trifluoromethoxyphenyloxy)-{4-[trans-4-(trans-4-ethylcyclohexyl)cyclohexyl]phenyl} methane
Difluoro-(4-trifluoromethoxyphenyloxy)-{4-[trans-4-(trans-4-propylcyclohexyl)cyclohexyl]phenyl} methane
Difluoro-(4-trifluoromethoxyphenyloxy)-{4-[trans-4-(trans-4-butylcyclohexyl)cyclohexyl]phenyl} methane
Difluoro-(4-trifluoromethoxyphenyloxy)-{4-[trans-4-(trans-4-pentylcyclohexyl)cyclohexyl]phenyl} methane
Difluoro-(4-difluoromethoxyphenyloxy)-{4-[trans-4-(trans-4-ethylcyclohexyl)cyclohexyl]phenyl} methane
Difluoro-(4-difluoromethoxyphenyloxy)-{4-[trans-4-(trans-4-propylcyclohexyl)cyclohexyl]phenyl} methane
Difluoro-(4-difluoromethoxyphenyloxy)-{4-[trans-4-(trans-4-butylcyclohexyl)cyclohexyl]phenyl} methane
Difluoro-(4-difluoromethoxyphenyloxy)-{4-[trans-4-(trans-4-pentylcyclohexyl)cyclohexyl]phenyl} methane
Difluoro-(4-trifluoromethylphenyloxy)-{4-[trans-4-(trans-4-ethylcyclohexyl)cyclohexyl]phenyl} methane
Difluoro-(4-trifluoromethylphenyloxy)-{4-[trans-4-(trans-4-propylcyclohexyl)cyclohexyl]phenyl} methane
Difluoro-(4-trifluoromethylphenyloxy)-{4-[trans-4-(trans-4-butylcyclohexyl)cyclohexyl]phenyl} methane
Difluoro-(4-trifluoromethylphenyloxy)-{4-[trans-4-(trans-4-pentylcyclohexyl)cyclohexyl]phenyl} methane
Difluoro-(3-fluoro-4-trifluoromethoxyphenyloxy)-{4-[trans-4-(trans-4-ethylcyclohexyl)cyclohexyl]phenyl} methane
Difluoro-(3-fluoro-4-trifluoromethoxyphenyloxy)-{4-[trans-4-(trans-4-propylcyclohexyl)cyclohexyl]phenyl} methane
Difluoro-(3-fluoro-4-trifluoromethoxyphenyloxy)-{4-[trans-4-(trans-4-butylcyclohexyl)cyclohexyl]phenyl} methane
Difluoro-(3-fluoro-4-trifluoromethoxyphenyloxy)-{4-[trans-4-(trans-4-pentylcyclohexyl)cyclohexyl]phenyl} methane
Difluoro-(3-fluoro-4-difluoromethoxyphenyloxy)-{4-[trans-4-(trans-4-ethylcyclohexyl)cyclohexyl]phenyl} methane
Difluoro-(3-fluoro-4-difluoromethoxyphenyloxy)-{4-[trans-4-(trans-4-propylcyclohexyl)cyclohexyl]phenyl} methane
Difluoro-(3-fluoro-4-difluoromethoxyphenyloxy)-{4-[trans-4-(trans-4-butylcyclohexyl)cyclohexyl]phenyl} methane
Difluoro-(3-fluoro-4-difluoromethoxyphenyloxy)-{4-[trans-4-(trans-4-pentylcyclohexyl)cyclohexyl]phenyl} methane
Difluoro-(3-fluoro-4-trifluoromethylphenyloxy)-{4-[trans-4-(trans-4-ethylcyclohexyl)cyclohexyl]phenyl} methane
Difluoro-(3-fluoro-4-trifluoromethylphenyloxy)-{4-[trans-4-(trans-4-propylcyclohexyl)cyclohexyl]phenyl} methane
Difluoro-(3,5-difluoro-4-trifluoromethoxyphenyloxy)-{4-[trans-4-(trans-4-ethylcyclohexyl)cyclohexyl]phenyl} methane
Difluoro-(3,5-difluoro-4-trifluoromethoxyphenyloxy)-{4-[trans-4-(trans-4-propylcyclohexyl)cyclohexyl]phenyl} methane
Difluoro-(3,5-difluoro-4-trifluoromethoxyphenyloxy)-{4-[trans-4-(trans-4-butylcyclohexyl)cyclohexyl]phenyl} methane
Difluoro-(3,5-difluoro-4-trifluoromethoxyphenyloxy)-{4-[trans-4-(trans-4-pentylcyclohexyl)cyclohexyl]phenyl} methane
Difluoro-(3,5-difluoro-4-difluoroinethoxyphenyloxy)-{4-[trans-4-(trans-4-ethylcyclohexyl)cyclohexyl]phenyl} methane
Difluoro-(3,5-difluoro-4-difluoromethoxyphenyloxy)-{4-[trans-4-(trans-4-propylcyclohexyl)cyclohexyl]phenyl} methane
Difluoro-(3,5-difluoro-4-difluoromethoxyphenyloxy)-{4-[trans-4-(trans-4-butylcyclohexyl)cyclohexyl]phenyl} methane
Difluoro-(3,5-difluoro-4-difluoromethoxyphenyloxy)-{4-[trans-4-(trans-4-pentylcyclohexyl)cyclohexyl]phenyl} methane
Difluoro-(3,5-difluoro-4-trifluoromethylphenyloxy)-{4-[trans-4-trans-4-ethylcyclohexyl)cyclohexyl]phenyl} methane
Difluoro-(3,5-difluoro-4-trifluoromethylphenyloxy)-{4-[trans-4-(trans-4-propylcyclohexyl)cyclohexyl]phenyl} methane
Difluoro-(3,5-difluoro-4-trifluoromethylphenyloxy)-{4-[trans-4-(trans-4-butylcyclohexyl)cyclohexyl]phenyl} methane
Difluoro-(3,5-difluoro-4-trifluoromethylphenyloxy)-{4-[trans-4-(trans-4-pentylcyclohexyl)cyclohexyl]phenyl} methane
Difluoro-(3,4,5-trifluorophenyloxy)-{2-fluoro-4-[trans-4-(trans4-ethylcyclohexyl)cyclohexyl]phenyl} methane
Difluoro-(3,4,5-trifluorophenyloxy)-{2-fluoro-4-[trans-4-(trans4-propylcyclohexyl)cyclohexyl]phenyl} methane
Difluoro-(3,4,5-trifluorophenyloxy)-{2-fluoro-4-[trans-4-(trans4-butylcyclohexyl)cyclohexyl]phenyl} methane
Difluoro-(3,4,5-trifluorophenyloxy)-{2-fluoro-4-[trans-4-(trans4-pentylcyclohexyl)cyclohexyl]phenyl} methane
Difluoro-(3,5-difluoro-4-trifluoromethoxyphenyloxy)-{2-fluoro-4-[trans-4-(trans-4-ethylcyclohexyl)cyclohexyl]phenyl} methane
Difluoro-(3,5-difluoro-4-trifluoromethoxyphenyloxy)-{2-fluoro-4-[trans-4-(trans-4-propylcyclohexyl)cyclohexyl]phenyl} methane
Difluoro-(3,5-difluoro-4-trifluoromethoxyphenyloxy)-{2-fluoro-4-[trans-4-(trans-4-butylcyclohexyl)cyclohexyl]phenyl} methane
Difluoro-(3,5-difluoro-4-trifluoromethoxyphenyloxy)-{2-fluoro-4-[trans-4-(trans-4-pentylcyclohexyl)cyclohexyl]phenyl} methane
Difluoro-(3,5-difluoro-4-difluoromethoxyphenyloxy)-{2-fluoro-4-[trans-4-(trans-4-ethylcyclohexyl)cyclohexyl]phenyl} methane Difluoro-(3,5-difluoro-4-difluoromethoxyphenyloxy)-{2-fluoro-4-[trans-4-(trans-4-propylcyclohexyl)cyclohexyl]phenyl} methane Difluoro-(3,5-difluoro-4-difluoromethoxyphenyloxy)-{2-fluoro-4-[trans-4-(trans-4-butylcyclohexyl)cyclohexyl]phenyl} methane Difluoro-(3,5-difluoro-4-difluoromethoxyphenyloxy)-{2-fluoro-4-[trans-4-(trans-4-pentylcyclohexyl)cyclohexyl]phenyl} methane Difluoro-(3,5-difluoro-4-trifluoromethylphenyloxy)-{2-fluoro-4-[trans-4-(trans-4-ethylcyclohexyl)cyclohexyl]phenyl} methane Difluoro-(3,5-difluoro-4-trifluoromethylphenyloxy)-{2-fluoro-4-[trans-4-(trans-4-propylcyclohexyl)cyclohexyl]phenyl} methane Difluoro-(3,5-difluoro-4-trifluoromethylphenyloxy)-{2-fluoro-4-[trans-4-(trans-4-butylcyclohexyl)cyclohexyl]phenyl} methane Difluoro-(3,5-difluoro-4-trifluoromethylphenyloxy)-{2-fluoro-4-[trans-4-(trans-4-pentylcyclohexyl)cyclohexyl]phenyl} methane Difluoro-(3,4,5-trifluorophenyloxy)-{2,6-difluoro-4-[trans-4-(trans-4-ethylcyclohexyl)cyclohexyl]phenyl} methane Difluoro-(3,4,5-trifluorophenyloxy)-{2,6-difluoro-4-[trans-4-(trans-4-propylcyclohexyl)cyclohexyl]phenyl} methane Difluoro-(3,4,5-trifluorophenyloxy)-{2,6-difluoro-4-[trans-4-(trans-4-butylcyclohexyl)cyclohexyl]phenyl} methane Difluoro-(3,4,5-trifluorophenyloxy)-{2,6-difluoro-4-[trans-4-(trans-4-pentylcyclohexyl)cyclohexyl]phenyl} methane Difluoro-(3,5-difluoro-4-trifluoromethoxyphenyloxy)-{2,6-difluoro-4-[trans-4-(trans-4-ethylcyclohexyl)cyclohexyl]phenyl}methane Difluoro-(3,5-difluoro-4-trifluoromethoxyphenyloxy)-{2,6-difluoro-4-[trans-4-(trans-4-propylcyclohexyl)cyclohexyl]phenyl} methane Difluoro-(3,5-difluoro-4-trifluoromethoxyphenyloxy)-{2,6-difluoro-4-[trans-4-(trans-4-butylcyclohexyl)cyclohexyl]phenyl} methane Difluoro-(3,5-difluoro-4-trifluoromethoxyphenyloxy)-{2,6-difluoro-4-[trans-4-(trans-4-pentylcyclohexyl)cyclohexyl]phenyl} methane Difluoro-(3,5-difluoro-4-difluoromethoxyphenyloxy)-{2,6-difluoro-4-[trans-4-(trans-4-ethylcyclohexyl)cyclohexyl]phenyl} methane Difluoro-(3,5-difluoro-4-difluoromethoxyphenyloxy)-{2,6-difluoro-4-[trans-4-(trans-4-propylcyclohexyl)cyclohexyl]phenyl} methane Difluoro-(3,5-difluoro-4-difluoromethoxyphenyloxy)-{2,6-difluoro-4-[trans-4-(trans-4-butylcyclohexyl)cyclohexyl]phenyl} methane Difluoro-(3,5-difluoro-4-difluoromethoxyphenyloxy)-{2,6-difluoro-4-[trans-4-(trans-4-pentylcyclohexyl)cyclohexyl]phenyl} methane Difluoro-(3,5-difluoro-4-trifluoromethylphenyloxy)-{2,6-difluoro-4-[trans-4-(trans-4-ethylcyclohexyl)cyclohexyl]phenyl} methane Difluoro-(3,5-difluoro-4-trifluoromethylphenyloxy)-{2,6-difluoro-4-[trans-4-(trans-4-propylcyclohexyl)cyclohexyl]phenyl} methane Difluoro-(3,5-difluoro-4-trifluoromethylphenyloxy)-{2,6-difluoro-4-[trans-4-(trans-4-butylcyclohexyl)cyclohexyl]phenyl} methane Difluoro-(3,5-difluoro-4-trifluoromethylphenyloxy)-{2,6-difluoro-4-[trans-4-(trans-4-pentylcyclohexyl)cyclohexyl]phenyl} methane Difluoro-(3,4,5-trifluorophenyloxy)-{4-[trans-4-[2-(trans-4-ethylcyclohexyl)ethyl]cyclohexyl]phenyl} methane Difluoro-(3,4,5-trifluorophenyloxy)-{4-[trans-4-[2-(trans-4-propylcyclohexyl)ethyl]cyclohexyl]phenyl} methane Difluoro-(3,4,5-trifluorophenyloxy)-{4-[trans-4-[2-(trans-4-butylcyclohexyl)ethyl]cyclohexyl]phenyl} methane Difluoro-(3,4,5-trifluorophenyloxy)-{4-[trans-4-[2-(trans-4-pentylcyclohexyl)ethyl]cyclohexyl]phenyl} methane Difluoro-(4-trifluoromethoxyphenyloxy)-{4-[trans-4-[2-(trans-4-ethylcyclohexyl)ethyl]cyclohexyl]phenyl} methane Difluoro-(4-trifluoromethoxyphenyloxy)-{4-[trans-4-[2-(trans-4-propylcyclohexyl)ethyl]cyclohexyl]phenyl} methane Difluoro-(4-trifluoromethoxyphenyloxy)-{4-[trans-4-[2-(trans-4-butylcyclohexyl)ethyl]cyclohexyl]phenyl} methane Difluoro-(4-trifluoromethoxyphenyloxy)-{4-[trans-4-[2-(trans-4-pentylcyclohexyl)ethyl]cyclohexyl]phenyl} methane Difluoro-(4-difluoromethoxyphenyloxy)-{4-[trans-4-[2-(trans-4-ethylcyclohexyl)ethyl]cyclohexyl]phenyl} methane Difluoro-(4-difluoromethoxyphenyloxy)-{4-[trans-4-[2-(trans-4-propylcyclohexyl)ethyl]cyclohexyl]phenyl} methane Difluoro-(4-difluoromethoxyphenyloxy)-{4-[trans-4-[2-(trans-4-butylcyclohexyl)ethyl]cyclohexyl]phenyl} methane Difluoro-(4-difluoromethoxyphenyloxy)-{4-[trans-4-[2-(trans-4-pentylcyclohexyl)ethyl]cyclohexyl]phenyl} methane Difluoro-(4-trifluoromethylphenyloxy)-{4-[trans-4-[2-(trans-4-ethylcyclohexyl)ethyl]cyclohexyl]phenyl} methane Difluoro-(4-trifluoromethylphenyloxy)-{4-[trans-4-[2-(trans-4-propylcyclohexyl)ethyl]cyclohexyl]phenyl} methane Difluoro-(4-trifluoromethylphenyloxy)-{4-[trans-4-[2-(trans-4-butylcyclohexyl)ethyl]cyclohexyl]phenyl} methane Difluoro-(4-trifluoromethylphenyloxy)-{4-[trans-4-[2-(trans-4-pentylcyclohexyl)ethyl]cyclohexyl]phenyl} methane Difluoro-(3,4,5-trifluorophenyloxy)-{4-[2-[trans-4-(trans-4-ethylcyclohexyl)cyclohexyl]ethyl]phenyl} methane Difluoro-(3,4,5-trifluorophenyloxy)-{4-[2-[trans-4-(trans-4-propylcyclohexyl)cyclohexyl]ethyl]phenyl} methane Difluoro-(3,4,5-trifluorophenyloxy)-{4-[2-[trans-4-(trans-4-butylcyclohexyl)cyclohexyl]ethyl]phenyl} methane Difluoro-(3,4,5-trifluorophenyloxy)-{4-[2-[trans-4-(trans-4-pentylcyclohexyl)cyclohexyl]ethyl]phenyl} methane Difluoro-(4-trifluoromethoxyphenyloxy)-{4-[2-[trans-4-(trans-4-ethylcyclohexyl)cyclohexyl]ethyl]phenyl} methane Difluoro-(4-trifluoromethoxyphenyloxy)-{4-[2-[trans-4-(trans-4-propylcyclohexyl)cyclohexyl]ethyl]phenyl} methane Difluoro-(4-trifluoromethoxyphenyloxy)-{4-[2-[trans-4-(trans-4-butylcyclohexyl)cyclohexyl]ethyl]phenyl} methane Difluoro-(4-trifluoromethoxyphenyloxy)-{4-[2-[trans-4-(trans-4-pentylcyclohexyl)cyclohexyl]ethyl]phenyl} methane Difluoro-(4-difluoromethoxyphenyloxy)-{4-[2-[trans-4-(trans-4-ethylcyclohexyl)cyclohexyl]ethyl]phenyl} methane Difluoro-(4-difluoromethoxyphenyloxy)-{4-[2-[trans-4-(trans-4-propylcyclohexyl)cyclohexyl]ethyl]phenyl} methane Difluoro-(4-difluoromethoxyphenyloxy)-{4-[2-[trans-4-(trans-4-butylcyclohexyl)cyclohexyl]ethyl]phenyl} methane Difluoro-(4-difluoromethoxyphenyloxy)-{4-[2-[trans-4-(trans-4-pentylcyclohexyl)cyclohexyl]ethyl]phenyl} methane Difluoro-(4-trifluoromethylphenyloxy)-{4-[2-[trans-4-(trans-4-ethylcyclohexyl)cyclohexyl]ethyl]phenyl} methane Difluoro-(4-trifluoromethylphenyloxy)-{4-[2-[trans-4-(trans-4-propylcyclohexyl)cyclohexyl]ethyl]phenyl} methane Difluoro-(4-trifluoromethylphenyloxy)-{4-[2-[trans-4-(trans-4-butylcyclohexyl)cyclohexyl]ethyl]phenyl} methane Difluoro-(4-trifluoromethylphenyloxy)-{4-[2-[trans-4-(trans-4-pentylcyclohexyl)cyclohexyl]ethyl]phenyl} methane Difluoro-(3,4,5-trifluorophenyloxy)-[4'-(trans-4-ethylcyclohexyl) biphenyl]methane Difluoro-(3,4,5-trifluorophenyloxy)-[4'-(trans-4-propylcyclohexyl)biphenyl]methane Difluoro-(3,4, 5-trifluorophenyloxy)-[4'-(trans-4-butylcyclohexyl) biphenyl]methane Difluoro-(3,4,5-trifluorophenyloxy)-[4'-(trans-4-pentylcyclohexyl)biphenyl]methane Difluoro-(4-trifluoromethoxyphenyloxy)-[4'-(trans-4-ethylcyclohexyl)biphenyl]methane Difluoro-(4-trifluoromethoxyphenyloxy)-[4'-(trans-4-propylcyclohexyl)biphenyl]methane Difluoro-(4-trifluoromethoxyphenyloxy)-[4'-(trans-4-butylcyclohexyl)biphenyl]methane Difluoro-(4-trifluoromethoxyphenyloxy)-[4'-(trans-4-pentylcyclohexyl)biphenyl]methane Difluoro-(4-difluoromethoxyphenyloxy)-[4'-(trans-4-ethylcyclohexyl)biphenyl]methane Difluoro-(4-difluoromethoxyphenyloxy)-[4'-(trans-4-propylcyclohexyl)biphenyl]methane Difluoro-(4-difluoromethoxyphenyloxy)-[4'-(trans-4-butylcyclohexyl)biphenyl]methane Difluoro-(4-difluoromethoxyphenyloxy)-[4'-(trans-4-pentylcyclohexyl)biphenyl]methane Difluoro-(4-trifluoromethylphenyloxy)-[4'-(trans-4-ethylcyclohexyl)biphenyl]methane Difluoro-(4-trifluoromethylphenyloxy)-[4'-(trans-4-propylcyclohexyl)biphenyl]methane Difluoro-(4-trifluoromethylphenyloxy)-[4'-(trans-4-butylcyclohexyl)biphenyl]methane Difluoro-(4-trifluoromethylphenyloxy)-[4'-(trans-4-pentylcyclohexyl)biphenyl]methane Difluoro-(3,4,5-trifluorophenyloxy)-{4'-[2-(trans-4-ethylcyclohexyl)ethyl]biphenyl} methane Difluoro-(3,4,5-trifluorophenyloxy)-{4'-[2-(trans-4-propylcyclohexyl)ethyl]biphenyl} methane Difluoro-(3,4,5-trifluorophenyloxy)-{4'-[2-(trans-4-butylcyclohexyl)ethyl]biphenyl} methane Difluoro-(3,4,5-trifluorophenyloxy)-(4'-[2-(trans-4-pentylcyclohexyl)ethyl]biphenyl} methane Difluoro-(4-trifluoromethoxyphenyloxy)-{4'-[2-(trans-4-ethylcyclohexyl)ethyl]biphenyl} methane Difluoro-(4-trifluoromethoxyphenyloxy)-{4'-[2-(trans-4-propylcyclohexyl)ethyl]biphenyl} methane Difluoro-(4-trifluoromethoxyphenyloxy)-{4'-[2-(trans-4-butylcyclohexyl)ethyl]biphenyl} methane Difluoro-(4-trifluoromethoxyphenyloxy)-{4'-[2-(trans-4-pentylcyclohexyl)ethyl]biphenyl} methane Difluoro-(4-difluoromethoxyphenyloxy)-{4'-[2-(trans-4-ethylcyclohexyl)ethyl]biphenyl} methane Difluoro-(4-difluoromethoxyphenyloxy)-{4'-[2-(trans-4-propylcyclohexyl)ethyl]biphenyl} methane Difluoro-(4-difluoromethoxyphenyloxy)-{4'-[2-(trans-4-butylcyclohexyl)ethyl]biphenyl} methane Difluoro-(4-difluoromethoxyphenyloxy)-{4'-[2-(trans-4-pentylcyclohexyl)ethyl]biphenyl} methane Difluoro-(4-trifluoromethylphenyloxy)-{4'-[2-(trans-4-ethylcyclohexyl)ethyl]biphenyl} methane Difluoro-(4-trifluoromethylphenyloxy)-{4'-[2-(trans-4—propylcyclohexyl)ethyl]biphenyl} methane Difluoro-(4-trifluoromethylphenyloxy)-{4'-[2-(trans-4-butylcyclohexyl)ethyl]biphenyl} methane Difluoro-(4-trifluoromethylphenyloxy)-{4'-[2-(trans-4-pentylcyclohexyl)ethyl]biphenyl} methane

EXAMPLE 11

Preparation of difluoro-(3',4',5'-trifluorobiphenyloxy)-[4-(trans-4-propylcyclohexyl)phenyl]methane (Compound expressed by the formula (I) wherein R=$C_3H_7$, l=n=1, m=0, ring $A_1$ is trans-1,4-cyclohexylene group, ring $A_3$ is 1,4-phenylene group, $Z_1$, $Z_2$ and $Z_3$ are covalent bond, $L_1=L_2=$H, $L_3=L_4=$F, and X=F.)

In a 500 ml three neck distillation flask provided with a stirrer, thermometer, dropping funnel, and nitrogen gas introducing pipe, 15.0 g (60.9 mmol) of 4-(trans-4-propylcyclohexyl)benzoic acid, 15.1 g (73.1 mmol) of DCC, and 0.27 g (2.2 mmol) of DMAP were dissolved in 300 ml of dichloromethane under nitrogen gas atmosphere, and then the solution which was prepared by dissolving 16.4 g (73.1 mmol) of the 4-(3',4',5-trifluorophenol) phenol prepared according to the procedures described in Example 6 in 80 ml of dichloromethane was added dropwise in the flask at room temperature in 20 min while stirring. After the dropping, the solution was stirred at room temperature for 10 hours. Reaction solution was added with 200 ml of water, and dichloromethane insoluble matter was filtered off, the dichloromethane layer was separated, and the water layer was further extracted with 200 ml of dichloromethane. Extracted layers were mixed, washed with 200 ml×2 of water, 100 ml of saturated aqueous solution of sodium hydrogencarbonate, and 200 ml×2 of water in turn, dried over anhydrous magnesium sulfate, and then concentrated under a reduced pressure to obtain 26.9 g of reaction product. Reaction product was purified by a column chromatography using silica gel as filler and using toluene as developing solvent, and further recrystallized from a mixed solvent of heptane-ethanol to obtain 22.8 g of colorless crystal product. This product was (3',4',5'-trifluorobiphenyl)-4-(trans-4-cyclohexyl)benzoate.

Subsequently, in a 1000 ml egg-plant type flask provided with a nitrogen gas introducing pipe and cooling pipe, 22.8 g (50.5 mmol) of the (3',4',5'-trifluorobiphenyl)-4-(trans-4-cyclohexyl)benzoate obtained by the procedures mentioned above and 40.9 g (101.1 mmol) of Lawesson's reagent were dissolved in 500 ml of toluene, and the solution was refluxed while stirring under nitrogen gas stream for 60 hours. After the reaction solution was cooled down to room temperature, 200 ml of water was added to the reaction solution, the toluene layer was separated, and then the water layer was further extracted with 200 ml of toluene. Organic layers were mixed, and washed with 200 ml×2 of water, 100 ml of saturated sodium hydrogencarbonate, 100 ml of 10% aqueous solution of sodium hydrogensulfite, and 200 ml×2 of water in turn, dried over anhydrous magnesium sulfate, and then concentrated under a reduced pressure to obtain 23.4 g of brown crystalline mixture. Reaction product was purified by a column chromatography using silica gel as filler and using heptane as developing solvent, and then recrystallized from heptane to obtain 8.3 g of yellow needle-like crystal product. This product was 4-(trans-4-propylcyclohexyl) phenylcarbothio acid-O-3',4',51-trifluorobiphenyl.

In a 100 ml egg-plant type flask provided with a nitrogen gas introducing pipe, 8.3 g (17.7 mmol) of 4-(trans-4-propylcyclohexyl)phenylcarbothio acid-O-3',4',5'-trifluorobiphenyl was dissolved in 80 ml of dichloromethane at room temperature, and then 8.5 g (53.0 mmol) of DAST was added to the solution and the solution was stirred at room temperature for 40 hours. Reaction solution was added with 50 ml of water, the dichloromethane layer was separated, and the water layer was further extracted with 50 ml of dichloromethane. Extracted layers were mixed, washed with 50 ml×2 of water, 30 ml of saturated aqueous solution of sodium hydrogencarbonate, and 50 ml×2 of water in turn, dried over anhydrous magnesium sulfate, and then concentrated under a reduced pressure to obtain 8.1 g of brown crystal product. Reaction product was purified by a column chromatography using silica gel as filler and using heptane as developing solvent, and then recrystallized from heptane to obtain 1.9 g of colorless needle-like crystal product. This product was difluoro-(3',4',5'-trifluorobiphenyloxy)-[4-(trans-4-propylcyclohexyl)phenyl]methane.

Following compounds can be prepared according to the preparation method mentioned above by using 4-(trans-4-alkylcyclohexyl)benzoic acids having a different alkyl chain in place of 4-(trans-4-propylcyclohexyl)benzoic acid:

Difluoro(3',4',5'-trifluorobiphenyloxy)-[4-(trans-4-methylcyclohexyl)phenyl]methane Difluoro(3',4',5'-trifluorobiphenyloxy)-[4-(trans-4-ethylcyclohexyl)phenyl]methane Difluoro(3',4',5'-trifluorobiphenyloxy)-[4-(trans-4-butylcyclohexyl)phenyl]methane Difluoro(3',4',5'-trifluorobiphenyloxy)-[4-(trans-4-pentylcyclohexyl)phenyl]methane
Cr 73.8–74.4N 163.4–164.0 Iso Difluoro(3',4',5'-trifluorobiphenyloxy)-[4-(trans-4-hexylcyclohexyl)phenyl]methane Difluoro(3',4',5'-trifluorobiphenyloxy)-[4-(trans-4-heptylcyclohexyl)phenyl]methane Difluoro(3',4',5'-trifluorobiphenyloxy)-[4-(trans-4-octylcyclohexyl)phenyl]methane Difluoro(3',4',5'-trifluorobiphenyloxy)-[4-(trans-4-nonylcyclohexyl)phenyl]methane Difluoro(3',4',5'-trifluorobiphenyloxy)-[4-(trans-4-decylcyclohexyl)phenyl]methane Following compounds can be prepared according to the preparation method mentioned above by selectively using several known benzoic acid derivatives and several known phenol derivatives, including the compounds preparation examples of which are described in detail in the Examples mentioned above, in place of 4-(trans-4-propylcyclohexyl) benzoic acid or 3',4',5'-trifluorobiphenol:

Difluoro-(4'-trifluoromethoxybiphenyloxy)-[4-(trans-4-ethylcyclohexyl)phenyl]methane Difluoro-(4'-trifluoromethoxybiphenyloxy)-[4-(trans-4-propylcyclohexyl)phenyl]methane Difluoro-(4'-trifluoromethoxybiphenyloxy)-[4-(trans-4-butylcyclohexyl)phenyl]methane Difluoro-(4'-trifluoromethoxybiphenyloxy)-[4-(trans-4-pentylcyclohexyl)phenyl]methane Difluoro-(4'-difluoromethoxybiphenyloxy)-[4-(trans-4-ethylcyclohexyl)phenyl]methane Difluoro-(4'-difluoromethoxybiphenyloxy)-[4-(trans-4-propylcyclohexyl)phenyl]methane Difluoro-(4'-difluoromethoxybiphenyloxy)-[4-(trans-4-butylcyclohexyl)phenyl]methane Difluoro-(4'-difluoromethoxybiphenyloxy)-[4-(trans-4-pentylcyclohexyl)phenyl]methane Difluoro-(4'-trifluoromethylbiphenyloxy)-[4-(trans-4-ethylcyclohexyl)phenyl]methane Difluoro-(4'-trifluoromethylbiphenyloxy)-[4-(trans-4-propylcyclohexyl)phenyl]methane Difluoro-(4'-trifluoromethylbiphenyloxy)-[4-(trans-4-butylcyclohexyl)phenyl]methane Difluoro-(4'-trifluoromethylbiphenyloxy)-[4-(trans-4-pentylcyclohexyl)phenyl]methane Difluoro-(3'-fluoro-4'-trifluoromethoxybiphenyloxy)-[4-(trans-4-ethylcyclohexyl)phenyl]methane Difluoro-(3'-fluoro-4'-trifluoromethoxybiphenyloxy)-[4-(trans-4-propylcyclohexyl)phenyl]methane Difluoro-(3'-fluoro-4'-trifluoromethoxybiphenyloxy)-[4-(trans-4-butylcyclohexyl)phenyl]methane Difluoro-(3'-fluoro-4'-trifluoromethoxybiphenyloxy)-[4-(trans-4-pentylcyclohexyl)phenyl]methane Difluoro-(3'-fluoro-4'-difluoromethoxybiphenyloxy)-[4-(trans-4-ethylcyclohexyl)phenyl]methane Difluoro-(3'-fluoro-4'-difluoromethoxybiphenyloxy)-[4-(trans-4-propylcyclohexyl)phenyl]methane Difluoro-(3'-fluoro-4'-difluoromethoxybiphenyloxy)-[4-(trans-4-butylcyclohexyl)phenyl]methane Difluoro-(3'-fluoro-4'-difluoromethoxybiphenyloxy)-[4-(trans-4-pentylcyclohexyl)phenyl]methane Difluoro-(3'-fluoro-4'-trifluoromethylbiphenyloxy)-[4-(trans-4-ethylcyclohexyl)phenyl]methane Difluoro-(3'-fluoro-4'-trifluoromethylbiphenyloxy)-[4-(trans-4-propylcyclohexyl)phenyl]methane Difluoro-(3'-fluoro-4'-trifluoromethylbiphenyloxy)-[4-(trans-4-butylcyclohexyl)phenyl]methane Difluoro-(3'-fluoro-4'-trifluoromethylbiphenyloxy)-[4-(trans-4-pentylcyclohexyl)phenyl]methane Difluoro-(3',5'-difluoro-4'-trifluoromethoxybiphenyloxy)-[4-(trans-4-ethylcyclohexyl)phenyl]methane Difluoro-(3',5'-difluoro-4'-trifluoromethoxybiphenyloxy)-[4-(trans-4-propylcyclohexyl)phenyl]methane Difluoro-(3',5'-difluoro-4'-trifluoromethoxybiphenyloxy)-[4-(trans-4-butylcyclohexyl)phenyl]methane Difluoro-(3,5',-difluoro-4'-trifluoromethoxybiphenyloxy)-[4-(trans-4-pentylcyclohexyl)phenyl]methane Difluoro-(3',5'-difluoro-4', -difluoromethoxybiphenyloxy)-[4-(trans-4-ethylcyclohexyl)phenyl]methane Difluoro-(3',5'-difluoro-4'-difluoromethoxybiphenyloxy)-[4-(trans-4-propylcyclohexyl)phenyl]methane Difluoro-(3',5'-difluoro-4'-difluoromethoxybiphenyloxy)-[4-(trans-4-butylcyclohexyl)phenyl]methane Difluoro-(3',5'-difluoro-4', -difluoromethoxybiphenyloxy)-[4-(trans-4-pentylcyclohexyl)phenyl]methane Difluoro-(3',5'-difluoro-4'-trifluoromethylbiphenyloxy)-[4-(trans-4-ethylcyclohexyl)phenyl]methane Difluoro-(3',5'-difluoro-4'-trifluoromethylbiphenyloxy)-[4-(trans-4-propylcyclohexyl)phenyl]methane Difluoro-(3',5'-difluoro-4'-trifluoromethylbiphenyloxy)-[4-(trans-4-butylcyclohexyl)phenyl]methane Difluoro-(3',5'-difluoro-4'-trifluoromethylbiphenyloxy)-[4-(trans-4-pentylcyclohexyl)phenyl]methane Difluoro-(3',4',5'-trifluorobiphenyloxy)-[2-fluoro-4-(trans-4-ethylcyclohexyl)phenyl]methane Difluoro-(3',4',5'-trifluorobiphenyloxy)-[2-fluoro-4-(trans-4-propylcyclohexyl)phenyl]methane Difluoro-(3',4',5'-trifluorobiphenyloxy)-[2-fluoro-4-(trans-4-butylcyclohexyl)phenyl]methane Difluoro-(3',4',5'-trifluorobiphenyloxy)-[2-fluoro-4-(trans-4-pentylcyclohexyl)phenyl]methane Difluoro-(3',5'-difluoro-4'-trifluoromethoxybiphenyloxy)-[2-fluoro-4-(trans-4-ethylcyclohexyl)phenyl]methane
Difluoro-(3',5'-difluoro-4'-trifluoromethoxybiphenyloxy)-[2-fluoro-4-(trans-4-propylcyclohexyl)phenyl]methane
Difluoro-(3',5'-difluoro-4'-trifluoromethoxybiphenyloxy)-[2-fluoro-4-(trans-4-butylcyclohexyl)phenyl]methane
Difluoro-(3',5'-difluoro-4'-trifluoromethoxybiphenyloxy)-[2-fluoro-4-(trans-4-pentylcyclohexyl)phenyl]methane
Difluoro-(3',5'-difluoro-4'-difluoromethoxybiphenyloxy)-[2-fluoro-4-(trans-4-ethylcyclohexyl)phenyl]methane
Difluoro-(3',5'-difluoro-4'-difluoromethoxybiphenyloxy)-[2-fluoro-4-(trans-4-propylcyclohexyl)phenyl]methane
Difluoro-(3',5'-difluoro-4'-difluoromethoxybiphenyloxy)-[2-fluoro-4-(trans-4-butylcyclohexyl)phenyl]methane
Difluoro-(3',5'-difluoro-4'-difluoromethoxybiphenyloxy)-[2-fluoro-4-(trans-4-pentylcyclohexyl)phenyl]methane
Difluoro-(3',5'-difluoro-4'-trifluoromethylbiphenyloxy)-[2-fluoro-4-(trans-4-ethylcyclohexyl)phenyl]methane
Difluoro-(3',5'-difluoro-4'-trifluoromethylbiphenyloxy)-[2-fluoro-4-(trans-4-propylcyclohexyl)phenyl]methane
Difluoro-(3',5'-difluoro-4'-trifluoromethylbiphenyloxy)-[2-fluoro-4-(trans-4-butylcyclohexyl)phenyl]methane
Difluoro-(3',5'-difluoro-4'-trifluoromethylbiphenyloxy)-[2-fluoro-4-(trans-4-pentylcyclohexyl)phenyl]methane
Difluoro-(3',4',5'-trifluorobiphenyloxy)-[2,6-difluoro-4-(trans-4-ethylcyclohexyl)phenyl]methane
Difluoro-(3',4',5'-trifluorobiphenyloxy)-[2,6-difluoro-4-(trans-4-propylcyclohexyl)phenyl]methane
Difluoro-(3',4',5'-trifluorobiphenyloxy)-[2,6-difluoro-4-(trans-4-butylcyclohexyl)phenyl]methane
Difluoro-(3',4',5'-trifluorobiphenyloxy)-[2,6-difluoro-4-(trans-4-pentylcyclohexyl)phenyl]methane
Difluoro-(3',5'-difluoro-4'-trifluoromethoxybiphenyloxy)-[2,6-difluoro-4-(trans-4-ethylcyclohexyl)phenyl]methane
Difluoro-(3',5'-difluoro-4'-trifluoromethoxybiphenyloxy)-[2,6-difluoro-4-(trans-4-propylcyclohexyl)phenyl]methane
Difluoro-(3',5'-difluoro-4'-trifluoromethoxybiphenyloxy)-[2,6-difluoro-4-(trans-4-butylcyclohexyl)phenyl]methane
Difluoro-(3',5'-difluoro-4'-trifluoromethoxybiphenyloxy)-[2,6-difluoro-4-(trans-4-pentylcyclohexyl)phenyl]methane
Difluoro-(3',5'-difluoro-4'-difluoromethoxybiphenyloxy)-[2,6-difluoro-4-(trans-4-ethylcyclohexyl)phenyl]methane
Difluoro-(3',5'-difluoro-4'-difluoromethoxybiphenyloxy)-[2,6-difluoro-4-(trans-4-propylcyclohexyl)phenyl]methane
Difluoro-(3',5'-difluoro-4'-difluoromethoxybiphenyloxy)-[2,6-difluoro-4-(trans-4-butylcyclohexyl)phenyl]methane
Difluoro-(3',5'-difluoro-4'-difluoromethoxybiphenyloxy)-[2,6-difluoro-4-(trans-4-pentylcyclohexyl)phenyl]methane
Difluoro-(3',5'-difluoro-4'-trifluoromethybiphenyloxy)-[2,6-difluoro-4-(trans-4-ethylcyclohexyl)phenyl]methane
Difluoro-(3',5'-difluoro-4'-trifluoromethylbiphenyloxy)-[2,6-difluoro-4-(trans-4-propylcyclohexyl)phenyl]methane
Difluoro-(3',5'-difluoro-4'-trifluoromethylbiphenyloxy)-[2,6-difluoro-4-(trans-4-butylcyclohexyl)phenyl]methane
Difluoro-(3',5'-difluoro-4'-trifluoromethylbiphenyloxy)-[2,6-difluoro-4-(trans-4-pentylcyclohexyl)phenyl]methane
Difluoro-(3',4',5'-trifluorobiphenyloxy)-{4-[2-(trans-4-ethylcyclohexyl)ethyl]phenyl} methane
Difluoro-(3',4',5'-trifluorobiphenyloxy)-{4-[2-(trans-4-propylcyclohexyl)ethyl]phenyl} methane
Difluoro-(3',4',5'-trifluorobiphenyloxy)-{4-[2-(trans-4-butylcyclohexyl)ethyl]phenyl} methane
Difluoro-(3',4',5'-trifluorobiphenyloxy)-{4-[2-(trans-4-pentylcyclohexyl)ethyl]phenyl} methane
Difluoro-(4'-trifluoromethoxybiphenyloxy)-{4-[2-(trans-4-ethylcyclohexyl)ethyl]phenyl} methane
Difluoro-(4'-trifluoromethoxybiphenyloxy)-{4-[2-(trans-4-propylcyclohexyl)ethyl]phenyl} methane
Difluoro-(4'-trifluoromethoxybiphenyloxy)-{4-[2-(trans-4-butylcyclohexyl)ethyl]phenyl} methane
Difluoro-(4'-trifluoromethoxybiphenyloxy)-{4-[2-(trans-4-pentylcyclohexyl)ethyl]phenyl} methane
Difluoro-(4'-difluoromethoxybiphenyloxy)-{4-[2-(trans-4-ethylcyclohexyl)ethyl]phenyl} methane
Difluoro-(4'-difluoromethoxybiphenyloxy)-{4-[2-(trans-4-propylcyclohexyl)ethyl]phenyl} methane
Difluoro-(4'-difluoromethoxybiphenyloxy)-{4-[2-(trans-4-butylcyclohexyl)ethyl]phenyl} methane
Difluoro-(4'-difluoromethoxybiphenyloxy)-{4-[2-(trans-4-pentylcyclohexyl)ethyl]phenyl} methane
Difluoro-(4'-trifluoromethylbiphenyloxy)-{4-[2-(trans-4-ethylcyclohexyl)ethyl]phenyl} methane
Difluoro-(4'-trifluoromethylbiphenyloxy)-{4-[2-(trans-4-propylcyclohexyl)ethyl]phenyl} methane
Difluoro-(4'-trifluoromethylbiphenyloxy)-{4-[2-(trans-4-butylcyclohexyl)ethyl]phenyl} methane
Difluoro-(4'-trifluoromethylbiphenyloxy)-{4-[2-(trans-4-pentylcyclohexyl)ethyl]phenyl} methane
Difluoro-(3',5'-difluoro-4'-trifluoromethylbiphenyloxy)-{4-[2-(trans-4-ethylcyclohexyl)ethyl]phenyl} methane
Difluoro-(3',5'-difluoro-4'-trifluoromethylbiphenyloxy)-{4-[2-(trans-4-propylcyclohexyl)ethyl]phenyl} methane
Cr 101.8–102.1N 134.4–135.0 Iso
Difluoro-(3',5'-difluoro-4'-trifluoromethylbiphenyloxy)-{4-[2-(trans-4-butylcyclohexyl)ethyl]phenyl} methane
Difluoro-(3',5'-difluoro-4'-trifluoromethylbiphenyloxy)-{(2-(trans-4-pentylcyclohexyl)ethyl]phenyl} methane EXAMPLE 12 (Use Example 1)

Clearing point (Cp) of the nematic liquid crystal composition having the following chemical composition was 72.4° C.:

| | |
|---|---|
| 4-(trans-4-propylcyclohexyl)benzonitrile | 24% |
| (Symbol % is by weight. This rule applies even hereinafter.) | |
| 4-(trans-4-pentylcyclohexyl)benzonitrile | 36% |
| 4-(trans-4-heptylcyclohexyl)benzonitrile | 25% |
| 4-(4-propylphenyl)benzonitrile | 15% |

This liquid crystal composition enclosed in a TN cell (twisted nematic cell) of 9 $\mu$m cell thickness had a driving threshold voltage ($V_{th}$) of 1.78 V, value of dielectric anisotropy ($\Delta\epsilon$) of +11.0, optical anisotropy ($\Delta\epsilon$) of 0.137, and viscosity at 20° C. ($\eta_{20}$) of 27.0 cP. This liquid crystal composition, as mother liquid crystal, in an amount of 85 parts was mixed with 15 parts of difluoro-[4-(trans-4-propylcyclohexyl)phenyl]-(4-trifluoromethoxyphenyloxy) methane shown in Example 2, and physical properties of the mixture were determined. The results were as follows:

Cp: 70.1, $V_{th}$: 1.71, $\Delta\epsilon$: 10.8, $\Delta$n: 0.132, $\eta_{20}$: 23.5 cP.

While this composition was left in a freezer at –20° C. for 20 days, separation of crystal was not observed.

EXAMPLE 13 (Use Example 2)

Liquid crystal composition shown in Use Example 1, as mother liquid, in an amount of 85 parts was mixed with 15 parts of difluoro-[4-(trans-4-propylcyclohexyl)phenyl]-(3,4,5-trifluorophenyloxy)methane shown in Example 2, and physical properties of the mixture were determined. The results were as follows:

Cp: 64.5, $V_{th}$: 1.49, $\Delta\epsilon$: 11.6, $\Delta n$: 0.128, $\eta_{20}$: 26.6 cP.

While this composition was left in a freezer at −20° C. for 20 days, separation of crystal was not observed.

EXAMPLE 14 (Use Example 3)

Liquid crystal composition shown in Use Example 1, as mother liquid, in an amount of 85 parts was mixed with 15 parts of difluoro-[4-(trans-4-pentylcyclohexyl)phenyl]-(3,4,5-trifluorophenyloxy)methane shown in Example 2, and physical properties of the mixture were determined. The results were as follows:

Cp: 66.6, $V_{th}$: 1.48, $\Delta\epsilon$: 11.4, $\Delta n$: 0.126, $\eta_{20}$: 25.5 cP.

while this composition was left in a freezer at −20° C. for 20 days, separation of crystal was not observed.

EXAMPLE 15 (Use Example 4)

Liquid crystal composition shown in Use Example 1, as mother liquid, in an amount of 85 parts was mixed with 15 parts of difluoro-[4-(trans-4-pentylcyclohexyl)phenyl]-(3,4-difluorophenyloxy)methane shown in Example 2, and physical properties of the mixture were determined. The results were as follows:

Cp: 69.3, $V_{th}$: 1.68, $\Delta\epsilon$: 10.3, $\Delta n$: 0.130, $\eta_{20}$: 25.0 cP.

While this composition was left in a freezer at −20° C. for 20 days, separation of crystal was not observed.

Clearing point (Cp) of the nematic liquid crystal composition having the following chemical composition was 112.4° C.:

| | |
|---|---|
| 4-(trans-4-(trans-4-ethylcyclohexyl)cyclohexyl)-1,2-difluoro-benzene | 33.3% |
| (Symbol % is by weight. This rule applies even hereinafter.) | |
| 4-(trans-4-(trans-4-propylcyclohexyl)cyclohexyl)-1,2-difluoro-benzene | 33.3% |
| 4-(trans-4-(trans-4-pentylcyclohexyl)cyclohexyl)-1,2-difluoro-benzene | 33.3% |

This liquid crystal composition enclosed in a TN cell (twisted nematic cell) of 9 μm cell thickness had a value of dielectric anisotropy ($\Delta\epsilon$) of +5.0, optical anisotropy ($\Delta n$) of 0.080, and viscosity at 20° C. ($\eta_{20}$) of 24.3 cP. This liquid crystal composition, as mother liquid crystal, in an amount of 80 parts was mixed with 20 parts of difluoro-[4-(trans-4-pentylcyclohexyl)phenyl]-(3,4-difluorophenyloxy) methane mentioned above, and physical properties of the mixture were determined. The results were as follows:

Cp: 99.4, $\Delta\epsilon$: 5.6, $\Delta n$: 0.083, $\eta_{20}$: 21.6 cP.

While this composition was left in a freezer at −20° C. for 40 days, separation of crystal was not observed.

EXAMPLE 16 (Use Example 5)

Liquid crystal composition shown in Use Example 1, as mother liquid, in an amount of 85 parts was mixed with 15 parts of difluoro-[4-(trans-4-pentylcyclohexyl)phenyl]-(4-trifluoromethyl phenyloxy)methane shown in Example 2, and physical properties of the mixture were determined. The results were as follows:

Cp: 69.0, $V_{th}$: 1.65, $\Delta\epsilon$: 11.4, $\Delta n$: 0.131, $\eta_{20}$: 27.0 cP.

While this composition was left in a freezer at −20° C. for 20 days, separation of crystal was not observed.

EXAMPLE 17 (Use Example 6)

Liquid crystal composition shown in Use Example 1, as mother liquid, in an amount of 85 parts was mixed with 15 parts of difluoro-[4-(trans-4-propylcyclohexyl)phenyl]-(3-trifluoro-4-cyanophenyloxy)methane shown in Example 2, and physical properties of the mixture were determined. The results were as follows:

Cp: 74.6, $V_{th}$: 1.64, $\Delta\epsilon$: 12. 3, $\Delta n$: 0.140, $\eta_{20}$: 30.9 cP.

While this composition was left in a freezer at −20° C. for 20 days, separation of crystal was not observed.

EXAMPLE 18 (Use Example 7)

Liquid crystal composition shown in Use Example 1, as mother liquid, in an amount of 85 parts was mixed with 15 parts of difluoro-{4-[2-(trans-4-propylcyclohexyl)ethyl]phenyl}-(3,4,5-trifluorophenyloxy)methane shown in Example 3, and physical properties of the mixture were determined. The results were as follows:

Cp: 65.8, $V_{th}$: 1.61, $\Delta\epsilon$: 11.3, $\Delta n$: 0.129, $\eta_{20}$: 25.4 cP.

While this composition was left in a freezer at −20° C. for 20 days, separation of crystal was not observed.

EXAMPLE 19 (Use Example 8)

Liquid crystal composition shown in Use Example 1, as mother liquid, in an amount of 85 parts was mixed with 15 parts of difluoro-{4-[2-(trans-4-propylcyclohexyl)ethyl]phenyl}-(4-trifluoromethoxyphenyloxy)methane shown in Example 3, and physical properties of the mixture were determined. The results were as follows:

Cp: 69.8, $V_{th}$: 1.79, $\Delta\epsilon$: 10.4, $\Delta n$: 0.131, $\eta_{20}$: 24.2 cP.

While this composition was left in a freezer at −20° C. for 20 days, separation of crystal was not observed.

EXAMPLE 20 (Use Example 9)

Liquid crystal composition shown in Use Example 1, as mother liquid, in an amount of 85 parts was mixed with 15 parts of difluoro-{4-[2-(trans-4-propylcyclohexyl)ethyl]phenyl}-(3-fluoro-4-trifluoromethoxyphenyloxy)methane shown in Example 3, and physical properties of the mixture were determined. The results were as follows:

Cp: 68.9, $V_{th}$: 1.69, $\Delta\epsilon$: 10.9, $\Delta n$: 0.131, $\eta_{20}$: 25.3 cP.

While this composition was left in a freezer at −20° C. for 20 days, separation of crystal was not observed.

EXAMPLE 21 (Use Example 10)

Liquid crystal composition shown in Use Example 1, as mother liquid, in an amount of 85 parts was mixed with 15 parts of difluoro-(3',4',5'-trifluorobiphenyloxy)-[4-(trans-4-pentylcyclohexyl)phenyl]methane shown in Example 10, and physical properties of the mixture were determined. The results were as follows:

Cp: 80.4, $V_{th}$: 1.62, $\Delta\epsilon$: 10.3, $\Delta n$: 0.140, $\eta_{20}$: 28.8 cP.

While this composition was left in a freezer at −20° C. for 20 days, separation of crystal was not observed.

EXAMPLE 22 (Use Example 11)

Liquid crystal composition shown in Use Example 1, as mother liquid, in an amount of 85 parts was mixed with 15 parts of difluoro-(3',5'-difluoro-4-trifluoromethylbiphenyloxy)-{4-[2-(trans-4-propylcyclohexyl)ethyl]phenyl} methane shown in Example 10, and physical properties of the mixture were determined. The results were as follows:

Cp: 76.6, $V_{th}$: 1.75, $\Delta\epsilon$: 11.9, $\Delta n$: 0.139, $\eta_{20}$: 29.8 cP.

While this composition was left in a freezer at −20° C. for 20 days, separation of crystal was not observed.

As the nematic liquid crystal compositions containing the compounds of the present invention, the followings (use Examples 12 to 28) can be mentioned. In the following lists, compounds in the compositions are indicated by the abbreviations according to the rules shown in the following Table. That is, left side terminal groups are indicated by s, sO, sOt, Vs, or sVt, bonding groups by 2, E, T, or CF2O, ring structures by B, B(F), B(F,F), H, or Py, and right side terminal groups are indicated by F, CL, OCF3, w, or Ow.

TABLE 1

| Left side terminal group | Symbol | Bonding group | Symbol |
|---|---|---|---|
| $C_sH_{2s+1}-$ | s— | $-CH_2CH_2-$ | 2 |
| $C_sH_{2s+1}O-$ | sO— | $-COO-$ | E |
| $C_sH_{2s+1}OC_tH_{2t}-$ | sOt— | $-C\equiv C-$ | T |
| $CH_2=CHC_sH_{2s}-$ | Vs— | $-CF_2O-$ | CF2O |
| $C_sH_{2s+1}CH=CHC_tH_{2t}-$ | sVt— | | |

| Ring structure | Symbol | Right side terminal group | Symbol |
|---|---|---|---|
| 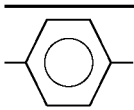 | B | $-F$ | $-F$ |
| 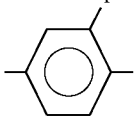 | B(F) | $-Cl$ | $-CL$ |
| 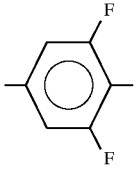 | B(F, F) | $-CN$ | $-C$ |
|  | H | $-OCF_3$ | $-OCF3$ |
|  | Py | $-C_wH_{2w+1}$ | $-w$ |
| | | $-OC_wH_{2w+1}$ | $-Ow$ |

| Example 23 (Use Example 12) | |
|---|---|
| 3-HBCF2OB-OCF3 | 10.0% |
| 5-HBCF2OB-OCF3 | 8.0% |
| 3O1-BEB(F)-C | 5.0% |
| 2-HB-C | 5.0% |
| 3-HB-C | 15.0% |
| 2-HHB-C | 5.0% |
| 3-HHB-C | 5.0% |
| 4-HHB-C | 5.0% |
| 3-PyBB-F | 5.0% |
| 3-HH-4 | 10.0% |
| 3-HH-5 | 3.0% |
| 2-BTB-O1 | >3.0% |
| 3-BTB-O1 | 3.0% |
| 4-BTB-O1 | 3.0% |
| 4-BTB-O2 | 3.0% |
| 5-BTB-O1 | 3.0% |
| 3-HHB-1 | 6.0% |
| 3-HHB-O1 | 3.0% |

| Example 23 (Use Example 12) | |
|---|---|
| Clearing point (°C.) | 92.2 |
| Viscosity (mPa · s) | 20.9 |
| Optical anisotropy | 0.142 |
| Dielectric anisotropy | 8.6 |
| Threshold voltage (V) | 1.83 |

| Example 24 (Use Example 13) | |
|---|---|
| 3-HBCF2OB-OCF3 | 10.0% |
| 3-HBCF2OB-(F,F)-F | 5.0% |
| 5-HBCF2OB-(F,F)-F | 5.0% |
| V2-HB-C | 7.0% |
| 1V2-HB-C | 7.0% |
| 3-HB-C | 5.0% |
| 3-HHB-C | 5.0% |
| 3-PyBB-F | 8.0% |
| 2-PyBH-3 | 4.0% |
| 3-PyBH-3 | 4.0% |
| 4-PyBB-3 | 4.0% |
| 3-HH-4 | 10.0% |
| 1O1-HH-3 | 6.0 |
| 2-BTB-1 | 4.0% |
| 1-BTB-6 | 8.0% |
| 4-BTB-4 | 4.0% |
| 3-HHB-1 | 4.0% |
| Clearing point (°C.) | 83.5 |
| Viscosity (mPa · s) | 26.8 |
| Optical anisotropy | 0.148 |
| Dielectric anisotropy | 7.0 |
| Threshold voltage (V) | 2.02 |

| Example 25 (Use Example 14) | |
|---|---|
| 3-HBCF2OB(F,F)-F | 8.0% |
| 5-HBCF2OB(F,F)-F | 8.0% |
| 2-BB-C | 7.0% |
| 1O1-HB-C | 8.0% |
| 2O1-HB-C | 7.0% |
| 2-BEB-C | 4.0% |
| 5-PyB-F | 5.0% |
| 3-PyBB-F | 5.0% |
| 2-PyB-2 | 3.0% |
| 3-PyB-2 | 3.0% |
| 4-PyB-2 | 3.0% |
| 2-PyBH-3 | 5.0% |
| 3-PyBH-3 | 5.0% |
| 4-PyBH-3 | 5.0% |
| 3-PyB-O2 | 5.0% |
| 2-HHB-1 | 4.0% |
| 3-HHB-1 | 6.0% |
| 3-HHB-3 | 9.0% |
| Clearing point (°C.) | 71.5 |
| Viscosity (mPa · s) | 32.5 |
| Optical anisotropy | 0.142 |
| Dielectric anisotropy | 10.2 |
| Threshold voltage (V) | 1.44 |

| Example 26 (Use Example 15) | |
|---|---|
| 3-HBCF2OB-OCF3 | 10.0% |
| 5-HBCF2OB-CF3 | 5.0% |
| 3-PyB(F)-F | 6.0% |
| 3-PyBB-F | 4.0% |
| 4-PyBB-F | 4.0% |
| 5-PyBB-F | 4.0% |
| 2-PyB-2 | 6.0% |
| 3-PyB-2 | 6.0% |
| 4-PyB-2 | 6.0% |

Example 26 (Use Example 15)

| | |
|---|---|
| 3-HEB-O4 | 6.0% |
| 4-HEB-O2 | 6.0% |
| 5-HEB-O1 | 6.0% |
| 2-H2BTB-4 | 4.0% |
| 3-H2BTB-4 | 4.0% |
| 3-HHB-1 | 7.0% |
| 3-HHB-3 | 7.0% |
| 3-HHEBB-C | 3.0% |
| 5-HHEBB-C | 3.0% |
| 3-HBEBB-C | 3.0% |
| Clearing point (°C.) | 99.3 |
| Viscosity (mPa · s) | 30.1 |
| Optical anisotropy | 0.156 |
| Dielectric anisotropy | 5.3 |
| Threshold voltage (V) | 2.36 |

Example 27 (Use Example 16)

| | |
|---|---|
| 5-HBCF2OB(F,F)-CF3 | 10.0% |
| 3-HBCF2OB(F,F)-F | 7.0% |
| 5-HBCF2OB(F,F)-F | 7.0% |
| 2O1-BEB(F)-C | 2.0% |
| 3O1-BEB(F)-C | 8.0% |
| 2-HB(F)-C | 5.0% |
| 3-HB(F)-C | 7.0% |
| 3-HHB(F)-C | 3.0% |
| 2-HHB(F)-F | 5.0% |
| 3-HHB(F)-F | 5.0% |
| 5-HHB(F)-F | 5.0% |
| 3-HHB-1 | 6.0% |
| 3-HHB-3 | 3.0% |
| 3-HHB-O1 | 3.0% |
| 3-H2BTB-2 | 4.0% |
| 3-H2BTB-3 | 4.0% |
| 3-H2BTB-4 | 4.0% |
| 3-HB(F)TB-2 | 4.0% |
| 3-HB(F)TB-3 | 4.0% |
| 3-HB(F)TB-4 | 4.0% |
| Clearing point (°C.) | 94.3 |
| Viscosity (mPa · s) | 32.9 |
| Optical anisotropy | 0.137 |
| Dielectric anisotropy | 12.8 |
| Threshold voltage (V) | 1.46 |

Example 28 (Use Example 17)

| | |
|---|---|
| 3-HBCF2OB-OCF3 | 6.0% |
| 5-HBCF2OB-OCF3 | 5.0% |
| 5-HBCF2OB-CF3 | 5.0% |
| V2-HB-C | 8.0% |
| 1V2-HB-C | 8.0% |
| 3-HB-C | 13.0% |
| 5-HB-C | 7.0% |
| 1O1-HB-C | 4.0% |
| 2O1-HB-C | 4.0% |
| 3-HHB-F | 4.0% |
| 3-HH-4 | 4.0% |
| 2-BTB-O1 | 8.0% |
| 3-HHB-O1 | 4.0% |
| 3-HHB-1 | 6.0% |
| 3-HHB-3 | 10.0% |
| 3-HB(F)TB-2 | 4.0% |
| Clearing point (°C.) | 80.5 |
| Viscosity (mPa · s) | 19.4 |
| Optical anisotropy | 0.130 |
| Dielectric anisotropy | 8.2 |
| Threshold voltage (V) | 1.86 |

Example 29 (Use Example 18)

| | |
|---|---|
| 3-HBCF2OB(F,F)-F | 9.0% |
| 5-HBCF2OB(F,F)-OCF3 | 9.0% |
| 2-BEB-C | 5.0% |
| 2-BB-C | 11.0% |
| 3-HB-C | 5.0% |
| 1O-BEB-2 | 10.0% |
| 3-HEB-O4 | 10.0% |
| 4-HEB-O2 | 10.0% |
| 5-HEB-O1 | 10.0% |
| 3-HBEB-F | 5.0% |
| 3-HHEB-F | 5.0% |
| 5-HHEB-F | 5.0% |
| 3-HEBEB-F | 3.0% |
| 3-HEBEB-1 | 3.0% |
| Clearing point (°C.) | 71.7 |
| Viscosity (mPa · s) | 36.8 |
| Optical anisotropy | 0.117 |
| Dielectric anisotropy | 7.5 |
| Threshold voltage (V) | 1.52 |

Example 30 (Use Example 19)

| | |
|---|---|
| 3-HBCF2OB-OCF3 | 6.0% |
| 3-HBCF2OB(F,F)-F | 6.0% |
| 3-H2BCF2OBB(F,F)-CF3 | 5.0% |
| 2O1-BEB(F)-C | 2.0% |
| 3O1-BEB(F)-C | 6.0% |
| 4O1-BEB(F)-C | 3.0% |
| 2-HHB(F)-F | 4.0% |
| 3-HHB(F)-F | 4.0% |
| 5-HHB(F)-F | 4.0% |
| 3-HHEB-F | 3.0% |
| 5-HHEB-F | 3.0% |
| 3-HEB-F | 3.0% |
| 3-HH-EMe | 9.0% |
| 3-HEB-O4 | 4.0% |
| 4-HEB-3 | 4.0% |
| 4-HEB-4 | 4.0% |
| 2-PyBH-3 | 5.0% |
| 3-PyBH-3 | 5.0% |
| 4-PyBH-3 | 5.0% |
| 3-HB-O2 | 10.0% |
| 3-HHP-1 | 5.0% |
| Clearing point (°C.) | 83.6 |
| Viscosity (mPa · s) | 32.9 |
| Optical anisotropy | 0.105 |
| Dielectric anisotropy | 7.1 |
| Threshold voltage (V) | 1.83 |

Example 31 (Use Example 20)

| | |
|---|---|
| 5-HBCF2OB-CF3 | 5.0% |
| 5-HBCF2OB(F,F)-CF3 | 10.0% |
| 3-DB-C | 4.0% |
| 4-DB-C | 4.0% |
| 1O1-HB-C | 5.0% |
| 2-PyB-2 | 9.0% |
| 3-PyB-2 | 9.0% |
| 4-PyB-2 | 9.0% |
| 2-PyBH-3 | 7.0% |
| 3-PyBH-3 | 6.0% |
| 4-PyBH-3 | 6.0% |
| 1O1-HH-5 | 8.0% |
| 3-HB(F)TB-2 | 6.0% |
| 3-HB(F)TB-3 | 6.0% |
| 3-HB(F)TB-4 | 6.0% |
| Clearing point (°C.) | 71.0 |
| Viscosity (mPa · s) | 25.5 |
| Optical anisotropy | 0.149 |

Example 31 (Use Example 20)

| | |
|---|---|
| Dielectric anisotropy | 6.0 |
| Threshold voltage (V) | 1.78 |

Example 32 (Use Example 21)

| | |
|---|---|
| 3-HBCF2OB(F,F)-F | 14.0% |
| 5-HBCF2OB(F,F)-F | 14.0% |
| 5-HBCF2OB(F)-OCF3 | 4.0% |
| 1V2-BEB(F,F)-C | 12.0% |
| 3O1-BEB(F)-C | 11.0% |
| 3-HB-C | 9.0% |
| 3-HB(F)-C | 7.0% |
| 3-HHB(F)-C | 6.0% |
| 3-PyBB-F | 8.0% |
| 4-PyBB-F | 8.0% |
| 5-PyBB-F | 7.0% |
| Clearing point (°C.) | 57.6 |
| Viscosity (mPa · s) | 52.0 |
| Optical anisotropy | 0.144 |
| Dielectric anisotropy | 24.4 |
| Threshold voltage (V) | 0.77 |

Example 33 (Use Example 22)

| | |
|---|---|
| 3-HBCF2OB-OCF3 | 10.0% |
| 5-HBCF2OB-OCF3 | 5.0% |
| 2-HB(F)-C | 10.0% |
| 3-HB(F)-C | 10.0% |
| 3O1-BEB(F)-C | 7.0% |
| 3-HHEB-F | 4.0% |
| 5-HHEB-F | 4.0% |
| 3-HHEB(F,F)-F | 15.0% |
| 5-HHEB(F,F)-F | 10.0% |
| 3-HBEB(F,F)-F | 5.0% |
| 5-HBEB(F,F)-F | 5.0% |
| 3-HHB-1 | 8.0% |
| 3-HHB-O1 | 4.0% |
| 3-HHB-3 | 3.0% |
| Clearing point (°C.) | 83.2 |
| Viscosity (mPa · s) | 33.2 |
| Optical anisotropy | 0.096 |
| Dielectric anisotropy | 13.6 |
| Threshold voltage (V) | 1.16 |

Example 34 (Use Example 23)

| | |
|---|---|
| 3-HBCF26B-OCF3 | 10.0% |
| 5-HBCF2OB-OCF3 | 5.0% |
| 1V-HB-C | 9.0% |
| 1V2-HB-C | 9.0% |
| 3-HB-C | 14.0% |
| 2-HHB-C | 3.0% |
| 3-HHB-C | 4.0% |
| V2-HH-3 | 10.0% |
| 1O1-HH-5 | 8.0% |
| 2-BTB-O1 | 11.0% |
| V-HHB-1 | 8.0% |
| V-HBB-2 | 5.0% |
| 1V2-HBB-2 | 4.0% |
| Clearing point (°C.) | 83.6 |
| Viscosity (mPa · s) | 17.1 |
| Optical anisotropy | 0.134 |
| Dielectric anisotropy | 7.0 |

Example 35 (Use Example 24)

| | |
|---|---|
| 3-HBCF2OB(F,F)-F | 10.0% |
| 5-HBCF2OB(F,F)-F | 10.0% |
| 2-HB(F)-C | 7.0% |
| 3-HB(F)-C | 10.0% |
| 3-HHB-F | 5.0% |
| 3-HB-O2 | 10.0% |
| V-HH-5 | 5.0% |
| V2-HH-3 | 5.0% |
| 2-BTB-O1 | 8.0% |
| V-HHB-1 | 8.0% |
| V-HBB-2 | 5.0% |
| 1V2-HBB-2 | 5.0% |
| 3-HHB-O1 | 4.0% |
| 3-H2BTB-2 | 4.0% |
| 3-H2BTB-3 | 4.0% |
| Clearing point (°C.) | 71.6 |
| Viscosity (mPa · s) | 16.9 |
| Optical anisotropy | 0.121 |
| Dielectric anisotropy | 6.1 |
| Threshold voltage (V) | 1.81 |

Example 36 (Use Example 25)

| | |
|---|---|
| 3-HBCF2OB(F,F)-F | 5.0% |
| 5-HBCF2OB(F,F)-F | 10.0% |
| 5-HBCF2OB-CF3 | 5.0% |
| 5-HBCF2OB(F)-F | 5.0% |
| 3-HBCF2OB-OCF3 | 5.0% |
| 7-HB(F,F)-F | 8.0% |
| 3-HHB(F,F)-F | 6.0% |
| 4-HHB(F,F)-F | 3.0% |
| 3-H2HB(F,F)-F | 10.0% |
| 4-H2HB(F,F)-F | 6.0% |
| 5-H2HB(F,F)-F | 6.0% |
| 3-HH2B(F,F)-F | 10.0% |
| 5-HH2B(F,F)-F | 5.0% |
| 3-HBB(F,F)-F | 5.0% |
| 5-HBB(F,F)-F | 5.0% |
| 3-HHBB(F,F)-F | 3.0% |
| 3-HH2BB(F,F)-F | 3.0% |
| Clearing point (°C.) | 61.8 |
| Viscosity (mPa · s) | 23.6 |
| Optical anisotropy | 0.083 |
| Dielectric anisotropy | 8.4 |
| Threshold voltage (V) | 1.50 |

Example 37 (Use Example 26)

| | |
|---|---|
| 3-HBCF2OB(F,F)-F | 5.0% |
| 3-HBCF2OB-OCF3 | 5.0% |
| 3-HB-CL | 4.0% |
| 5-HB-CL | 4.0% |
| 7-HB-CL | 5.0% |
| 2-HHB-CL | 6.0% |
| 3-HHB-CL | 7.0% |
| 5-HHB-CL | 6.0% |
| 2-HBB(F)-F | 6.0% |
| 3-HBB(F)-F | 6.0% |
| 5-HBB(F)-F | 12.0% |
| 3-HBB(F,F)-F | 13.0% |
| 5-HBB(F,F)-F | 13.0% |
| 3-H2HB(F)-CL | 3.0% |
| 3-HB(F)TB-2 | 3.0% |
| 3-HB(F)VB-2 | 2.0% |
| Clearing point (°C.) | 89.3 |
| Viscosity (mPa · s) | 21.9 |
| Optical anisotropy | 0.128 |
| Dielectric anisotropy | 6.4 |
| Threshold voltage (V) | 2.08 |

| Example 38 (Use Example 27) | |
|---|---|
| 5-HBCF2OB(F,F)-F | 10.0% |
| 5-HBCF2OB-CF3 | 5.0% |
| 3-HBCF2OB-OCF3 | 5.0% |
| 2-HBB(F)-F | 3.0% |
| 3-HBB(F)-F | 3.0% |
| 5-HBB(F)-F | 6.0% |
| 2-HBB-F | 3.0% |
| 3-HBB-F | 3.0% |
| 3-H2HB(F,F)-F | 6.0% |
| 4-H2HB(F,F)-F | 6.0% |
| 5-H2HB(F,F)-F | 6.0% |
| 3-HHB(F,F)-F | 3.0% |
| 4-HHB(F,F)-F | 3.0% |
| 3-HH2B(F,F)-F | 12.0% |
| 5-HH2B(F,F)-F | 6.0% |
| 3-HBB(F,F)-F | 6.0% |
| 5-HBB(F,F)-F | 6.0% |
| 3-HHB-CL | 4.0% |
| 5-HHB-CL | 4.0% |
| Clearing point (°C.) | 82.8 |
| Viscosity (mPa · s) | 24.8 |
| Optical anisotropy | 0.100 |
| Dielectric anisotropy | 8.0 |
| Threshold voltage (V) | 1.69 |

| Example 39 (Use Example 28) | |
|---|---|
| 3-HBCF2OB(F,F)-F | 3.0% |
| 5-HBCF2OB(F,F)-F | 8.0% |
| 3-HBCF2OB-OCF3 | 5.0% |
| 2-HBB(F)-F | 8.0% |
| 3-HBB(F)-F | 8.0% |
| 5-HBB(F)-F | 16.0% |
| 5-HB-F | 6.0% |
| 7-HB-F | 6.0% |

| Example 39 (Use Example 28) | |
|---|---|
| 5-HHB-OCF3 | 8.0% |
| 3-H2HB-OCF3 | 8.0% |
| 5-H2HB-OCF3 | 8.0% |
| 3-HH2B-OCF3 | 8.0% |
| 5-HH2B-OCF3 | 8.0% |
| Clearing point (°C.) | 84.9 |
| Viscosity (mPa · s) | 16.6 |
| Optical anisotropy | 0.101 |
| Dielectric anisotropy | 5.5 |
| Threshold voltage (V) | 2.12 |

COMPARATIVE EXAMPLE

Among the compounds expressed by the formula (b-1) or (b-4) (U.S. Pat. No. 5,032,313) described in the paragraph of BACKGROUND ART, 1,2,6-trifluoro-4-[4-(trans-4-propylcyclohexyl)phenyl]benzene (compound expressed by the formula (b-1) wherein R=C$_3$H$_7$) was selected as comparative compound to the present invention.

This compound was actually synthesized according to the Example described in the U.S. Pat. No. 5,032,313.

Liquid crystal composition shown in Example 12(Use Example 1) in an amount of 85 parts, as mother liquid crystal, was mixed with 15 parts of the 1,2,6-trifluoro-4-[4-(trans-4-propylcyclohexyl) phenyl]benzene or 4-(trans-4-propylcyclohexyl)phenyl-(3,4,5-trifulorophenyloxy) methane, and physical properties of the mixtures were determined. The physical properties are shown in Table 2 together with the results of (Use Example 1) and Example 13 (Use Example 2). In the Table, numerical values in parentheses are ones obtained by extrapolation.

TABLE 2

| | Cp(°C.) | Δε | η$_{20}$ (cP) | V$_{th}$(V) |
|---|---|---|---|---|
| Mother liquid crystal | 72.4 | 11.0 | 27.0 | 1.78 |
| 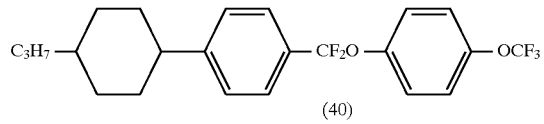 (40) | 70.1(57.1) | 10.8(9.7) | 23.5(3.7) | 1.71 |
| 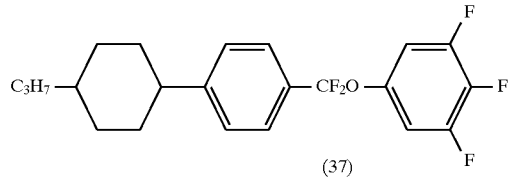 (37) | 64.5(19.7) | 11.6(15.0) | 26.6(24.3) | 1.49 |
| 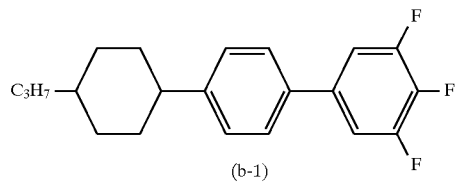 (b-1) | 68.7(47.7) | 11.1(11.7) | 28.8(39.0) | 1.51 |

TABLE 2-continued

| | Cp(°C.) | Δε | η₂₀ (cP) | V_th(V) |
|---|---|---|---|---|
| 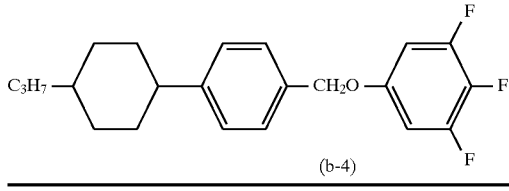 (b-4) | 61.2(1.7) | 10.4(7.0) | 30.5(54.3) | 1.61 |

From Table 2, it can be seen that compound (37) of the present invention has excellent characteristics compared with comparative compound (b-i) having the same molecular skeleton in that the inventive compound exhibits an extremely low viscosity ($\eta_{20}$) as low as about 60% of the compound (b-1) whereas the inventive compound has a value of dielectric anisotropy ($\Delta\epsilon$) 1.28 times as large as the compound (b-1) when compared based on extrapolated values. Also, in comparison between compound (37) of the present invention and the compound (b-4) in which fluorine atoms at benzyl position in compound (37) were substituted with hydrogen atoms, the inventive compound has an extremely low viscosity ($\eta_{20}$) as low as about 40% of the compound (b-4). From this fact, it can be seen that the —CF₂O—bonding group which crosslinked two benzene rings, as a characteristic of the present invention, contributes to the increase of the value of dielectric anisotropy ($\Delta\epsilon$) as well as to the reduction of viscosity. Further, it is seen that compound (40) of the present invention having a trifluoromethoxy group at the terminal of its molecule is as extremely low as 3.7 cP in the extrapolated value of viscosity and that the compound reduces only viscosity by even about 13% without lowering clearing point or the value of dielectric anisotropy, compared with the mother liquid crystal. Thus, the present compound can be said to be highly useful even as viscosity reducing agent.

INDUSTRIAL APPLICABILITY

Difluorooxymethane derivatives of the present invention and liquid crystal compositions containing the compound are useful, as liquid crystal material for low voltages in several modes, for example, active matrix mode and STN mode.

We claim:
1. A difluorooxymethane derivative expressed by the general formula (I)

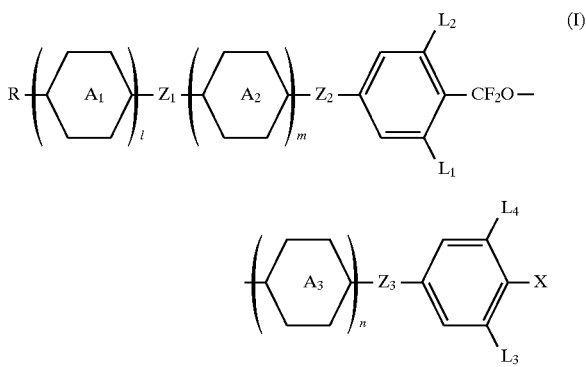

wherein each of l, m, and n is 0 or 1, rings A and A₂ independently represent trans-1,4-cyclohexylene group, 1,4-phenylene group one or more hydrogen atoms in which six-membered ring may be replaced by a halogen atom, trans-1,3-dioxane-2,5-diyl, or pyrimidine-2,5-diyl, ring A₃ represents 1,4-phenylene group one or more hydrogen atoms in which six-membered ring may be replaced by a halogen atom, trans-1,3-dioxane-2,5-diyl, or pyrimidine-2,5-diyl, Z₁, Z₂, and Z₃ independently represent a covalent bond, —CH₂CH₂—, —COO—, —CF₂O—, —OCF₂—, —CH₂O—, —OCH₂—, —CH=CH—, or —C≡C—, L₁, L₂, L₃, and L₄ independently represent hydrogen atom or a halogen atom, respectively, X represents a halogen atom, CN, CF₃, OCF₃, OCHF₂, OCH₂F, or a linear or branched alkyl group or alkoxy group having 1 to 10 carbon atoms, or a linear or branched alkenyl group having 2 to 10 carbon atoms, and R represents a linear or branched alkyl group having 1 to 10 carbon atoms or a linear or branched alkenyl group having 2 to 10 carbon atoms, one or not adjacent 2 or more CH₂, groups in the R may be replaced by oxygen atom, provided that in no case is X an alkyl group, alkoxy group, or alkenyl group, except in the case where Z₁, Z₂, or Z₃ is —CF₂O—or —OCF₂—; that in the case where l is 0, then Z₁ represents a covalent bond, in the case where m is 0,then Z₂ represents a covalent bond, and in the case where n is 0, then Z₃ represents a covalent bond; that when X represents other than CN group, at least one of L₁ and L₂ represents a halogen atom except in the case where both l and m are 1; and that in the case where both L₁ and L₂ represent hydrogen atom and X represents CN group, then at least one of L₃ and L₄ represents a halogen atom.

2. The difluorooxymethane derivative according to claim 1 wherein l=1, m=0, n is 0 or 1, Z₁ is covalent bond or —CH—CH₂—, both Z₂ and Z₃ are covalent bond, A₁ is trans-1,4-cyclohexylene group, A₃ is 1,4-phenylene group, and R is a linear alkyl group or alkenyl group having 1 to 10 carbon atoms, in the general formula (I).

3. The difluorooxymethane derivative according to claim 1 or 2 wherein at least one of L₃ and L₄ is halogen atom.

4. The difluorooxymethane derivative according to claim 1 wherein l=m=n=0, and all of Z₁, Z₂, and Z₃ are covalent bond, in the general formula (I).

5. The difluorooxymethane derivative according to claim 1 wherein l=1, m=n=0, and both of Z₂ and Z₃ are covalent bond, in the general formula (I).

6. The difluorooxymethane derivative according to any one of claims 1 2, 4 or 5 wherein all of L₃, L₄, and X are fluorine atom, in the general formula (I).

7. The difluorooxymethane derivative according to claim 5 wherein X is OCF₃, in the general formula (I).

8. The difluorooxymethane derivative according to claim 5 wherein X is CN, in the general formula (I).

9. The difluorooxymethane derivative according to claim 1 wherein l=1, ring A₁ is 1,4-phenylene group one or more hydrogen atom in which 6-membered ring may be replaced by halogen atom, $Z_1$ is —OCF$_2$—, both of $Z_2$ and $Z_3$ are covalent bond, and X is a linear or branched alkyl group, alkenyl group, or alkoxy group having 1 to 10 carbon atoms, in the general formula (I).

10. The difluorooxymethane derivative according to claim 1 wherein l=m=0, n=1, both of $Z_1$ and $Z_2$ are covalent bond, and ring $A_3$ is 1,4-phenylene group, in the general formula (I).

11. The difluorooxymethane derivative according to claim 10 wherein $Z_3$ is covalent bond, in the general formula (I).

12. The difluorooxymethane derivative according to claim 10 wherein $Z_3$ is —CH$_2$CH$_2$—, in the general formula (I).

13. A liquid crystal composition containing at least one kind of difluorooxymethane derivative defined in any one of claims 1,2,4,5 or 7 to 12.

14. A liquid crystal composition containing, as a first component, at least one kind of difluorooxymethane derivative defined in any one of claims 1,4,5 or 7 to 12 and containing, as a second component, at least one kind of compound selected from the group of compounds expressed by general formula (II), (III), or (IV)

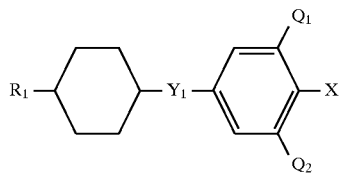
(II)

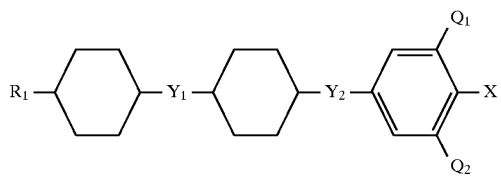
(III)

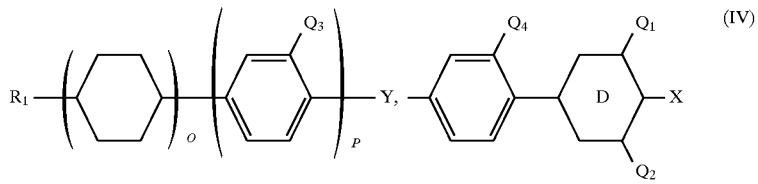
(IV)

wherein $R_1$, represents an alkyl group having 1 to 10 carbon atoms, X represents F, Cl, CF$_3$, OCF$_3$, OCF$_2$H, or an alkyl group having 1 to 10 carbon atoms, $Q_1$, $Q_2$, $Q_3$ and $Q_4$ independently represent H or F, o represents 1 or 2, p represents 0 or 1, $Y_1$ and $Y_2$ independently represent —CH$_2$CH$_2$—, —CH=CH—, or covalent bond, and ring D represents trans-1,4-cyclohexylene group or 1,4-phenylene group.

15. A liquid crystal composition containing, as a first component, at least one kind of difluorooxymethane derivative defined in any one of claims 1, 2, 4, 5 or 7 to 12, containing, as a second component, at least one kind of compound selected from the group of compounds expressed by general formula (V), (VI), (VII), (VIII), or (IX)

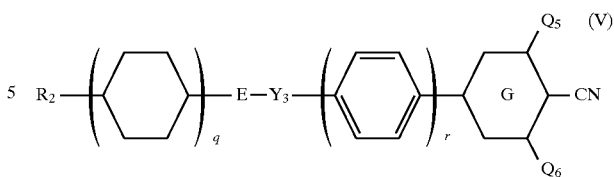
(V)

wherein $R_2$ represents fluorine atom, an alkyl group having 1 to 10 carbon atoms, or an alkenyl group having 2 to 10 carbon atoms, in any case, one or not adjacent two or more CH$_2$ groups in the alkyl or alkenyl group may be replaced by oxygen atom, $Y_3$ represents —CH$_2$CH$_2$—, —COO—, or covalent bond, $Q_5$ and $Q_6$ independently represent hydrogen atom or fluorine atom, E represents trans-1,4-cyclohexylene, 1,4-phenylene, or trans-1,3-dioxane-2,5-diyl, ring G represents trans-1,4-cyclohexylene or 1,4-phenylene, and q and r independently represent 0 or 1,

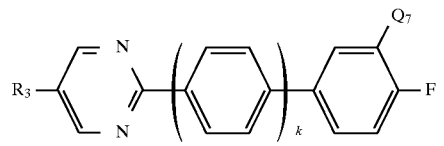
(VI)

wherein $R_3$ represents an alkyl group having 1 to 10 carbon atoms, $Q_7$ represents hydrogen atom or fluorine atom, and k represents 0 or 1,

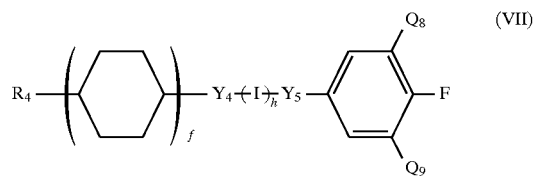
(VII)

wherein $R_4$ represents an alkyl group having 1 to 10 carbon atoms, I represents trans-1,4-cyclohexylene or 1,4-phenylene, $Q_8$ and $Q_9$ represent hydrogen atom or fluorine atom, $Y_4$ represents —COO— or —C≡C—, and f and h independently represent 0 or 1,

wherein $R_5$ and $R_6$ independently represent an alkyl group, alkoxy group, or alkoxymethyl group having 1 to 10 carbon atoms, J represents trans-1,4-cyclohexylene, 1,3-pyrimidine-2,5-diyl, or 1,4-phenylene, K represents trans-1,4-cyclohexylene or 1,4-phenylene, $Y_6$ represents —C≡C—, —COO—, —CH$_2$CH$_2$—, or covalent bond,

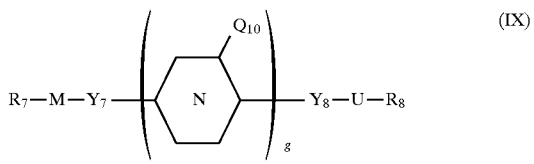

wherein $R_7$ represents an alkyl group or alkoxy group having 1 to 10 carbon atoms, $R_8$ represents an alkyl group having 1 to 10 carbon atoms, one or not adjacent two or more CH$_2$ groups in which alkyl group may be replaced by oxygen atom, M represents trans-1,4-cyclohexylene or 1,3-pyrimidine-2,5-diyl, rings N and U independently represent trans-1,4-cyclohexylene or 1,4-phenylene, $Y_7$ represents —CH$_2$CH$_2$—, —COO—, or covalent bond, $Y_8$ represents —C≡C—, —COO—, or covalent bond, g represents 0 or 1, and $Q_{10}$ represents hydrogen atom or fluorine atom.

16. A liquid crystal composition containing, as a first component, at least one kind of difluorooxymethane derivative defined in any one of claims 1,2,4,5 or 7 to 12, containing, as a part of the second component, at least one kind of compound selected from a group of compounds expressed by the general formula (II), (III), or (IV), and containing, as other part of the second component, at least one compound selected from a group of compounds expressed by the general formula (V), (VI), (VII), (VIII), or (IX).

17. A liquid crystal display device composed by using a liquid crystal composition defined in claim 13.

18. The difluorooxymethane derivative according to claim 3 wherein all of $L_3$, $L_4$, and X are fluorine atom, in the general formula (I).

19. A liquid crystal composition containing at least one kind of difluorooxymethane derivative defined in claim 3.

20. A liquid crystal composition containing at least one kind of difluorooxymethane derivative defined in claim 6.

21. A liquid crystal composition containing, as a first component, at least one kind of difluorooxymethane derivative defined in claim 3 and containing, as a second component, at least one kind of compound selected from the group of compounds expressed by general formula (II), (III), or (IV)

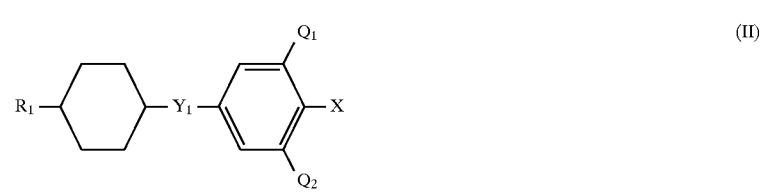

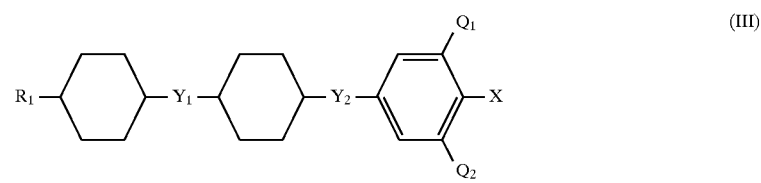

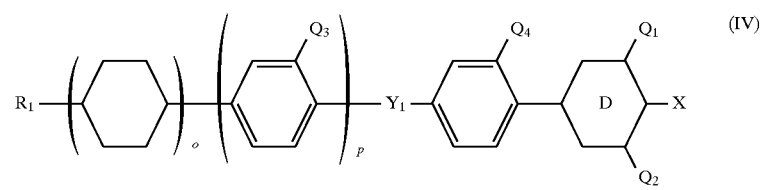

wherein $R_1$ represents an alkyl group having 1 to 10 carbon atoms, X represents F, Cl, CF$_3$, OCF$_3$, OCF$_2$H or an alkyl group having 1 to 10 carbon atoms, $Q_1$, $Q_2$, $Q_3$, and $Q_4$ independently represent H or F, o represents 1 or 2, p represents 0 or 1, $Y_1$ and $Y_2$ independently represent —CH$_2$CH$_2$—, —CH=CH—, or covalent bond, and ring D represents trans-1,4-cyclohexylene group or 1,4-phenylene group.

22. A liquid crystal composition containing, as a first component, at least one kind of difluorooxymethane derivative defined in claim 6 and containing, as a second component, at least one kind of compound selected from the group of compounds expressed by general formula (II), (III), or (IV)

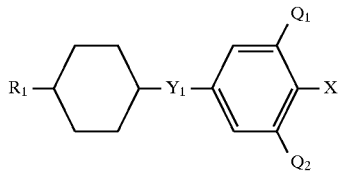

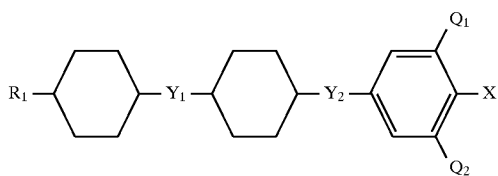

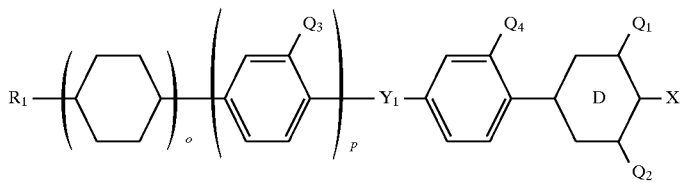

wherein $R_1$ represents an alkyl group having 1 to 10 carbon atoms, X represents F, Cl, $CF_3$, $OCF_3$, $OCF_2H$ or an alkyl group having 1 to 10 carbon atoms, $Q_1$, $Q_2$, $Q_3$, and $Q_4$ independently represent H or F, o represents 1 or 2, p represents 0 or 1, $Y_1$ and $Y_2$ independently represent —$CH_2CH_2$—, —CH=CH—, or covalent bond, and ring D represents trans-1,4-cyclohexylene group or 1,4-phenylene group.

23. A liquid crystal composition containing, as a first component, at least one kind of difluorooxymethane derivative defined in claim 3, containing, as a second component, at least one kind of compound selected from the group of compounds expressed by general formula (V), (VI), (VII), (VIII), or (IX)

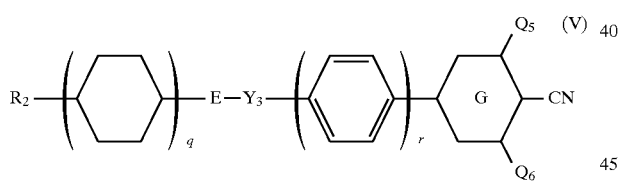

wherein $R_2$ represents fluorine atom, an alkyl group having 1 to 10 carbon atoms, or an alkenyl group having 2 to 10 carbon atoms, in any case, one or not adjacent two or more $CH_2$ groups in the alkyl or alkenyl group may be replaced by oxygen atom, $Y_3$ represents —$CH_2CH_2$—, —COO—, or covalent bond, $Q_5$ and $Q_6$ independently represent hydrogen atom or fluorine atom, E represents trans-1,4-cyclohexylene, 1,4-phenylene, or trans-1,3-dioxane-2,5-diyl, ring G represents trans-1,4-cyclohexylene or 1,4-phenylene, and q and r independently represent 0 or 1,

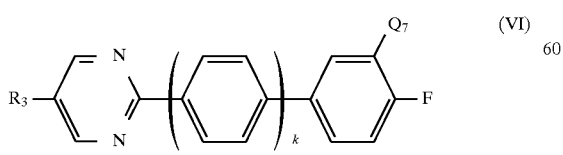

wherein $R_3$ represents an alkyl group having 1 to 10 carbon atoms, $Q_7$ represents hydrogen atom or fluorine atom, and k represents 0 or 1,

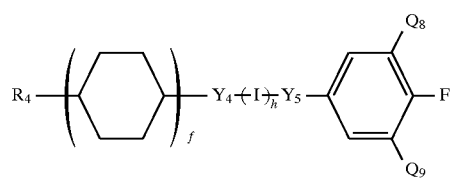

wherein $R_4$ represents an alkyl group having 1 to 10 carbon atoms, I represents trans-1,4-cyclohexylene or 1,4-phenylene, $Q_8$ and $Q_9$ represent hydrogen atom or fluorine atom, $Y_4$ represents —COO—or —C≡C—, and f and h independently represent 0 or 1, $R_5$—J—$Y_6$—K—$R_6$ (VIII)

wherein $R_5$ and $R_6$ independently represent an alkyl group, alkoxy group, or alkoxymethyl group having 1 to 10 carbon atoms, J represents trans-1,4-cyclohexylene, 1,3-pyrimidine-2,5-diyl, or 1,4-phenylene, K represents trans-1,4-cyclohexylene or 1,4-phenylene, $Y_6$ represents —C≡C—, —COO—, —$CH_2CH_2$—, or covalent bond,

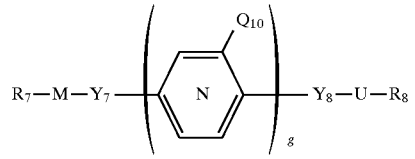

wherein $R_7$ represents an alkyl group or alkoxy group having 1 to 10 carbon atoms, $R_8$ represents an alkyl group having 1 to 10 carbon atoms, one or not adjacent two or more $CH_2$ groups in which alkyl group may be replaced by oxygen atom, M represents trans-1,4-cyclohexylene or 1,3-pyrimidine-2,5-diyl, rings N and U independently represent trans-1,4-cyclohexylene or 1,4-phenylene, $Y_7$ represents —$CH_2CH_2$—, —COO—, or covalent bond, $Y_8$ represents —C≡C—, —COO—, or covalent bond, g represents 0 or 1, and $Q_{10}$ represents hydrogen atom or fluorine atom.

24. A liquid crystal composition containing, as a first component, at least one kind of difluorooxymethane derivative defined in claim 6, containing, as a second component, at least one kind of compound selected from the group of compounds expressed by general formula (V), (VI), (VII), (VIII), or (IX)

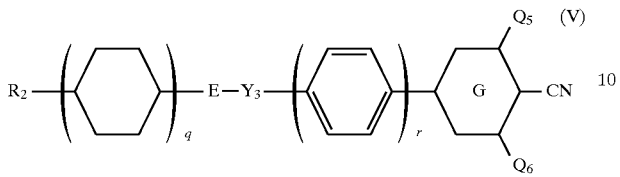 (V)

wherein $R_2$ represents fluorine atom, an alkyl group having 1 to 10 carbon atoms, or an alkenyl group having 2 to 10 carbon atoms, in any case, one or not adjacent two or more $CH_2$ groups in the alkyl or alkenyl group may be replaced by oxygen atom, $Y_3$ represents —$CH_2CH_2$—, —COO—, or covalent bond, $Q_5$ and $Q_6$ independently represent hydrogen atom or fluorine atom, E represents trans-1,4-cyclohexylene, 1,4-phenylene, or trans-1,3-dioxane-2,5-diyl, ring G represents trans-1,4-cyclohexylene or 1,4-phenylene, and q and r independently represent 0 or 1,

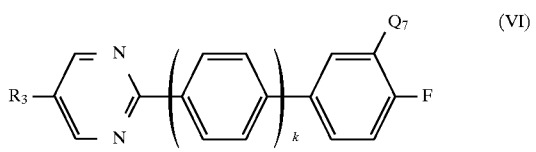 (VI)

wherein $R_3$ represents an alkyl group having 1 to 10 carbon atoms, $Q_7$ represents hydrogen atom or fluorine atom, and k represents 0 or 1,

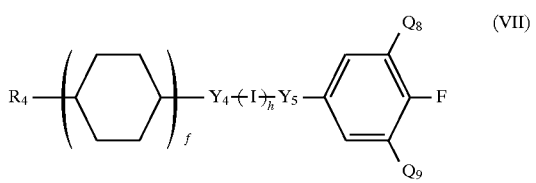 (VII)

wherein $R_4$ represents an alkyl group having 1 to 10 carbon atoms, I represents trans-1,4-cyclohexylene or 1,4-phenylene, $Q_8$ and $Q_9$ represent hydrogen atom or fluorine atom, $Y_4$ represents —COO— or —C≡C—, and f and h independently represent 0 or 1,

 (VIII)

wherein $R_5$ and $R_6$ independently represent an alkyl group, alkoxy group, or alkoxymethyl group having 1 to 10 carbon atoms, J represents trans-1,4-cyclohexylene, 1,3-pyrimidine-2,5-diyl, or 1,4-phenylene, K represents trans-1,4-cyclohexylene or 1,4-phenylene, $Y_6$ represents —C≡C—, —COO—, —$CH_2CH_2$—, or covalent bond,

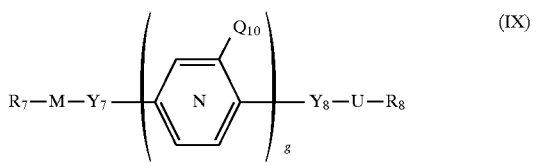 (IX)

wherein $R_7$ represents an alkyl group or alkoxy group having 1 to 10 carbon atoms, $R_8$ represents an alkyl group having 1 to 10 carbon atoms, one or not adjacent two or more $CH_2$ groups in which alkyl group may be replaced by oxygen atom, M represents trans-1,4-cyclohexylene or 1,3-pyrimidine-2,5-diyl, rings N and U independently represent trans-1,4-cyclohexylene or 1,4-phenylene, $Y_7$ represents —$CH_2CH_2$—, —COO—, or covalent bond, $Y_8$ represents —C≡C—, —COO—, or covalent bond, g represents 0 or 1, and $Q_{10}$ represents hydrogen atom or fluorine atom.

25. A liquid crystal composition containing, as a first component, at least one kind of difluorooxymethane derivative defined in claim 3, containing, as a part of the second component, at least one kind of compound selected from a group of compounds expressed by the general formula (II), (III), or (IV), and containing, as other part of the second component, at least one compound selected from a group of compounds expressed by the general formula (V), (VI), (VII), (VIII), or (IX).

26. A liquid crystal composition containing, as a first component, at least one kind of difluorooxymethane derivative defined in claim 6, containing, as a part of the second component, at least one kind of compound selected from a group of compounds expressed by the general formula (II), (III), or (IV), and containing, as other part of the second component, at least one compound selected from a group of compounds expressed by the general formula (V), (VI), (VII), (VIII), or (IX).

27. A liquid crystal display device composed by using a liquid crystal composition defined in claim 14.

28. A liquid crystal display device composed by using a liquid crystal composition defined in claim 15.

29. A liquid crystal display device composed by using a liquid crystal composition defined in claim 16.

30. A liquid crystal display device composed by using a liquid crystal composition defined in claim 19.

31. A liquid crystal display device composed by using a liquid crystal composition defined in claim 20.

32. A liquid crystal display device composed by using a liquid crystal composition defined in claim 21.

33. A liquid crystal display device composed by using a liquid crystal composition defined in claim 22.

34. A liquid crystal display device composed by using a liquid crystal composition defined in claim 23.

35. A liquid crystal display device composed by using a liquid crystal composition defined in claim 24.

36. A liquid crystal display device composed by using a liquid crystal composition defined in claim 25.

37. A liquid crystal display device composed by using a liquid crystal composition defined in claim 26.

38. The difluorooxymethane derivative according to claim 1 wherein all of l, m, and n are 0; and X is CN group.

39. The difluorooxymethane derivative according to claim 1 wherein l and m are 1, and n is 0.

40. The difluorooxymethane derivative according to claim 39 wherein all of $Z_1$, $Z_2$, and $Z_3$ are covalent bond.

* * * * *